(12) United States Patent
Martinez Botella et al.

(10) Patent No.: US 10,774,108 B2
(45) Date of Patent: Sep. 15, 2020

(54) COMPOSITIONS AND METHODS FOR TREATING CNS DISORDERS

(71) Applicant: Sage Therapeutics, Inc., Cambridge, MA (US)

(72) Inventors: Gabriel Martinez Botella, Wayland, MA (US); Boyd L. Harrison, Princeton Junction, NJ (US); Albert Jean Robichaud, Boston, MA (US); Francesco G. Salituro, Marlborough, MA (US); Richard Thomas Beresis, Shanghai (CN)

(73) Assignee: Sage Therapeutics, Inc., Cambridge, MA (US)

( * ) Notice: Subject to any disclaimer, the term of this patent is extended or adjusted under 35 U.S.C. 154(b) by 46 days.

(21) Appl. No.: 15/531,313

(22) PCT Filed: Nov. 27, 2015

(86) PCT No.: PCT/CN2015/095765
§ 371 (c)(1),
(2) Date: May 26, 2017

(87) PCT Pub. No.: WO2016/082789
PCT Pub. Date: Jun. 2, 2016

(65) Prior Publication Data
US 2017/0342102 A1 Nov. 30, 2017

(30) Foreign Application Priority Data
Nov. 27, 2014 (WO) .............. PCT/CN2014/092369

(51) Int. Cl.
| | |
|---|---|
| *C07J 41/00* | (2006.01) |
| *C07J 9/00* | (2006.01) |
| *C07J 33/00* | (2006.01) |
| *C07J 43/00* | (2006.01) |
| *C07J 3/00* | (2006.01) |
| *C07J 17/00* | (2006.01) |
| *C07J 31/00* | (2006.01) |
| *A61K 45/06* | (2006.01) |
| *A61K 31/56* | (2006.01) |

(52) U.S. Cl.
CPC .......... *C07J 41/0055* (2013.01); *A61K 31/56* (2013.01); *A61K 45/06* (2013.01); *C07J 3/00* (2013.01); *C07J 9/00* (2013.01); *C07J 17/00* (2013.01); *C07J 31/006* (2013.01); *C07J 33/002* (2013.01); *C07J 43/00* (2013.01); *C07J 43/003* (2013.01); *C07J 31/00* (2013.01)

(58) Field of Classification Search
CPC ... C07J 31/00; C07J 43/00; C07J 17/00; C07J 33/002; C07J 43/003; C07J 41/0055; C07J 3/00; C07J 9/00; C07J 45/06; A61K 31/56; A61K 45/06
See application file for complete search history.

(56) References Cited

U.S. PATENT DOCUMENTS

| | | |
|---|---|---|
| 2,856,415 A | 10/1958 | Mihina |
| 3,169,134 A | 2/1965 | Klimstra et al. |
| 3,206,459 A | 9/1965 | Cross |
| 3,580,937 A | 5/1971 | Campbell et al. |

(Continued)

FOREIGN PATENT DOCUMENTS

| | | |
|---|---|---|
| CA | 2831054 A1 | 12/2013 |
| CN | 1190404 A | 8/1998 |

(Continued)

OTHER PUBLICATIONS

International Search Report and Written Opinion for Corresponding International Application No. PCT/US15/36500 dated Sep. 11, 2015.

(Continued)

*Primary Examiner* — Barbara P Badio
(74) *Attorney, Agent, or Firm* — Catherine M. McCarty; Christopher K. Haley; Goodwin Procter LLP

(57) ABSTRACT

Described herein are neuroactive steroids of the Formula (II): or a pharmaceutically acceptable salt thereof; wherein A, $R^1$, $R^{2a}$, $R^{2b}$, $R^{3a}$, $R^{3b}$, $R^{4a}$, $R^{4b}$, $R^5$, $R^6$ and ----- are as defined herein. Such compounds are envisioned, in certain embodiments, to behave as GABA modulators. The present invention also provides pharmaceutical compositions comprising a compound of the present invention and methods of use and treatment, e.g., such for inducing sedation and/or anesthesia.

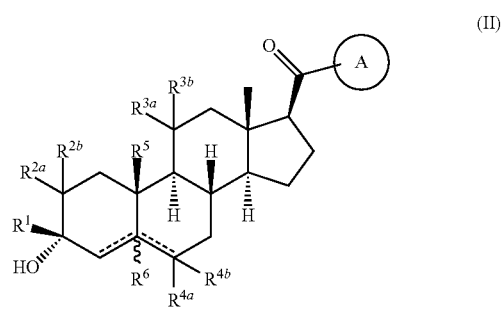

(II)

18 Claims, No Drawings

(56) References Cited

U.S. PATENT DOCUMENTS

| | | |
|---|---|---|
| 3,943,124 A | 3/1976 | Phillipps et al. |
| 3,983,111 A | 9/1976 | Phillipps et al. |
| 3,998,829 A | 12/1976 | Phillips et al. |
| 4,029,777 A | 6/1977 | Engelfried et al. |
| 4,071,625 A | 1/1978 | Grunwell et al. |
| 4,179,336 A | 12/1979 | Weber et al. |
| 4,192,871 A | 3/1980 | Phillipps et al. |
| 4,389,345 A | 6/1983 | Lenz |
| 5,593,983 A | 1/1997 | Campbell |
| 5,721,227 A | 2/1998 | Melloni et al. |
| 5,925,630 A | 7/1999 | Upasani et al. |
| 5,935,545 A | 8/1999 | Leary et al. |
| 5,939,545 A | 8/1999 | Upasani et al. |
| 6,133,280 A | 10/2000 | Brodie et al. |
| 6,143,736 A | 11/2000 | Upasani et al. |
| 6,277,838 B1 | 8/2001 | Upasani et al. |
| 6,717,002 B2 | 4/2004 | Yano et al. |
| 6,844,456 B2 | 1/2005 | Covey |
| 7,064,116 B2 | 6/2006 | Calogeropoulou et al. |
| 7,781,421 B2 | 8/2010 | Covey et al. |
| 8,759,330 B2 | 6/2014 | Covey et al. |
| 8,939,545 B2 | 1/2015 | Tunmore et al. |
| 9,156,876 B2 | 10/2015 | Covey |
| 9,365,611 B2 | 6/2016 | Martinez Botella et al. |
| 9,512,165 B2 | 12/2016 | Martinez Botella et al. |
| 9,630,986 B2 | 4/2017 | Covey et al. |
| 9,725,481 B2 | 8/2017 | Martinez Botella et al. |
| 9,765,110 B2 | 9/2017 | Covey |
| 10,246,482 B2 | 4/2019 | Harrison et al. |
| 2002/0091112 A1 | 7/2002 | Menzenbach et al. |
| 2005/0176976 A1 | 8/2005 | Calogeropoulou et al. |
| 2006/0094696 A1 | 5/2006 | Leese et al. |
| 2007/0014719 A1 | 1/2007 | Reading et al. |
| 2008/0269183 A1 | 10/2008 | Mellon et al. |
| 2009/0048218 A1 | 2/2009 | Kuhnke et al. |
| 2010/0152840 A1 | 6/2010 | Seguin et al. |
| 2010/0234335 A1 | 9/2010 | Gravanis et al. |
| 2010/0317638 A1 | 12/2010 | Covey et al. |
| 2011/0152840 A1 | 6/2011 | Lee et al. |
| 2011/0172242 A1 | 7/2011 | Helton et al. |
| 2014/0017675 A1 | 1/2014 | Ito |
| 2014/0050789 A1 | 2/2014 | Rogawski et al. |
| 2014/0094619 A1 | 4/2014 | Runyon et al. |
| 2014/0148412 A1 | 5/2014 | Hogenkamp |
| 2014/0235600 A1 | 8/2014 | Covey et al. |
| 2014/0249120 A1 | 9/2014 | Covey et al. |
| 2014/0275241 A1 | 9/2014 | Covey |
| 2015/0291654 A1 | 10/2015 | Upasani et al. |
| 2015/0315230 A1 | 11/2015 | Covey et al. |
| 2016/0068563 A1 | 3/2016 | Martinez Botella et al. |
| 2016/0083418 A1 | 3/2016 | Martinez Botella et al. |
| 2016/0108080 A1 | 4/2016 | Martinez Botella et al. |
| 2016/0229887 A1 | 8/2016 | Martinez Botella et al. |
| 2017/0233433 A1 | 8/2017 | Martinez Botella et al. |
| 2017/0246191 A1 | 8/2017 | Martinez Botella et al. |
| 2018/0071315 A1 | 3/2018 | Cashman et al. |
| 2019/0160078 A1 | 5/2019 | Masuoka et al. |

FOREIGN PATENT DOCUMENTS

| | | |
|---|---|---|
| CN | 101412742 A | 4/2009 |
| CN | 101624414 A | 1/2010 |
| CN | 104136452 A | 11/2014 |
| CN | 108727453 A | 11/2018 |
| DE | 2330342 A1 | 1/1974 |
| DE | 2526373 A1 | 12/1976 |
| DE | 2700267 A1 | 7/1977 |
| DE | 2632677 A1 | 1/1978 |
| EP | 0104489 A1 | 4/1984 |
| EP | 0554436 A1 | 8/1993 |
| EP | 0656365 A1 | 6/1995 |
| EP | 0701444 A1 | 3/1996 |
| EP | 1038880 A2 | 9/2000 |
| FR | 1994 M | 9/1963 |
| GB | 1380246 A | 1/1975 |
| GB | 1430942 A | 4/1976 |
| GB | 1494097 A | 12/1977 |
| GB | 1538869 A | 1/1979 |
| GB | 1570394 A | 7/1980 |
| GB | 1581234 A | 12/1980 |
| GB | 1581235 A | 12/1980 |
| RU | 2194712 C2 | 12/2002 |
| RU | 2243232 C2 | 12/2004 |
| RU | 2010100334 A | 7/2011 |
| RU | 2675855 C2 | 12/2018 |
| WO | 1991016897 A1 | 11/1991 |
| WO | 9303732 A1 | 3/1993 |
| WO | 9305786 A1 | 4/1993 |
| WO | 9318053 A1 | 9/1993 |
| WO | 9427608 A1 | 12/1994 |
| WO | 1995021617 A1 | 8/1995 |
| WO | 1996003421 A1 | 2/1996 |
| WO | 1996016076 A1 | 5/1996 |
| WO | 9640043 A2 | 12/1996 |
| WO | 9805337 A1 | 2/1998 |
| WO | 0066614 A1 | 11/2000 |
| WO | 2005051972 A1 | 6/2005 |
| WO | 2005105822 A2 | 11/2005 |
| WO | 2006037016 A2 | 4/2006 |
| WO | 2006131392 A1 | 12/2006 |
| WO | 2008151745 A1 | 12/2008 |
| WO | 2008157460 A1 | 12/2008 |
| WO | 2010003391 A2 | 1/2010 |
| WO | 2010054158 A2 | 5/2010 |
| WO | 2010107815 A1 | 9/2010 |
| WO | 2012013816 A1 | 2/2012 |
| WO | 2012083090 A2 | 6/2012 |
| WO | 2012109752 A1 | 8/2012 |
| WO | 2012110010 A1 | 8/2012 |
| WO | 2012116290 A2 | 8/2012 |
| WO | 2013019711 A2 | 2/2013 |
| WO | 2013036835 A1 | 3/2013 |
| WO | 2013056181 A1 | 4/2013 |
| WO | 2013188792 A2 | 12/2013 |
| WO | 2013192097 A1 | 12/2013 |
| WO | 2014058736 A1 | 4/2014 |
| WO | 2014071449 A1 | 5/2014 |
| WO | 2014100228 A1 | 6/2014 |
| WO | 2014108808 A2 | 7/2014 |
| WO | 2014122480 A1 | 8/2014 |
| WO | 2014169831 A1 | 10/2014 |
| WO | 2014169832 A1 | 10/2014 |
| WO | 2014169833 A1 | 10/2014 |
| WO | 2014169836 A1 | 10/2014 |
| WO | 2015010054 A2 | 1/2015 |
| WO | 2015027227 A1 | 2/2015 |
| WO | 2015180679 A1 | 12/2015 |
| WO | 2015195962 A1 | 12/2015 |
| WO | 2016036724 A1 | 3/2016 |
| WO | 2016061527 A1 | 4/2016 |
| WO | 2016061537 A1 | 4/2016 |
| WO | 2016082789 A1 | 6/2016 |
| WO | 2016123056 A1 | 8/2016 |
| WO | 2016131414 A1 | 8/2016 |
| WO | 2016134301 A2 | 8/2016 |
| WO | 2016209847 A1 | 12/2016 |
| WO | 2017044659 A1 | 3/2017 |
| WO | 2017066626 A1 | 4/2017 |
| WO | 2017087864 A1 | 5/2017 |
| WO | 2017156103 A1 | 9/2017 |
| WO | 2017156418 A1 | 9/2017 |
| WO | 2018013613 A1 | 1/2018 |
| WO | 2018013615 A1 | 1/2018 |
| WO | 2018039378 A1 | 3/2018 |
| WO | 2019018119 A1 | 1/2019 |
| WO | 2019045121 A1 | 3/2019 |
| WO | 2019051264 A1 | 3/2019 |
| WO | 2019094724 A1 | 5/2019 |

OTHER PUBLICATIONS

International Search Report and Written Opinion for Corresponding International Application No. PCT/US15/56054 dated Feb. 9, 2016.

(56) References Cited

OTHER PUBLICATIONS

International Search Report and Written Opinion for Corresponding International Application No. PCT/US2013/076214 dated Aug. 29, 2016.
International Search Report and Written Opinion for Corresponding International Application No. PCT/US2014/052417 dated Nov. 19, 2014.
International Search Report and Written Opinion for Corresponding International Application No. PCT/US2014/092369 dated Aug. 25, 2015.
International Search Report and Written Opinion for Corresponding International Application No. PCT/US2015/056066 dated Feb. 8, 2016.
International Search Report and Written Opinion for Corresponding International Application No. PCT/US2016/014835 dated Jun. 9, 2016.
International Search Report and Written Opinion for Corresponding International Application No. PCT/US2016/018748 dated Aug. 29, 2016.
International Search Report and Written Opinion for Corresponding International Application No. PCT/US2016/062874 dated Jan. 30, 2017.
International Search Report and Written Opinion for Corresponding International Application No. PCT/US2017/041600 dated Dec. 1, 2017.
International Search Report and Written Opinion for Corresponding International Application No. PCT/US2017/041605 dated Dec. 12, 2017.
International Search Report and Written Opinion for Corresponding International Application No. PCT/US2017/048267 dated Aug. 29, 2016.
International Search Report and Written Opinion for International Application No. PCT/CN2013/074312 dated Jan. 23, 2014.
International Search Report and Written Opinion for International Application No. PCT/CN2013/074319 dated Jan. 23, 2014.
International Search Report and Written Opinion for International Application No. PCT/CN2013/074323 dated Jan. 30, 2014.
International Search Report and Written Opinion for International Application No. PCT/CN2013/074325 dated Jan. 23, 2014.
International Search Report and Written Opinion for International Application No. PCT/CN2014/075585 dated Aug. 4, 2014.
International Search Report and Written Opinion for International Application No. PCT/CN2014/075593 dated Jul. 22, 2014.
International Search Report and Written Opinion for International Application No. PCT/CN2014/075594 dated Jul. 16, 2014.
International Search Report and Written Opinion for International Application No. PCT/CN2014/075600 dated Jul. 29, 2014.
International Search Report and Written Opinion for International Application No. PCT/US14/47246, dated Jan. 22, 2015.
International Search Report for International Application No. PCT/US2012/060136 dated Mar. 27, 2013.
Jiang et al., "Neurosteroid analogues. 9. Conformationally constrained pregnanes: structure-activity studies of 13,24-cyclo-18, 21-dinorcholane analogues of the GABA modulatory and anesthetic steroids (3a,5a)- and (3a,5a)-3-hydroxypregnan-20-one", Journal of Medicinal Chemistry, 2003, vol. 46, pp. 5334-5348.
Jungmann et al., "7-Keto-5b-ätiansäure-Derivate. über Gallensäuren and verwandte Stoffe, 51 Mitteilung [Bile acids and related substances. LI. 7-0xo-5. beta.-etianic acid derivatives]", Helvetica Chimica Acta, vol. 41, No. 5, (1958), pp. 1206-1233.
Kaji et al., "Synthesis of 3-epi-6, 7- dideoxyxestobergsterol A", Chem. & Pharm. Bulletin, 2000, vol. 48, No. 10, pp. 1480-1483.
Katona et al., "Neurosteroid analogues. 12. Potent enhancement of GABA-mediated chloride currents at GABAA receptors by ent-androgens", European Journal of Medicinal Chemistry, 2008, vol. 43, pp. 107-113.
Knox et al., "Steroids. CCLXXVIII. Reductions of 19-substituted androst-4-en-3-ones and related compounds", Journal of Organic Chemistry, 1965, vol. 30, No. 7, pp. 2198-2205.

Krafft et al., "Synthesis of the C/D/E and A/B Rings of Xestobergsterol—(A)", Journal of Organic Chemistry, American Chemical Society, vol. 64, No. 7, (1999), pp. 2475-2485.
Krishnan et al., "Neurosteroid Analogues. Chapter 17. Inverted Binding Orientations of Androsterone Enantiomers at the Steroid Potentiation Site on y-Aminobutyric Acid Type A Receptors", Journal of Medicinal Chemistry, 2012, vol. 55, No. 3, pp. 1334-1345.
Lan et al., "Neurosteroid Analogues. 4. The Effect of Methyl Substitution at the C-5 and C-10 Positions of Neurosteroids on Electrophysiological Activity at GABAA Receptors", Journal of Medicinal Chemistry, (1996), vol. 39, pp. 4218-4232.
Lehmann et al., "Schweinegallensäuren Der Abbau von Hyocholsäure zu Pregnanderivaten", vol. 32, No. 3-4, (1966), pp. 217-224.
Lewbart et al., "Oxidation of Steroidal a-Ketols to Glyoxals with Cupric Acetate", Journal of Organic Chemistry, (1963), vol. 28, No. 8, pp. 2001-2006.
Li et al., "Neuroactive Steroids and Human Recombinant p1 GABAc Receptors", Journal of Pharmacology and Experimental Therapeutics, (2007), vol. 323, pp. 236-247.
Mangialasche et al., "Alzheimer's disease: clinical trials and drug development", Lance Neurology, vol. 9 (2010), pp. 702-716.
Matsui et al., "Comparative fate of testosterone and testosterone sulfate in female rats: C19O2 and C19O3 steroid metabolites in the bile", Journal of Steroid Biochemistry, 1977, 8(4), pp. 323-328.
Mok et al., "Evidence that 5a-pregnan-3a-ol-20-one is the metabolite responsible for progesterone anesthesia", Brain Research (1990), 533(1), pp. 42-45.
Morrow et al., "Characterization of Steroid Interactions with gamma-Aminobutyric Acid Receptor-Gated Chloride Ion Channels: Evidence for Multiple Steroid Recognition Sites", 1989, Molecular Pharmacology, 37, pp. 263-270.
Nilsson et al., "Neurosteroid analogues. 6. The synthesis and GABAA receptor pharmacology of enantiomers of dehydroepiandrosterone sulfate, pregnenolone sulfate, and (3a,5b)-3-hydroxypregnan-20-one sulfate", Journal of Medicinal Chemistry, 1998, vol. 41, pp. 2604-2613.
Notification of Transmittal of the International Search Report and the Written Opinion of the International Searching authority, or the Declaration, International Application No. PCT/US13/45933, dated Dec. 3, 2013, 5 Pages.
Paradiso et al., "Steroid Inhibition of Rat Neuronal Nicotinic a4B2 Receptors Expressed in HEK 293 Cells", Journal of Molecular Pharmacology, (2000), vol. 58, pp. 341-351.
Paul et al., "Neuroactive Steroids", The Journal of the Federation of American Societies for Experimental Biology, (1992), pp. 2311-2322.
Peart et al., "Hydroxylation of steroids by Fusarium oxysporum, Exophiala jeanselmei and Ceratocystis paradoxa", Steroids, vol. 76, No. 12, (2011), pp. 1317-1330.
Pechet et al., "Metabolism of 19-hydroxycorticosterone. Isolation and characterization of three metabolites", Journal of Thological Chemistry, Jan. 1, 1961, vol. 236, No. 10, pp. PC68-PC69.
Phillipps et al., "A New Series of Steroidal Antidysrhythmic Agents," J. Steroid Biochem. 19(1):759-765 (1983).
Phillipps et al., "Water-soluble Steroidal Anaesthetics", Journal of Steroid Biochemistry 11:79-86 (1979).
Phillipps, "Structure-Activity Relationships in Steroidal Anaesthetics", Journal of Steroid Biochemistry, (1975), vol. 6, pp. 607-613.
Phillipps, "Structure-Activity Relationships in Steroidal Anaesthetics", Nol. Mech. Gen. Anaesth. Glaxo Symposium, (1974), pp. 32-47.
PubChem-70249446 (2012), entire document.
Purdy et al., "Synthesis, Metabolism, and Pharmacological Activity of 3a-Hydroxy Steroids Which Potentiate GABA-Receptor-Mediated Chloride Ion Uptake in Rat Cerebral Cortical Synaptoneurosomes", Journal of Medicinal Chemistry, (1990), vol. 33, pp. 1572-1581.
Qian et al., "Neurosteroid Analogues, 18. Structure-Activity Studies of ent-Steroid Potentiators of y-Aminobutyric Acid Type A Receptors and Comparison of Their Activities with Those of Alphaxalone and Allopregnanolone", Journal of Medicinal Chemistry, 2014, vol. 57, No. 1, pp. 171-190.

(56) References Cited

OTHER PUBLICATIONS

Qian et al., "The efficient and enantiospecific total synthesis of cyclopenta[b]phenanthrenes structurally related to neurosteroids", Adv. Syn. & Cata., 2010, vol. 352, Nos. 11-12, pp. 2057-2061.
Rogawski et al., "Neuroactive steroids for the treatment of status epilepticus", Epilepsia, 54:(2013), pp. 93-98.
Runyon et al., "17b-Nitro-5a-androstan-3a-ol and its 3b-methyl derivative: Neurosteroid analogs with potent anticonvulsant and anxiolytic activities", European Journal of Pharmacology 617, (2009), pp. 68-73.
Ruzicka et al., "Steroids and sex hormones. CXXXIX. The relation between constitution and odor of steroids. Methylandrostane and allopregnane derivatives", Helvetica Chimica Acta, 1947, vol. 30, pp. 867-878.
Rychnovsky et al., "Synthesis of ent-cholesterol, the unnatural enantiomer", Journal of Organic Chemistry, 1992, vol. 57, No. 9, pp. 2732-2736.
Santaniello & Caspi, "Reduction of certain steroidal 19-sulfonic esters with metal hydrides", J. of Ster. Biochem, 1976, vol. 7, No. 3, pp. 223-227.
Sarett., "A new method for the preparation of 17(alpha)-hydroxy-20-ketopregnanes", J. Am. Chem. Soc., 1948, vol. 70, pp. 1454-1458.
Scaglione et al., "Neurosteroid Analogues. 14. Alternative Ring System Scaffolds: GABA Modulatory and Anesthetic Actions of Cyclopenta[b]phenanthrenes and Cyclopenta[b]anthracenes", 2008, Journal of Medicinal Chemistry, vol. 51, pp. 1309-1318.
Shen et al., "Microbial aromatization of 19-hydroxymethylepidehydroandrosterone acetate by Corynebacterium simplex", Huaxue Xuebao, 1983, vol. 41, No. 5, pp. 473-474.
Shu et al., "Characteristics of concatemeric GABM receptors containing alpha4/d subunits expressed in Xenopus oocytes" British Journal of Pharmacology (2012) 165, 2228-2243.
Slavíková et al., "Allopregnanolone (3a-Hydroxy-5a-pregnan-20-one) Derivatives with a Polar Chain in Position 16a: Synthesis and Activity", Journal of Medicinal Chemistry, vol. 52, No. 7, (2009), 2119-2125.
Spiegel et al., "Use of Nonaqueous Solvents in Parenteral Products", Journal of Pharmaceutical Sciences, 1963, vol. 52, No. 10, pp. 917-927.
Starnes et al., "Thin-Layer Chromatography of 17-Kelosteroid 2,4-Dinitrophenylhydrazones", Journal of Clinical Endocrinology and Metabolism, 1966, vol. 26, No. 11, pp. 1245-1250.
Stastna et al., "Neurosteroid Analogues. 16. A New Explanation for the Lack of Anesthetic Effects in D16—Alphaxalone and Identification of a D17(20) Analogue with Potent Anesthetic Activity", Journal of Medicinal Chemistry, 2011, vol. 54, No. 11, pp. 3926-3934.
Stastna et al., "Stereoselectivity of sodium borohydride reduction of saturated steroidal ketones utilizing conditions of Luche reduction", Steroids, 2010, vol. 75, No. 10, pp. 721-725.
Stastna et al., "Synthesis of C3, C5, and C7 pregnane derivatives and their effect on NMDA receptor responses in cultured rat hippocampal neurons", Steroids, Elsevier Science Publishers, vol. 74, No. 2, (2008), pp. 256-263.
Stastna et al., "The use of symmetry in enantioselective synthesis: Four pairs of chrysene enantiomers prepared from 19-nortestosterone", Org. Biomol. Chem., 2011, vol. 9, pp. 4685-4694.
Supplemental European Search Report, European Patent Application No. 14826212.4, dated Feb. 16, 2017.
Tsai et al., "Synthesis and antiproliferative activity of 3a-hydroxyl-3b-methoxymethyl-5a-pregnan-20-one with a C-21 hydrophilic substituent", Heteroatom Chemistry, (2017), pp. 1-9.
Upasani et al., "3a-Hydroxy-311-(phenylethynyl)-5ß-pregnan-20-ones: Synthesis and Pharmacological Activity of Neuroactive Steroids with High Affinity for GABAA Receptors", J. Med. Chem. (1997) vol. 40, No. 1, pp. 73-84.
Vanover et al., "Behavioral characterization of Co 134444 (3a-hydroxy-21-(1'-imidazolyl)-3b-methoxymethyl-5a-pregnan-20-one), a novel sedative-hypnotic neuroactive steroid", Psychopharmacology (2001), vol. 155, pp. 285-291.
Vanover et al., "Characterization of the Anxiolytic Properties of a Novel Neuroactive Steroid, Co 2-6749 (GMA-839; WAY-141839; 3a, 21-Dihydroxy-3b-trifluoromethyl-19-nor-5b-pregnan-20-one), a Selective Modulator of y-Aminobutyric AcidA Receptors", The Journal of Pharmacology and Experimental Therapeutics, (2000), vol. 295, No. 1, pp. 337-345.
Vanover et al., "Response-Rate Suppression in Operant Paradigm as Predictor of Soporific Potency in Rats and Identification of Three Novel Sedative-Hypnotic Neuroactive Steroids", Journal of Pharmacology and Experimental Therapeutics, (1999), vol. 291, No. 3, pp. 1317-1323.
Wicha et al., "Transformations of steroidal neopentyl systems. II. Migration of acetate from the 3beta-to the 19-hydroxyl in delta 5 and A/B-trans steroids", Canadian Journal of Chemistry, 1967, vol. 45, No. 7, pp. 707-711.
Wicha et al., "Transformations of steroidal neopentyl systems. IV. Stereochemistry of Products of Reaction of Methyllithium with Steroidal A5-19-aldehydes", Journal of the Chemical Society (Section) C: Organic, 1968, vol. 14, 1740-1746.
Wicha et al., "Transformations of steroidal neopentyl systems. V. Synthesis and proof of the configuration of 19amethyl-195-alcohols", Journal of the Chemical Society [Section] C: Organic, 1969, vol. 6, pp. 947-951.
Wicha et al., "Transformations of steroidal neopentyl systems. VI. Intramolecular Claisen condensation of 19R-acetoxy-19A-methyl-3-ones of the 5alpha series", Tetrahedron, 1969, vol. 25, No. 17, pp. 3961-3968.
Wicha et al., "Transformations of steroidal neopentyl systems. VII. Mechanism of the transformation of (19R)-(19)-hydroxy-19-methyl-3-oxo-5alpha-to 3alpha-hydroxy-19-methyl-19-oxo-5alpha-analogs", Journal of Organic Chemistry, 1973, vol. 38 No. 7, pp. 1280-1283.
Wu, "A New Classification of Prodrugs: Regulatory Perspectives", Pharmaceuticals, 2009, vol. 2, pp. 77-81.
Zeng et al., "Neurosteroid Analogues. 10. The Effect of Methyl Group Substitution at the C-6 and C-7 Positions on the GABA Modulatory and Anesthetic Actions of (3a,5a) -and (3a, 5b)-3-Hydroxypregnan-20-one", Journal of Medicinal Chemistry, (2005). vol. 48, pp. 3051-3059.
Zonana et al., "The Neurobiology of Postpartum Depression", CNS Spectrums, (2005), pp. 792-799, 805.
Zorumski et al., "Enantioselective Modulation of GABAergic Synaptic Transmission by Steroids and Benz[dindenes in Hippocampal Microcultures", Synapse, (1998), vol. 29, pp. 162-171.
Anderson et al., "Anesthetic Activity of Novel Water-Soluble 2b-Morpholinyl Steroids and Their Modulatory Effects at GABA-A Receptors", Journal of Medicinal Chemistry., 1997, vol. 40, pp. 1668-1681.
Anderson et al., "Conformationally Constrained Anesthetic Steroids That Modulate GABAA Receptors," Journal of Medicinal Chemistry, 2000, vol. 43, No. 22, pp. 4118-4125.
Atack, "Development of Subtype-Selective GABAA Receptor Compounds for the Treatment of Anxiety, Sleep Disorders and Epilepsy", GABA and Sleep. Molecular, Functional and Clinical Aspects. 2010, pp. 25-72.
Banday et al., "D-ring substituted 1,2,3-triazolyl 20-keto pregnenanes as potential anticancer agents: Synthesis and biological evaluation", Steroids, (2010), vol. 75, No. 12, pp. 801-804, Abstract.
Bandyopadhyaya et al., "Neurosteroid Analogs. 15. A Comparative Study of the Anesthetic and GABAergic Actions of Alphaxalone, D16-Alphaxalone and Their Corresponding 17-Carbonitrile Analogs," Bioorganic & Medicinal Chemistry Letters 20:6680-6684 (2010).
Berge et al., J. Pharmaceutical Sciences, 1977, vol. 66, pp. 1-19.
Bernstein, "Rett Syndrome Medication", Medscape, (2017).
Bjorkhem et al., "Steroid hormone metabolism in developing rates", Eur. J.Biochem., 1972, vol. 27, No. 2, pp. 318-326.
Botella et al., "Neuroactive Steroids. 1. Positive Allosteric Modulators of the (g-Aminobutyric Acid)A Receptor: Structure-Activity Relationships of Heterocyclic Substitution at C-21", Journal of Medical Chemistry, 2015, pp. 3500-3511.

(56) References Cited

OTHER PUBLICATIONS

Botella et al., "Neuroactive Steroids. 2. 3a-Hydroxy-3b-methyl-21-(4-cyano-1H-pyrazol-1-yl)-19-nor-5b-pregnan-20-one (SAGE-217): A Clinical Next Generation Neuroactive Steroid Positive Allosteric Modulator of the (g-Aminobutyric Acid) A Receptor" Journal of Medical Chemistry, 2017, 10 pp. A-J.
Caspi et al., "Stereochemistry of 19-hydroxy-19alpha-methyl steroids," Chemical Communications, 1966, vol. 7, pp. 209-210.
Cerny et al., "Syntheses of 19-[O-(carboxymethyl)oxime] haptens of epipregnanolone and pregnanolone", Steroids, 2006, vol. 71(2), pp. 120-128.
Cerny et al., "Synthetic approach to 5alpha-pregnanolone 19-[O-(carboxymethyl) oxime] derivatives", Collection of Czechoslovak Chemical Communications, 2004, vol. 69, No. 9, pp. 1805-1817.
Chodounska et al., "Epalons: Synthesis of 3a, 7a-Dihydroxy-5a-Pregnan-20-One", Collection Symposium Series, vol. 53, No. 10, (1998), pp. 1543-1548.
Database CAPLUS in STN, Acc. No. 1995:986323, Upasani et al., WO 9521617 A1 (Aug. 17, 1995) (abstract). [Upasani, Ravindra B. "Androstanes and pregnanes for allosteric modulation of GABA receptor, and preparation and therapeutic uses of compounds".].
Database CAPLUS in STN, Acc. No. 1998:112239, Lan, WO 9805337 A1 (Feb. 12, 1998) (abstract). [Lan, Nancy C., "Use of GABA agonists and NMDA receptor antagonists for the treatment of migraine headache".].
Deluca et al., "Synthesis of 3b-Hydroxy[21-14C]-5b-pregn-8(14)-en-20-one from Chenodeoxycholic Acid", Helvetica Chemic Acta, vol. 69, (1986), pp. 1844-1850.
Deniau et al., "Synthesis of fluorinated analogues of the neurosteroid GABA receptor antagonist, 17-PA", Journal of Fluorine Chemistry, (2008), vol. 129, No. 9, pp. 881-887.
Dorwald, "Side Reactions in Organic Synthesis", 2005, Wiley-VCH, Preface, Pg. IX.
Edgar et al., "CCD-3693: An Orally Bioavailable Analog of the Endogenous Neuroactive Steroid, Pregnanolone, Demonstrates Potent Sedative Hypnotic Actions in the Rat" The Journal of Pharmacology and Experimental Therapeutics (1997) vol. 282, No. 1, pp. 420-429.
Evers et al., "A Synthetic 18-Norsleroid Distinguishes Between Two Neuroactive Steroid Binding Sites on GABAA Receptors", Journal of Pharmacology and Experimental Therapeutics, 2010, vol. 333, No. 2, pp. 404-413.
Extended European Search Report for application PCT/CN2014075593 dated Aug. 26, 2016.
Extended European Search Report for application PCT/CN2014075594 dated Aug. 26, 2016.
Fajkos et al., "Steroids. XXIII. Synthesis and configuration of the two stereoisomeric 3b-hydroxy-16-acetylandrostanes", Chemicke Listy pro Vedu a Prumysl, 1956, vol. 50, pp. 791-799.
Fesik et al., "Geometric Requirements for Membrane Perturbation and Anesthetic Activity", Molecular Pharmacology, 1985, vol. 27, pp. 624-629.
Gasior et al., "Neuroactive steroids: potential therapeutic use in neurological and psychiatric disorders", Trends in Pharmacological Science, (1999), vol. 20, No. 3, pp. 107-112.
Green et al., "The nonfeminizing enantiomer of 17b-estradiol exerts protective effects in neuronal cultures and a rat model of cerebral ischemia", Endocrinology, 2001, vol. 142, pp. 400-406.
Gustafsson et al., "Steroid excretion patterns in urine from ovariectomized and adrenalectomized rats", Biochmica ET Biophysica ACTA—Lipids and Lipid Metabolism, Elsevier Science BV, 1972, vol. 280, No. 1, pp. 182-186.
Gustafsson et al., "Steroids in Germfree and Conventional Rats. 7. Identification of C19 and C21 Steroids in faeces from Conventional Rats", European Journal of Biochemistry, 1968, vol. 6, No. 2, pp. 248-255.
Gyermek et al., "Steroids, CCCX. 1 Structure-Activity Relationship of Some Steroidal Hypnotic Agents", Journal of Medicinal Chemistry, 1968, vol. 11, No. 1, pp. 117-125.
Han et al., "Neurosteroid Analogs. 3. The Synthesis and Electrophysiological Evaluation of Benz[e]indene Congeners of Neuroactive Steroids Having the 5b-Configuration", Journal of of Medicinal Chemistry, 1995, vol. 38, No. 22, pp. 4548-4556.
Harrison et al., "Structure-Activity Relationships for Steroid Interaction with the y-Aminobutyric AcidA Receptor Complex" The Journal of Pharmacology and Experimental Therapeutics (1987) vol. 241, No. 1, pp. 346-353.
Hauser et al., "Steroids. CCV. Fragmentations and intramolecular abstractions of tertiary hydrogen atoms by primary oxy radicals with fixed reaction centers", Helv. Chim. Acta, 1964, vol. 47, pp. 1961-1979.
Hawkinson et al., "3a-Hydroxy-3b-trifluoromethyl-5a-pregnan-20-one (Co 2-1970): A Partial Agonist at the Neuroactive Steroid Site of the y-Aminobutyric acidA Receptor" Molecular Pharmacology (1996) vol. 49, pp. 897-906.
Hawkinson et al., "Correlation of Neuroactive Steroid Modulation of [35S]t-Butylbicyclophosphorothionate and [3H] Flunitrazepam Binding and y-Aminobutyric AcidA Receptor Function", Molecular Pharmacology (1994) vol. 46, pp. 977-985.
Hawkinson et al., "Substituted 3b-Phenylethynyl Derivatives of 3a-Hydroxy-5a-pregnan-20-one: Remarkably Potent Neuroactive Steroid Modulators of y-Aminobutyric AcidA Receptors", The Journal of Pharmacology and Experimental Therapeutics(1998), vol. 287, No. 1, pp. 198-207.
Heard et al., "Steroids VII. Preparation of of androstan-3(b)-ol-7-one from from dehydroisoandrosterone", Journal of Biological Chemistry, 1946, vol. 165, pp. 677-685.
Hewett et al., "Amino steroids. Part III. 2- and 3-Amino-5a-androstanes", Journal of the Chemical Society, 1968, vol. 9, pp 1134-1140.
Hill et al., "Pholochemische Reaktionen. 32 Milleilung. UV-Bestrahlung von gesattigten and bela,gamma-ngesalligten, homoallylisch konjugierten steroidaldehyden", Helvetica Chimica Acta, 1946, vol. 49, No. 1, pp. 292-311.
Hogenkamp et al., "Pharmacological profile of a 17b-heteroaryl-substituted neuroactive steroid", Psychopharmacology, vol. 231, (2014), pp. 3517-3524.
Hogenkamp et al., "Synthesis and in Vitro Activity of 3b-Substituted-3a-hydroxypregnan-20-ones: Allosteric Modulators of the GABAA Receptor", Journal of Medicinal Chemistry, (1997), vol. 40, pp. 61-72.
Hu et al., "Neurosteroid analogues. Part 5. Enantiomers of neuroactive steroids and benz[e]indenes: total synthesis, 18 electrophysiological effects on GABAA receptor function and anesthetic actions in tadpoles", J. Chem. Soc. Perkin Trans 1, 1997, pp. 3665-3671.
Hu et al., "Neurosteroid Analogues: Structure-Activity Studies of Benz(e] indene Modulators of GABAA Receptor Function. 1. The Effect of 6-Melhyl Substitution on the Electrophysiological Activity of 7-Substituted Benz[e]indene-3-carbonitriles", Journal of Medicinal Chemistry, (1993), pp. 3956-3967.
Im et al., "Studies on the Mechanism of Interactions between Anesthetic Steroids and y-Aminobutyric AcidA Receptors", Molecular Pharmacology (1990), 37(3), pp. 429-434.
International Search Report and Written Opinion for Corresponding International Application No. PCT/CN2014/078820 dated Feb. 27, 2015.
International Search Report and Written Opinion for Corresponding International Application No. PCT/CN2015/080216 dated Aug. 3, 2015.
International Search Report and Written Opinion for Corresponding International Application No. PCT/CN2015/095765 dated Mar. 4, 2016.
Adams et al., "The estrogenic activity and enzymic oxidation of 17b-estradiol-17a-d1", Steroids, Elsevier Science Publishers, (1965), pp. 75-84.
Anonymous: "Archive History for NCT03000530", Aug. 4, 2017, Retrieved from the Internet: <URL:https://www.clinicaltrials.gov/ct2/his> tory/NCT03000530?V-_6=View#StudyPageTop; [retrieved on Nov. 20, 2018].
Chen et al., "The mechanism investigation in substitution of 21-bromo-3a-hydroxy-3b-methoxymethyl-5a-pregnan-20-one with nucleophiles", Steroids, vol. 71, (2006), pp. 942-948.

(56) References Cited

OTHER PUBLICATIONS

D'hulst et al., "Expression of the GABAergic system in animal models for fragile X syndrome and fragile X associated tremor/ataxia syndrome (FXTAS)", Brain Research, 2008, vol. 1253, pp. 176-183.
Database Medline, US National Library of Medicine, Bethesda, MD, 1984, Welling: "Intentions affecting drug absorption", Database accession No. NLM6388952, abstract.
Durán et al., "Synthesis of 6-thia analogs of the natural neurosteroid allopregnanolone", Tetrahedron, Elsevier Science Publishers, 2006, vol. 62, No. 20, pp. 4762-4768.
Eimon et al., "Brain activity patterns in high-throughput electrophysiology screen predict both drug efficacies and side effects", Nature Communications, (2018) 9:219, pp. 1-14.
Gottesmann, "GABA Mechanisms and Sleep", Neuroscience, (2002), vol. 111, No. 2, pp. 231-239.
Guardia et al., "GABAergic and Glutamatergic Modulation in Binge Eating: Therapeutic Approach", Current pharmaceutical design, 2011, vol. 17, No. 14, pp. 1396-1409.
Gunduz-Bruce et al.,"Sage-217 in Major Depressive Disorder: A Multicenter, Randomized, Double-Blind, Phase 2 Placebo-Controlled Trial", European Nueuropsychopharmacology, vol. 29, 2019, pp. S59-S-60, Abstract.
Gunduz-Bruce et al.,"Sage-217 in Subjects with Major Depressive Disorder: Efficacy and Safety Results from Open-Label Part A of a Phase 2a Study", Poster, (Presented on Sep. 2-5, 2017 at the 30th ECNP Congress, Paris, France.
Hawkins et al., "The synthetic neuroactive steroid SGE-516 reduces seizure burden and improves survival in a Dravet syndrome mouse model", Science Reports, (2017), pp. 1-8.
International Search Report and Written Opinion for Corresponding International Application No. PCT/US2018/050012 dated Dec. 7, 2018.
International Search Report and Written Opinion for Corresponding International Application No. PCT/US2018/051048 dated Jan. 11, 2019.
International Search Report and Written Opinion for Corresponding International Application No. PCT/US2018/064546 dated Apr. 9, 2019.
International Search Report and Written Opinion for Corresponding International Application No. PCT/US2019/036848 dated Aug. 22, 2019.
International Search Report and Written Opinion International Application No. PCT/US2018/067277 dated May 24, 2019.
International Search Report and Written Opinion for International Application No. PCT/US2018/067306 dated May 28, 2019.
International Search Report and Written Opinion for International Application No. PCT/US2019/013315 dated Jun. 14, 2019.
Itoh et al., "On the acid-catalyzed d-homoannulation of pregnanetriol 20-sulfate and its c-20 isomeric sulfate", Chemical and Pharmaceutical Bulletin. 1994, vol. 42, No. 9, pp. 1736-1744.
Kanes et al., "A multiple-ascending dose study of the neuroactive steroid Sage-217", Biological Psychiatry, vol. 81, No. 10, 2017, pp. S347.
Kanes et al., "A single-ascending dose study of the neuroactive steroid Sage-217", Biological Psychiatry, vol. 81, No. 10, 2017, pp. S31.
Kasal et al., "Neurosteroid analogues: synthesis of 6-aza-allopregnanolone", Tetrahedron, Elsevier Science Publishers, 2005, vol. 61, No. 9, pp. 2269-2278.
Mariangela et al., "The influence of neuroactive steroid lipophilicity on gabaa receptor modulation: Evidence for a low-affinity interaction", Journal of Neurophysiology, 2009, vol. 102, No. 2, pp. 1254-1264.
Möhler, "The GABA system in anxiety and depression and its therapeutic potential", Neuropharmacology, (2012) 62; pp. 42-53.
Nicoletti et al., "Synthesis and GABAA receptor activity of 6-oxa-analogs of neurosteroids", Steroids, Elsevier Science Publishers 2000, vol. 65, No. 6, pp. 349-356.
Rongone et al., "In vivo metabolism of d-homotestosterone", Steroids, vol. 1, No. 6, 1963, pp. 664-669.
Sage Therapeutics: "Sage Therapeutics Advances SAGE-217 into Placebo-Controlled Phase 2 Clinical Trial in Major Depressive Disorder", Feb. 13, 2017, Retrieved from the Internet: <URL:https://investor.sagerx.com/static-fil>es/80fflf35-fc4c-4eb2-9456-3228ec891a59; [retrieved on Dec. 21, 2018].
Saporito et al., "Intravenously Administered Ganaxolone Blocks Diazepam-Resistant Lithium-Pilocarpine-Induced Status Epilepticus in Rats: Comparison with Allopregnanolone", Journal of Pharmacology Exp. Ther. 2019, 368(3), pp. 326-327.
Shu et al., "Photodynamic effects of steroid-conjugated fluorophores on gabaa receptors", Molecular Pharmacology, 2009, vol. 76, No. 4, pp. 754-765.
Sunöl et al., "Activity of b-nor analogues of neurosteroids on the gabaa receptor in primary neuronal cultures", Journal of Medicinal Chemistry, 2006, vol. 49, No. 11, pp. 3225-3234.
Suthoff et al., "Assessment of Health-Related Quality of Life by the SF36V2 in a Phase 2, Randomized Placebo-Controlled Trial of the GABAA Receptor Positive Allosteric Modulator Sage-217 in Major Depressive Disorder", Value in Health, vol. 21, No. Suppl. 3, 2018, Abstract.
Veleiro et al., "Structure-activity relationships of neuroactive steroids acting on the gabaa receptor", Current Medicinal Chemistry, 2009, vol. 16, No. 4, pp. 455-472.
Welling, "Interactions affecting drug absorption", Clinical Pharmacokinetics, vol. 9, No. 5, Sep. 1984 (Sep. 1984), pp. 404-434.

COMPOSITIONS AND METHODS FOR TREATING CNS DISORDERS

RELATED APPLICATIONS

This application is a U.S. National Stage Application filed under 35 U.S.C. § 371 of International Patent Application No. PCT/CN2015/095765, filed Nov. 27, 2015, which claims the benefit of and priority to PCT/CN2014/092369, filed Oct. 27, 2014, the contents of each of which are hereby incorporated by reference in their entirety.

BACKGROUND OF THE INVENTION

Brain excitability is defined as the level of arousal of an animal, a continuum that ranges from coma to convulsions, and is regulated by various neurotransmitters. In general, neurotransmitters are responsible for regulating the conductance of ions across neuronal membranes. At rest, the neuronal membrane possesses a potential (or membrane voltage) of approximately −70 mV, the cell interior being negative with respect to the cell exterior. The potential (voltage) is the result of ion ($K^+$, $Na^+$, $Cl^-$, organic anions) balance across the neuronal semipermeable membrane. Neurotransmitters are stored in presynaptic vesicles and are released under the influence of neuronal action potentials. When released into the synaptic cleft, an excitatory chemical transmitter such as acetylcholine will cause membrane depolarization, e.g., a change of potential from −70 mV to −50 mV. This effect is mediated by postsynaptic nicotinic receptors which are stimulated by acetylcholine to increase membrane permeability to $Na^+$ ions. The reduced membrane potential stimulates neuronal excitability in the form of a postsynaptic action potential.

In the case of the GABA receptor complex (GRC), the effect on brain excitability is mediated by GABA, a neurotransmitter. GABA has a profound influence on overall brain excitability because up to 40% of the neurons in the brain utilize GABA as a neurotransmitter. GABA regulates the excitability of individual neurons by regulating the conductance of chloride ions across the neuronal membrane. GABA interacts with its recognition site on the GRC to facilitate the flow of chloride ions down an electrochemical gradient of the GRC into the cell. An intracellular increase in the levels of this anion causes hyperpolarization of the transmembrane potential, rendering the neuron less susceptible to excitatory inputs, i.e., reduced neuron excitability. In other words, the higher the chloride ion concentration in the neuron, the lower the brain excitability and level of arousal.

It is well-documented that the GRC is responsible for the mediation of anxiety, seizure activity, and sedation. Thus, GABA and drugs that act like GABA or facilitate the effects of GABA (e.g., the therapeutically useful barbiturates and benzodiazepines (BZs), such as Valium®) produce their therapeutically useful effects by interacting with specific regulatory sites on the GRC. Accumulated evidence has now indicated that in addition to the benzodiazepine and barbiturate binding site, the GRC contains a distinct site for neuroactive steroids. See, e.g., Lan, N. C. et al., *Neurochem. Res.* (1991) 16:347-356.

Neuroactive steroids can occur endogenously. The most potent endogenous neuroactive steroids are 3α-hydroxy-5-reduced pregnan-20-one and 3α-21-dihydroxy-5-reduced pregnan-20-one, metabolites of hormonal steroids progesterone and deoxycorticosterone, respectively. The ability of these steroid metabolites to alter brain excitability was recognized in 1986 (Majewska, M. D. et al., *Science* 232:1004-1007 (1986); Harrison, N. L. et al., *J Pharmacol. Exp. Ther.* 241:346-353 (1987)).

The ovarian hormone progesterone and its metabolites have been demonstrated to have profound effects on brain excitability (Backstrom, T. et al., *Acta Obstet. Gynecol. Scand. Suppl.* 130:19-24 (1985); Pfaff, D. W and McEwen, B. S., *Science* 219:808-814 (1983); Gyermek et al., *J Med Chem.* 11: 117 (1968); Lambert, J. et al., *Trends Pharmacol. Sci.* 8:224-227 (1987)). The levels of progesterone and its metabolites vary with the phases of the menstrual cycle. It has been well documented that the levels of progesterone and its metabolites decrease prior to the onset of menses. The monthly recurrence of certain physical symptoms prior to the onset of menses has also been well documented. These symptoms, which have become associated with premenstrual syndrome (PMS), include stress, anxiety, and migraine headaches (Dalton. K., *Premenstrual Syndrome and Progesterone Therapy,* 2nd edition, Chicago Yearbook, Chicago (1984)). Subjects with PMS have a monthly recurrence of symptoms that are present in premenses and absent in postmenses.

In a similar fashion, a reduction in progesterone has also been temporally correlated with an increase in seizure frequency in female epileptics, i.e., catamenial epilepsy (Laidlaw, J., *Lancet,* 1235-1237 (1956)). A more direct correlation has been observed with a reduction in progesterone metabolites (Rosciszewska et al., *J. Neurol. Neurosurg. Psych.* 49:47-51 (1986)). In addition, for subjects with primary generalized petit mal epilepsy, the temporal incidence of seizures has been correlated with the incidence of the symptoms of premenstrual syndrome (Backstrom, T. et al., *J. Psychosom. Obstet. Gynaecol.* 2:8-20 (1983)). The steroid deoxycorticosterone has been found to be effective in treating subjects with epileptic spells correlated with their menstrual cycles (Aird, R. B. and Gordan, G., *J. Amer. Med. Soc.* 145:715-719 (1951)).

A syndrome also related to low progesterone levels is postnatal depression (PND). Immediately after birth, progesterone levels decrease dramatically leading to the onset of PND. The symptoms of PND range from mild depression to psychosis requiring hospitalization. PND is also associated with severe anxiety and irritability. PND-associated depression is not amenable to treatment by classic antidepressants, and women experiencing PND show an increased incidence of PMS (Dalton, K., *Premenstrual Syndrome and Progesterone Therapy,* 2nd edition, Chicago Yearbook, Chicago (1984)).

Collectively, these observations imply a crucial role for progesterone and deoxycorticosterone and more specifically their metabolites in the homeostatic regulation of brain excitability, which is manifested as an increase in seizure activity or symptoms associated with catamenial epilepsy, PMS, and PND. The correlation between reduced levels of progesterone and the symptoms associated with PMS, PND, and catamenial epilepsy (Backstrom, T. et al, *J Psychosom. Obstet. Gynaecol.* 2:8-20 (1983)); Dalton, K., Premenstrual Syndrome and Progesterone Therapy, 2nd edition, Chicago Yearbook, Chicago (1984)) has prompted the use of progesterone in their treatment (Mattson et al., "Medroxyprogesterone therapy of catamenial epilepsy," in *Advances in Epileptology: XVth Epilepsy International Symposium,* Raven Press, New York (1984), pp. 279-282, and Dalton, K., *Premenstrual Syndrome and Progesterone Therapy,* 2nd edition, Chicago Yearbook, Chicago (1984)). However, progesterone is not consistently effective in the treatment of the aforementioned syndromes. For example, no dose-response relationship exists for progesterone in the treatment of PMS (Maddocks et al., *Obstet. Gynecol.* 154:573-581 (1986); Dennerstein et al., *Brit. Med J* 290:16-17 (1986)).

New and improved neuroactive steroids are needed that act as modulating agents for brain excitability, as well as agents for the prevention and treatment of CNS-related diseases. The compounds, compositions, and methods described herein are directed toward this end.

SUMMARY OF THE INVENTION

Provided herein are C21-substituted neuroactive steroids designed, for example, to act as GABA modulators. In certain embodiments, such compounds are envisioned to be useful as therapeutic agents for the inducement of anesthesia and/or sedation in a subject. In some embodiments, such compounds are envisioned to be useful as therapeutic agents for treating a CNS-related disorder (e.g., sleep disorder, a mood disorder, a schizophrenia spectrum disorder, a convulsive disorder, a disorder of memory and/or cognition, a movement disorder, a personality disorder, autism spectrum disorder, pain, traumatic brain injury, a vascular disease, a substance abuse disorder and/or withdrawal syndrome, or tinnitus) in a subject in need (e.g., a subject with Rett syndrome, Fragile X syndrome, or Angelman syndrome).

In one aspect, provided is a compound of Formula (II):

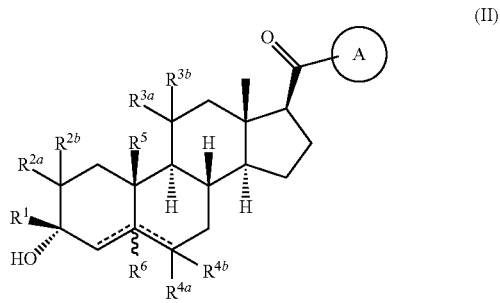

(II)

or a pharmaceutically acceptable salt thereof; wherein: Ring A is substituted or unsubstituted aryl or heteroaryl; $R^1$ is hydrogen, or substituted or unsubstituted $C_{1-6}$ alkyl, substituted or unsubstituted $C_{2-6}$ alkenyl, substituted or unsubstituted $C_{2-6}$ alkynyl, or substituted or unsubstituted $C_{3-6}$ carbocyclyl; each of $R^{2a}$ and $R^{2b}$ is independently selected from hydrogen, halogen, substituted or unsubstituted $C_{1-6}$alkyl, substituted or unsubstituted $C_{2-6}$ alkenyl, substituted or unsubstituted $C_{2-6}$ alkynyl, substituted or unsubstituted $C_{3-6}$ carbocyclyl, substituted or unsubstituted aryl, substituted or unsubstituted heteroaryl, $—N(R^A)(R^B)$, or $—OR^{A2}$, wherein each of $R^A$ and $R^B$ is independently hydrogen, substituted or unsubstituted $C_{1-6}$ alkyl, substituted or unsubstituted $C_{2-6}$alkenyl, substituted or unsubstituted $C_{2-6}$ alkynyl, substituted or unsubstituted $C_{3-6}$ carbocyclyl, substituted or unsubstituted heterocyclyl, substituted or unsubstituted aryl, or substituted or unsubstituted heteroaryl, or $R^A$ and $R^B$, together with the nitrogen atom to which they are attached form a ring (e.g., heteroaryl, heterocyclyl), or $R^{2a}$ and $R^{2b}$, together with the carbon atom to which they are attached form a ring; $R^{A2}$ is hydrogen or substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{3-6}$ carbocyclyl, substituted or unsubstituted aryl, or substituted or unsubstituted heteroaryl; $R^{3a}$ is hydrogen, $—N(R^A)(R^B)$, or $—OR^{A3}$, wherein $R^{A3}$ is hydrogen, substituted or unsubstituted $C_{1-6}$ alkyl, substituted or unsubstituted $C_{2-6}$ alkenyl, substituted or unsubstituted $C_{2-6}$ alkynyl, or substituted or unsubstituted $C_{3-6}$ carbocyclyl, substituted or unsubstituted aryl, substituted or unsubstituted heteroaryl, and $R^{3b}$ is hydrogen or $—N(R^A)C(O)R^{A3}$; or $R^{3a}$ and $R^{3b}$ are joined to form an oxo (=O) group; each of $R^{4a}$ and $R^{4b}$ is independently selected from hydrogen or halogen; $R^5$ is hydrogen, unsubstituted $C_{1-6}$ alkyl, or $—CH_2OR^{A5}$, wherein $R^{A5}$ is hydrogen, substituted or unsubstituted $C_{1-6}$ alkyl, substituted or unsubstituted $C_{2-6}$ alkenyl, substituted or unsubstituted $C_{2-6}$ alkynyl, or substituted or unsubstituted $C_{3-6}$ carbocyclyl, substituted or unsubstituted aryl, substituted or unsubstituted heteroaryl; $R^6$ is absent or hydrogen; and ==== represents a single or double bond, wherein when one of ---- is a double bond, the other ---- is a single bond; and when one of the ---- is a double bond, $R^6$ is absent.

Also provided herein are pharmaceutical compositions comprising a compound of the present invention and methods of use and treatment, e.g., such as for inducing sedation and/or anesthesia, for treating a CNS-related disorder.

Steroids of Formula (I), sub-genera thereof, and pharmaceutically acceptable salts thereof are collectively referred to herein as "compounds of the present invention."

In another aspect, provided is a pharmaceutical composition comprising a compound of the present invention and a pharmaceutically acceptable excipient. In certain embodiments, the compound of the present invention is provided in an effective amount in the pharmaceutical composition. In certain embodiments, the compound of the present invention is provided in a therapeutically effective amount. In certain embodiments, the compound of the present invention is provided in a prophylactically effective amount.

Compounds of the present invention as described herein, act, in certain embodiments, as GABA modulators, e.g., effecting the $GABA_A$ receptor in either a positive or negative manner. As modulators of the excitability of the central nervous system (CNS), as mediated by their ability to modulate $GABA_A$ receptor, such compounds are expected to have CNS-activity.

Thus, in another aspect, provided are methods of treating a CNS-related disorder in a subject in need thereof, comprising administering to the subject an effective amount of a compound of the present invention. In certain embodiments, the CNS-related disorder is selected from the group consisting of a sleep disorder, a mood disorder, a schizophrenia spectrum disorder, a convulsive disorder, a disorder of memory and/or cognition, a movement disorder, a personality disorder, autism spectrum disorder, pain, traumatic brain injury, a vascular disease, a substance abuse disorder and/or withdrawal syndrome, and tinnitus. In certain embodiments, the compound is administered orally, subcutaneously, intravenously, or intramuscularly. In certain embodiments, the compound is administered chronically. In certain embodiments, the compound is administered continuously, e.g., by continuous intravenous infusion.

Other objects and advantages will become apparent to those skilled in the art from a consideration of the ensuing Detailed Description, Examples, and Claims.

Definitions

Chemical Definitions

Definitions of specific functional groups and chemical terms are described in more detail below. The chemical elements are identified in accordance with the Periodic Table of the Elements, CAS version, *Handbook of Chemistry and*

*Physics*, 75*th* Ed., inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Smith and March, *March's Advanced Organic Chemistry*, 5*th* Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3*rd* Edition, Cambridge University Press, Cambridge, 1987.

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, NY, 1962); and Wilen, *Tables of Resolving Agents and Optical Resolutions* p. 268 (E.L. Eliel, Ed., Univ. of Notre Dame Press, Notre Dame, Ind. 1972). The invention additionally encompasses compounds described herein as individual isomers substantially free of other isomers, and alternatively, as mixtures of various isomers.

As used herein a pure enantiomeric compound is substantially free from other enantiomers or stereoisomers of the compound (i.e., in enantiomeric excess). In other words, an "S" form of the compound is substantially free from the "R" form of the compound and is, thus, in enantiomeric excess of the "R" form. The term "enantiomerically pure" or "pure enantiomer" denotes that the compound comprises more than 75% by weight, more than 80% by weight, more than 85% by weight, more than 90% by weight, more than 91% by weight, more than 92% by weight, more than 93% by weight, more than 94% by weight, more than 95% by weight, more than 96% by weight, more than 97% by weight, more than 98% by weight, more than 98.5% by weight, more than 99% by weight, more than 99.2% by weight, more than 99.5% by weight, more than 99.6% by weight, more than 99.7% by weight, more than 99.8% by weight or more than 99.9% by weight, of the enantiomer. In certain embodiments, the weights are based upon total weight of all enantiomers or stereoisomers of the compound.

In the compositions provided herein, an enantiomerically pure compound can be present with other active or inactive ingredients. For example, a pharmaceutical composition comprising enantiomerically pure R-compound can comprise, for example, about 90% excipient and about 10% enantiomerically pure R-compound. In certain embodiments, the enantiomerically pure R-compound in such compositions can, for example, comprise, at least about 95% by weight R-compound and at most about 5% by weight S-compound, by total weight of the compound. For example, a pharmaceutical composition comprising enantiomerically pure S-compound can comprise, for example, about 90% excipient and about 10% enantiomerically pure S-compound. In certain embodiments, the enantiomerically pure S-compound in such compositions can, for example, comprise, at least about 95% by weight S-compound and at most about 5% by weight R-compound, by total weight of the compound. In certain embodiments, the active ingredient can be formulated with little or no excipient or carrier.

Compound described herein may also comprise one or more isotopic substitutions. For example, H may be in any isotopic form, including $^1$H, $^2$H (D or deuterium), and $^3$H (T or tritium); C may be in any isotopic form, including $^{12}$C, $^{13}$C, and $^{14}$C; O may be in any isotopic form, including $^{16}$O and $^{18}$O; and the like.

The articles "a" and "an" may be used herein to refer to one or to more than one (i.e. at least one) of the grammatical objects of the article. By way of example "an analogue" means one analogue or more than one analogue.

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

The following terms are intended to have the meanings presented therewith below and are useful m understanding the description and intended scope of the present invention.

"Alkyl" refers to a radical of a straight-chain or branched saturated hydrocarbon group having from 1 to 20 carbon atoms ("$C_{1-20}$ alkyl"). In some embodiments, an alkyl group has 1 to 12 carbon atoms ("$C_{1-12}$ alkyl"). In some embodiments, an alkyl group has 1 to 8 carbon atoms ("$C_{1-8}$ alkyl"). In some embodiments, an alkyl group has 1 to 6 carbon atoms ("$C_{1-6}$ alkyl", also referred to herein as "lower alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_8$) and the like. Unless otherwise specified, each instance of an alkyl group is independently optionally substituted, i.e., unsubstituted (an "unsubstituted alkyl") or substituted (a "substituted alkyl") with one or more substituents; e.g., for instance from 1 to 5 substituents, 1 to 3 substituents, or 1 substituent. In certain embodiments, the alkyl group is unsubstituted $C_{1-10}$ alkyl (e.g., —CH$_3$). In certain embodiments, the alkyl group is substituted $C_{1-10}$ alkyl. Common alkyl abbreviations include Me (—CH$_3$), Et (—CH$_2$CH$_3$), iPr (—CH(CH$_3$)$_2$), nPr (—CH$_2$CH$_2$CH$_3$), n-Bu (—CH$_2$CH$_2$CH$_2$CH$_3$), or i-Bu (—CH$_2$CH(CH$_3$)$_2$).

"Alkenyl" refers to a radical of a straight-chain or branched hydrocarbon group having from 2 to 20 carbon atoms, one or more carbon-carbon double bonds, and no triple bonds ("$C_{2-20}$ alkenyl"). In some embodiments, an alkenyl group has 2 to 10 carbon atoms ("$C_{2-10}$ alkenyl"). In some embodiments, an alkenyl group has 2 to 8 carbon atoms ("$C_{2-8}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like Unless otherwise specified, each instance of an alkenyl group is independently optionally substituted, i.e., unsubstituted (an "unsubstituted alkenyl") or substituted (a "substituted alkenyl") with one or more substituents e.g., for instance from 1 to 5 substituents, 1 to 3 substituents, or 1 substituent. In certain embodiments, the alkenyl group is unsubstituted $C_{2-10}$ alkenyl. In certain embodiments, the alkenyl group is substituted $C_{2-10}$ alkenyl.

"Alkynyl" refers to a radical of a straight-chain or branched hydrocarbon group having from 2 to 20 carbon atoms, one or more carbon-carbon triple bonds, and optionally one or more double bonds ("$C_{2-20}$ alkynyl"). In some embodiments, an alkynyl group has 2 to 10 carbon atoms ("$C_{2-10}$ alkynyl"). In some embodiments, an alkynyl group has 2 to 8 carbon atoms ("$C_{2-8}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-6}$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently optionally substituted, i.e., unsubstituted (an "unsubstituted alkynyl") or substituted (a "substituted alkynyl") with one or more substituents, e.g., for instance from 1 to 5 substituents, 1 to 3 substituents, or 1 substituent. In certain embodiments, the alkynyl group is unsubstituted $C_{2-10}$ alkynyl. In certain embodiments, the alkynyl group is substituted $C_{2-10}$ alkynyl.

"Aryl" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms provided in the aromatic ring system ("$C_{6-14}$ aryl"). In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{14}$ aryl"; e.g., anthracyl) "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Aryl groups include, but are not limited to, phenyl, naphthyl, indenyl, and tetrahydronaphthyl. Unless otherwise specified, each instance of an aryl group is independently optionally substituted, i.e., unsubstituted (an "unsubstituted aryl") or substituted (a "substituted aryl") with one or more substituents. In certain embodiments, the aryl group is unsubstituted $C_{6-14}$ aryl. In certain embodiments, the aryl group is substituted $C_{6-14}$ aryl.

In certain embodiments, an aryl group substituted with one or more of groups selected from halo, $C_1$-$C_8$ alkyl, $C_1$-$C_8$ haloalkyl, cyano, hydroxy, $C_1$-$C_8$ alkoxy, and amino.

Examples of representative substituted aryls include the following

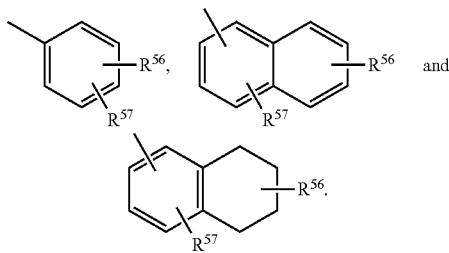

wherein one of $R^{56}$ and $R^{57}$ may be hydrogen and at least one of $R^{56}$ and $R^{57}$ is each independently selected from $C_1$-$C_8$ alkyl, $C_1$-$C_8$ haloalkyl, 4-10 membered heterocyclyl, alkanoyl, $C_1$-$C_8$ alkoxy, heteroaryloxy, alkylamino, arylamino, heteroarylamino, $NR^{58}COR^{59}$, $NR^{58}SOR^{59}NR^{58}SO_2R^{59}$, COOalkyl, COOaryl, $CONR^{58}R^{59}$, $CONR^{58}OR^{59}$, $NR^{58}R^{59}$, $SO_2NR^{58}R^{59}$, S-alkyl, SOalkyl, $SO_2$alkyl, Saryl, SOaryl, $SO_2$aryl; or $R^{56}$ and $R^{57}$ may be joined to form a cyclic ring (saturated or unsaturated) from 5 to 8 atoms, optionally containing one or more heteroatoms selected from the group N, O, or S. $R^{60}$ and $R^{61}$ are independently hydrogen, $C_1$-$C_8$ alkyl, $C_1$-$C_4$ haloalkyl. $C_3$-$C_{10}$ cycloalkyl, 4-10 membered heterocyclyl, $C_6$-$C_{10}$ aryl, substituted $C_6$-$C_{10}$ aryl, 5-10 membered heteroaryl, or substituted 5-10 membered heteroaryl.

Other representative aryl groups having a fused heterocyclyl group include the following:

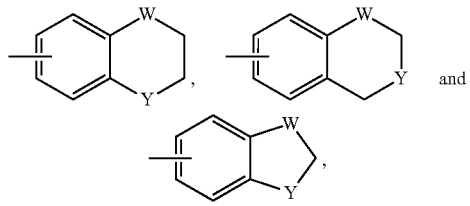

wherein each W is selected from $C(R^{66})_2$, $NR^{66}$, O, and S; and each Y is selected from carbonyl, $NR^{66}$, O and S, and $R^{66}$ is independently hydrogen, $C_1$-$C_8$ alkyl, $C_3$-$C_{10}$ cycloalkyl, 4-10 membered heterocyclyl, $C_6$-$C_{10}$ aryl, and 5-10 membered heteroaryl.

"Halo" or "halogen," independently or as part of another substituent, mean, unless otherwise stated, a fluorine (F), chlorine (Cl), bromine (Br), or iodine (I) atom. The term "halide" by itself or as part of another substituent, refers to a fluoride, chloride, bromide, or iodide atom. In certain embodiments, the halo group is either fluorine or chlorine.

"Haloalkyl" and "haloalkoxy" can include alkyl and alkoxy structures that are substituted with one or more halo groups or with combinations thereof. For example, the terms "fluoroalkyl" and "fluoroalkoxy" include haloalkyl and haloalkoxy groups, respectively, in which the halo is fluorine.

"Heteroaryl" refers to a radical of a 5-10 membered monocyclic or bicyclic 4n+2 aromatic ring system (e.g., having 6 or 10 π electrons shared in a cyclic array) having ring carbon atoms and 1-4 ring heteroatoms provided in the aromatic ring system, wherein each heteroatom is independently selected from nitrogen, oxygen and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently optionally substituted, i.e., unsubstituted (an "unsubstituted heteroaryl") or substituted (a "substituted heteroaryl") with one or more substituents. In certain embodiments, the heteroaryl group is unsubstituted 5-14 membered heteroaryl. In certain embodiments, the heteroaryl group is substituted 5-14 membered heteroaryl.

Exemplary 5-membered heteroaryl groups containing one heteroatom include, without limitation, pyrrolyl, furanyl and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl.

Examples of representative heteroaryls include the following formulae:

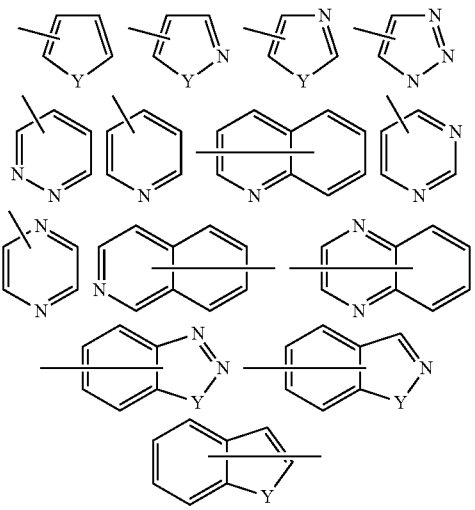

wherein each Y is selected from carbonyl, N, NR$^{65}$, O, and S; and R$^{65}$ is independently hydrogen, C$_1$-C$_8$ alkyl, C$_3$-C$_{10}$ cycloalkyl, 4-10 membered heterocyclyl, C$_6$-C$_{10}$ aryl, and 5-10 membered heteroaryl.

"Carbocyclyl" or "carbocyclic" refers to a radical of a non-aromatic cyclic hydrocarbon group having from 3 to 10 ring carbon atoms ("C$_{3-10}$ carbocyclyl") and zero heteroatoms in the non-aromatic ring system. In some embodiments, a carbocyclyl group has 3 to 8 ring carbon atoms ("C$_{3-8}$ carbocyclyl"). In some embodiments, a carbocyclyl group has 3 to 6 ring carbon atoms ("C$_{3-6}$ carbocyclyl"). In some embodiments, a carbocyclyl group has 3 to 6 ring carbon atoms ("C$_{3-6}$ carbocyclyl"). In some embodiments, a carbocyclyl group has 5 to 10 ring carbon atoms ("C$_{5-10}$ carbocyclyl"). Exemplary C$_{3-6}$ carbocyclyl groups include, without limitation, cyclopropyl (C$_3$), cyclopropenyl (C$_3$), cyclobutyl (C$_4$), cyclobutenyl (C$_4$), cyclopentyl (C$_5$), cyclopentenyl (C$_5$), cyclohexyl (C$_6$), cyclohexenyl (C$_6$), cyclohexadienyl (C$_6$), and the like. Exemplary C$_{3-8}$ carbocyclyl groups include, without limitation, the aforementioned C$_{3-6}$ carbocyclyl groups as well as cycloheptyl (C$_7$), cycloheptenyl (C$_7$), cycloheptadienyl (C$_7$), cycloheptatrienyl (C$_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or contain a fused, bridged or spiro ring system such as a bicyclic system ("bicyclic carbocyclyl") and can be saturated or can be partially unsaturated. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently optionally substituted, i.e., unsubstituted (an "unsubstituted carbocyclyl") or substituted (a "substituted carbocyclyl") with one or more substituents. In certain embodiments, the carbocyclyl group is unsubstituted $C_{3-10}$ carbocyclyl. In certain embodiments, the carbocyclyl group is a substituted $C_{3-10}$ carbocyclyl.

In some embodiments, "carbocyclyl" is a monocyclic, saturated carbocyclyl group having from 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is unsubstituted $C_{3-10}$ cycloalkyl. In certain embodiments, the cycloalkyl group is substituted $C_{3-10}$ cycloalkyl.

"Heterocyclyl" or "heterocyclic" refers to a radical of a 3- to 10-membered non-aromatic ring system having ring carbon atoms and 1 to 4 ring heteroatoms, wherein each heteroatom is independently selected from nitrogen, oxygen, sulfur, boron, phosphorus, and silicon ("3-10 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged or spiro ring system such as a bicyclic system ("bicyclic heterocyclyl"), and can be saturated or can be partially unsaturated. Heterocyclyl bicyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently optionally substituted, i.e., unsubstituted (an "unsubstituted heterocyclyl") or substituted (a "substituted heterocyclyl") with one or more substituents. In certain embodiments, the heterocyclyl group is unsubstituted 3-10 membered heterocyclyl. In certain embodiments, the heterocyclyl group is substituted 3-10 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, sulfur, boron, phosphorus, and silicon ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has one ring heteroatom selected from nitrogen, oxygen, and sulfur.

Exemplary 3-membered heterocyclyl groups containing one heteroatom include, without limitation, azirdinyl, oxiranyl, thiorenyl. Exemplary 4-membered heterocyclyl groups containing one heteroatom include, without limitation, azetidinyl, oxetanyl and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl and pyrrolyl-2,5-dione. Exemplary 5-membered heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, tetrahydropyranyl, dihydropyridinyl, and thianyl. Exemplary 6-membered heterocyclyl groups containing two heteroatoms include, without limitation, piperazinyl, morpholinyl, dithianyl, dioxanyl. Exemplary 6-membered heterocyclyl groups containing two heteroatoms include, without limitation, triazinanyl. Exemplary 7-membered heterocyclyl groups containing one heteroatom include, without limitation, azepanyl, oxepanyl and thiepanyl. Exemplary 8-membered heterocyclyl groups containing one heteroatom include, without limitation, azocanyl, oxecanyl and thiocanyl. Exemplary 5-membered heterocyclyl groups fused to a $C_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary 6-membered heterocyclyl groups fused to an aryl ring (also referred to herein as a 6,6-bicyclic heterocyclic ring) include, without limitation, tetrahydroquinolinyl, tetrahydroisoquinolinyl, and the like.

Particular examples of heterocyclyl groups are shown in the following illustrative examples:

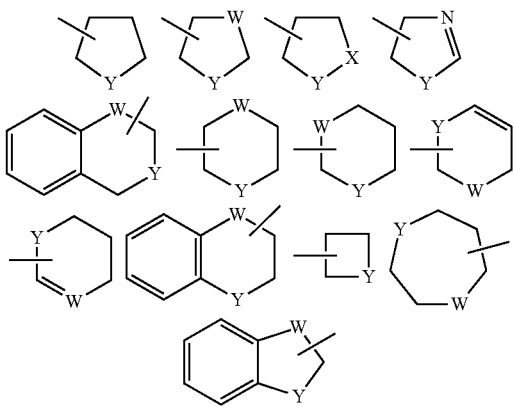

wherein each W is selected from CR$^{67}$, C(R$^{67}$)$_2$, NR$^{67}$, O, and S; and each Y is selected from NR$^{67}$, O, and S; and R$^{67}$ is independently hydrogen, C$_1$-C$_8$ alkyl, C$_3$-C$_{10}$ cycloalkyl, 4-10 membered heterocyclyl, C$_6$-C$_{10}$ aryl, and 5-10-membered heteroaryl. These heterocyclyl rings may be optionally substituted with one or more groups selected from the group consisting of acyl, acylamino, acyloxy, alkoxy, alkoxycarbonyl, alkoxycarbonylamino, amino, substituted amino, aminocarbonyl (e.g., amido), aminocarbonylamino, aminosulfonyl, sulfonylamino, aryl, aryloxy, azido, carboxyl, cyano, cycloalkyl, halogen, hydroxy, keto, nitro, thiol, —S-alkyl, —S-aryl, —S(O)-alkyl, —S(O)-aryl, —S(O)$_2$-alkyl, and —S(O)$_2$-aryl. Substituting groups include carbonyl or thiocarbonyl which provide, for example, lactam and urea derivatives.

"Acyl" refers to a radical —C(O)R$^{20}$, where R$^{20}$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl, as defined herein. "Alkanoyl" is an acyl group wherein R$^{20}$ is a group other than hydrogen. Representative acyl groups include, but are not limited to, formyl (—CHO), acetyl (—C(=O)CH$_3$), cyclohexylcarbonyl, cyclohexylmethylcarbonyl, benzoyl (—C(=O)Ph), benzylcarbonyl (—C(=O)CH$_2$Ph), —C(O)—C$_1$-C$_8$ alkyl, —C(O)—(CH$_2$)$_t$(C$_6$-C$_{10}$ aryl), —C(O)—(CH$_2$)$_t$ (5-10 membered heteroaryl), —C(O)—(CH$_2$)$_t$(C$_3$-C$_{10}$ cycloalkyl), and —C(O)—(CH$_2$)$_t$ (4-10 membered heterocyclyl), wherein t is an integer from 0 to 4. In certain embodiments, R$^{21}$ is C$_1$-C$_8$ alkyl, substituted with halo or hydroxy; or C$_3$-C$_{10}$ cycloalkyl, 4-10 membered heterocyclyl, C$_6$-C$_{10}$ aryl, arylalkyl, 5-10 membered heteroaryl or heteroarylalkyl, each of which is substituted with unsubstituted C$_1$-C$_4$ alkyl, halo, unsubstituted C$_1$-C$_4$ alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxy.

"Acylamino" refers to a radical —NR$^{22}$C(O)R$^{23}$, where each instance of R$^{22}$ and R$^{23}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl, as defined herein, or R$^{22}$ is an amino protecting group. Exemplary "acylamino" groups include, but are not limited to, formylamino, acetylamino, cyclohexylcarbonylamino, cyclohexylmethyl-carbonylamino, benzoylamino and benzylcarbonylamino. Particular exemplary "acylamino" groups are —NR$^{24}$C(O)—C$_1$-C$_8$alkyl, —NR$^{24}$C(O)—(CH$_2$)$_t$(C$_6$-C$_{10}$ aryl), —NR$^{24}$C(O)—(CH$_2$)$_t$ (5-10 membered heteroaryl), —NR$^4$C(O)—(CH$_2$)$_t$(C$_3$-C$_{10}$ cycloalkyl), and —NR$^{24}$C(O)—(CH$_2$)$_t$ (4-10 membered heterocyclyl), wherein t is an integer from 0 to 4, and each R$^{24}$ independently represents hydrogen or C$_1$-C$_8$ alkyl. In certain embodiments, R$^{25}$ is H, C$_1$-C$_8$ alkyl, substituted with halo or hydroxy; C$_3$-C$_{10}$ cycloalkyl, 4-10 membered heterocyclyl, C$_6$-C$_{10}$ aryl, arylalkyl, 5-10 membered heteroaryl or heteroarylalkyl, each of which is substituted with unsubstituted C$_1$-C$_4$ alkyl, halo, unsubstituted C$_1$-C$_4$ alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxy; and R$^{26}$ is H, C$_1$-C$_8$ alkyl, substituted with halo or hydroxy; C$_3$-C$_{10}$ cycloalkyl, 4-10-membered heterocyclyl, C$_6$-C$_{10}$ aryl, arylalkyl, 5-10-membered heteroaryl or heteroarylalkyl, each of which is substituted with unsubstituted C$_1$-C$_4$ alkyl, halo, unsubstituted C$_1$-C$_4$ alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxy, provided at least one of R$^{25}$ and R$^{26}$ is other than H.

"Acyloxy" refers to a radical —OC(O)R$^{27}$, where R$^{27}$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl, as defined herein. Representative examples include, but are not limited to, formyl, acetyl, cyclohexylcarbonyl, cyclohexylmethylcarbonyl, benzoyl, and benzylcarbonyl. In certain embodiments. R$^{28}$ is C$_1$-C$_8$ alkyl, substituted with halo or hydroxy; C$_3$-C$_{10}$ cycloalkyl, 4-10 membered heterocyclyl, C$_6$-C$_{10}$ aryl, arylalkyl, 5-10-membered heteroaryl or heteroarylalkyl, each of which is substituted with unsubstituted C$_1$-C$_4$ alkyl, halo, unsubstituted C$_1$-C$_4$ alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxy.

"Alkoxy" refers to the group —OR$^{29}$ where R$^{29}$ is substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl. Particular alkoxy groups are methoxy, ethoxy, n-propoxy, isopropoxy, n-butoxy, tert-butoxy, sec-butoxy, n-pentoxy, n-hexoxy, and 1,2-dimethylbutoxy. Particular alkoxy groups are lower alkoxy, i.e., with between 1 and 6 carbon atoms. Further particular alkoxy groups have between 1 and 4 carbon atoms.

In certain embodiments, R$^{29}$ is a group that has 1 or more substituents, for instance from 1 to 5 substituents, and particularly from 1 to 3 substituents, in particular 1 substituent, selected from the group consisting of amino, substituted amino, C$_6$-C$_{10}$ aryl, aryloxy, carboxyl, cyano, C$_3$-C$_{10}$ cycloalkyl, 4-10 membered heterocyclyl, halogen, 5-10 membered heteroaryl, hydroxy, nitro, thioalkoxy, thioaryloxy, thiol, alkyl-S(O)—, aryl-S(O)—, alkyl-S(O)$_2$— and aryl-S(O)$_2$—. Exemplary "substituted alkoxy" groups include, but are not limited to, —O—(CH$_2$)$_t$(C$_6$-C$_{10}$ aryl), —O—(CH$_2$)$_t$(5-10 membered heteroaryl), —O—(CH$_2$)$_t$(C$_3$-C$_{10}$ cycloalkyl), and —O—(CH$_2$)$_t$(4-10 membered heterocyclyl), wherein t is an integer from 0 to 4 and any aryl, heteroaryl, cycloalkyl or heterocyclyl groups present, may themselves be substituted by unsubstituted C$_1$-C$_4$ alkyl, halo, unsubstituted C$_1$-C$_4$ alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxy. Particular exemplary 'substituted alkoxy' groups are —OCF$_3$, —OCH$_2$CF$_3$, —OCH$_2$Ph, —OCH$_2$-cyclopropyl, —OCH$_2$CH$_2$OH, and —OCH$_2$CH$_2$NMe$_2$.

"Amino" refers to the radical —NH$_2$.

"Substituted amino" refers to an amino group of the formula —N(R$^{38}$) wherein R$^{38}$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or an amino protecting group, wherein at least one of R$^{38}$ is not a hydrogen. In certain embodiments, each R$^{38}$ is independently selected from hydrogen, C$_1$-C$_8$ alkyl, C$_3$-C$_8$ alkenyl, C$_3$-C$_8$ alkynyl, C$_6$-C$_{10}$ aryl, 5-10 membered heteroaryl, 4-10 membered heterocyclyl, or C$_3$-C$_{10}$ cycloalkyl; or C$_1$-C$_8$ alkyl, substituted with halo or hydroxy; C$_3$-C$_8$ alkenyl, substituted with halo or hydroxy; C$_3$-C$_8$ alkynyl, substituted with halo or hydroxy, or —(CH$_2$)$_t$(C$_6$-C$_{10}$ aryl), —(CH$_2$)$_t$(5-10 membered heteroaryl), —(CH$_2$)$_t$(C$_3$-C$_{10}$ cycloalkyl), or —(CH$_2$)$_t$(4-10 membered heterocyclyl), wherein t is an integer between 0 and 8, each of which is substituted by unsubstituted C$_1$-C$_4$ alkyl, halo, unsubstituted C$_1$-C$_4$ alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxy; or both R$^{38}$ groups are joined to form an alkylene group.

Exemplary "substituted amino" groups include, but are not limited to, —NR$^{39}$—C$_1$-C$_8$ alkyl, —NR$^{39}$—(CH$_2$)$_t$(C$_6$-C$_{10}$ aryl), —NR$^{39}$—(CH$_2$)$_t$(5-10 membered heteroaryl), —NR$^{39}$—(CH$_2$)$_t$(C$_3$-C$_{10}$ cycloalkyl), and —NR$^{39}$—(CH$_2$)$_t$(4-10 membered heterocyclyl), wherein t is an integer from 0 to 4, for instance 1 or 2, each R$^{39}$ independently represents hydrogen or C$_1$-C$_8$ alkyl; and any alkyl groups present, may themselves be substituted by halo, substituted or unsubstituted amino, or hydroxy; and any aryl, heteroaryl, cycloalkyl, or heterocyclyl groups present, may themselves be substituted by unsubstituted C$_1$-C$_4$ alkyl, halo, unsubstituted C$_1$-C$_4$ alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxy. For the avoidance of doubt the term 'substituted amino' includes the groups alkylamino, substituted alkylamino, alkylarylamino, substituted alkylarylamino, arylamino, substituted arylamino, dialkylamino, and substituted dialkylamino as defined below. Substituted amino encompasses both monosubstituted amino and disubstituted amino groups.

"Azido" refers to the radical —N$_3$.

"Carbamoyl" or "amido" refers to the radical —C(O)NH$_2$.

"Substituted carbamoyl" or "substituted amido" refers to the radical —C(O)N(R$^{62}$)$_2$ wherein each R$^{62}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or an amino protecting group, wherein at least one of R$^{62}$ is not a hydrogen. In certain embodiments, R$^{62}$ is selected from H, C$_{1-8}$ alkyl, C$_3$-C$_{10}$ cycloalkyl, 4-10 membered heterocyclyl, C$_6$-C$_{10}$ aryl, and 5-10 membered heteroaryl; or C$_1$-C$_8$ alkyl substituted with halo or hydroxy; or C$_3$-C$_{10}$ cycloalkyl, 4-10 membered heterocyclyl, C$_6$-C$_{10}$ aryl, or 5-10 membered heteroaryl, each of which is substituted by unsubstituted C$_1$-C$_4$ alkyl, halo, unsubstituted C$_1$-C$_4$ alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxy; provided that at least one R$^{62}$ is other than H.

"Carboxy" refers to the radical —C(O)OH.

"Cyano" refers to the radical —CN.

"Hydroxy" refers to the radical —OH.

"Nitro" refers to the radical —NO$_2$.

"Ethenyl" refers to substituted or unsubstituted —(C=C)—. "Ethylene" refers to substituted or unsubstituted —(C—C)—. "Ethynyl" refers to —(C≡C)—.

"Nitrogen-containing heterocyclyl" group means a 4- to 7-membered non-aromatic cyclic group containing at least one nitrogen atom, for example, but without limitation, morpholine, piperidine (e.g. 2-piperidinyl, 3-piperidinyl and 4-piperidinyl), pyrrolidine (e.g. 2-pyrrolidinyl and 3-pyrrolidinyl), azetidine, pyrrolidone, imidazoline, imidazolidinone, 2-pyrazoline, pyrazolidine, piperazine, and N-alkyl piperazines such as N-methyl piperazine. Particular examples include azetidine, piperidone and piperazone.

Alkyl, alkenyl, alkynyl, carbocyclyl, heterocyclyl, aryl, and heteroaryl groups, as defined herein, are optionally substituted (e.g., "substituted" or "unsubstituted" alkyl, "substituted" or "unsubstituted" alkenyl, "substituted" or "unsubstituted" alkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$$^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$ —C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)$_2$R$^{aa}$, —OP(=O)$_2$R$^{aa}$, —P(=O)(R$^{aa}$)$_2$, —OP(=O)(R$^{aa}$)$_2$, —OP(=O)(OR$^{cc}$)$_2$, —P(=O)$_2$N(R$^{bb}$)$_2$, —OP(=O)$_2$N(R$^{bb}$)$_2$, —P(=O)(NR$^{bb}$)$_2$, —OP(=O)(NR$^{bb}$)$_2$, —NR$^{bb}$P(=O)(OR$^{cc}$)$_2$, —NR$^{bb}$P(=O)(NR$^{bb}$)$_2$, —P(R$^{cc}$)$_2$, —P(R$^{cc}$)$_3$, —OP(R$^{cc}$)$_2$, —OP(R$^{cc}$)$_3$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, $C_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 $R^{dd}$ groups;

each instance of $R^{aa}$ is, independently, selected from $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^{aa}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups;

each instance of $R^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$), —P(=O)(NR$^{cc}$)$_2$, $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^{bb}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups;

each instance of $R^{cc}$ is, independently, selected from hydrogen, $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^{cc}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups;

each instance of $R^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3$$^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —SC(=S)SR$^{ee}$, —SC(=S)SR$^{ee}$, —P(=O)$_2$R$^{ee}$, —P(=O)(R$^{ee}$)$_2$, —OP(=O)(R$^{ee}$)$_2$, —OP(=O)(OR$^{ee}$)$_2$, $C_{1-6}$ alkyl, $C_{1-6}$ perhaloalkyl, $C_{2-6}$ alkenyl, $C_{2-6}$ alkynyl, $C_{3-10}$ carbocyclyl, 3-10 membered heterocyclyl, $C_{6-10}$ aryl, 5-10 membered heteroaryl, wherein each alkyl, alkenyl, alkynyl, carbocyclyl, heterocyclyl, aryl, and heteroaryl is independently substituted with 0, 1, 2, 3, 4, or 5 $R^{gg}$ groups;

each instance of $R^{ee}$ is, independently, selected from $C_{1-6}$ alkyl, $C_{1-6}$ perhaloalkyl, $C_{2-6}$ alkenyl, $C_{2-6}$ alkynyl, $C_{3-10}$ carbocyclyl, $C_{6-10}$ aryl, 3-10 membered heterocyclyl, and 3-10 membered heteroaryl, wherein each alkyl, alkenyl, alkynyl, carbocyclyl, heterocyclyl, aryl, and heteroaryl is independently substituted with 0, 1, 2, 3, 4, or 5 $R^{gg}$ groups;

each instance of $R^{ff}$ is, independently, selected from hydrogen, $C_{1-6}$ alkyl, $C_{1-6}$ perhaloalkyl, $C_{2-6}$ alkenyl, $C_{2-6}$ alkynyl, $C_{3-10}$ carbocyclyl, 3-10 membered heterocyclyl, $C_{6-10}$ aryl and 5-10 membered heteroaryl, or two R$^{ff}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{gg}$ groups; and each instance of $R^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3$$^+$X$^-$, —NH(C$_{1-6}$ alkyl)$_2$$^+$X$^-$, —NH$_2$(C$_{1-6}$ alkyl)$^+$X$^-$, —NH$_3$$^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$-C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)(C$_{1-6}$ alkyl), —P(=O)(C$_{1-6}$ alkyl)$_2$, —OP(=O)(C$_{1-6}$ alkyl)$_2$, —OP(=O)(OC$_{1-6}$ alkyl)$_2$, $C_{1-6}$ alkyl, $C_{1-6}$ perhaloalkyl, $C_{2-6}$ alkenyl, $C_{2-6}$ alkynyl, $C_{3-10}$ carbocyclyl, $C_{6-10}$ aryl, 3-10 membered heterocyclyl, 5-10 membered heteroaryl; wherein X$^-$ is a counterion.

A "counterion" or "anionic counterion" is a negatively charged group associated with a cationic quaternary amino group in order to maintain electronic neutrality. Exemplary counterions include halide ions (e.g., F$^-$, Cl$^-$, Br$^-$, I$^-$), NO$_3$$^-$, ClO$_4$$^-$, OH$^-$, H$_2$PO$_4$$^-$, HSO$_4$$^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), and carboxylate ions (e.g., acetate, ethanoate, propanoate, benzoate, glycerate, lactate, tartrate, glycolate, and the like).

Nitrogen atoms can be substituted or unsubstituted as valency permits, and include primary, secondary, tertiary, and quarternary nitrogen atoms. Exemplary nitrogen atom substituents include, but are not limited to, hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{bb}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14-membered heteroaryl, or two R$^{cc}$ groups attached to a nitrogen atom are joined to form a 3-14-membered heterocyclyl or 5-14-membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined above.

In certain embodiments, the substituent present on a nitrogen atom is an amino protecting group (also referred to herein as a nitrogen protecting group). Amino protecting groups include, but are not limited to, —OH, —OR$^{aa}$, —N(R$^{cc}$)$_2$, —C(=O)R$^{aa}$, —C(=O)OR$^{aa}$, —C(=O)N(R$^{cc}$)$_2$, —S(=O)$_2$R$^{aa}$, —C(=NR$^{cc}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, $C_{1-10}$ alkyl, $C_{2-10}$ alkenyl, $C_{2-10}$ alkynyl, $C_{3-10}$ carbocyclyl, 3-14-membered heterocyclyl, $C_{6-14}$ aryl, and 5-14-membered heteroaryl groups, wherein each alkyl, alkenyl, alkynyl, carbocyclyl, heterocyclyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined herein. Amino protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

Exemplary amino protecting groups include, but are not limited to amide groups (e.g., —C(=O)$R^{aa}$), which include, but are not limited to, formamide and acetamide; carbamate groups (e.g., —C(=O)O$R^{aa}$), which include, but are not limited to, 9-fluorenylmethyl carbamate (Fmoc), t-butyl carbamate (BOC), and benzyl carbamate (Cbz); sulfonamide groups (e.g., —S(=O)$_2$$R^{aa}$), which include, but are not limited to, p-toluenesulfonamide (Ts), methanesulfonamide (Ms), and N-[2-(trimethylsilyl)ethoxy]methylamine (SEM).

In certain embodiments, the substituent present on an oxygen atom is an oxygen protecting group (also referred to as a hydroxyl protecting group). Oxygen protecting groups include, but are not limited to, —$R^{aa}$, —N($R^{bb}$)$_2$, —C(=O)S$R^{aa}$, —C(=O)$R^{aa}$, —CO$_2$$R^{aa}$, —C(=O)N($R^{bb}$)$_2$, —C(=N$R^{bb}$)$R^{aa}$, —C(=N$R^{bb}$)O$R^{aa}$, —C(=N$R^{bb}$)N($R^{bb}$)$_2$, —S(=O)$R^{aa}$, —SO$_2$$R^{aa}$, —Si($R^{aa}$)$_3$, —P($R^{cc}$)$_2$, —P($R^{cc}$)$_3$, —P(=O)$_2$$R^{aa}$, —P(=O)($R^{aa}$)$_2$, —P(=O)(O$R^{cc}$)$_2$, —P(=O)$_2$N($R^{bb}$)$_2$, and —P(=O)(N$R^{bb}$)$_2$, wherein $R^{aa}$, $R^{bb}$, and $R^{cc}$ are as defined herein. Oxygen protecting groups are well known in the art and include those described in detail in *Protecting Groups in Organic Synthesis*, T. W. Greene and P. G. M Wuts, 3$^{rd}$ edition, John Wiley & Sons, 1999, incorporated herein by reference.

Exemplary oxygen protecting groups include, but are not limited to, methyl, methoxylmethyl (MOM), 2-methoxyethoxymethyl (MEM), benzyl (Bn), triisopropylsilyl (TIPS), t-butyldimethylsilyl (TBDMS), t-butylmethoxyphenylsilyl (TBMPS), methanesulfonate (mesylate), and tosylate (Ts).

In certain embodiments, the substituent present on an sulfur atom is an sulfur protecting group (also referred to as a thiol protecting group). Sulfur protecting groups include, but are not limited to, —$R^{aa}$, —N($R^{bb}$)$_2$, —C(=O)S$R^{aa}$, —C(=O)$R^{aa}$, —CO$_2$$R^{aa}$, —C(=O)N($R^{bb}$), —C(=N$R^{bb}$)$R^{aa}$, —C(=N$R^{bb}$)O$R^{aa}$, —C(=N$R^{bb}$)N($R^{bb}$)$_2$, —S(=O)$R^{aa}$, —SO$_2$$R^{aa}$, —Si($R^{aa}$)$_3$, —P($R^{cc}$)$_2$, —P($R^{cc}$)$_3$, —P(=O)$_2$$R^{aa}$, —P(=O)($R^{aa}$)$_2$, —P(=O)(O$R^{cc}$)$_2$, —P(=O)$_2$N($R^{bb}$)$_2$, and —P(=O)(N$R^{bb}$)$_2$, wherein $R^{aa}$, $R^{bb}$, and $R^{cc}$ are as defined herein. Sulfur protecting groups are well known in the art and include those described in detail in *Protecting Groups in Organic Synthesis*, T W. Greene and P. G. M. Wuts, 3$^{rd}$ edition, John Wiley & Sons, 1999, incorporated herein by reference.

These and other exemplary substituents are described in more detail in the Detailed Description, Examples, and Claims. The invention is not intended to be limited in any manner by the above exemplary listing of substituents.

Other Definitions

As used herein, the term "modulation" refers to the inhibition or potentiation of GABA receptor function. A "modulator" (e.g., a modulator compound) may be, for example, an agonist, partial agonist, antagonist, or partial antagonist of the GABA receptor.

"Pharmaceutically acceptable" means approved or approvable by a regulatory agency of the Federal or a state government or the corresponding agency in countries other than the United States, or that is listed in the U.S. Pharmacopoeia or other generally recognized pharmacopoeia for use in animals, and more particularly, in humans.

"Pharmaceutically acceptable salt" refers to a salt of a compound of the invention that is pharmaceutically acceptable and that possesses the desired pharmacological activity of the parent compound. In particular, such salts are non-toxic may be inorganic or organic acid addition salts and base addition salts. Specifically, such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, N-methylglucamine and the like. Salts further include, by way of example only, sodium, potassium, calcium, magnesium, ammonium, tetraalkylammonium, and the like; and when the compound contains a basic functionality, salts of non-toxic organic or inorganic acids, such as hydrochloride, hydrobromide, tartrate, mesylate, acetate, maleate, oxalate and the like. The term "pharmaceutically acceptable cation" refers to an acceptable cationic counterion of an acidic functional group. Such cations are exemplified by sodium, potassium, calcium, magnesium, ammonium, tetraalkylammonium cations, and the like. See, e.g., Berge, et al., *J. Pharm. Sci.* (1977) 66(1): 1-79.

"Solvate" refers to forms of the compound that are associated with a solvent or water (also referred to as "hydrate"), usually by a solvolysis reaction. This physical association includes hydrogen bonding. Conventional solvents include water, ethanol, acetic acid, and the like. The compounds of the invention may be prepared e.g. in crystalline form and may be solvated or hydrated. Suitable solvates include pharmaceutically acceptable solvates, such as hydrates, and further include both stoichiometric solvates and non-stoichiometric solvates. In certain instances the solvate will be capable of isolation, for example when one or more solvent molecules are incorporated in the crystal lattice of the crystalline solid. "Solvate" encompasses both solution-phase and isolable solvates. Representative solvates include hydrates, ethanolates and methanolates.

As used herein, the term "isotopic variant" refers to a compound that contains unnatural proportions of isotopes at one or more of the atoms that constitute such compound. For example, an "isotopic variant" of a compound can contain one or more non-radioactive isotopes, such as for example, deuterium ($^2$H or D), carbon-13 ($^{13}$C), nitrogen-15 ($^{15}$N), or the like. It will be understood that, in a compound where such isotopic substitution is made, the following atoms, where present, may vary, so that for example, any hydrogen may be $^2$H/D, any carbon may be $^{13}$C, or any nitrogen may be $^{15}$N, and that the presence and placement of such atoms may be determined within the skill of the art. Likewise, the invention may include the preparation of isotopic variants with radioisotopes, in the instance for example, where the resulting compounds may be used for drug and/or substrate tissue distribution studies. The radioactive isotopes tritium, i.e., $^3$H, and carbon-14, i.e., $^{14}$C, are particularly useful for this purpose in view of their ease of incorporation and ready means of detection. Further, compounds may be prepared that are substituted with positron emitting isotopes, such as $^{11}$C, $^{18}$F, $^{15}$O, and $^{13}$N, and would be useful in Positron Emission Topography (PET) studies for examining substrate receptor occupancy. All isotopic variants of the compounds provided herein, radioactive or not, are intended to be encompassed within the scope of the invention.

"Stereoisomers": It is also to be understood that compounds that have the same molecular formula but differ in the nature or sequence of bonding of their atoms or the arrangement of their atoms in space are termed "isomers." Isomers that differ in the arrangement of their atoms in space are termed "stereoisomers." Stereoisomers that are not mirror images of one another are termed "diastereomers" and those that are non-superimposable mirror images of each other are termed "enantiomers." When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

"Tautomers" refer to compounds that are interchangeable forms of a particular compound structure, and that vary in the displacement of hydrogen atoms and electrons. Thus, two structures may be in equilibrium through the movement of π electrons and an atom (usually H). For example, enols and ketones are tautomers because they are rapidly interconverted by treatment with either acid or base. Another example of tautomerism is the aci- and nitro-forms of phenylnitromethane, that are likewise formed by treatment with acid or base. Tautomeric forms may be relevant to the attainment of the optimal chemical reactivity and biological activity of a compound of interest.

A "subject" to which administration is contemplated includes, but is not limited to, humans (i.e., a male or female of any age group, e.g., a pediatric subject (e.g. infant, child, adolescent) or adult subject (e.g., young adult, middle-aged adult or senior adult)) and/or a non-human animal, e.g., a mammal such as primates (e.g., cynomolgus monkeys, rhesus monkeys), cattle, pigs, horses, sheep, goats, rodents, cats, and/or dogs. In certain embodiments, the subject is a human. In certain embodiments, the subject is a non-human animal. The terms "human," "patient," and "subject" are used interchangeably herein.

Disease, disorder, and condition are used interchangeably herein.

As used herein, and unless otherwise specified, the terms "treat," "treating" and "treatment" contemplate an action that occurs while a subject is suffering from the specified disease, disorder or condition, which reduces the severity of the disease, disorder or condition, or retards or slows the progression of the disease, disorder or condition ("therapeutic treatment"), and also contemplates an action that occurs before a subject begins to suffer from the specified disease, disorder or condition ("prophylactic treatment").

In general, the "effective amount" of a compound refers to an amount sufficient to elicit the desired biological response, e.g., to treat a CNS-related disorder, is sufficient to induce anesthesia or sedation. As will be appreciated by those of ordinary skill in this art, the effective amount of a compound of the invention may vary depending on such factors as the desired biological endpoint, the pharmacokinetics of the compound, the disease being treated, the mode of administration, and the age, weight, health, and condition of the subject. An effective amount encompasses therapeutic and prophylactic treatment.

As used herein, and unless otherwise specified, a "therapeutically effective amount" of a compound is an amount sufficient to provide a therapeutic benefit in the treatment of a disease, disorder or condition, or to delay or minimize one or more symptoms associated with the disease, disorder or condition. A therapeutically effective amount of a compound means an amount of therapeutic agent, alone or in combination with other therapies, which provides a therapeutic benefit in the treatment of the disease, disorder or condition. The term "therapeutically effective amount" can encompass an amount that improves overall therapy, reduces or avoids symptoms or causes of disease or condition, or enhances the therapeutic efficacy of another therapeutic agent.

As used herein, and unless otherwise specified, a "prophylactically effective amount" of a compound is an amount sufficient to prevent a disease, disorder or condition, or one or more symptoms associated with the disease, disorder or condition, or prevent its recurrence. A prophylactically effective amount of a compound means an amount of a therapeutic agent, alone or in combination with other agents, which provides a prophylactic benefit in the prevention of the disease, disorder or condition. The term "prophylactically effective amount" can encompass an amount that improves overall prophylaxis or enhances the prophylactic efficacy of another prophylactic agent.

DETAILED DESCRIPTION OF CERTAIN EMBODIMENTS OF THE INVENTION

As generally described herein, the present invention provides C21-substituted neuroactive steroids designed, for example, to act as GABA modulators. In certain embodiments, such compounds are envisioned to be useful as therapeutic agents for the inducement of anesthesia and/or sedation in a subject. In certain embodiments, such compounds are envisioned to be useful as therapeutic agents for treating a CNS-related disorder.

Compounds

In one aspect, provided is a compound of Formula (I):

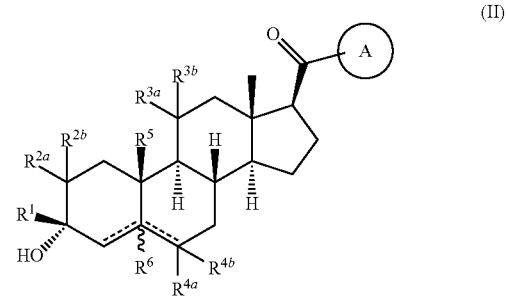

(II)

or a pharmaceutically acceptable salt thereof; wherein: Ring A is substituted or unsubstituted aryl or heteroaryl; $R^1$ is hydrogen, or substituted or unsubstituted C$_{1-6}$ alkyl, substituted or unsubstituted C$_{2-6}$ alkenyl, substituted or unsubstituted C$_{2-6}$ alkynyl, or substituted or unsubstituted C$_{3-6}$ carbocyclyl; each of R$^{2a}$ and R$^{2b}$ is independently selected from hydrogen, halogen, substituted or unsubstituted C$_{1-6}$alkyl, substituted or unsubstituted C$_{2-6}$ alkenyl, substituted or unsubstituted C$_{1-6}$ alkynyl, substituted or unsubstituted C$_{3-6}$ carbocyclyl, substituted or unsubstituted aryl, substituted or unsubstituted heteroaryl, —N(R$^A$)(R$^B$), or —OR$^{A2}$, wherein each of R$^A$ and R$^B$ is independently hydrogen, substituted or unsubstituted C$_{1-6}$ alkyl, substituted or unsubstituted C$_{2-6}$ alkenyl, substituted or unsubstituted C$_{2-6}$ alkynyl, substituted or unsubstituted C$_{3-6}$ carbocyclyl, substituted or unsubstituted heterocyclyl, substituted or unsubstituted aryl, or substituted or unsubstituted heteroaryl, or R$^A$ and R$^B$, together with the nitrogen atom to which they are attached form a ring (e.g., heteroaryl, heterocyclyl), or R$^{2a}$ and R$^{2b}$, together with the carbon atom to which they are attached form a ring; R$^{A2}$ is hydrogen or substituted or unsubstituted C$_{1-6}$ alkyl, substituted or unsubstituted C$_{2-6}$ alkenyl, substituted or unsubstituted C$_{2-6}$ alkynyl, substituted or unsubstituted C$_{3-6}$ carbocyclyl, substituted or unsubstituted aryl, or substituted or unsubstituted heteroaryl; R$^{3a}$ is hydrogen, —N(R$^A$)(R$^B$), or —OR$^{A3}$, wherein R$^{A3}$ is hydrogen, substituted or unsubstituted C$_{1-6}$ alkyl, substituted or unsubstituted C$_{2-6}$ alkenyl, substituted or unsubstituted C$_{2-6}$ alkynyl, or substituted or unsubstituted C$_{3-6}$ carbocyclyl, substituted or unsubstituted aryl, substituted or unsubstituted heteroaryl, and R$^{3b}$ is hydrogen or —N(R$^A$)C(O)R$^{A3}$; or R$^{3a}$ and R$^{3b}$ are joined to form an oxo (=O) group; each of R$^{4a}$ and R$^{4b}$ is independently selected from hydrogen or halogen; R$^5$ is hydrogen, unsubstituted C$_{1-6}$ alkyl, or —CH$_2$OR$^{A5}$, wherein R$^{A5}$ is hydrogen, substituted or unsubstituted C$_{1-6}$ alkyl, substituted or unsubstituted C$_{2-6}$ alkenyl, substituted or unsubstituted C$_{2-6}$ alkynyl, or substituted or unsubstituted C$_{3-6}$ carbocyclyl, substituted or unsubstituted aryl, substituted or unsubstituted heteroaryl; R$^6$ is absent or hydrogen; and ----- represents a single or double bond, wherein one of ----- is a double bond, the other ----- is a single bond; and when one of the ----- is a double bond, R$^6$ is absent.

In one aspect, provided is a compound of Formula (I):

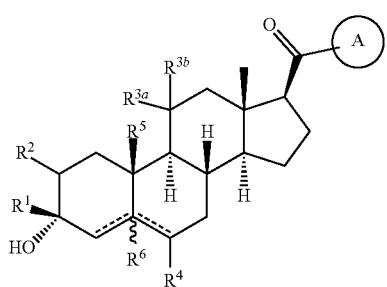

(I)

or a pharmaceutically acceptable salt thereof; wherein: Ring A is substituted or unsubstituted aryl or heteroaryl; R$^1$ is hydrogen, or substituted or unsubstituted C$_{1-6}$ alkyl, substituted or unsubstituted C$_{2-6}$ alkenyl, or substituted or unsubstituted C$_{3-6}$ carbocyclyl. R$^2$ is hydrogen, halogen, substituted or unsubstituted C$_{1-6}$ alkyl, substituted or unsubstituted C$_{2-6}$ alkenyl, substituted or unsubstituted C$_{2-6}$ alkynyl, substituted or unsubstituted C$_{3-6}$ carbocyclyl, —N(R$^A$)(R$^B$), or —OR$^{A2}$, wherein each of R$^A$ and R$^B$ is independently hydrogen, substituted or unsubstituted C$_{1-6}$ alkyl, substituted or unsubstituted C$_{2-6}$ alkenyl, substituted or unsubstituted C$_{2-6}$ alkynyl, substituted or unsubstituted C$_{3-6}$ carbocyclyl, or substituted or unsubstituted heterocyclyl, or R$^A$ and R$^B$, together with the nitrogen atom to which they are attached form a ring (e.g., heteroaryl, heterocyclyl); R$^{A2}$ is hydrogen or substituted or unsubstituted C$_{1-6}$alkyl, substituted or unsubstituted C$_{2-6}$ alkenyl, substituted or unsubstituted C$_{2-6}$ alkynyl, or substituted or unsubstituted C$_{3-6}$ carbocyclyl; R$^{3a}$ is hydrogen, —N(R$^A$)(R$^B$), or —OR$^{A3}$, wherein R$^{A3}$ is hydrogen, substituted or unsubstituted C$_{1-6}$ alkyl, substituted or unsubstituted C$_{2-6}$ alkenyl, substituted or unsubstituted C$_{2-6}$ alkynyl, or substituted or unsubstituted C$_{3-6}$ carbocyclyl, and R$^{3b}$ is hydrogen or —N(R$^A$)C(O)R$^{A3}$; or R$^{3a}$ and R$^{3b}$ are joined to form an oxo (=O) group; R$^4$ is hydrogen or halogen; R$^5$ is hydrogen, unsubstituted C$_{1-6}$alkyl, or —CH$_2$OR$^{A5}$, wherein R$^{A5}$ is hydrogen, substituted or unsubstituted C$_{1-6}$ alkyl, substituted or unsubstituted C$_{2-6}$ alkenyl, substituted or unsubstituted C$_{2-6}$ alkynyl, or substituted or unsubstituted C$_{3-6}$ carbocyclyl; R$^6$ is absent or hydrogen; and ----- represents a single or double bond, wherein when one of ----- is a double bond, the other ----- is a single bond; and when one of the ----- is a double bond, R$^6$ is absent.

In some embodiments, the compound of Formula (I) is a compound of Formula (I-a):

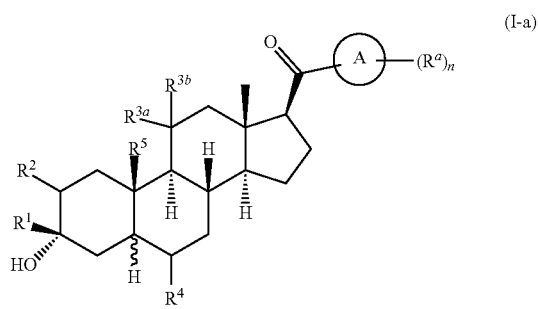

(I-a)

wherein: n is 0, 1, 2, 3, 4, 5, or 6; and each R$^a$ is independently halogen, cyano, C$_{1-6}$ alkyl, —N(R$^A$)(R$^B$), —N(R$^A$)C(O)R$^{AA}$, —N(R$^A$)C(O)OR$^{AA}$, —SR$^{AA}$ or —OR$^{AA}$, wherein R$^{AA}$ is hydrogen, substituted or unsubstituted C$_{1-6}$ alkyl, substituted or unsubstituted C$_{2-6}$ alkenyl, substituted or unsubstituted C$_{2-6}$ alkynyl, substituted or unsubstituted C$_{3-6}$ carbocyclyl, substituted or unsubstituted aryl, or substituted or unsubstituted heteroaryl; or two R$^a$ groups, together with the atoms with which they are attached form a ring.

In some embodiments, the compound of Formula (I) is a compound of Formula (I-b):

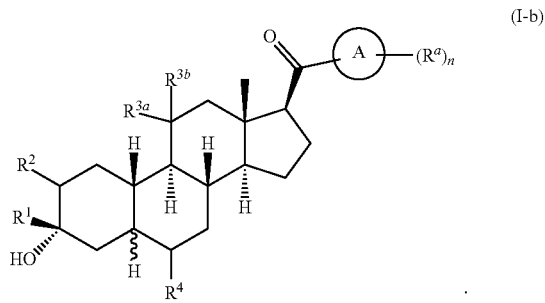

(I-b)

In some embodiments, the compound of Formula (I) is a compound of Formula (I-b-i) or (I-b-ii):

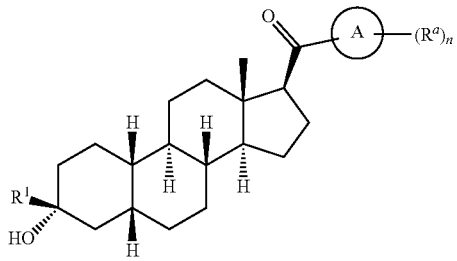
(I-b-i)

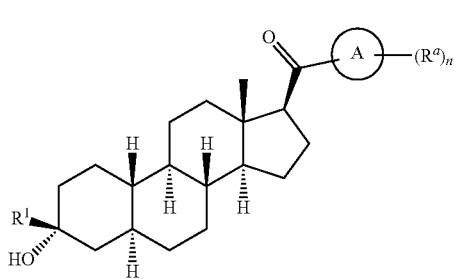
(I-b-ii)

In some embodiments, the compound of Formula (I) is a compound of Formula (I-c):

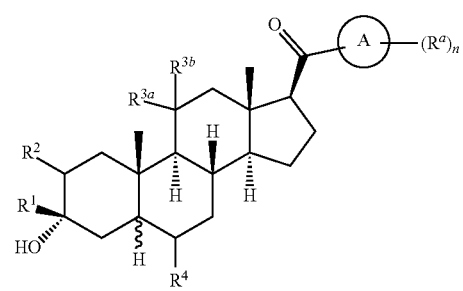
(I-c)

In some embodiments, the compound of Formula (I) is a compound of Formula (I-c-i) or (I-c-ii):

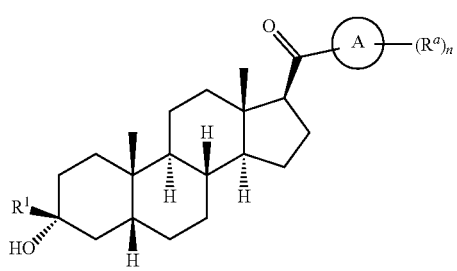
(I-c-i)

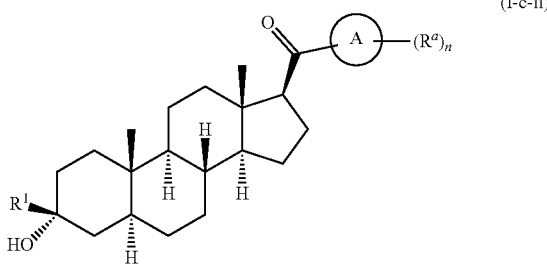
(I-c-ii)

In some embodiments, the compound of Formula (I) is a compound of Formula (I-f):

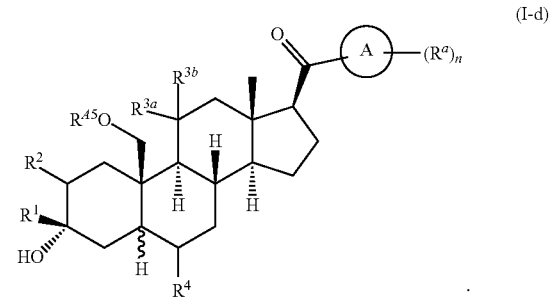
(I-d)

In some embodiments, the compound of Formula (I) is a compound of Formula (I-d-i) or (I-d-ii):

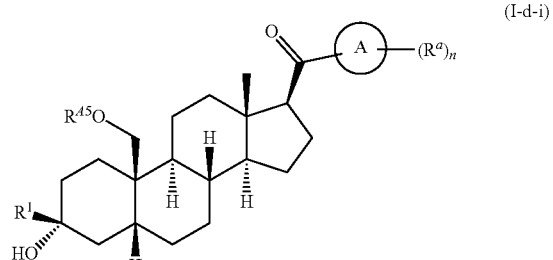
(I-d-i)

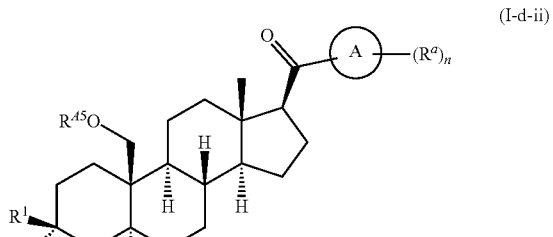
(I-d-ii)

In some embodiments, A is a 5-10-membered ring. In some embodiments, A is phenyl, naphthyl, furan, thiophene, thiazole, pyrrole, imidazole, pyrazole, or triazole.

In some embodiments. A is a fused bicyclic ring. In some embodiments, A is benzofuran, benzoimidazole, indole, benzothiazole, or benzothiophene.

In some embodiments, A is linked through a carbon atom.

In some embodiments, $R^1$ is hydrogen or substituted or unsubstituted $C_{1-6}$ alkyl.

In some embodiments, R¹ is unsubstituted $C_{1-6}$ alkyl. In some embodiments, R¹ is —$CH_3$.

In some embodiments, R¹ is hydrogen.

In some embodiments, R² is hydrogen or halogen. In some embodiments, R² is hydrogen.

In some embodiments, $R^{3a}$ is —$N(R^A)(R^B)$. In some aspects of these embodiments, each of $R^A$ and $R^B$ is independently hydrogen or substituted or unsubstituted $C_{1-6}$ alkyl. In some embodiments, $R^{3a}$ is —$NH_2$. In some embodiments, $R^{3a}$ is —$NHCH_3$ or —$NHCH_2CH_3$. In some embodiments, $R^{3a}$ is —$N(CH_3)(CH_2CH_3)$, —$N(CH_2CH_3)_2$ or —$N(CH_3)_2$. In some aspects of these embodiments, $R^A$ and $R^B$, together with the nitrogen atom to which they are attached form a ring (e.g., heteroaryl, heterocyclyl). In some embodiments, $R^A$ and $R^B$, together with the nitrogen atom to which they are attached form a 3-7-membered ring (e.g., pyrrolidine, imidazolidine, piperidine, piperazine, morpholine, pyrrole, imidazole, triazole, tetrazole).

In some embodiments, $R^{3b}$ is hydrogen.

In some embodiments, $R^{3b}$ is —$N(R^A)C(O)R^{A3}$. In some aspects of these embodiments, $R^A$ is hydrogen or substituted or unsubstituted $C_{1-6}$ alkyl. In some aspects of these embodiments, $R^{A3}$ is hydrogen or substituted or unsubstituted $C_{1-6}$ alkyl.

In some embodiments, R⁴ is hydrogen.

In some embodiments, R⁵ is hydrogen or unsubstituted $C_{1-6}$ alkyl. In some embodiments, R⁵ is —$CH_2OR^{A5}$. In some aspects of these embodiments, $R^{A5}$ is hydrogen or substituted or unsubstituted $C_{1-6}$ alkyl.

In some embodiments, n is 0, 1, or 2. In some embodiments, n is 0 or 1.

In some embodiments, n is 0, 1, or 2, and each $R^a$ is independently halogen, $C_{1-6}$ alkyl, or —$OR^{AA}$. In some aspects of these embodiments, $R^{AA}$ is hydrogen, or substituted or unsubstituted $C_{1-6}$ alkyl. In some embodiments, $R^a$ is —$CH_3$.

In some embodiments, $R^a$ is $C_{1-6}$ alkyl.

In some embodiments, $R^a$ is —$N(R^A)(R^B)$. In some aspects of these embodiments, each of $R^A$ and $R^B$ is independently hydrogen or substituted or unsubstituted $C_{1-6}$ alkyl. In some embodiments, $R^a$ is —$NH_2$. In some embodiments, $R^a$ is —$NHCH_3$ or —$NHCH_2CH_3$. In some embodiments, $R^a$ is —$N(CH_3)(CH_2CH_3)$, —$N(CH_2CH_3)_2$ or —$N(CH_3)_2$. In some aspects of these embodiments, $R^A$ and $R^B$, together with the nitrogen atom to which they are attached form a ring (e.g., heteroaryl, heterocyclyl). In some embodiments, $R^A$ and $R^B$, together with the nitrogen atom to which they are attached form a 3-7-membered ring (e.g., pyrrolidine, imidazolidine, piperidine, piperazine, morpholine, pyrrole, imidazole, triazole, tetrazole).

In some embodiments, R is —$N(R^A)C(O)R^{AA}$. In some aspects of these embodiments, $R^A$ is hydrogen or substituted or unsubstituted $C_{1-6}$ alkyl. In some aspects of these embodiments, $R^{AA}$ is hydrogen or substituted or unsubstituted $C_{1-6}$ alkyl.

In some embodiments, $R^a$ is —$N(R^A)C(O)OR^{AA}$. In some aspects of these embodiments, $R^A$ is hydrogen or substituted or unsubstituted $C_{1-6}$ alkyl. In some aspects of these embodiments, $R^{AA}$ is hydrogen or substituted or unsubstituted $C_{1-6}$ alkyl.

In some embodiments, $R^a$ is —$OR^{AA}$. In some embodiments, $R^a$ is —$OCH_3$, —$OCH_2CH_3$.

In some embodiments, the compound is:

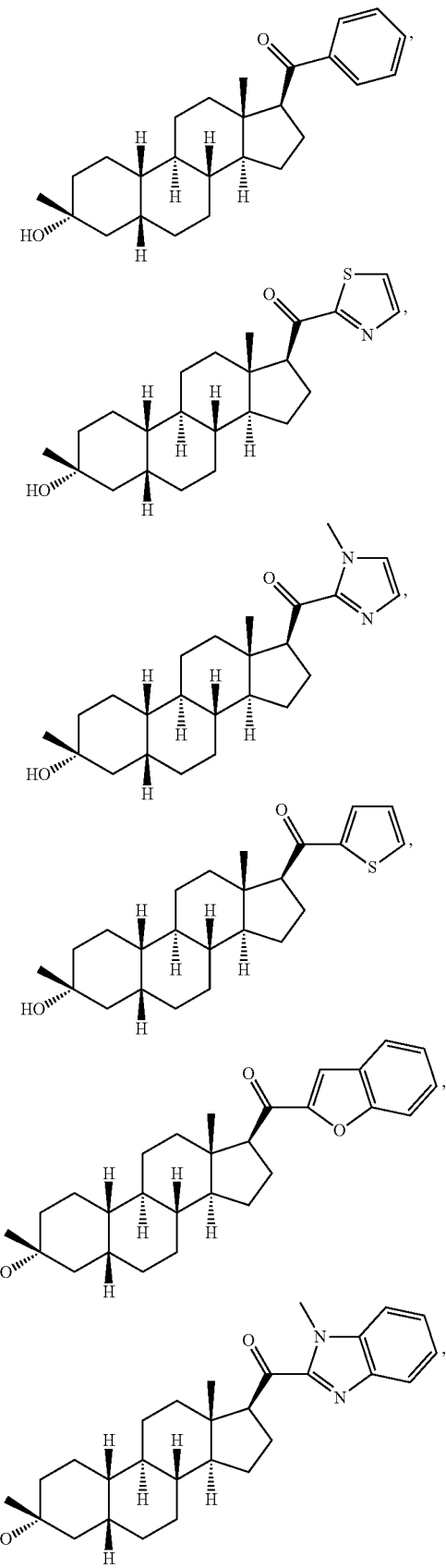

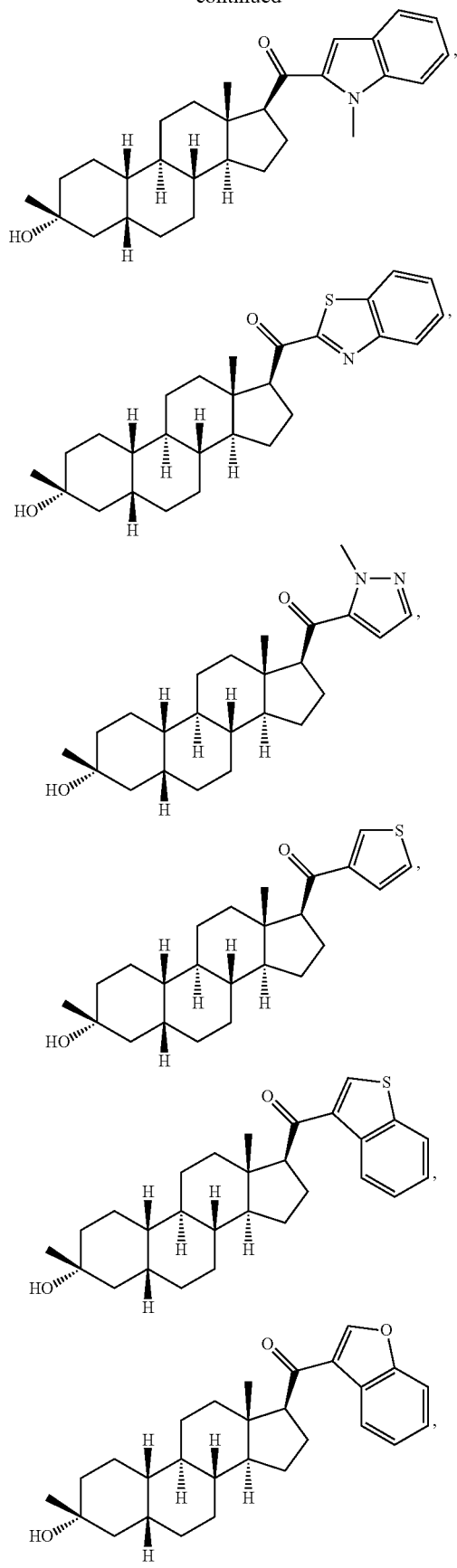
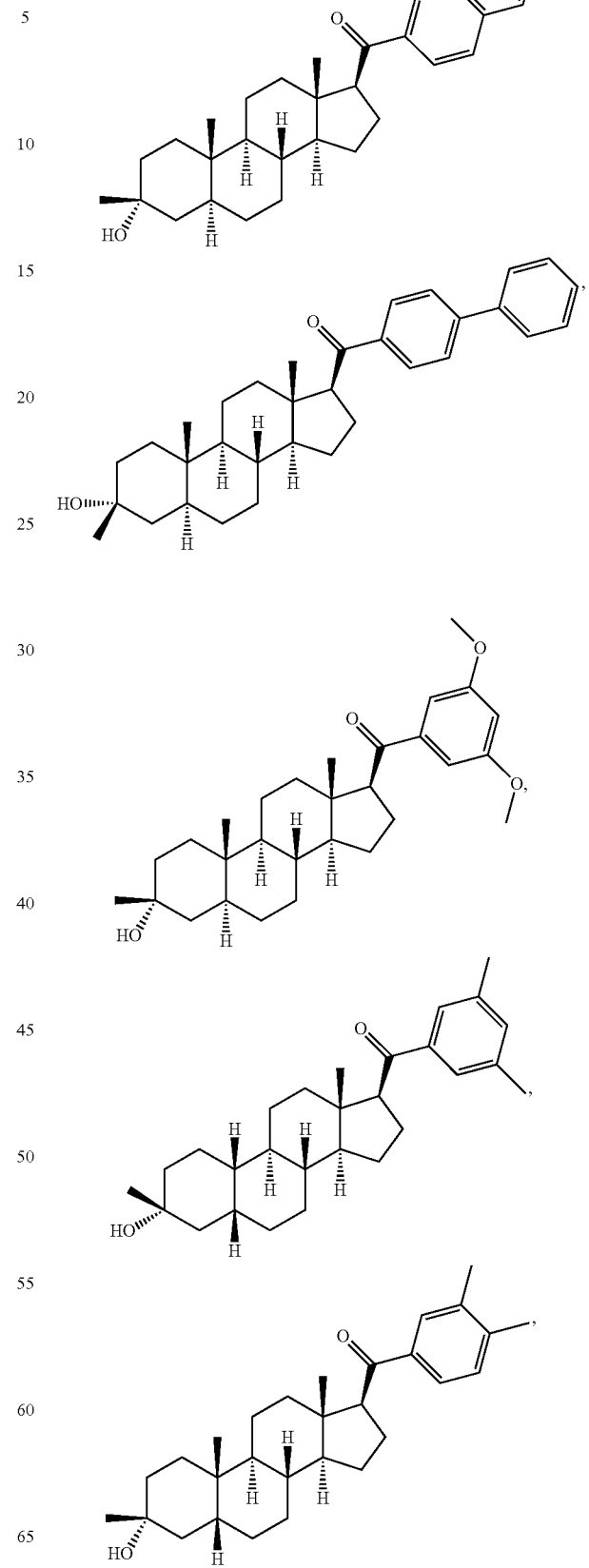

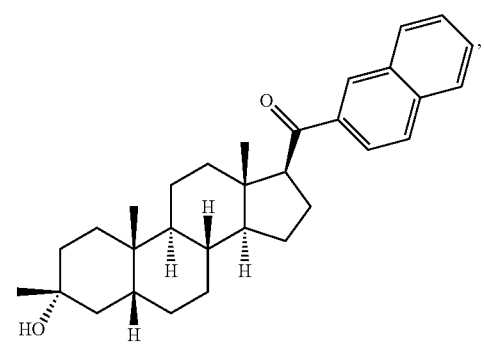
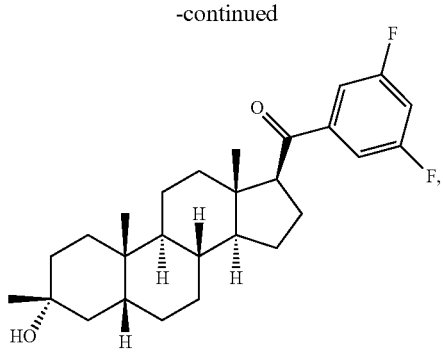
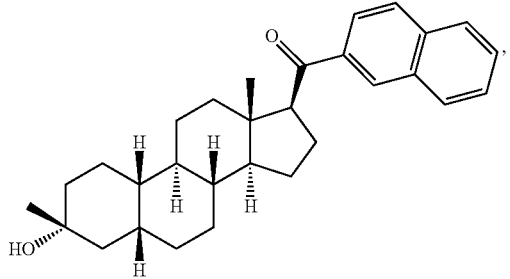
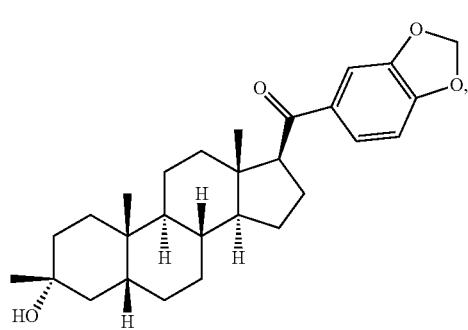
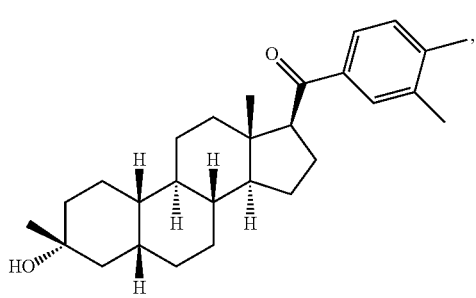
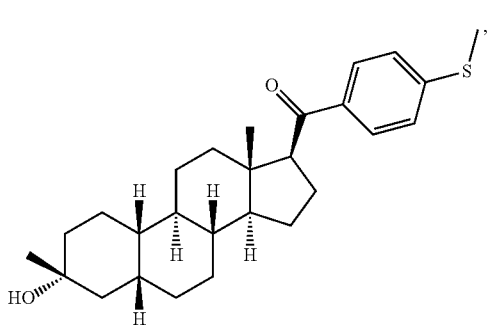
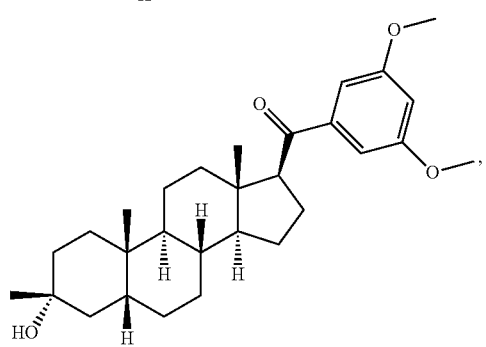
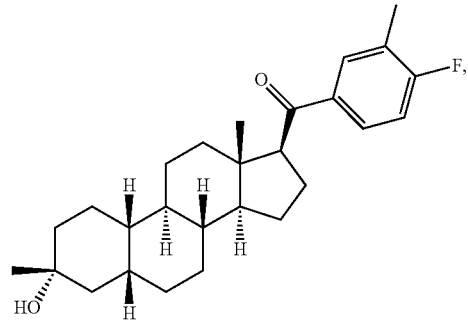
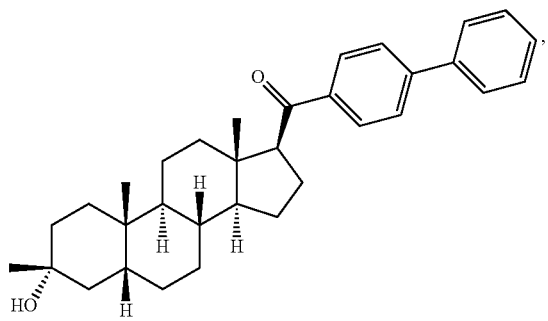
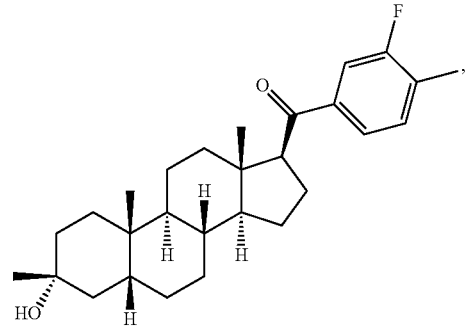

33
-continued
34
-continued
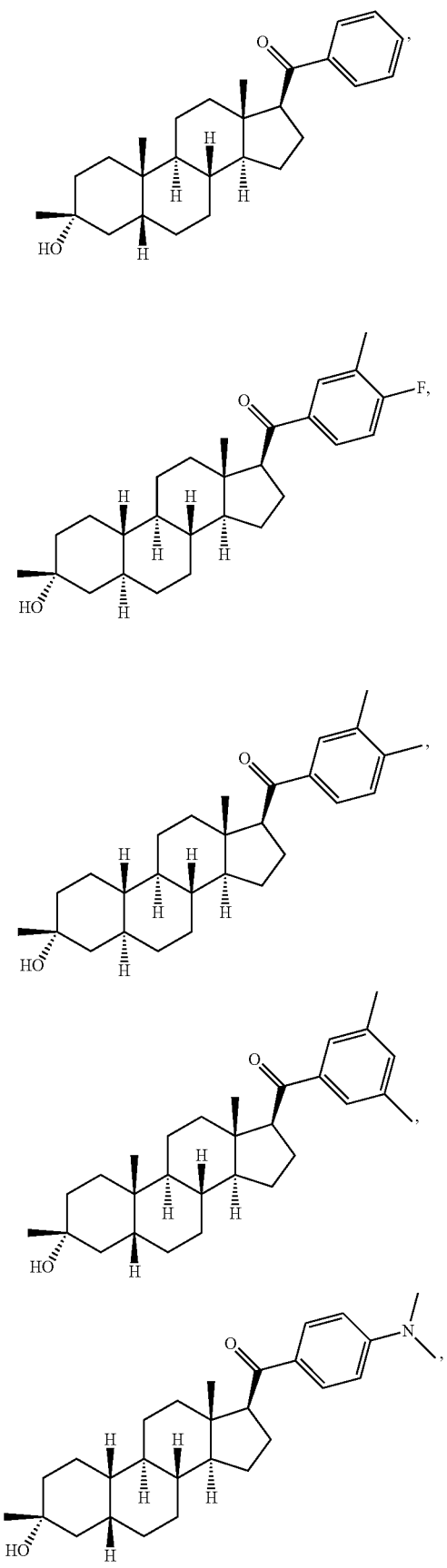
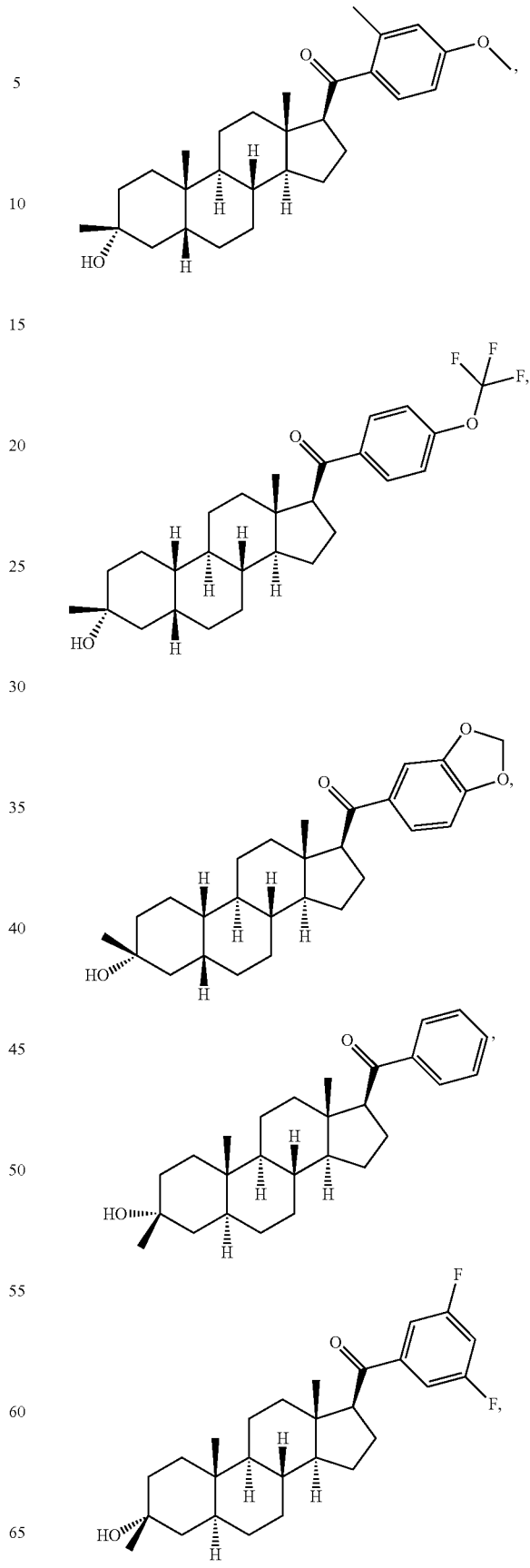

35
-continued
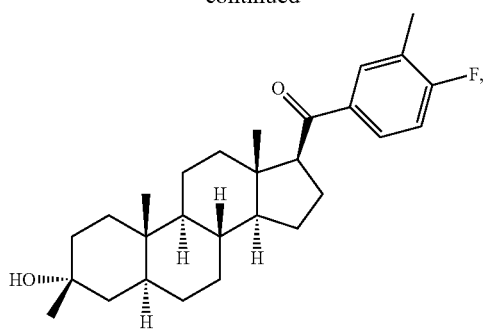
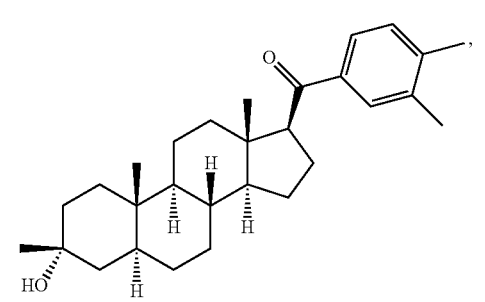
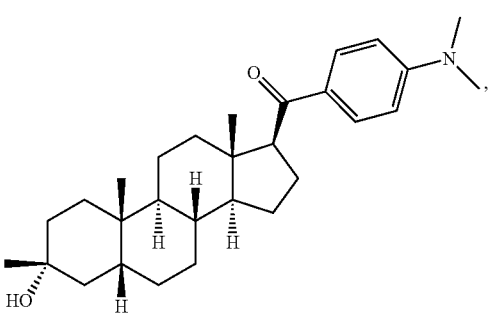
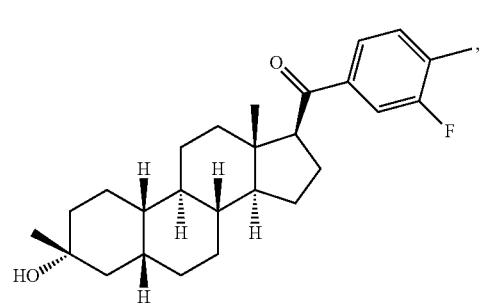
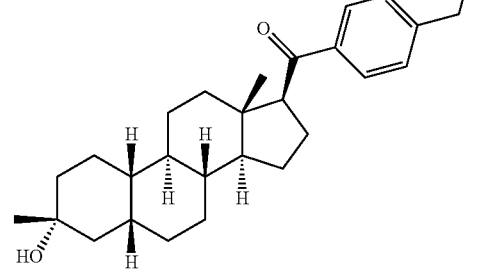
36
-continued
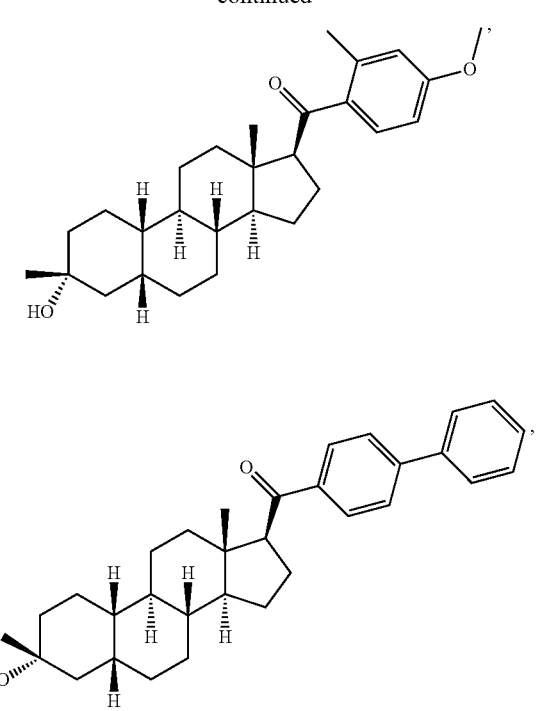
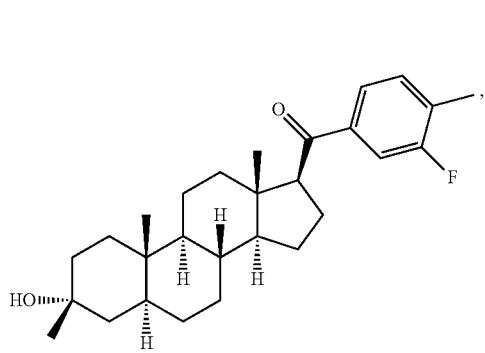
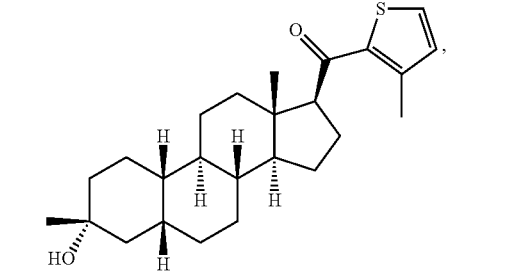
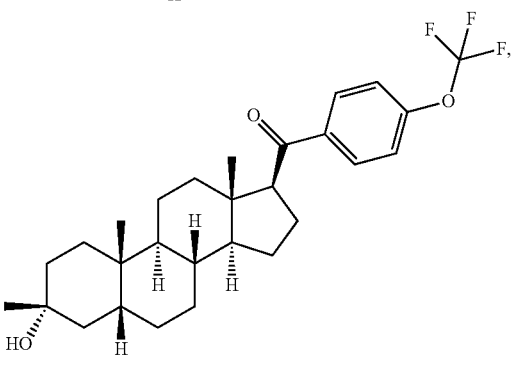

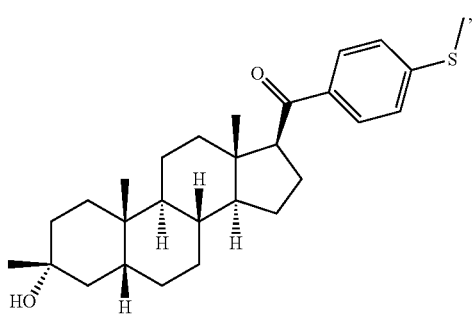
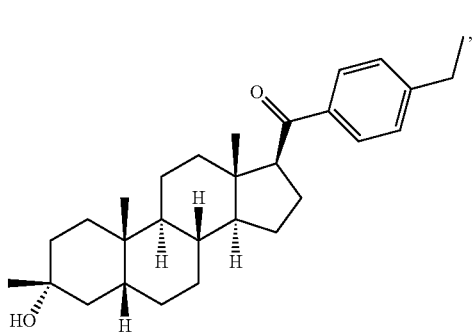
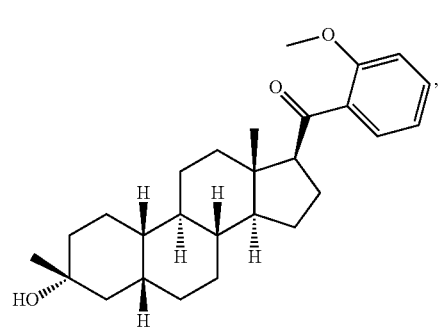
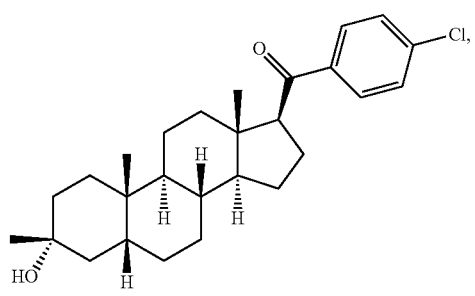
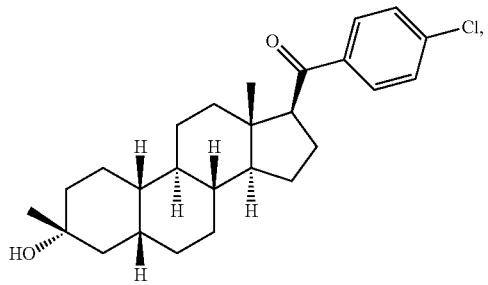
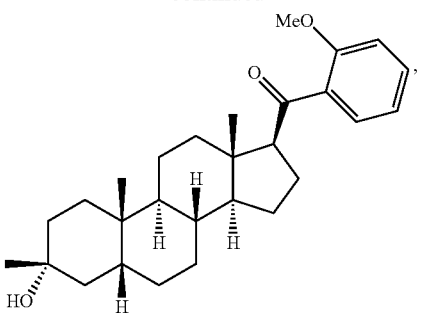
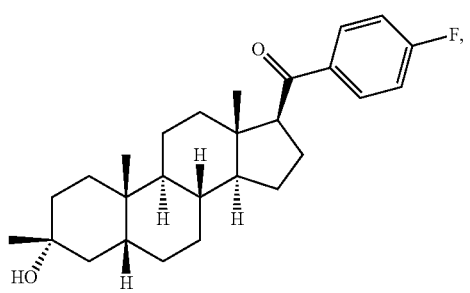
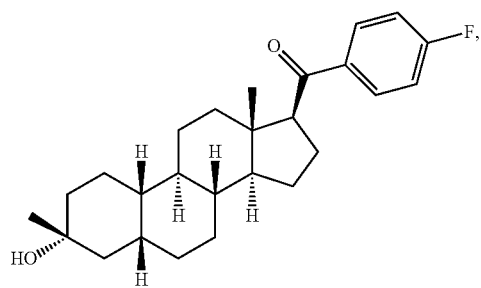
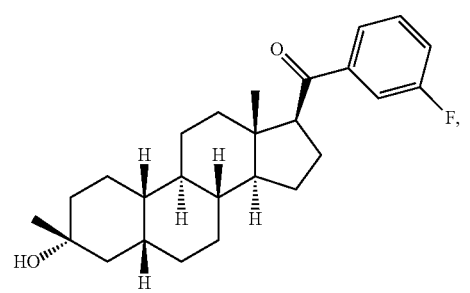
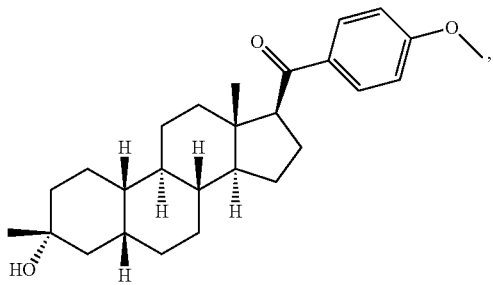

-continued
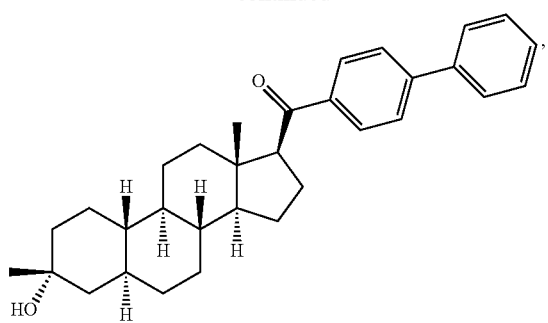
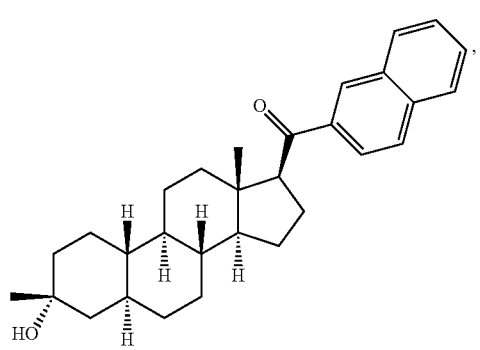
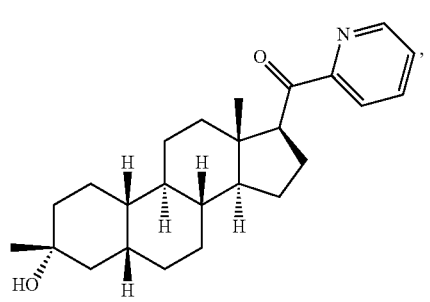
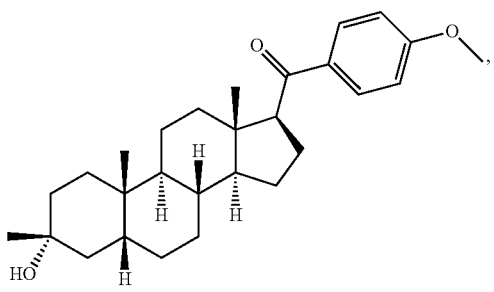
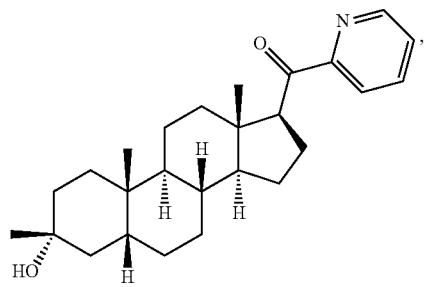
-continued
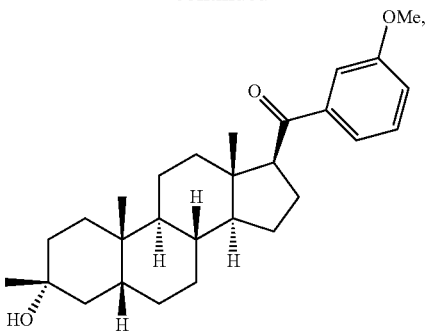
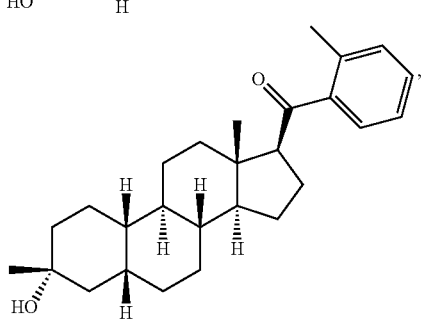
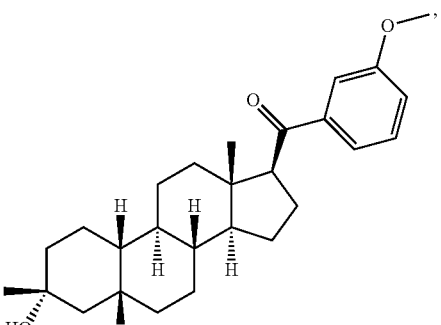
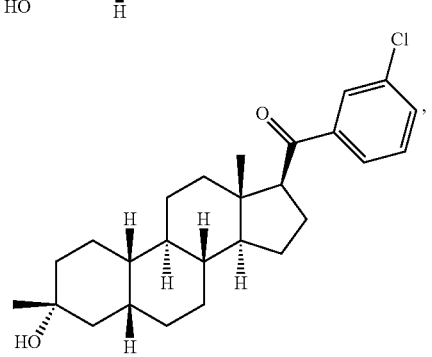
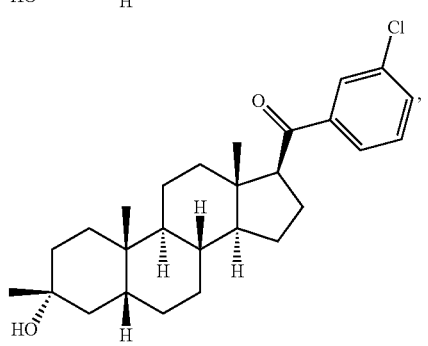

41
-continued
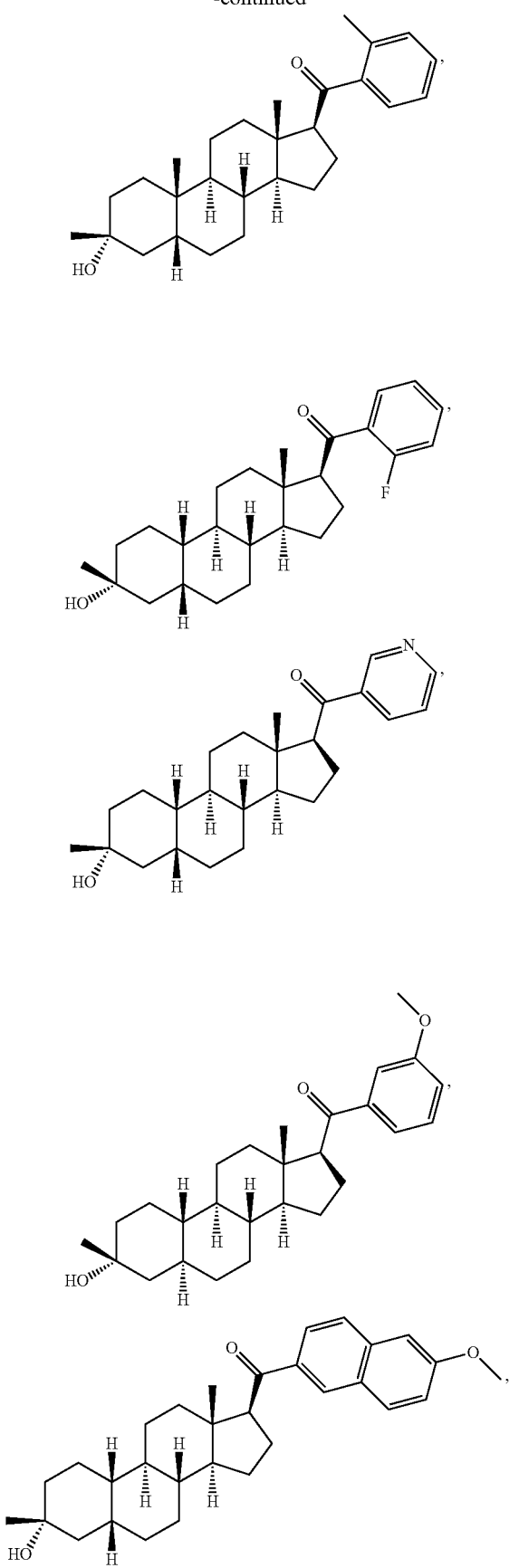
42
-continued
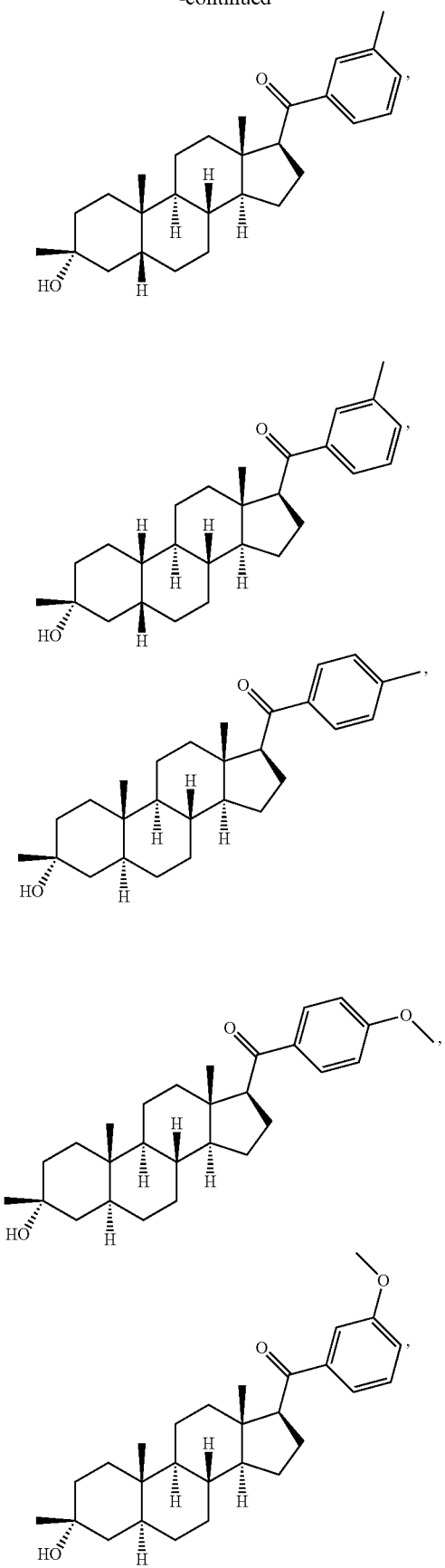

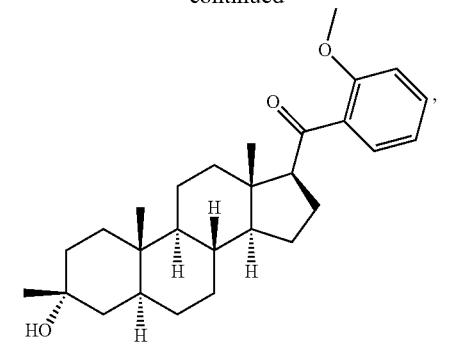
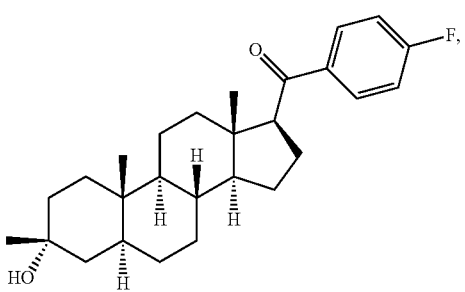
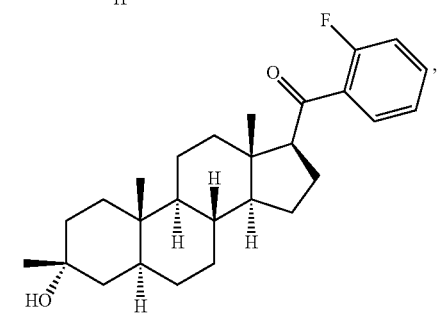
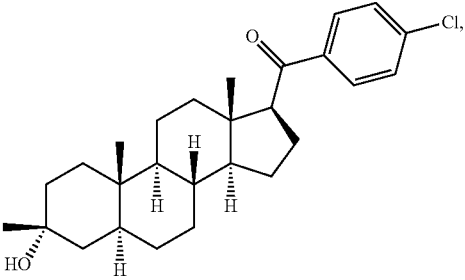
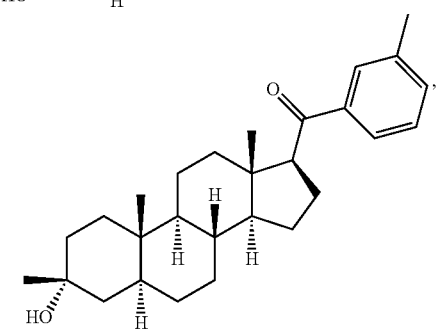
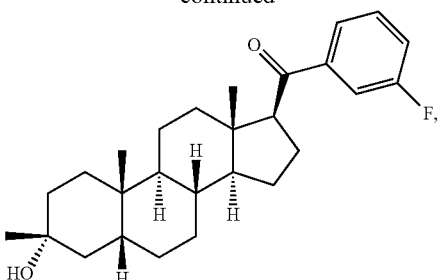
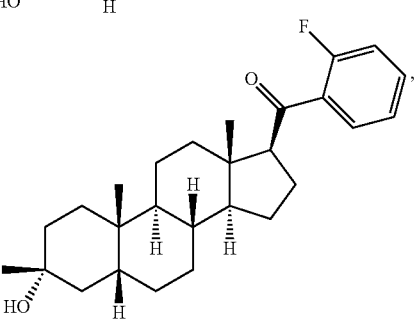
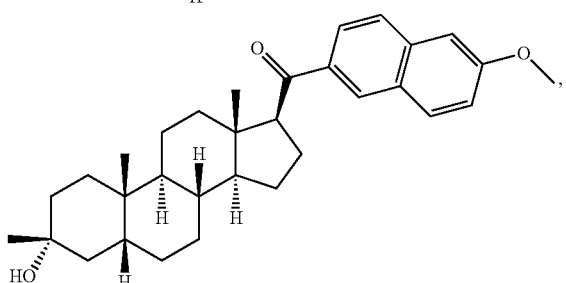
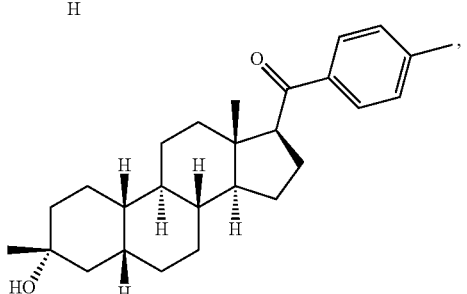
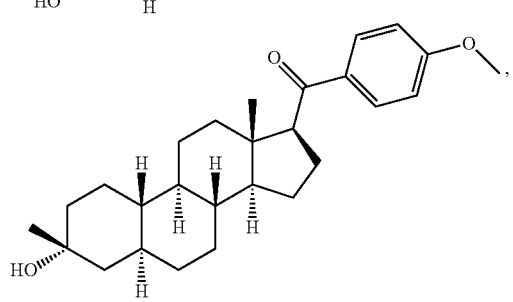
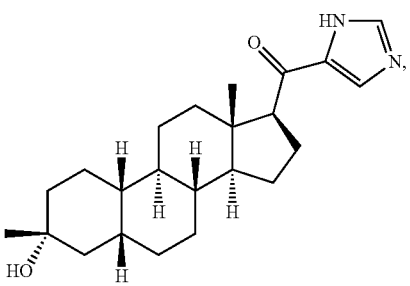

-continued
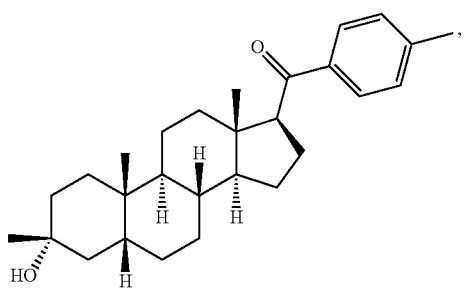
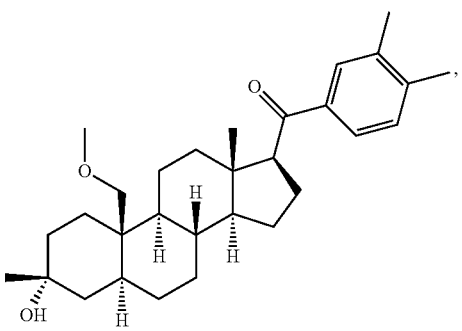
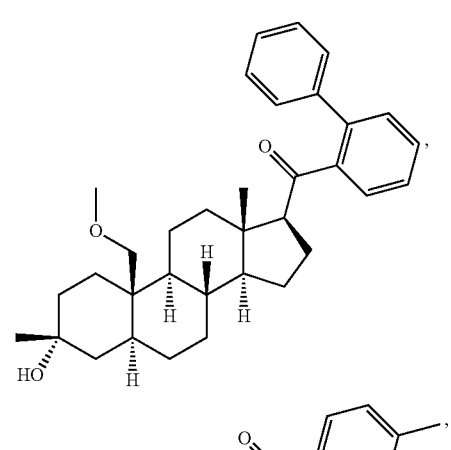
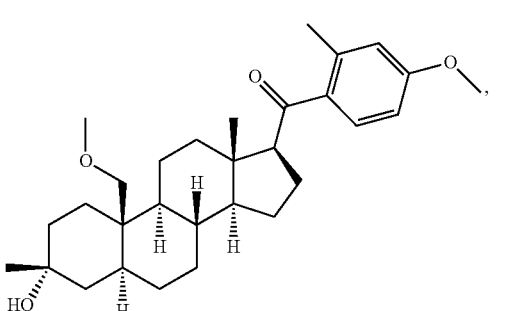
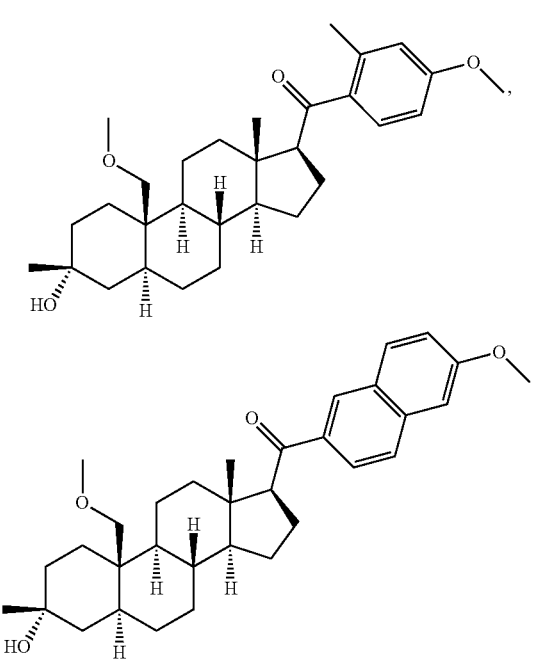
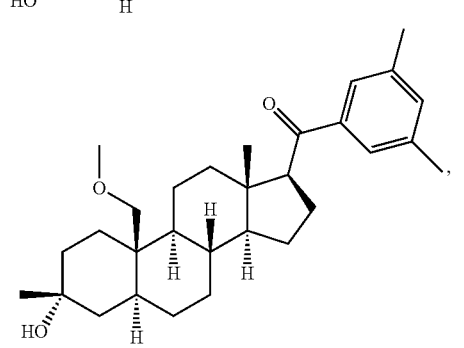
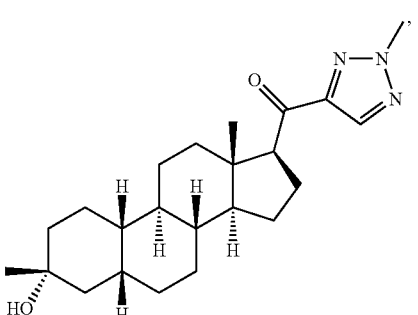
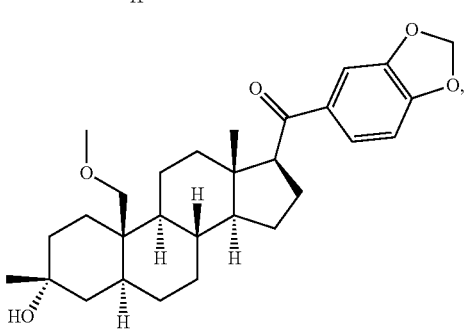
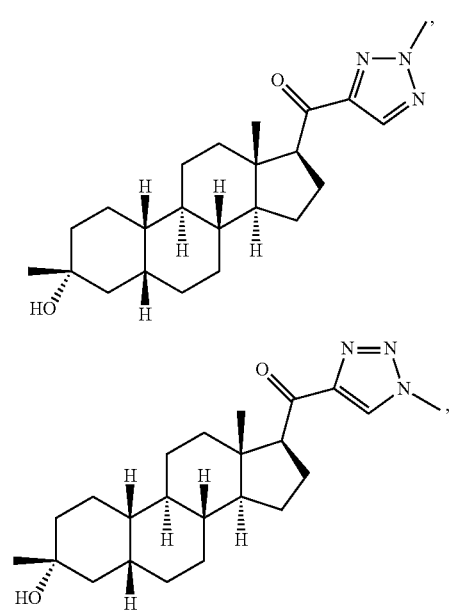

-continued
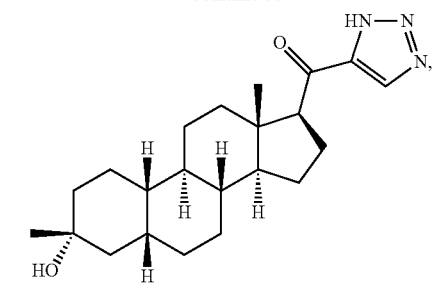
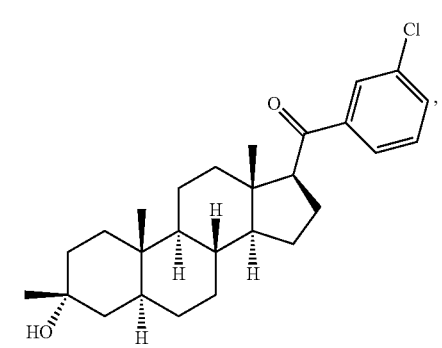
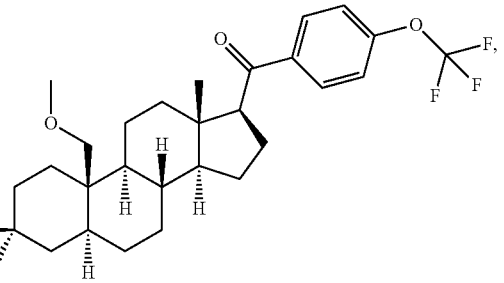
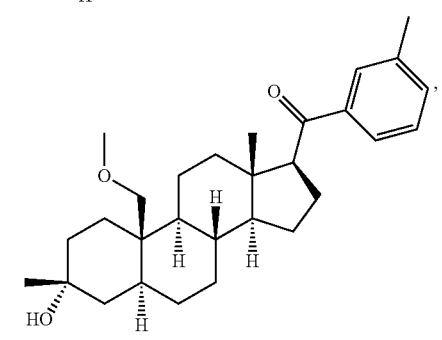
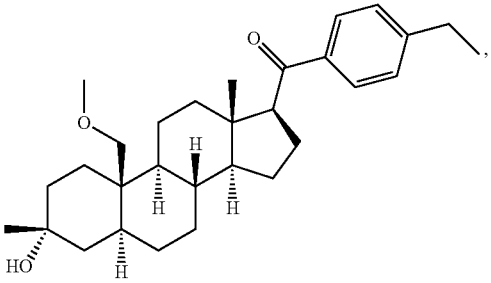
-continued
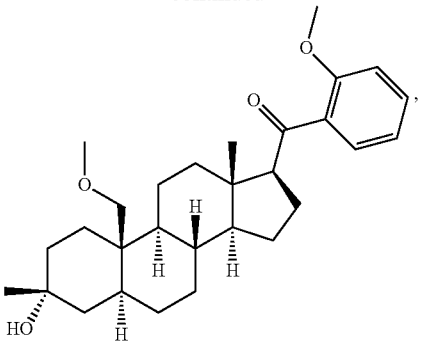
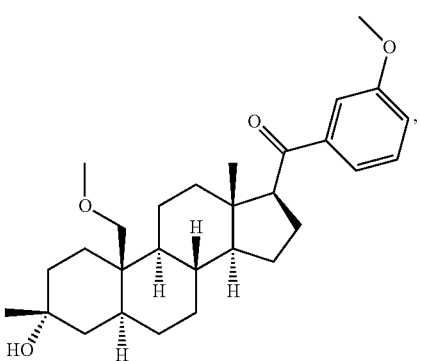
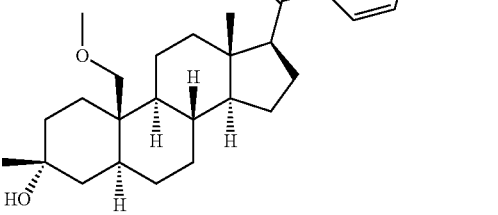
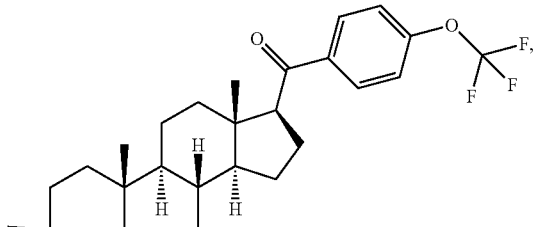
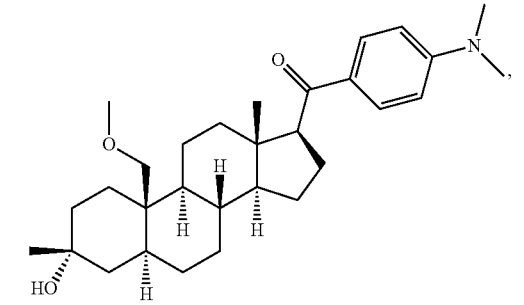

49
-continued
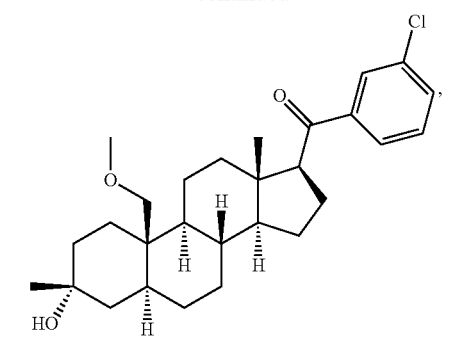
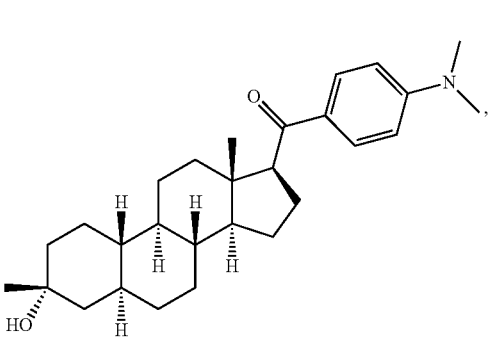
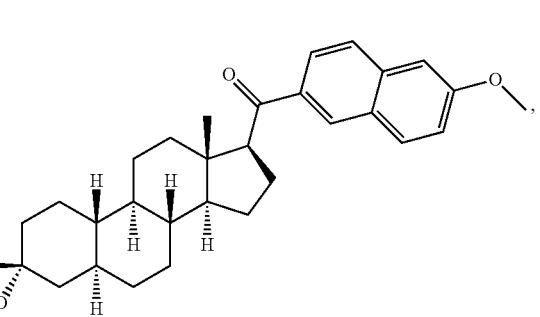
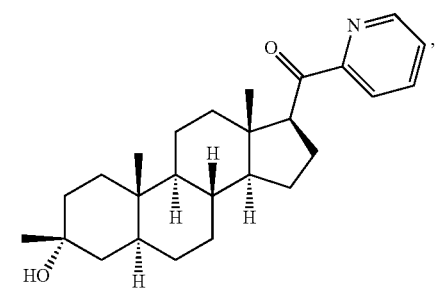
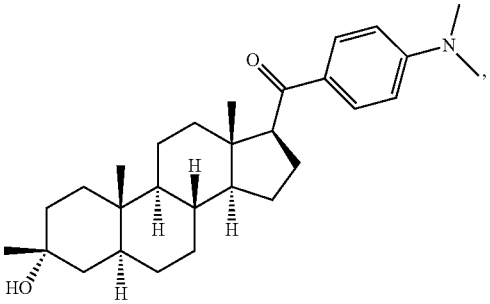
50
-continued
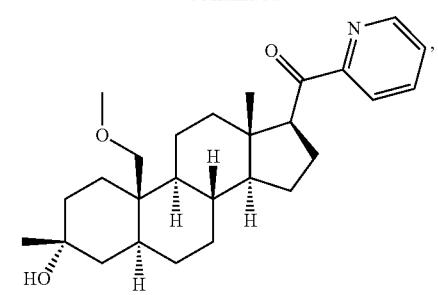
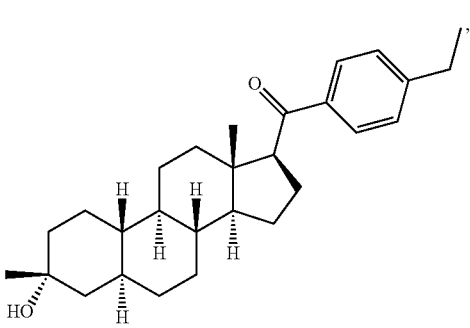
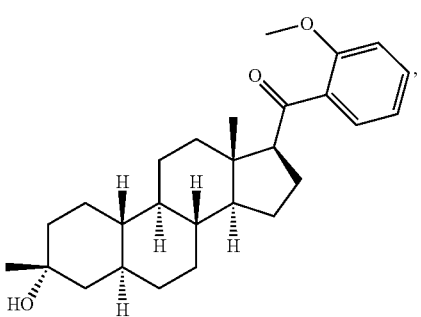
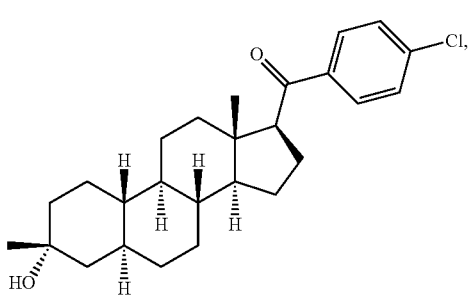
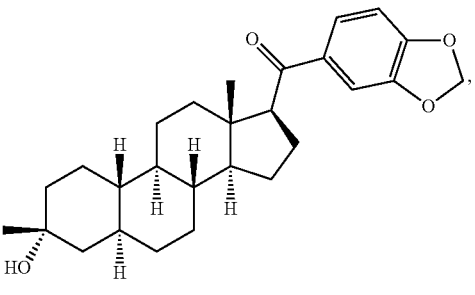

51
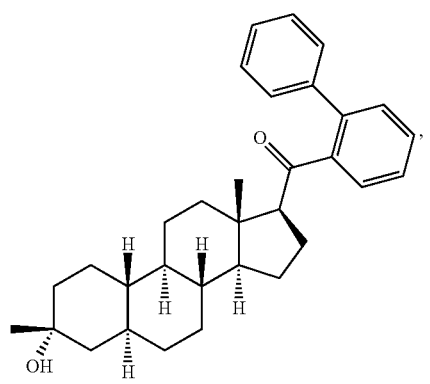
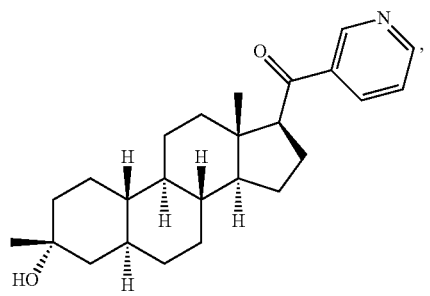
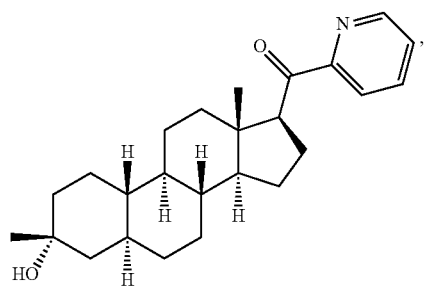
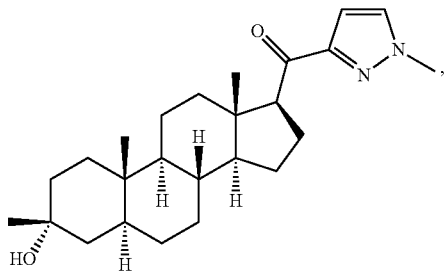
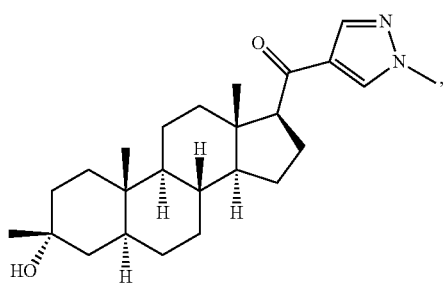
52
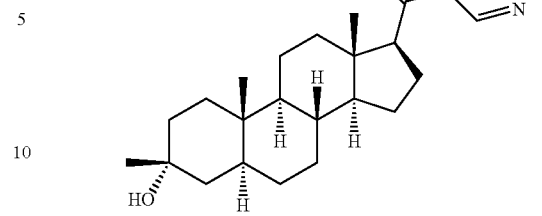
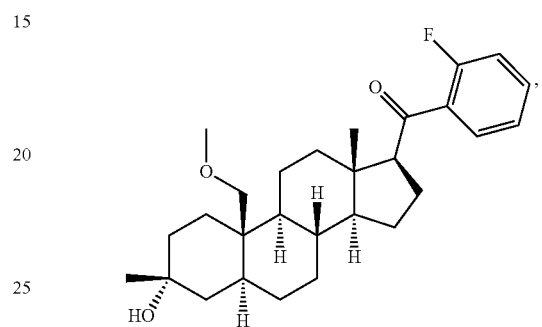
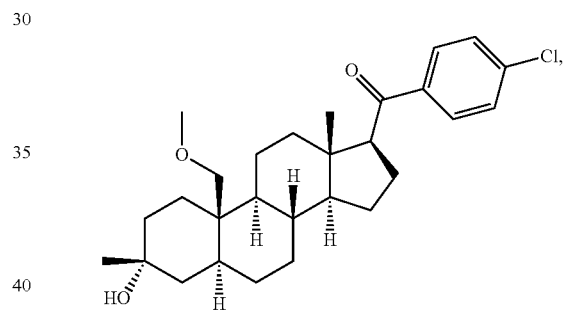
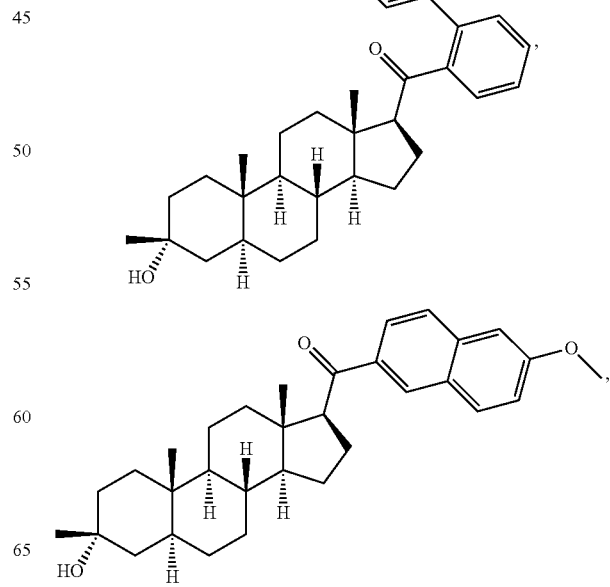

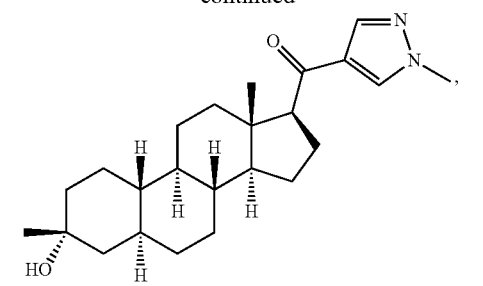
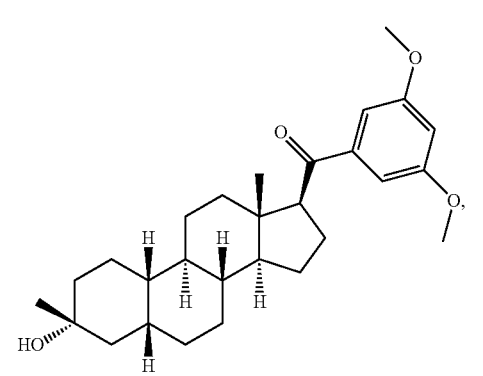
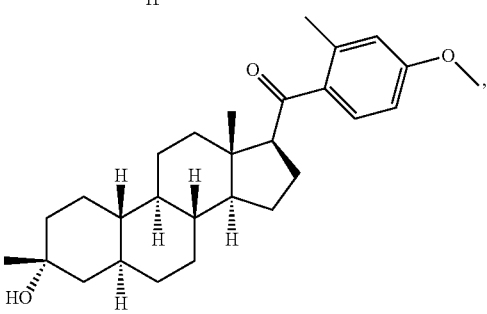
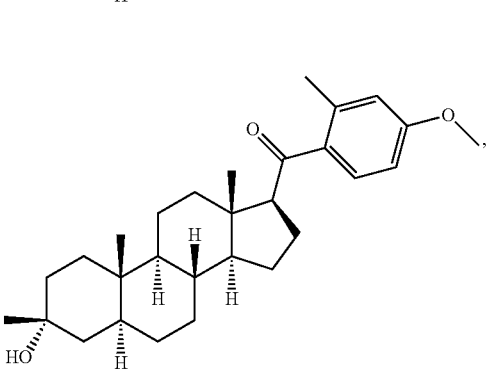
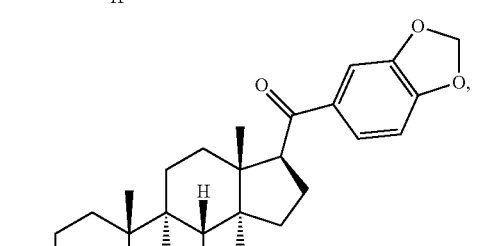
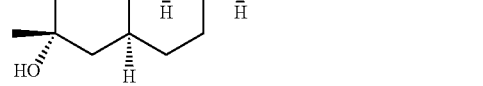
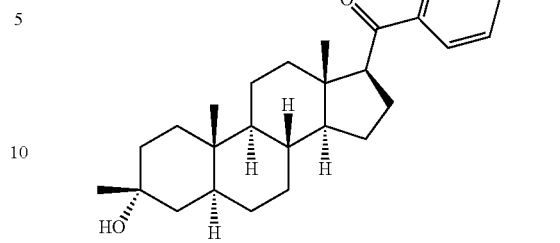
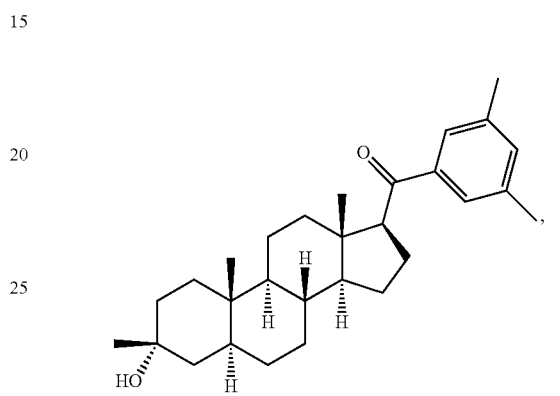
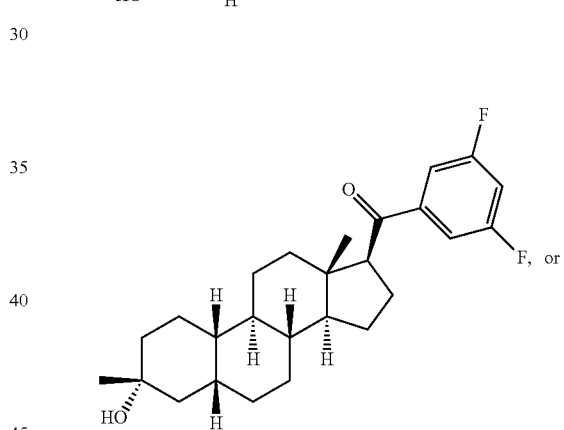
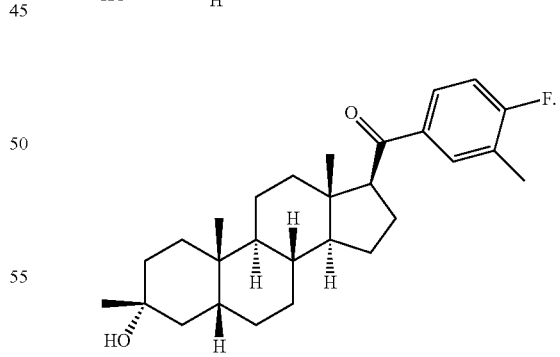
In one aspect, provided is a pharmaceutical composition comprising a compound of Formula (I) and a pharmaceutically acceptable excipient.
In one aspect, provided is a method of inducing sedation and/or anesthesia in a subject, comprising administering to the subject an effective amount of a compound of the Formula (II):

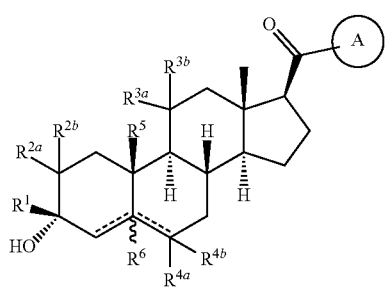

(II)

or a pharmaceutically acceptable salt thereof; wherein: Ring A is substituted or unsubstituted aryl or heteroaryl; $R^1$ is hydrogen, or substituted or unsubstituted $C_{1-6}$ alkyl, substituted or unsubstituted $C_{2-6}$ alkenyl, substituted or unsubstituted $C_{2-6}$ alkynyl, or substituted or unsubstituted $C_{3-6}$ carbocyclyl; each of $R^{2a}$ and $R^{2b}$ is independently selected from hydrogen, halogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{3-6}$ carbocyclyl, substituted or unsubstituted aryl, substituted or unsubstituted heteroaryl, —N($R^A$)($R^B$), or —O$R^{A2}$, wherein each of $R^A$ and $R^B$ is independently hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{3-6}$ carbocyclyl, substituted or unsubstituted heterocyclyl, substituted or unsubstituted aryl, or substituted or unsubstituted heteroaryl, or $R^A$ and $R^B$, together with the nitrogen atom to which they are attached form a ring (e.g., heteroaryl, heterocyclyl), or $R^{2a}$ and $R^{2b}$, together with the carbon atom to which they are attached form a ring; $R^{A2}$ is hydrogen or substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{3-6}$ carbocyclyl, substituted or unsubstituted aryl, or substituted or unsubstituted heteroaryl; $R^{3a}$ is hydrogen, —N($R^A$)$R^B$), or —O$R^{A3}$, wherein $R^{A3}$ is hydrogen, substituted or unsubstituted $C_{1-6}$ alkyl, substituted or unsubstituted $C_{2-6}$ alkenyl, substituted or unsubstituted $C_{2-6}$ alkynyl, or substituted or unsubstituted $C_{3-6}$ carbocyclyl, substituted or unsubstituted aryl, substituted or unsubstituted heteroaryl, and $R^{3b}$ is hydrogen or —N($R^A$)C(O)$R^A$; or $R^{3a}$ and $R^{3b}$ are joined to form an oxo (=O) group; each of $R^{4a}$ and $R^{4b}$ is independently selected from hydrogen or halogen; $R^5$ is hydrogen, unsubstituted $C_{1-6}$ alkyl, or —CH$_2$O$R^{A5}$, wherein $R^{A5}$ is hydrogen, substituted or unsubstituted $C_{1-6}$ alkyl, substituted or unsubstituted $C_{2-6}$ alkenyl, substituted or unsubstituted $C_{2-6}$ alkynyl, or substituted or unsubstituted $C_{3-6}$ carbocyclyl, substituted or unsubstituted aryl, substituted or unsubstituted heteroaryl; $R^6$ is absent or hydrogen; and ----- represents a single or double bond, wherein when one of ----- is a double bond, the other ----- is a single bond; and when one of the ----- is a double bond, $R^6$ is absent.

In one aspect, provided is a method of administering an effective amount of a compound, a pharmaceutically acceptable salt thereof, or pharmaceutical composition of a compound of Formula (I), to a subject in need thereof, wherein the subject experiences sedation and/or anesthesia within two hours of administration.

In some embodiments, the subject experiences sedation and/or anesthesia within one hour of administration. In some embodiments, the subject experiences sedation and/or anesthesia instantaneously.

In some embodiments, compound is administered by intravenous administration.

In some embodiments, compound is administered chronically.

In some embodiments, the subject is a mammal. In some embodiments, the subject is a human.

In some embodiments, the compound is administered in combination with another therapeutic agent.

In one aspect, provided is a method for treating seizure in a subject, comprising administering to the subject an effective amount of a compound of the Formula (II):

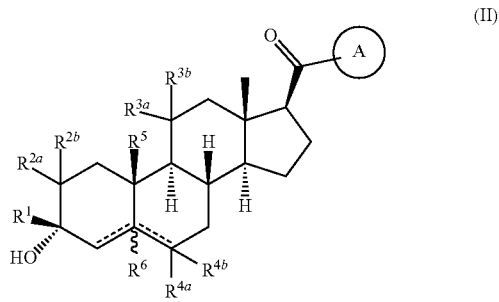

(II)

or a pharmaceutically acceptable salt thereof; wherein: Ring A is substituted or unsubstituted aryl or heteroaryl; $R^1$ is hydrogen, or substituted or unsubstituted $C_{1-6}$ alkyl, substituted or unsubstituted $C_{2-6}$ alkenyl, substituted or unsubstituted $C_{2-6}$ alkynyl, or substituted or unsubstituted $C_{3-6}$ carbocyclyl; each of $R^{2a}$ and $R^{2b}$ is independently selected from hydrogen, halogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{3-6}$ carbocyclyl, substituted or unsubstituted aryl, substituted or unsubstituted heteroaryl, —N($R^A$)($R^B$), or —O$R^{A2}$, wherein each of $R^A$ and $R^B$ is independently hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{3-6}$ carbocyclyl, substituted or unsubstituted heterocyclyl, substituted or unsubstituted aryl, or substituted or unsubstituted heteroaryl, or $R^A$ and $R^B$, together with the nitrogen atom to which they are attached form a ring (e.g., heteroaryl, heterocyclyl), or $R^{2a}$ and $R^{2b}$, together with the carbon atom to which they are attached form a ring; $R^{A2}$ is hydrogen or substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{3-6}$ carbocyclyl, substituted or unsubstituted aryl, or substituted or unsubstituted heteroaryl; $R^{3a}$ is hydrogen, —N($R^A$)($R^B$), or —O$R^{A3}$, wherein $R^{A3}$ is hydrogen, substituted or unsubstituted $C_{1-6}$ alkyl, substituted or unsubstituted $C_{2-6}$ alkenyl, substituted or unsubstituted $C_{2-6}$ alkynyl, or substituted or unsubstituted $C_{3-6}$ carbocyclyl, substituted or unsubstituted aryl, substituted or unsubstituted heteroaryl, and $R^{3b}$ is hydrogen or —N($R^A$)C(O)$R^{A3}$; or $R^{3a}$ and $R^{3b}$ are joined to form an oxo (=O) group; each of $R^{4a}$ and $R^{4b}$ is independently selected from hydrogen or halogen; $R^5$ is hydrogen, unsubstituted $C_{1-6}$ alkyl, or —CH$_2$O$R^{A5}$, wherein $R^{A5}$ is hydrogen, substituted or unsubstituted $C_{1-6}$ alkyl, substituted or unsubstituted $C_{2-6}$ alkenyl, substituted or unsubstituted $C_{2-6}$ alkynyl, or substituted or unsubstituted $C_{3-6}$ carbocyclyl, substituted or unsubstituted aryl, substituted or unsubstituted heteroaryl; $R^6$ is absent or hydrogen; an ----- represents a single or double bond, wherein when one of ---- is a double bond, the other ---- is a single bond; and when one of the ---- is a double bond, R⁶ is absent.

In one aspect, provided is a method for treating epilepsy or status or status epilepticus in a subject, the method comprising administering to the subject an effective amount of a compound of the Formula (II):

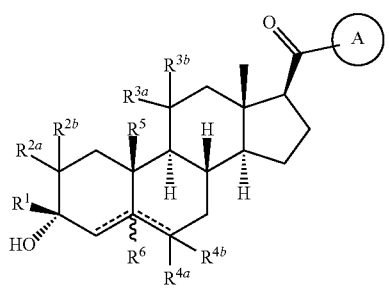

(II)

or a pharmaceutically acceptable salt thereof; wherein: Ring A is substituted or unsubstituted aryl or heteroaryl; $R^1$ is hydrogen, or substituted or unsubstituted $C_{1-6}$ alkyl, substituted or unsubstituted $C_{2-6}$ alkenyl, substituted or unsubstituted $C_{2-6}$ alkynyl, or substituted or unsubstituted $C_{3-6}$ carbocyclyl; each of $R^{2a}$ and $R^{2b}$ is independently selected from hydrogen, halogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{3-6}$ carbocyclyl, substituted or unsubstituted aryl, substituted or unsubstituted heteroaryl, —N($R^A$)($R^B$), or —O$R^{A2}$, wherein each of $R^A$ and $R^B$ is independently hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{3-6}$ carbocyclyl, substituted or unsubstituted heterocyclyl, substituted or unsubstituted aryl, or substituted or unsubstituted heteroaryl, or $R^A$ and $R^B$, together with the nitrogen atom to which they are attached form a ring (e.g., heteroaryl, heterocyclyl), or $R^{2a}$ and $R^{2b}$, together with the carbon atom to which they are attached form a ring; $R^{A2}$ is hydrogen or substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{3-6}$ carbocyclyl, substituted or unsubstituted aryl, or substituted or unsubstituted heteroaryl; $R^{3a}$ is hydrogen, —N($R^A$)($R^B$), or —O$R^{A3}$, wherein $R^{A3}$ is hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{3-6}$ carbocyclyl, substituted or unsubstituted aryl, substituted or unsubstituted heteroaryl, and $R^{3b}$ is hydrogen or —N($R^A$)C(O)$R^{A3}$; or $R^{3a}$ and $R^{3b}$ are joined to form an oxo (=O) group; each of $R^{4a}$ and $R^{4b}$ is independently selected from hydrogen or halogen; $R^5$ is hydrogen, unsubstituted $C_{1-6}$ alkyl, or —CH$_2$O$R^{A5}$, wherein $R^{A5}$ is hydrogen, substituted or unsubstituted $C_{1-6}$ alkyl, substituted or unsubstituted $C_{2-6}$ alkenyl, substituted or unsubstituted $C_{2-6}$ alkynyl, or substituted or unsubstituted $C_{3-6}$ carbocyclyl, substituted or unsubstituted aryl, substituted or unsubstituted heteroaryl; $R^6$ is absent or hydrogen; and ---- represents a single or double bond, wherein when one of ---- is a double bond, the other ---- is a single bond; and when one of the ---- is a double bond, R⁶ is absent.

In one aspect, provided is a method for treating disorders related to GABA function in a subject in need thereof, the method comprising administering to the subject a therapeutically effective amount of a compound, a pharmaceutically acceptable salt thereof, or pharmaceutical composition of one of a compound of Formula (II):

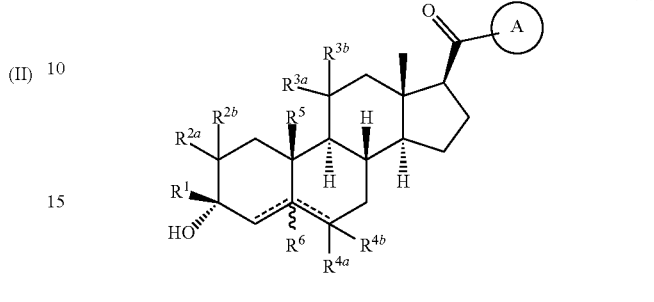

(II)

or a pharmaceutically acceptable salt thereof; wherein: Ring A is substituted or unsubstituted aryl or heteroaryl; $R^1$ is hydrogen, or substituted or unsubstituted $C_{1-6}$ alkyl, substituted or unsubstituted $C_{2-6}$ alkenyl, substituted or unsubstituted $C_{2-6}$ alkynyl, or substituted or unsubstituted $C_{3-6}$ carbocyclyl; each of $R^{2a}$ and $R^{2b}$ is independently selected from hydrogen, halogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{3-6}$ carbocyclyl, substituted or unsubstituted aryl, substituted or unsubstituted heteroaryl, —N($R^A$)($R^B$), or —O$R^{A2}$, wherein each of $R^A$ and $R^B$ is independently hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{3-6}$ carbocyclyl, substituted or unsubstituted heterocyclyl, substituted or unsubstituted aryl, or substituted or unsubstituted heteroaryl, or $R^A$ and $R^B$, together with the nitrogen atom to which they are attached form a ring (e.g., heteroaryl, heterocyclyl), or $R^{2a}$ and $R^{2b}$, together with the carbon atom to which they are attached form a ring; $R^{A2}$ is hydrogen or substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{3-6}$ carbocyclyl, substituted or unsubstituted aryl, or substituted or unsubstituted heteroaryl; $R^{3a}$ is hydrogen, —N($R^A$)($R^B$), or —O$R^{A3}$, wherein $R^{A3}$ is hydrogen, substituted or unsubstituted $C_{1-6}$ alkyl, substituted or unsubstituted $C_{2-6}$ alkenyl, substituted or unsubstituted $C_{2-6}$ alkynyl, or substituted or unsubstituted $C_{3-6}$ carbocyclyl, substituted or unsubstituted aryl, substituted or unsubstituted heteroaryl, and $R^{3b}$ is hydrogen or —N($R^A$)C(O)$R^{A3}$; or $R^{3a}$ and $R^{3b}$ are joined to form an oxo (=O) group; each of $R^{4a}$ and $R^{4b}$ is independently selected from hydrogen or halogen; $R^5$ is hydrogen, unsubstituted $C_{1-6}$ alkyl, or —CH$_2$O$R^{A5}$, wherein $R^{A5}$ is hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{3-6}$ carbocyclyl, substituted or unsubstituted aryl, substituted or unsubstituted heteroaryl; $R^6$ is absent or hydrogen; and ---- represents a single or double bond, wherein when one of ---- is a double bond, the other ---- is a single bond; and when one of the ---- is a double bond, R⁶ is absent.

In one aspect, provided is a method for treating a CNS-related disorder in a subject in need thereof, comprising administering to the subject an effective amount of a compound of Formula (I), or a pharmaceutically acceptable salt thereof.

In some embodiments, the CNS-related disorder is a sleep disorder, a mood disorder, a schizophrenia spectrum disorder, a convulsive disorder, a disorder of memory and/or cognition, a movement disorder, a personality disorder, autism spectrum disorder, pain, traumatic brain injury, a vascular disease, a substance abuse disorder and/or withdrawal syndrome, or tinnitus.

In some embodiments, the disorder is tremor (e.g., essential tremor).

In some embodiments, the disorder is depression (e.g., postpartum depression).

In some embodiments, the compound is administered orally. In some embodiments, the compound is administered parenterally. In some embodiments, the compound is administered intravaneously. In some embodiments, the compound is administered intramuscularly.

In some embodiments, the subject is a subject with Rett syndrome, Fragile X syndrome, or Angelman syndrome.

In one aspect, provided is a method for treating a subject having an injury resulting from exposure to a warfare agent (e.g., a chemical warfare agent), the method comprising administering to the subject a compound described herein (e.g., a GABA modulator such as a compound (e.g., neuroactive steroid) described herein).

In one aspect, provided is a method of treating an injury in a subject who has been exposed to a chemical warfare agent, the method comprising administering to the subject a compound described herein (e.g., GABA modulator such as a compound (e.g., neuroactive steroid) described herein).

In one aspect, provided is a method of treating a subject, the method comprising: identifying a subject that has been exposed to a chemical warfare agent such as a nerve agent or toxin; and administering to the subject a compound described herein (e.g., GABA modulator such as a neuroactive steroid described herein).

In some embodiments, the injury is a seizure. In some embodiments, the injury is a myoclonic seizure (e.g., sporadic jerks).

In some embodiments, the injury is status epilepticus.

In some embodiments, the administration is within 1 week; 6, 5, 4, 3, 2, 1 day; 24, 22, 20, 18, 16, 14, 12, 10, 8, 7, 6, 5, 4, 3, 2, 1 hour, 45, 30, 20, 10, or 5 minutes of exposure to the chemical warfare agent.

In some embodiments, the compound is administered parenterally. In some embodiments, the compound is administered by intravenous administration.

In some embodiments, the subject is a human.

In some embodiments, the chemical warfare agent is a nerve agent or toxin. In some embodiments, the chemical warfare agent is a nerve agent. In some embodiments, the nerve agent is a phosphorus-containing organic chemical. In some embodiments, the nerve agent is a G agent (e.g., tabun (GA), sarin (GB), soman (GD), cyclosarin (GF), and GV). In some embodiments, the nerve agent is a V agent (e.g., VE, VG, VM, VX, and Novichok agents). In some embodiments, the toxin is abrin, ricin, or saxitoxin.

In one aspect, provided is a kit comprising a solid composition comprising a compound of Formula (II):

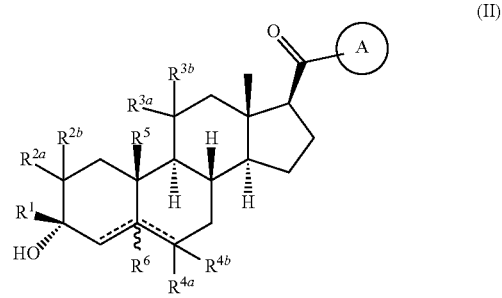

or a pharmaceutically acceptable salt thereof; wherein: Ring A is substituted or unsubstituted aryl or heteroaryl; $R^1$ is hydrogen, or substituted or unsubstituted $C_{1-6}$ alkyl, substituted or unsubstituted $C_{2-6}$ alkenyl, substituted or unsubstituted $C_{2-6}$ alkynyl, or substituted or unsubstituted $C_{3-6}$ carbocyclyl; each of $R^{2a}$ and $R^{2b}$ is independently selected from hydrogen, halogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{3-6}$ carbocyclyl, substituted or unsubstituted aryl, substituted or unsubstituted heteroaryl, —N($R^A$)($R^B$), or —O$R^{42}$, wherein each of $R^A$ and $R^B$ is independently hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{3-6}$ carbocyclyl, substituted or unsubstituted heterocyclyl, substituted or unsubstituted aryl, or substituted or unsubstituted heteroaryl, or $R^A$ and $R^B$, together with the nitrogen atom to which they are attached form a ring (e.g., heteroaryl, heterocyclyl), or $R^{2a}$ and $R^{2b}$, together with the carbon atom to which they are attached form a ring; $R^{42}$ is hydrogen or substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{3-6}$ carbocyclyl, substituted or unsubstituted aryl, or substituted or unsubstituted heteroaryl; $R^{3a}$ is hydrogen, —N($R^A$)($R^B$), or —O$R^{43}$, wherein $R^{43}$ is hydrogen, substituted or unsubstituted $C_{1-6}$ alkyl, substituted or unsubstituted $C_{2-6}$ alkenyl, substituted or unsubstituted $C_{2-6}$ alkynyl, or substituted or unsubstituted $C_{3-6}$ carbocyclyl, substituted or unsubstituted aryl, substituted or unsubstituted heteroaryl, and $R^{3b}$ is hydrogen or —N($R^A$)C(O)$R^{43}$; or $R^{3a}$ and $R^{3b}$ are joined to form an oxo (=O) group; each of $R^{4a}$ and $R^{4b}$ is independently selected from hydrogen or halogen; $R^5$ is hydrogen, unsubstituted $C_{1-6}$ alkyl, or —CH$_2$O$R^{45}$, wherein $R^{45}$ is hydrogen, substituted or unsubstituted $C_{1-6}$ alkyl, substituted or unsubstituted $C_{2-6}$ alkenyl, substituted or unsubstituted $C_{2-6}$ alkynyl, or substituted or unsubstituted $C_{3-6}$ carbocyclyl, substituted or unsubstituted aryl, substituted or unsubstituted heteroaryl; $R^6$ is absent or hydrogen; and ----- represents a single or double bond, wherein when one of ----- is a double bond, the other ----- is a single bond; and when one of the ----- is a double bond, $R^6$ is absent.

Pharmaceutical Compositions

In one aspect, the invention provides a pharmaceutical composition comprising a compound of the present invention (also referred to as the "active ingredient") and a pharmaceutically acceptable excipient. In certain embodiments, the pharmaceutical composition comprises an effective amount of the active ingredient. In certain embodiments, the pharmaceutical composition comprises a therapeutically effective amount of the active ingredient. In certain embodiments, the pharmaceutical composition comprises a prophylactically effective amount of the active ingredient.

The pharmaceutical compositions provided herein can be administered by a variety of routes including, but not limited to, oral (enteral) administration, parenteral (by injection) administration, rectal administration, transdermal administration, intradermal administration, intrathecal administration, subcutaneous (SC) administration, intravenous (IV) administration, intramuscular (IM) administration, and intranasal administration.

Generally, the compounds provided herein are administered in an effective amount. The amount of the compound actually administered will typically be determined by a physician, in the light of the relevant circumstances, including the condition to be treated, the chosen route of administration, the actual compound administered, the age, weight, and response of the individual patient, the severity of the patient's symptoms, and the like.

When used to prevent the onset of a CNS-disorder, the compounds provided herein will be administered to a subject at risk for developing the condition, typically on the advice and under the supervision of a physician, at the dosage levels described above. Subjects at risk for developing a particular condition generally include those that have a family history of the condition, or those who have been identified by genetic testing or screening to be particularly susceptible to developing the condition.

The pharmaceutical compositions provided herein can also be administered chronically ("chronic administration"). Chronic administration refers to administration of a compound or pharmaceutical composition thereof over an extended period of time, e.g., for example, over 3 months, 6 months, 1 year, 2 years, 3 years, 5 years, etc, or may be continued indefinitely, for example, for the rest of the subject's life. In certain embodiments, the chronic administration is intended to provide a constant level of the compound in the blood, e.g., within the therapeutic window over the extended period of time.

The pharmaceutical compostions of the present invention may be further delivered using a variety of dosing methods. For example, in certain embodiments, the pharmaceutical composition may be given as a bolus, e.g., in order to raise the concentration of the compound in the blood to an effective level. The placement of the bolus dose depends on the systemic levels of the active ingredient desired throughout the body, e.g., an intramuscular or subcutaneous bolus dose allows a slow release of the active ingredient, while a bolus delivered directly to the veins (e.g., through an IV drip) allows a much faster delivery which quickly raises the concentration of the active ingredient in the blood to an effective level. In other embodiments, the pharmaceutical composition may be administered as a continuous infusion, e.g., by IV drip, to provide maintenance of a steady-state concentration of the active ingredient in the subject's body. Furthermore, in still yet other embodiments, the pharmaceutical composition may be administered as first as a bolus dose, followed by continuous infusion.

The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampules or syringes of the liquid compositions or pills, tablets, capsules or the like in the case of solid compositions. In such compositions, the compound is usually a minor component (from about 0.1 to about 50% by weight or preferably from about 1 to about 40% by weight) with the remainder being various vehicles or excipients and processing aids helpful for forming the desired dosing form.

With oral dosing, one to five and especially two to four and typically three oral doses per day are representative regimens. Using these dosing patterns, each dose provides from about 0.01 to about 20 mg/kg of the compound provided herein, with preferred doses each providing from about 0.1 to about 10 mg/kg, and especially about 1 to about 5 mg/kg.

Transdermal doses are generally selected to provide similar or lower blood levels than are achieved using injection doses, generally in an amount ranging from about 0.01 to about 20% by weight, preferably from about 0.1 to about 20% by weight, preferably from about 0.1 to about 10% by weight, and more preferably from about 0.5 to about 15% by weight.

Injection dose levels range from about 0.1 mg/kg/hour to at least 20 mg/kg/hour, all for from about 1 to about 120 hours and especially 24 to 96 hours. A preloading bolus of from about 0.1 mg/kg to about 10 mg/kg or more may also be administered to achieve adequate steady state levels. The maximum total dose is not expected to exceed about 5 g/day for a 40 to 80 kg human patient.

Liquid forms suitable for oral administration may include a suitable aqueous or nonaqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Injectable compositions are typically based upon injectable sterile saline or phosphate-buffered saline or other injectable excipients known in the art. As before, the active compound in such compositions is typically a minor component, often being from about 0.05 to 10% by weight with the remainder being the injectable excipient and the like.

Transdermal compositions are typically formulated as a topical ointment or cream containing the active ingredient(s). When formulated as a ointment, the active ingredients will typically be combined with either a paraffinic or a water-miscible ointment base. Alternatively, the active ingredients may be formulated in a cream with, for example an oil-in-water cream base. Such transdermal formulations are well-known in the art and generally include additional ingredients to enhance the dermal penetration of stability of the active ingredients or Formulation. All such known transdermal formulations and ingredients are included within the scope provided herein.

The compounds provided herein can also be administered by a transdermal device. Accordingly, transdermal administration can be accomplished using a patch either of the reservoir or porous membrane type, or of a solid matrix variety.

The above-described components for orally administrable, injectable or topically administrable compositions are merely representative. Other materials as well as processing techniques and the like are set forth in Part 8 of *Remington's Pharmaceutical Sciences,* 17th edition, 1985, Mack Publishing Company, Easton, Pa., which is incorporated herein by reference.

The compounds of the present invention can also be administered in sustained release forms or from sustained release drug delivery systems. A description of representative sustained release materials can be found in *Remington's Pharmaceutical Sciences.*

The present invention also relates to the pharmaceutically acceptable acid addition salt of a compound of the present invention. The acid which may be used to prepare the pharmaceutically acceptable salt is that which forms a non-toxic acid addition salt, i.e., a salt containing pharmacologically acceptable anions such as the hydrochloride, hydroiodide, hydrobromide, nitrate, sulfate, bisulfate, phosphate, acetate, lactate, citrate, tartrate, succinate, maleate, fumarate, benzoate, para-toluenesulfonate, and the like.

In another aspect, the invention provides a pharmaceutical composition comprising a compound of the present invention and a pharmaceutically acceptable excipient, e.g., a composition suitable for injection, such as for intravenous (IV) administration.

Pharmaceutically acceptable excipients include any and all diluents or other liquid vehicles, dispersion or suspension aids, surface active agents, isotonic agents, preservatives, lubricants and the like, as suited to the particular dosage form desired, e.g., injection. General considerations in the formulation and/or manufacture of pharmaceutical compositions agents can be found, for example, in *Remington's Pharmaceutical Sciences*, Sixteenth Edition, E. W. Martin (Mack Publishing Co., Easton, Pa., 1980), and *Remington: The Science and Practice of Pharmacy,* $21^{st}$ Edition (Lippincott Williams & Wilkins, 2005).

For example, injectable preparations, such as sterile injectable aqueous suspensions, can be formulated according to the known art using suitable dispersing or wetting agents and suspending agents. Exemplary excipients that can be employed include, but are not limited to, water, sterile saline or phosphate-buffered saline, or Ringer's solution.

In certain embodiments, the pharmaceutical composition further comprises a cyclodextrin derivative. The most common cyclodextrins are α-, β- and γ-cyclodextrins consisting of 6, 7 and 8 α-1,4-linked glucose units, respectively, optionally comprising one or more substituents on the linked sugar moieties, which include, but are not limited to, substituted or unsubstituted methylated, hydroxyalkylated, acylated, and sulfoalkylether substitution. In certain embodiments, the cyclodextrin is a sulfoalkyl ether β-cyclodextrin, e.g., for example, sulfobutyl ether β-cyclodextrin, also known as Captisol®. See, e.g., U.S. Pat. No. 5,376,645. In certain embodiments, the composition comprises hexapropyl-β-cyclodextrin. In a more particular embodiment, the composition comprises hexapropyl-β-cyclodextrin (10-50% in water).

The injectable composition can be sterilized, for example, by filtration through a bacterial-retaining filter, or by incorporating sterilizing agents in the form of sterile solid compositions which can be dissolved or dispersed in sterile water or other sterile injectable medium prior to use.

Generally, the compounds provided herein are administered in an effective amount. The amount of the compound actually administered will typically be determined by a physician, in the light of the relevant circumstances, including the condition to be treated, the chosen route of administration, the actual compound administered, the age, weight, response of the individual patient, the severity of the patient's symptoms, and the like.

The compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include pre-filled, pre-measured ampules or syringes of the liquid compositions. In such compositions, the compound is usually a minor component (from about 0.1% to about 50% by weight or preferably from about 1% to about 40% by weight) with the remainder being various vehicles or carriers and processing aids helpful for forming the desired dosing form.

The compounds provided herein can be administered as the sole active agent, or they can be administered in combination with other active agents. In one aspect, the present invention provides a combination of a compound of the present invention and another pharmacologically active agent. Administration in combination can proceed by any technique apparent to those of skill in the art including, for example, separate, sequential, concurrent, and alternating administration.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation. General considerations in the formulation and/or manufacture of pharmaceutical compositions can be found, for example, in *Remington: The Science and Practice of Pharmacy* $21^{st}$ ed., Lippincott Williams & Wilkins, 2005.

Methods of Use and Treatment

As generally described herein, the present invention is directed to C21-substituted neuroactive steroids designed, for example, to act as GABA modulators. In certain embodiments, such compounds are envisioned to be useful as therapeutic agents for the inducement of anesthesia and/or sedation in a subject. In some embodiments, such compounds are envisioned to be useful as therapeutic agents for treating a CNS-related disorder (e.g., sleep disorder, a mood disorder, a schizophrenia spectrum disorder, a convulsive disorder, a disorder of memory and/or cognition, a movement disorder, a personality disorder, autism spectrum disorder, pain, traumatic brain injury, a vascular disease, a substance abuse disorder and/or withdrawal syndrome, or tinnitus) in a subject in need (e.g., a subject with Rett syndrome, Fragile X syndrome, or Angelman syndrome).

Thus, in one aspect, the present invention provides a method of inducing sedation and/or anesthesia in a subject, comprising administering to the subject an effective amount of a compound of the present invention or a composition thereof. In certain embodiments, the compound is administered by intravenous administration.

Earlier studies (see, e.g., Gee er al., *European Journal of Pharmacology,* 136:419-423 (1987)) demonstrated that certain 3α-hydroxylated steroids are orders of magnitude more potent as modulators of the GABA receptor complex (GRC) than others had reported (see, e.g., Majewska et al., *Science*

232:1004-1007 (1986); Harrison et al., *J Pharmacol. Exp. Ther.* 241:346-353 (1987)). Majewska et al. and Harrison et al. taught that 3α-hydroxylated-5-reduced steroids are only capable of much lower levels of effectiveness. In vitro and in vivo experimental data have now demonstrated that the high potency of these steroids allows them to be therapeutically useful in the modulation of brain excitability via the GRC (see, e.g., Gee et al., *European Journal of Pharmacology*, 136:419-423 (1987); Wieland et al., *Psychopharmacology* 118(1):65-71 (1995)).

Various synthetic steroids have also been prepared as neuroactive steroids. See, for example, U.S. Pat. No. 5,232,917, which discloses neuroactive steroid compounds useful in treating stress, anxiety, insomnia, seizure disorders, and mood disorders, that are amenable to GRC-active agents, such as depression, in a therapeutically beneficial manner. Furthermore, it has been previously demonstrated that these steroids interact at a unique site on the GRC which is distinct from other known sites of interaction (e.g., barbiturates, benzodiazepines, and GABA) where therapeutically beneficial effects on stress, anxiety, sleep, mood disorders and seizure disorders have been previously elicited (see, e.g., Gee, K. W. and Yamamura, H. I., "Benzodiazepines and Barbiturates: Drugs for the Treatment of Anxiety, Insomnia and Seizure Disorders," in *Central Nervous System Disorders*, Horvell, ed., Marcel-Dekker, New York (1985), pp. 123-147; Lloyd, K. G. and Morselli, P. L., "Psychopharmacology of GABAergic Drugs," in *Psychopharmacology: The Third Generation of Progress*, H. Y. Meltzer, ed., Raven Press, N.Y. (1987), pp. 183-195; and Gee et al., *European Journal of Pharmacology*, 136:419-423 (1987). These compounds are desirable for their duration, potency, and oral activity (along with other forms of administration).

Compounds of the present invention, as described herein, are generally designed to modulate GABA function, and therefore to act as neuroactive steroids for the treatment and prevention of CNS-related conditions in a subject. Modulation, as used herein, refers to the inhibition or potentiation of GABA receptor function. Accordingly, the compounds and pharmaceutical compositions provided herein find use as therapeutics for preventing and/or treating CNS conditions in mammals including humans and non-human mammals. Thus, and as stated earlier, the present invention includes within its scope, and extends to, the recited methods of treatment, as well as to the compounds for such methods, and to the use of such compounds for the preparation of medicaments useful for such methods.

Exemplary CNS conditions related to GABA-modulation include, but are not limited to, sleep disorders [e.g., insomnia], mood disorders [e.g., depression, dysthymic disorder (e.g., mild depression), bipolar disorder (e.g., I and/or II), anxiety disorders (e.g., generalized anxiety disorder (GAD), social anxiety disorder), stress, post-traumatic stress disorder (PTSD), compulsive disorders (e.g., obsessive compulsive disorder (OCD))], schizophrenia spectrum disorders [e.g., schizophrenia, schizoaffective disorder], convulsive disorders [e.g., epilepsy (e.g., status epilepticus (SE)), seizures], disorders of memory and/or cognition [e.g., attention disorders (e.g., attention deficit hyperactivity disorder (ADHD)), dementia (e.g., Alzheimer's type dementia, Lewis body type dementia, vascular type dementia], movement disorders [e.g., Huntington's disease, Parkinson's disease], personality disorders [e.g., anti-social personality disorder, obsessive compulsive personality disorder], autism spectrum disorders (ASD) [e.g., autism, monogenetic causes of autism such as synaptophathy's, e.g., Rett syndrome, Fragile X syndrome, Angelman syndrome], pain [e.g., neuropathic pain, injury related pain syndromes, acute pain, chronic pain], traumatic brain injury (TBI), vascular diseases [e.g., stroke, ischemia, vascular malformations], substance abuse disorders and/or withdrawal syndromes [e.g., addition to opiates, cocaine, and/or alcohol], and tinnitus.

In yet another aspect, provided is a combination of a compound of the present invention and another pharmacologically active agent. The compounds provided herein can be administered as the sole active agent or they can be administered in combination with other agents. Administration in combination can proceed by any technique apparent to those of skill in the art including, for example, separate, sequential, concurrent and alternating administration.

In another aspect, provided is a method of treating or preventing brain excitability in a subject susceptible to or afflicted with a condition associated with brain excitability, comprising administering to the subject an effective amount of a compound of the present invention to the subject.

In yet another aspect, provided is a method of treating or preventing stress or anxiety in a subject, comprising administering to the subject in need of such treatment an effective amount of a compound of the present invention, or a composition thereof.

In yet another aspect, provided is a method of alleviating or preventing seizure activity in a subject, comprising administering to the subject in need of such treatment an effective amount of a compound of the present invention.

In yet another aspect, provided is a method of alleviating or preventing insomnia in a subject, comprising administering to the subject in need of such treatment an effective amount of a compound of the present invention, or a composition thereof.

In yet another aspect, provided is a method of inducing sleep and maintaining substantially the level of REM sleep that is found in normal sleep, wherein substantial rebound insomnia is not induced, comprising administering an effective amount of a compound of the present invention.

In yet another aspect, provided is a method of alleviating or preventing PMS or PND in a subject, comprising administering to the subject in need of such treatment an effective amount of a compound of the present invention.

In yet another aspect, provided is a method of treating or preventing mood disorders in a subject, comprising administering to the subject in need of such treatment an effective amount of a compound of the present invention. In certain embodiments the mood disorder is depression.

In yet another aspect, provided is a method of inducing anesthesia in a subject, comprising administering to the subject an effective amount of a compound of the present invention.

In yet another aspect, provided is a method of cognition enhancement or treating memory disorder by administering to the subject a therapeutically effective amount of a compound of the present invention. In certain embodiments, the disorder is Alzheimer's disease. In certain embodiments, the disorder is Rett syndrome.

In yet another aspect, provided is a method of treating attention disorders by administering to the subject a therapeutically effective amount of a compound of the present invention. In certain embodiments, the attention disorder is ADHD.

In certain embodiments, the compound is administered to the subject chronically. In certain embodiments, the compound is administered to the subject orally, subcutaneously, intramuscularly, or intravenously.

Anesthesia/Sedation

Anesthesia is a pharmacologically induced and reversible state of amnesia, analgesia, loss of responsiveness, loss of skeletal muscle reflexes, decreased stress response, or all of these simultaneously. These effects can be obtained from a single drug which alone provides the correct combination of effects, or occasionally with a combination of drugs (e.g., hypnotics, sedatives, paralytics, analgesics) to achieve very specific combinations of results. Anesthesia allows patients to undergo surgery and other procedures without the distress and pain they would otherwise experience.

Sedation is the reduction of irritability or agitation by administration of a pharmacological agent, generally to facilitate a medical procedure or diagnostic procedure.

Sedation and analgesia include a continuum of states of consciousness ranging from minimal sedation (anxiolysis) to general anesthesia.

Minimal sedation is also known as anxiolysis. Minimal sedation is a drug-induced state during which the patient responds normally to verbal commands. Cognitive function and coordination may be impaired Ventilatory and cardiovascular functions are typically unaffected.

Moderate sedation/analgesia (conscious sedation) is a drug-induced depression of consciousness during which the patient responds purposefully to verbal command, either alone or accompanied by light tactile stimulation. No interventions are usually necessary to maintain a patent airway. Spontaneous ventilation is typically adequate. Cardiovascular function is usually maintained.

Deep sedation/analgesia is a drug-induced depression of consciousness during which the patient cannot be easily aroused, but responds purposefully (not a reflex withdrawal from a painful stimulus) following repeated or painful stimulation. Independent ventilatory function may be impaired and the patient may require assistance to maintain a patent airway. Spontaneous ventilation may be inadequate. Cardiovascular function is usually maintained.

General anesthesia is a drug-induced loss of consciousness during which the patient is not arousable, even to painful stimuli. The ability to maintain independent ventilatory function is often impaired and assistance is often required to maintain a patent airway. Positive pressure ventilation may be required due to depressed spontaneous ventilation or drug-induced depression of neuromuscular function. Cardiovascular function may be impaired.

Sedation in the intensive care unit (ICU) allows the depression of patients' awareness of the environment and reduction of their response to external stimulation. It can play a role in the care of the critically ill patient, and encompasses a wide spectrum of symptom control that will vary between patients, and among individuals throughout the course of their illnesses. Heavy sedation in critical care has been used to facilitate endotracheal tube tolerance and ventilator synchronization, often with neuromuscular blocking agents.

In some embodiments, sedation (e.g., long-term sedation, continuous sedation) is induced and maintained in the ICU for a prolonged period of time (e.g., 1 day, 2 days, 3 days, 5 days, 1 week, 2 week, 3 weeks, 1 month, 2 months). Long-term sedation agents may have long duration of action. Sedation agents in the ICU may have short elimination half-life.

Procedural sedation and analgesia, also referred to as conscious sedation, is a technique of administering sedatives or dissociative agents with or without analgesics to induce a state that allows a subject to tolerate unpleasant procedures while maintaining cardiorespiratory function.

Anxiety Disorders

Anxiety disorder is a blanket term covering several different forms of abnormal and pathological fear and anxiety. Current psychiatric diagnostic criteria recognize a wide variety of anxiety disorders.

Generalized anxiety disorder is a common chronic disorder characterized by long-lasting anxiety that is not focused on any one object or situation. Those suffering from generalized anxiety experience non-specific persistent fear and worry and become overly concerned with everyday matters. Generalized anxiety disorder is the most common anxiety disorder to affect older adults.

In panic disorder, a person suffers from brief attacks of intense terror and apprehension, often marked by trembling, shaking, confusion, dizziness, nausea, difficulty breathing. These panic attacks, defined by the APA as fear or discomfort that abruptly arises and peaks in less than ten minutes, can last for several hours and can be triggered by stress, fear, or even exercise; although the specific cause is not always apparent. In addition to recurrent unexpected panic attacks, a diagnosis of panic disorder also requires that said attacks have chronic consequences: either worry over the attacks' potential implications, persistent fear of future attacks, or significant changes in behavior related to the attacks. Accordingly, those suffering from panic disorder experience symptoms even outside of specific panic episodes. Often, normal changes in heartbeat are noticed by a panic sufferer, leading them to think something is wrong with their heart or they are about to have another panic attack. In some cases, a heightened awareness (hypervigilance) of body functioning occurs during panic attacks, wherein any perceived physiological change is interpreted as a possible life threatening illness (i.e. extreme hypochondriasis).

Obsessive compulsive disorder is a type of anxiety disorder primarily characterized by repetitive obsessions (distressing, persistent, and intrusive thoughts or images) and compulsions (urges to perform specific acts or rituals). The OCD thought pattern may be likened to superstitions insofar as it involves a belief in a causative relationship where, in reality, one does not exist. Often the process is entirely illogical; for example, the compulsion of walking in a certain pattern may be employed to alleviate the obsession of impending harm. And in many cases, the compulsion is entirely inexplicable, simply an urge to complete a ritual triggered by nervousness. In a minority of cases, sufferers of OCD may only experience obsessions, with no overt compulsions, a much smaller number of sufferers experience only compulsions.

The single largest category of anxiety disorders is that of Phobia, which includes all cases in which fear and anxiety is triggered by a specific stimulus or situation. Sufferers typically anticipate terrifying consequences from encountering the object of their fear, which can be anything from an animal to a location to a bodily fluid.

Post-traumatic stress disorder or PTSD is an anxiety disorder which results from a traumatic experience. Post-traumatic stress can result from an extreme situation, such as combat, rape, hostage situations, or even serious accident. It can also result from long term (chronic) exposure to a severe stressor, for example soldiers who endure individual battles but cannot cope with continuous combat. Common symptoms include flashbacks, avoidant behaviors, and depression.

Neurodegenerative Diseases and Disorders

The term "neurodegenerative disease" includes diseases and disorders that are associated with the progressive loss of structure or function of neurons, or death of neurons. Neurodegenerative diseases and disorders include, but are not limited to, Alzheimer's disease (including the associated symptoms of mild, moderate, or severe cognitive impairment); amyotrophic lateral sclerosis (ALS); anoxic and ischemic injuries; ataxia and convulsion (including for the treatment and prevention and prevention of seizures that are caused by schizoaffective disorder or by drugs used to treat schizophrenia); benign forgetfulness; brain edema; cerebellar ataxia including McLeod neuroacanthocytosis syndrome (MLS); closed head injury; coma; contusive injuries (e.g., spinal cord injury and head injury); dementias including multi-infarct dementia and senile dementia; disturbances of consciousness; Down syndrome; drug-induced or medication-induced Parkinsonism (such as neuroleptic-induced acute akathisia, acute dystonia, Parkinsonism, or tardive dyskinesia, neuroleptic malignant syndrome, or medication-induced postural tremor): epilepsy; fragile X syndrome; Gilles de la Tourette's syndrome; head trauma; hearing impairment and loss; Huntington's disease: Lennox syndrome; levodopa-induced dyskinesia; mental retardation; movement disorders including akinesias and akinetic (rigid) syndromes (including basal ganglia calcification, corticobasal degeneration, multiple system atrophy, Parkinsonism-ALS dementia complex, Parkinson's disease, postencephalitic parkinsonism, and progressively supranuclear palsy); muscular spasms and disorders associated with muscular spasticity or weakness including chorea (such as benign hereditary chorea, drug-induced chorea, hemiballism, Huntington's disease, neuroacanthocytosis, Sydenham's chorea, and symptomatic chorea), dyskinesia (including tics such as complex tics, simple tics, and symptomatic tics), myoclonus (including generalized myoclonus and focal cyloclonus), tremor (such as rest tremor, postural tremor, and intention tremor) and dystonia (including axial dystonia, dystonic writer's cramp, hemiplegic dystonia, paroxysmal dystonia, and focal dystonia such as blepharospasm, oromandibular dystonia, and spasmodic dysphonia and torticollis); neuronal damage including ocular damage, retinopathy or macular degeneration of the eye; neurotoxic injury which follows cerebral stroke, thromboembolic stroke, hemorrhagic stroke, cerebral ischemia, cerebral vasospasm, hypoglycemia, amnesia, hypoxia, anoxia, perinatal asphyxia and cardiac arrest; Parkinson's disease; seizure; status epilecticus; stroke; tinnitus; tubular sclerosis, and viral infection induced neurodegeneration (e.g., caused by acquired immunodeficiency syndrome (AIDS) and encephalopathies). Neurodegenerative diseases also include, but are not limited to, neurotoxic injury which follows cerebral stroke, thromboembolic stroke, hemorrhagic stroke, cerebral ischemia, cerebral vasospasm, hypoglycemia, amnesia, hypoxia, anoxia, perinatal asphyxia and cardiac arrest. Methods of treating or preventing a neurodegenerative disease also include treating or preventing loss of neuronal function characteristic of neurodegenerative disorder.

Epilepsy

Epilepsy is a brain disorder characterized by repeated seizures over time. Types of epilepsy can include, but are not limited to generalized epilepsy, e.g., childhood absence epilepsy, juvenile nyoclonic epilepsy, epilepsy with grand-mal seizures on awakening, West syndrome, Lennox-Gastaut syndrome, partial epilepsy, e.g., temporal lobe epilepsy, frontal lobe epilepsy, benign focal epilepsy of childhood.

Status Epilepticus (SE)

Status epilepticus (SE) can include, e.g., convulsive status epilepticus, e.g., early status epilepticus, established status epilepticus, refractory status epilepticus, super-refractory status epilepticus; non-convulsive status epilepticus, e.g., generalized status epilepticus, complex partial status epilepticus; generalized periodic epileptiform discharges; and periodic lateralized epileptiform discharges. Convulsive status epilepticus is characterized by the presence of convulsive status epileptic seizures, and can include early status epilepticus, established status epilepticus, refractory status epilepticus, super-refractory status epilepticus. Early status epilepticus is treated with a first line therapy Established status epilepticus is characterized by status epileptic seizures which persist despite treatment with a first line therapy, and a second line therapy is administered. Refractory status epilepticus is characterized by status epileptic seizures which persist despite treatment with a first line and a second line therapy, and a general anesthetic is generally administered. Super refractory status epilepticus is characterized by status epileptic seizures which persist despite treatment with a first line therapy, a second line therapy, and a general anesthetic for 24 hours or more.

Non-convulsive status epilepticus can include, e.g., focal non-convulsive status epilepticus, e.g., complex partial non-convulsive status epilepticus, simple partial non-convulsive status epilepticus, subtle non-convulsive status epilepticus; generalized non-convulsive status epilepticus, e.g., late onset absence non-convulsive status epilepticus, atypical absence non-convulsive status epilepticus, or typical absence non-convulsive status epilepticus.

Compositions described herein can also be administered as a prophylactic to a subject having a CNS disorder e.g., a traumatic brain injury, status epilepticus, e.g., convulsive status epilepticus, e.g., early status epilepticus, established status epilepticus, refractory status epilepticus, super-refractory status epilepticus; non-convulsive status epilepticus, e.g., generalized status epilepticus, complex partial status epilepticus; generalized periodic epileptiform discharges; and periodic lateralized epileptiform discharges; prior to the onset of a seizure.

Epileptogenesis

The compounds and methods described herein can be used to treat or prevent epileptogenesis. Epileptogenesis is a gradual process by which a normal brain develops epilepsy (a chronic condition in which seizures occur). Epileptogenesis results from neuronal damage precipitated by the initial insult (e.g., status epilepticus).

Seizure

A seizure is the physical findings or changes in behavior that occur after an episode of abnormal electrical activity in the brain. The term "seizure" is often used interchangeably with "convulsion." Convulsions are when a person's body shakes rapidly and uncontrollably. During convulsions, the person's muscles contract and relax repeatedly.

Based on the type of behavior and brain activity, seizures are divided into two broad categories: generalized and partial (also called local or focal). Classifying the type of seizure helps doctors diagnose whether or not a patient has epilepsy.

Generalized seizures are produced by electrical impulses from throughout the entire brain, whereas partial seizures are produced (at least initially) by electrical impulses in a relatively small part of the brain. The part of the brain generating the seizures is sometimes called the focus.

There are six types of generalized seizures. The most common and dramatic, and therefore the most well known, is the generalized convulsion, also called the grand-mal seizure. In this type of seizure, the patient loses consciousness and usually collapses. The loss of consciousness is followed by generalized body stiffening (called the "tonic"

phase of the seizure) for 30 to 60 seconds, then by violent jerking (the "clonic" phase) for 30 to 60 seconds, after which the patient goes into a deep sleep (the "postictal" or after-seizure phase). During grand-mal seizures, injuries and accidents may occur, such as tongue biting and urinary incontinence.

Absence seizures cause a short loss of consciousness (just a few seconds) with few or no symptoms. The patient, most often a child, typically interrupts an activity and stares blankly. These seizures begin and end abruptly and may occur several times a day. Patients are usually not aware that they are having a seizure, except that they may be aware of "losing time."

Myoclonic seizures consist of sporadic jerks, usually on both sides of the body. Patients sometimes describe the jerks as brief electrical shocks. When violent, these seizures may result in dropping or involuntarily throwing objects.

Clonic seizures are repetitive, rhythmic jerks that involve both sides of the body at the same time.

Tonic seizures are characterized by stiffening of the muscles.

Atonic seizures consist of a sudden and general loss of muscle tone, particularly in the arms and legs, which often results in a fall.

Seizures described herein can include epileptic seizures; acute repetitive seizures; cluster seizures; continuous seizures; unremitting seizures; prolonged seizures; recurrent seizures; status epilepticus seizures, e.g., refractory convulsive status epilepticus, non-convulsive status epilepticus seizures; refractory seizures; myoclonic seizures; tonic seizures; tonic-clonic seizures; simple partial seizures; complex partial seizures; secondarily generalized seizures; atypical absence seizures; absence seizures; atonic seizures; benign Rolandic seizures; febrile seizures; emotional seizures, focal seizures; gelastic seizures; generalized onset seizures; infantile spasms; Jacksonian seizures; massive bilateral myoclonus seizures; multifocal seizures, neonatal onset seizures; nocturnal seizures; occipital lobe seizures; post traumatic seizures; subtle seizures; Sylvan seizures; visual reflex seizures; or withdrawal seizures.

Chemical Warfare Agents

A subject may be exposed to a chemical warfare agent. If a compound described herein is administered, the symptoms or injuries resulting from the exposure to the chemical warfare agents can be reduced, prevented, or both. The compounds described herein can be administered to a subject before, during, or following such exposure and is therefore administered within 1 week; 6, 5, 4, 3, 2, 1 day; 24, 22, 20, 18, 16, 14, 12, 10, 8, 7, 6, 5, 4, 3, 2, 1 hour, 45, 30, 20, 10, or 5 minutes before or after such exposure. The compounds described herein can be administered prophylactically, when exposure to an agent is anticipated. It can also be administered after exposure to the chemical warfare agent (e.g., before or after symptoms of injury present in a subject).

Injuries resulting from the exposure to chemical warfare agents are known in the art and include any physical injuries, such as injuries to the central nervous system and peripheral nervous system. Exemplary symptoms or injuries resulting from the exposure to chemical warfare agents include inflammation, burn, itch, pain, rash, blisters, sweating, muscle twitching, nausea, vomiting, diarrhea, weakness, loss of consciousness, convulsions, muscular twitching, paralysis, secretions (from the mouth, nose, or lung for example), difficulty breathing, blurred vision, eye pain, lacrimation, red eyes, shortness of breath, coughing, phlegm production and narrowing of the airways, headaches, tremors, dizziness, numbness or tingling, anxiety, insomnia, depression, emotional instability, and even death. The term "chemical warfare agent" includes all of those agents classified as schedule 1, 2, and 3 agents under the Chemical Weapons Convention of 1993 and may be in liquid form, gas form, solid form, or combinations thereof. Exemplary agents are described in further detail below and include, for example, nerve agents and toxins.

Nerve Agents. Nerve agent poisoning typically leads to contraction of pupils, profuse salivation, convulsions, involuntary urination and defecation, and eventual death by asphyxiation as control is lost over respiratory muscles. For example, nerve agents can be phosphorus-containing organic chemicals (organophosphates) that disrupt the mechanism by which nerves transfer messages to organs. Exemplary agents include G agents such as tabun (GA), sarin (GB), soman (GD), cyclosarin (GF), and GV; V agents such as VE, VG, VM, VX, and Novichok agents.

Toxins. Exemplary toxins are abrin, ricin, and saxitoxin.

Equivalents and Scope

In the claims articles such as "a." "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

EXAMPLES

In order that the invention described herein may be more fully understood, the following examples are set forth. The synthetic and biological examples described in this application are offered to illustrate the compounds, pharmaceutical compositions and methods provided herein and are not to be construed in any way as limiting their scope.

Materials and Methods

The compounds provided herein can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art. For example, numerous protecting groups, and their introduction and removal, are described in T. W. Greene and P. G. M. Wuts, *Protecting Groups in Organic Synthesis*, Second Edition, Wiley, New York, 1991, and references cited therein.

The compounds provided herein may be isolated and purified by known standard procedures. Such procedures include (but are not limited to) recrystallization, column chromatography, HPLC, or supercritical fluid chromatography (SFC). The following schemes are presented with details as to the preparation of representative heteroaryls and heterocyclyls that have been listed herein. The compounds provided herein may be prepared from known or commercially available starting materials and reagents by one skilled in the art of organic synthesis. Exemplary chiral columns available for use in the separation/purification of the enantiomers/diastereomers provided herein include, but are not limited to, CHIRALPAK® AD-10, CHIRALCEL® OB, CHIRALCEL® OB-H, CHIRALCEL® OD, CHIRALCEL® OD-H, CHIRALCEL® OF, CHIRALCEL® OG, CHIRALCEL® OJ and CHIRALCEL® OK.

The stereochemistry assigned herein (e.g., the assignment of "R" or "S" to the C21 position of the steroid) may be tentatively (e.g., randomly) assigned. For example, a C21 position may be drawn in the "R" configuration when the C21 position is in the "S" configuration.

$^1$H-NMR reported herein (e.g., for intermediates) may be a partial representation of the full NMR spectrum of a compound, e.g., a compound described herein. For example, the reported $^1$H NMR may exclude the region between δ (ppm) of about 1 to about 2.5 ppm.

Exemplary general method for preparative HPLC: Column: Waters RBridge prep 10 μm C18, 19*250 mm. Mobile phase: acetonitrile, water (NH$_4$HCO$_3$) (30 L water, 24 g NH$_4$HCO$_3$, 30 mL NH$_3$.H$_2$O). Flow rate: 25 ml/min Exemplary general method for analytical HPLC: Mobile phase: A: water (10 mM NH$_4$HCO$_3$), B: acetonitrile Gradient: 5%-95% B in 1.6 or 2 min Flow rate: 1.8 or 2 mL/min; Column: XBridge C18, 4.6*50 mm, 3.5 μm at 45 C.

Synthetic Methods

Example 1

Synthesis of Intermediate A10

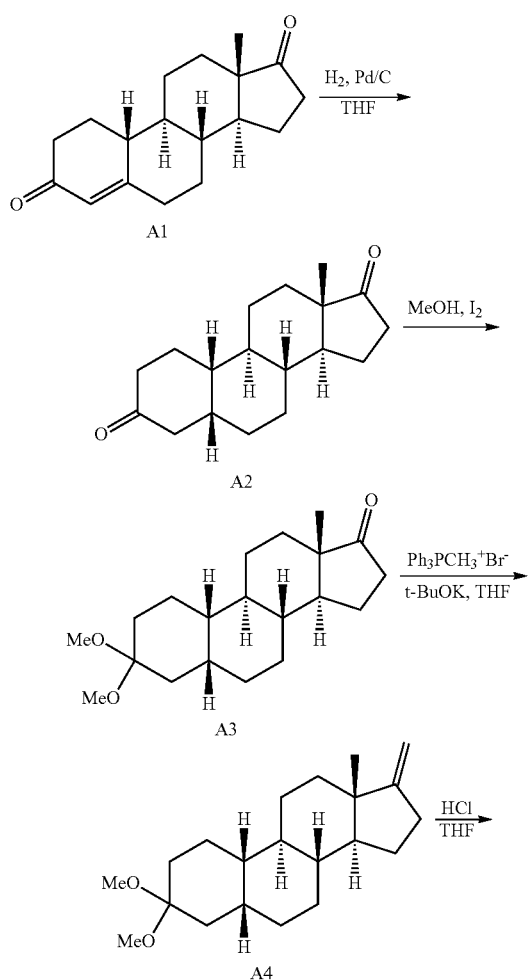

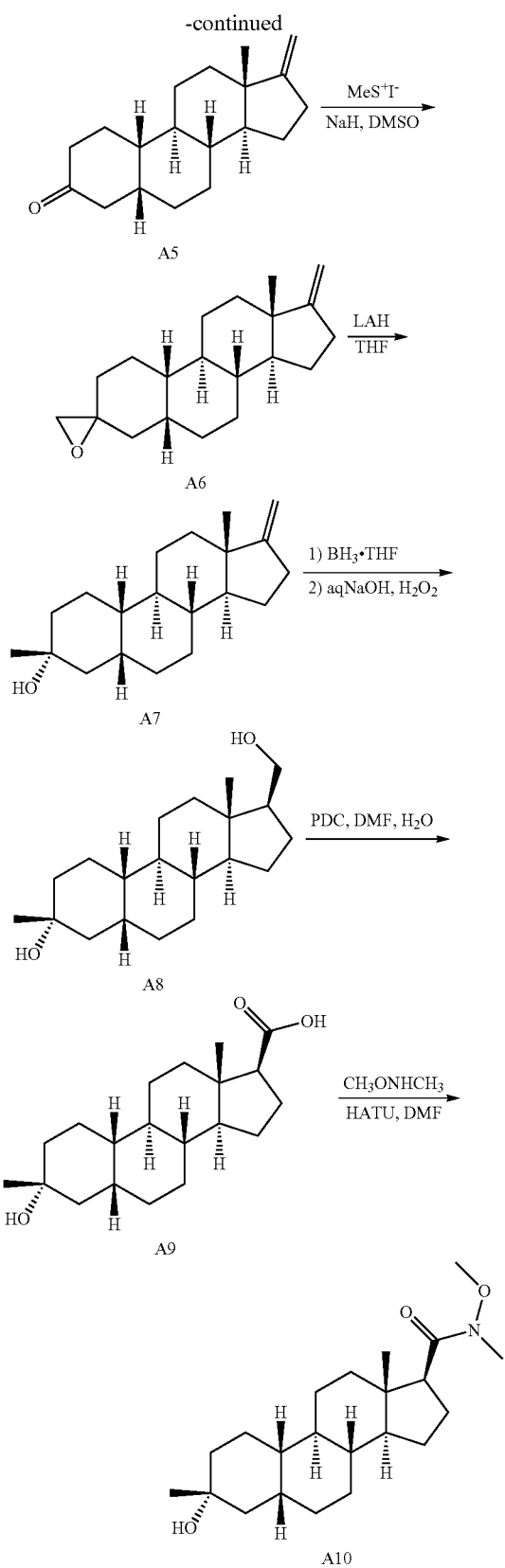

was hydrogenated with a hydrogen balloon at 1 atm. After stirring at room temperature for 24 h, the mixture was filtered through a pad of celite and the filtrate was concentrated in vacuo. Recrystallization from acetone to give compound A2 (367 mg, 1.34 mmol, 73%). $^1$H NMR (400 MHz, CDCl$_3$), δ (ppm), 2.61-2.54 (m, 1H), 2.58 (t, 1H, J=14 Hz), 2.45 (dd, 1H, J=19 Hz, 9 Hz), 0.98 (s, 3H).

Step 2. Synthesis of Compound A3. To a solution of compound A2 (274 mg, 1 mmol) in methanol (4 mL) was added iodine (0.1 mmol). After stirring at 60° C. for 12 h, TLC showed no SM and the solvent was removed in vacuo. The crude product was dissolved in dichloromethane (20 mL) and washed with saturated NaHCO$_3$ (15 mL), brine, dried over Na$_2$SO$_4$, filtered and concentrated. The residue was purified by chromatography on basic alumina (pertroleum ether/ethyl acetate=9:1) to give compound A3 (280 mg, 0.88 mmol, 88%), $^1$H NMR (400 MHz, CDCl3), δ (ppm), 3.19 (s, 3H), 3.13 (s, 3H), 2.43 (dd, 1H, J=19.2 Hz, 8.8 Hz), 0.83 (s, 3H).

Step 3. Synthesis of Compound A4. To a solution of methyltriphenylphosphonium bromide (10.26 g, 28.84 mmol) in 30 mL THF, was added KOt-Bu (3.23 g, 28.80 mmol). The reaction was heated to 60° C. for 1 h. A3 (3.23 g, 9.6 mmol) was added to the mixture, stirred at 60° C. for 15 h. The reaction mixture was extracted 500 ml EtOAc, washed with brine and evaporated in vacuo evaporated then purified by chromatography (PE:EA=3:1) to afford A4 as a solid (2.1 g).

Step 4. Synthesis of Compound A5. To a solution of A4 (1 g, 3.1 mmol) in 20 ml THF, was added 2 mL of 2 M HCl and reaction stirred at rt for 1 h. The reaction mixture was quenched with 5 mL H$_2$O and extracted with 100 mL EtOAc, washed with brine and evaporated in vacuo, then purified by chromatography (PE:EtOAc=10:1) to afford A5 as a solid (710 mg). $^1$H NMR (400 MHz, CDCl$_3$), δ (ppm), 4.65 (s, 1H), 4.63 (s, 1H), 0.82 (s, 3H).

Step 5. Synthesis of Compound A6. To a stirred solution of trimethylsulfonium iodide (6.4 g, 31.5 mmol) in 10 mL of DMSO was added NaH (60%; 800 mg, 31.5 mmol). After stirring at room temperature for 1 h, a suspension of A5 (870 mg, 3.2 mmol) in 5 mL of DMSO was added dropwise. After 15 h, the reaction mixture was poured into ice-cold water and extracted with 300 mL EtOAc, washed with 100 mL brine solution, dried and evaporated in vacuo, then purified by chromatography (PE:EtOAc=10:1) to afford A6 and its isomer as a solid (695 mg).

Step 6. Synthesis of Compound A7. To a solution of A6 and its isomer (129 mg, 0.45 mmol) in 10 mL THF, was added LiAlH$_4$ (50 mg, 1.35 mmol), stirred at rt for 1 h. The reaction mixture was quenched with 5 mL H$_2$O and extracted with 100 ml EtOAc, washed with brine solution and evaporated in vacuo then purified by chromatography (PE:EtOAc=3:1) to afford A7 as a solid (62 mg). $^1$H NMR (400 MHz, CDCl$_3$), δ (ppm), 4.63 (s, 1H), 4.61 (s, 1H), 0.82 (s, 3H), 1.25 (s, 3H).

Step 7. Synthesis of Compound A8. To a solution of A7 (86 mg, 0.3 mmol) in dry THF (5 mL) was added borane-tetrahydrofuran complex (1 mL; 1.0 M solution in THF). After stirring at room temperature for 1 hour, the reaction mixture was cooled in an ice bath then quenched slowly with 10% aqueous NaOH (1 mL) followed by 30% aqueous solution of H$_2$O$_2$ (1 mL). After stirring at room temperature for one hour, the mixture was extracted with EtOAc (3×100 mL). The combined organic layers were washed with 10% aqueous Na$_2$S$_2$O$_3$ (100 mL), brine (aq., 100 mL), dried over Step 1. Synthesis of Compound A2. Compound A1 (500 mg, 1.84 mmol) and 10% Pd/black (20 mg) in tetrahydrofuran (5 mL) and concentrated hydrobromic acid (0.02 mL)

MgSO₄, filtered and concentrated to afford A8 as a solid (83 mg, 91%). The crude product was used in the next step without further purification.

Step 8. Synthesis of Compound A9. To a solution of A8 (300 mg, 0.80 mmol) in 15 mL DMF, was added PDC (2.7 g, 7.2 mmol) and 1 mL H₂O, stirred at rt for 15 h. The reaction mixture was extracted 100 mL EtOAc, washed with brine and evaporated in vacuo then purified by chromatography (PE:EtOAc=1:1) to afford A9 as a solid 128 mg. ¹H NMR (400 MHz, DMSO-ds), δ (ppm), 11.90 (s, 1H), 4.22 (s, 1H), 2.28 (1H, t, J=7 Hz), 1.28 (s, 3H), 0.68 (s, 3H).

Step 9. Synthesis of Compound A10. To a solution of A9 (200 mg, 0.61 mmol) in 5 mL DMF, was added N,O-dimethylhydroxylamine HCl salt (60 mg, 0.62 mmol), HATU (236 mg, 0.62 mmol) and DIPEA 1 mL, stirred at rt for 3 h, The reaction mixture was extracted 100 mL EtOAc, washed with brine solution and evaporated in vacuo then purified by chromatography (PE:EtOAc=1:1) to afford A10 as a solid 110 mg. ¹H NMR (400 MHz, DMSO-d₆), δ (ppm), 3.64 (s, 3H), 3.19 (s, 3H), 2.70 (bs, 1H), 2.17 (t, J=7 Hz, 1H), 1.32 (s, 3H), 0.73 (s, 3H).

Example 2

Synthesis of Compound 1

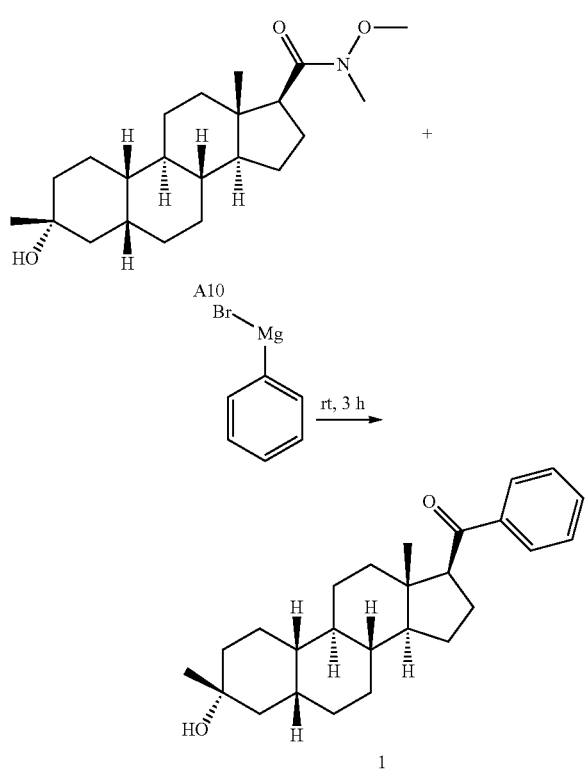

To a stirred solution of A10 (0.1 g, 0.275 mmol) in 5 mL of THF was added phenylmagnesium bromide (1 M; 1.375 mL, 1.375 mmol) dropwise at rt. After stirring at rt for 3 h, the reaction mixture was poured into ice-cold water and extracted with EtOAc (100 mL×3), washed with brine (100 mL×3), dried (MgSO₄), filtered, and evaporated in vacuo, then purified by prep-HPLC to afford 1 as a solid 24 mg. ¹H NMR (500 MHz, CDCl₃), δ (ppm), 7.86 (d, 2H, J=6.8 Hz), 7.52 (t, 1H, J=7.2 Hz), 7.43 (t, 2H, J=7.2 Hz), 3.49 (t, 1H, J=7.8 Hz), 2.43 (q, 1H, J=8.6 Hz), 1.25 (s, 3H), 0.60 (s, 3H). LCMS: Rt=2.618 min, MS (ESI) m/z 381 [M+H]⁺.

Example 3

Synthesis of Compound 2

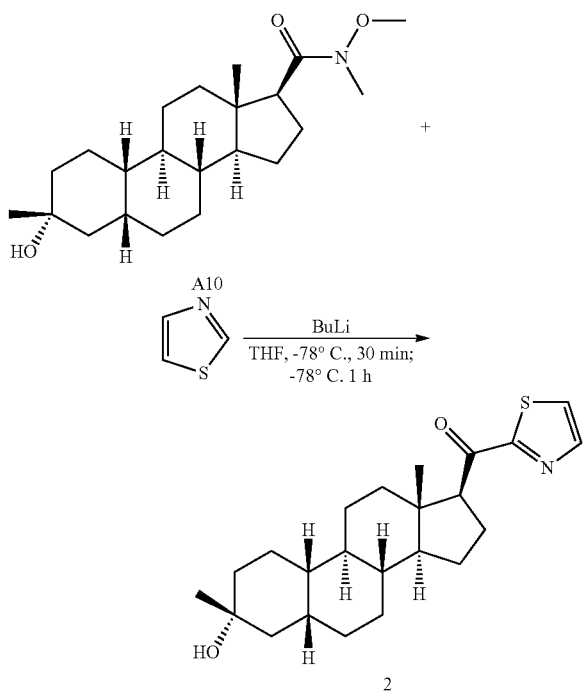

To a stirred solution of thiazole (117 mg, 1.375 mmol) in 10 mL of THF was added nBuLi (2.5 M, 0.55 ml, 1.375 mmol) at −78° C. After stirring at −78° C. for 30 min, a solution of A10 (0.1 g, 0.275 mmol) in 5 mL of THF was added dropwise at −78° C. After stirring at −78° C. for 1 h, the reaction mixture was poured into ice-cold water and extracted with EtOAc (100 mL×3), washed with brine (100 mL×3), dried (MgSO₄), filtered, and evaporated in vacuo, purified by prep-HPLC to afford 2 as a solid 44 mg. ¹H NMR (500 MHz, CDCl₃), δ (ppm), 7.97 (d, 1H, J=3.0 Hz), 7.63 (d, 1H, J=3.0 Hz), 3.87 (t, 1H, J=9.0 Hz), 1.26 (s, 3H), 0.69 (s, 3H). LCMS: Rt=2.564 min, MS (ESI) m/z: 388 [M+H]⁺.

Example 4

Synthesis of Compound 3

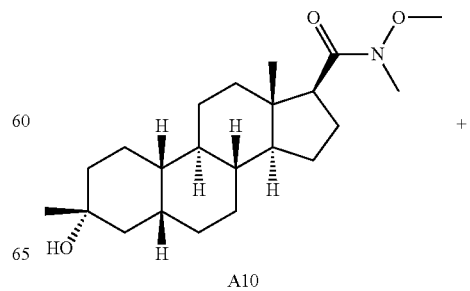

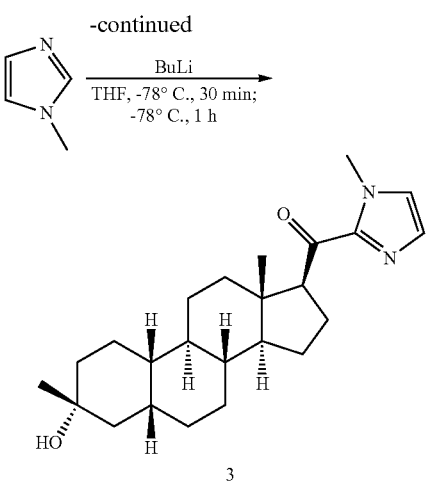

To a stirred solution of 1-methyl-1H-imidazole (113 mg, 1.375 mmol) in 10 mL of THF was added nBuLi (2.5 M, 0.55 ml, 1.375 mmol) at −78° C. After stirring at −78° C. for 30 min, a solution of A10 (0.1 g, 0.275 mmol) in 5 mL of THF was added dropwise at −78° C. After stirring at −78° C. for 1 h. the reaction mixture was poured into ice-cold water and extracted with EtOAc (100 mL×3), washed with brine (100 mL×3), dried (MgSO$_4$), filtered, and evaporated in vacuo, then purified by prep-HPLC to afford 3 as a solid 20 mg. $^1$H NMR (500 MHz, CDCl$_3$), δ$_H$ (ppm), 7.09 (d, 1H, J=0.5 Hz), 6.98 (d, 1H, J=0.5 Hz), 3.97 (s, 3H), 3.96 (t, 1H, J=8.6 Hz), 1.25 (s, 3H), 0.67 (s, 3H). LCMS: Rt=2.393 min, MS (ESI) m/z: 385 [M+H]$^+$.

Example 5

Synthesis of Compound 4

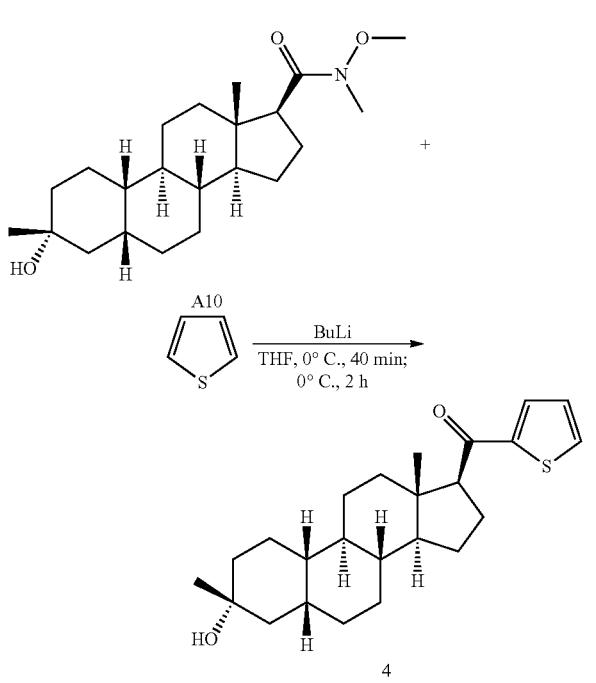

To a stirred solution of thiophene (115 mg, 1.375 mmol) in 10 mL of THF was added nBuLi (2.5 M; 0.55 mL, 1.375 mmol) at 0° C. After stirring at 0° C. for 40 min, a solution of A10 (0.1 g, 0.275 mmol) in 5 mL of THF was added dropwise at 0° C. After stirring at 0° C. for 2 h, the reaction mixture was poured into ice-cold water and extracted with EtOAc (100 mL×3), washed with brine (100 mL×3), dried (MgSO$_4$), filtered, and evaporated in vacuo, then purified by prep-HPLC to afford 4 as a solid 31 mg. $^1$H NMR (500 MHz, CDCl$_3$), δ (ppm), 7.66 (d, 1H), 7.61 (d, 1H), 7.11 (t, 1H), 3.27 (t, 1H), 1.26 (s, 3H), 0.67 (s, 3H). LCMS: Rt=2.541 min, MS (ESI) m/z: 387 [M+H]$^+$.

Example 6

Synthesis of Compound 5

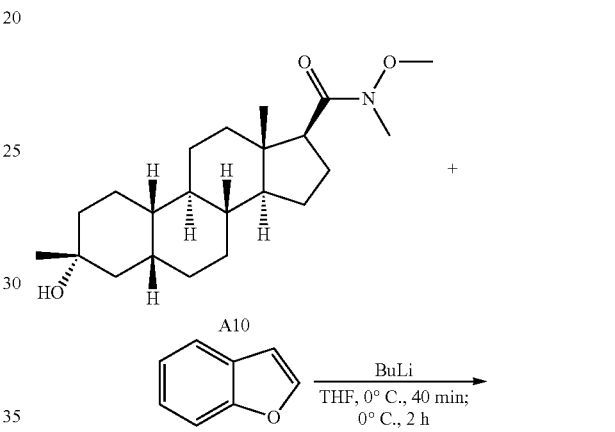

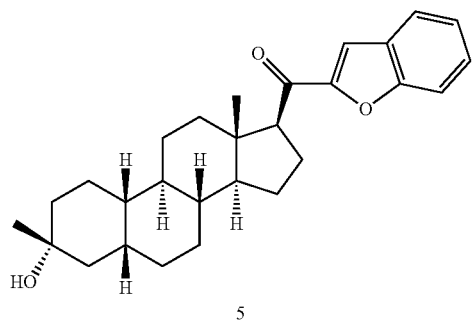

To a stirred solution of benzofuran (162 mg, 1.375 mmol) in 10 mL of THF was added nBuLi (2.5 M; 0.55 mL, 1.375 mmol) at 0° C. After stirring at 0° C. for 40 min, a solution of A10 (0.1 g, 0.275 mmol) in 5 mL of THF was added dropwise at 0° C. After stirring at 0° C. for 2 h, the reaction mixture was poured into ice-cold water and extracted with EtOAc (100 mL×3), washed with brine (100 mL×3), dried (MgSO$_4$), filtered, and evaporated in vacuo, then purified by prep-HPLC to afford 5 as a solid 47 mg. $^1$H NMR (500 MHz, CDCl$_3$), δ (ppm), 7.71 (d, 1H, J=7.8 Hz), 7.58 (d, 1H, J=7.8 Hz), 7.46 (t, 1H, J=7.8 Hz), 7.45 (s, 1H), 7.30 (t, 1H, J=7.8 Hz), 3.40 (t, 1H, J=8.2 Hz), 1.27 (s, 3H), 0.69 (s, 3H). LCMS: Rt=2.621 min, MS (ESI) m/z: 421 [M+H]$^+$.

Example 7

Synthesis of Compound 6

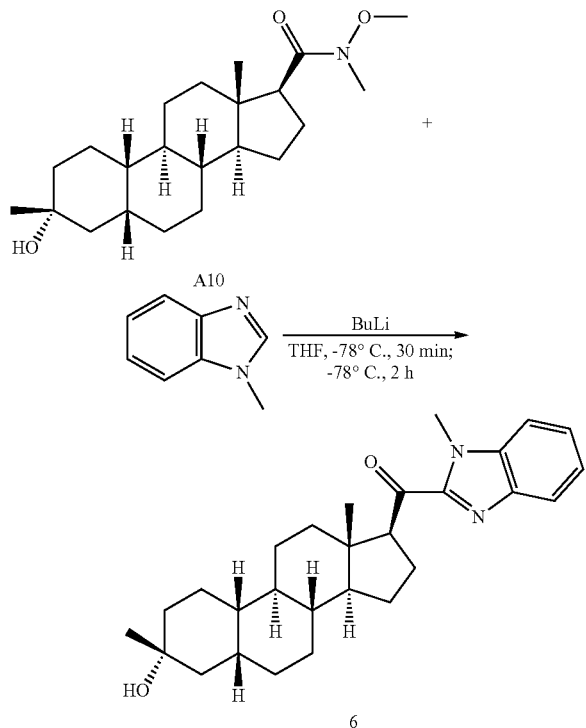

To a stirred solution of 1-methyl-1H-benzo[d]imidazole (181 mg, 1.375 mmol) in 10 mL of THF was added nBuLi (2.5 M; 0.55 mL, 1.375 mmol) at −78° C. After stirring at −78° C. for 30 min, a solution of A10 (0.1 g, 0.275 mmol) in 5 mL of THF was added dropwise at −78° C. After stirring at −78° C. for 2 h, the reaction mixture was poured into ice-cold water and extracted with EtOAc (100 mL×3), washed with brine (100 mL×3), dried (MgSO$_4$), filtered, and evaporated in vacuo, then purified by prep-HPLC to afford 6 as a solid 65 mg. $^1$H NMR (500 MHz, CDCl$_3$), δ (ppm), 7.89 (d, 1H, J=7.8 Hz), 7.44-7.40 (m, 2H), 7.36-7.33 (m, 1H), 4.19 (t, 1H, J=8.6 Hz), 4.10 (s, 3H), 1.25 (s, 3H), 0.69 (s, 3H). LCMS: Rt=2.607 min, MS (ESI) m/z: 435 [M+H]$^+$.

Example 8

Synthesis of Compound 7

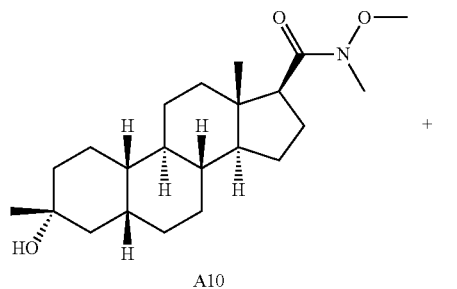

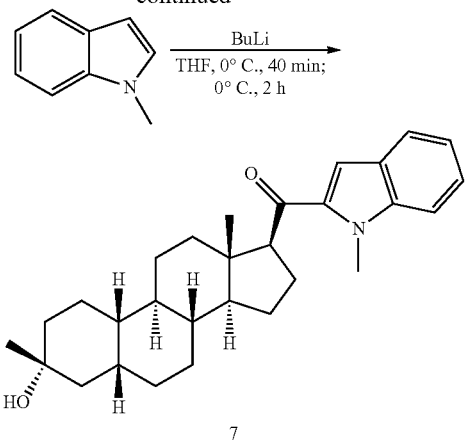

To a stirred solution of 1-methyl-1H-indole (180 mg, 1.375 mmol) in 10 mL of THF was added nBuLi (2.5 M; 0.55 mL, 1.375 mmol) at 0° C. After stirring at 0° C. for 40 min, a solution of A10 (0.1 g, 0.275 mmol) in 5 mL of THF was added dropwise at 0° C. After stirring at 0° C. for 2 h, the reaction mixture was poured into ice-cold water and extracted with EtOAc (100 mL×3), washed with brine (100 mL×3), dried (MgSO$_4$), filtered, and evaporated in vacuo, then purified by prep-HPLC to afford 7 as a solid 36 mg. $^1$H NMR (500 MHz, CDCl$_3$), δ (ppm), 7.70 (d, 1H, J=7.8 Hz), 7.38-7.34 (m, 2H), 7.23 (s, 1H), 7.15-7.13 (m, 1H), 4.06 (s, 3H), 3.40 (t, 1H, J=8.2 Hz), 1.26 (s, 3H), 0.68 (s, 3H). LCMS: Rt=2.742 min, MS (ESI) m/z: 434 [M+H]$^+$.

Example 9

Synthesis of Compound 8

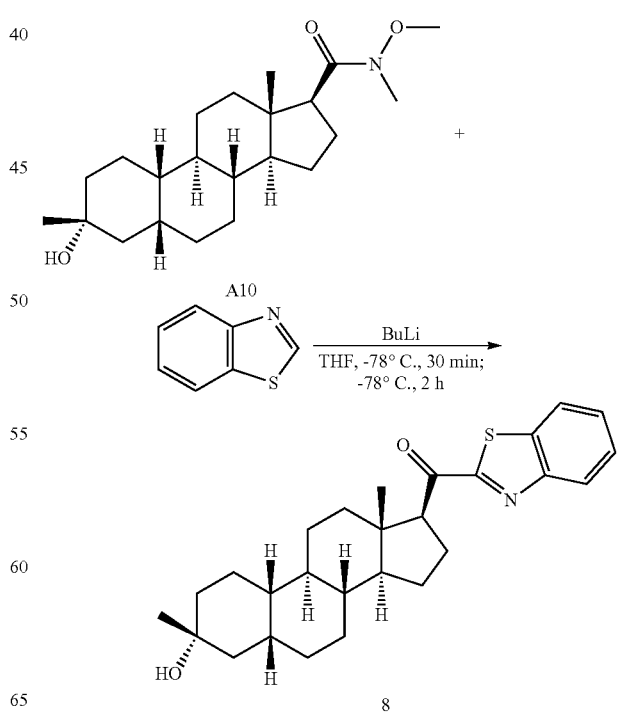

To a stirred solution of benzo[d]thiazole (185 mg, 1.375 mmol) in 10 mL of THF was added nBuLi (2.5 M; 0.55 mL, 1.375 mmol) at −78° C. After stirring at −78° C. for 30 min, a solution of A10 (0.2 g, 0.55 mmol) in 5 mL of THF was added dropwise at −78° C. After stirring at −78° C. for 2 h, the reaction mixture was poured into ice-cold water and extracted with EtOAc (100 mL×3), washed with brine (100 mL×3), dried (MgSO$_4$), filtered, and evaporated in vacuo, purified by prep-HPLC to afford 8 as a solid 100 mg. $^1$H NMR (500 MHz, CDCl$_3$), δ (ppm), 8.09 (d, 1H, J=7.8 Hz), 7.87 (d, 1H, J=7.8 Hz), 7.45 (t, 1H, J=7.8 Hz), 7.40 (t, 1H, J=7.8 Hz), 3.94 (t, 1H, J=8.6 Hz), 1.17 (s, 3H), 0.61 (s, 3H). LCMS: Rt=2.829 min, MS (ESI) m/z: 438 [M+H]$^+$.

Example 10

Synthesis of Compound 9

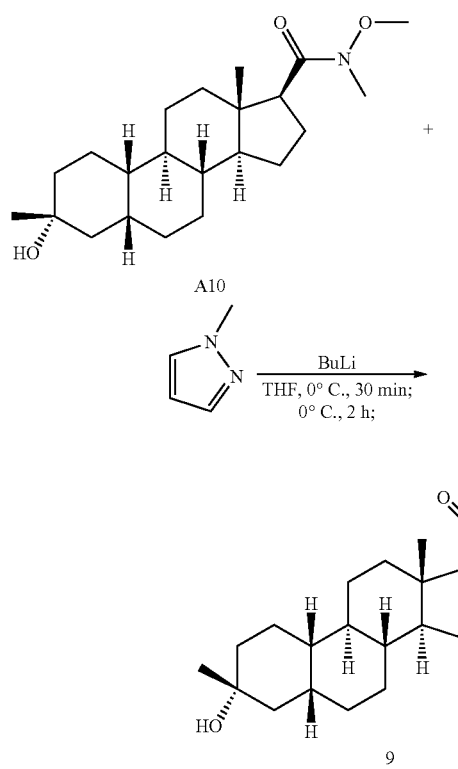

To a stirred solution of 1-methyl-1H-pyrazole (60 mg, 0.7 mmol) in 10 mL THF was added BuLi (2.5 M; 0.3 ml, 0.7 mmol) at 0° C. After stirring at 0° C. for 30 min, a solution of A10 (50 mg, 0.14 mmol) in 3 mL THF was added dropwise at −78° C. After stirring at 0° C. for 2 h, the reaction mixture was poured into ice-cold water and extracted with EtOAc (100 mL×3). The combined extracts were washed with brine (100 mL×3), dried (MgSO$_4$), filtered, evaporated in vacuo, and purified by prep-HPLC to afford 9 as a solid (23 mg, 0.06 mmol). $^1$H NMR (500 MHz, CDCl$_3$), δ(ppm), 7.44 (1H, d, J=2 Hz), 6.77 (1H, d, J=2 Hz), 4.15 (3H, s), 3.17 (1H, t, J=9 Hz), 2.35 (1H, dd, J=9 Hz, 8 Hz) 1.27 (s, 3H), 0.64 (s, 3H). LCMS: Rt=2.45 min, m/z=385.2 [M+H]

Example 11

Synthesis of Compound 10

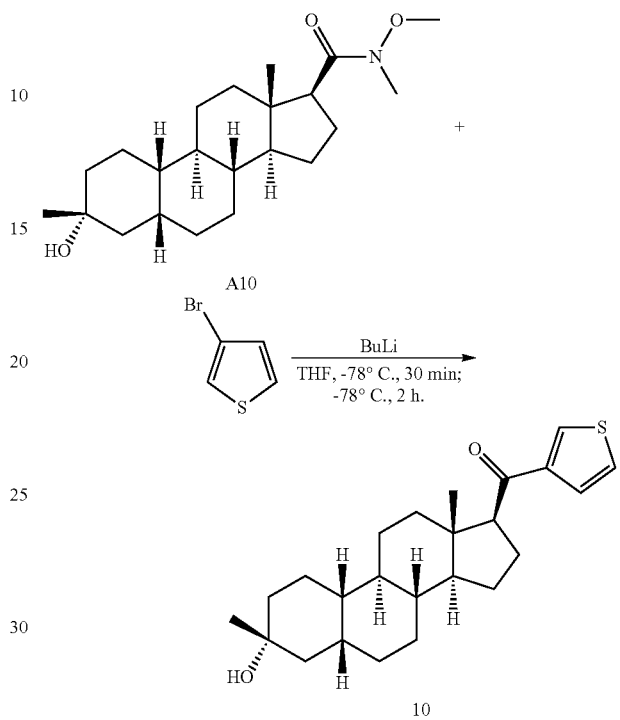

To a stirred solution of 3-bromothiophene (110 mg, 0.7 mmol) in 10 mL of THF was added BuLi (2.5 M; 0.3 ml, 0.7 mmol) at −78° C. After stirring at −78° C. for 30 min, a solution of A10 (50 mg, 0.14 mmol) in 3 mL of THF was added dropwise at −78° C. After stirring at −78° C. for 2 h, the reaction mixture was poured into ice-cold water and extracted with EtOAc (100 mL×3), washed with brine (100 mL×3), dried (MgSO$_4$), filtered, evaporated in vacuo, and purified by prep-HPLC to afford 10 as a solid (15 mg, 0.039 mmol). $^1$H NMR (500 MHz, CDCl$_3$), δ(ppm), 7.66 (1H, d, J=4 Hz), 7.61 (1H, dd, J=1 Hz), 7.11 (1H, t, J=4 Hz), 3.28 (1H, t, J=9 Hz), 2.42-2.36 (1H, m) 1.27 (s, 3H), 0.68 (s, 3H). LCMS: Rt=2.54 min, m/z=387.1 [M+H]

Example 12

Synthesis of Compound 11

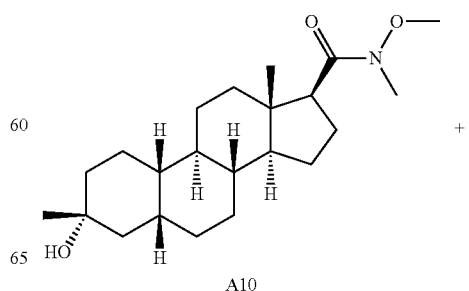

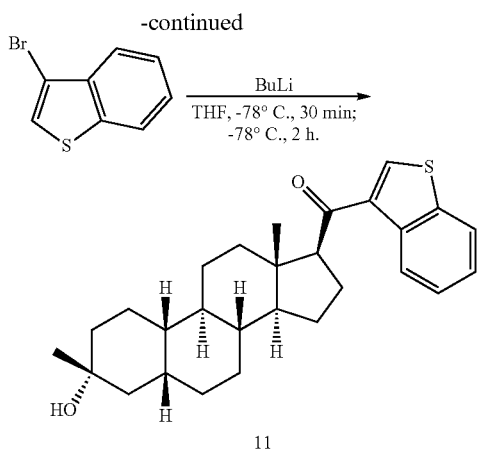

To a stirred solution of 3-bromobenzo[b]thiophene (230 mg, 1.1 mmol) in 10 mL THF was added BuLi (2.5 M; 0.45 ml, 1.1 mmol) at −78° C. After stirring at −78° C. for 30 min, a solution of A10 (80 mg, 0.22 mmol) in 3 mL THF was added dropwise at −78° C. After stirring at −78° C. for 2 h, the reaction mixture was poured into ice-cold water and extracted with EtOAc (100 mL×3), The combined extracts were washed with brine (100 mL×3), dried (MgSO4), filtered, evaporated in vacuo, and purified by prep-HPLC to afford 11 as a solid (52 mg, 0.12 mmol). $^{1}$H NMR (500 MHz, CDCl$_3$), δ(ppm), 7.90-7.89 (2H, s), 7.85 (1H, d, J=9 Hz), 7.44 (1H, t, J=7 Hz), 7.39 (1H, t, J=7 Hz), 3.40 (1H, t, J=9 Hz), 2.43-2.39 (1H, m) 1.27 (s, 3H), 0.69 (s, 3H). LCMS: rt=2.73 min, m/z=437.2 [M+H]

Example 13

Synthesis of Compound 12

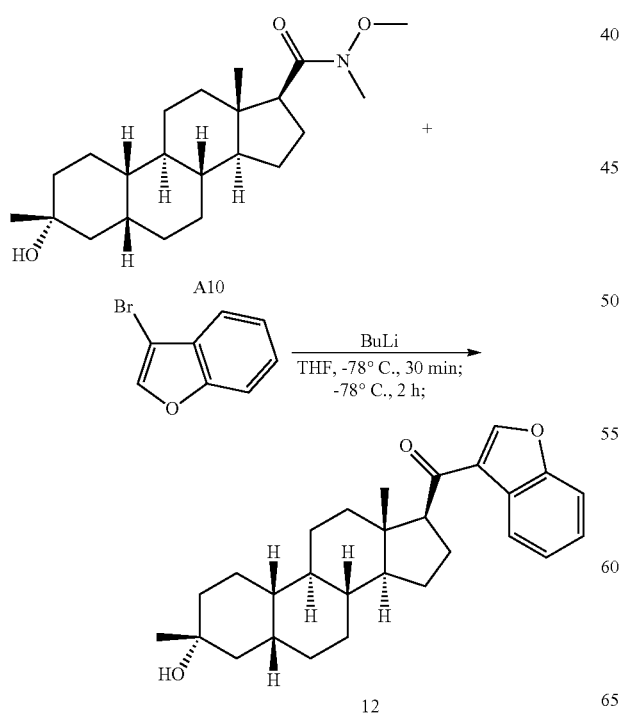

To a stirred solution of 3-bromobenzofuran (140 mg, 0.7 mmol) in 10 mL THF was added BuLi (2.5 M; 0.3 ml, 0.7 mmol) at −78° C. After stirring at −78° C. for 30 min, a solution of A10 (50 mg, 0.14 mmol) in 3 mL of THF was added dropwise at −78° C. After stirring at −78° C. for 2 h, the reaction mixture was poured into ice-cold water and extracted with EtOAc (100 mL×3). The combined extracts were washed with brine (100 mL×3), dried (MgSO$_4$), filtered, evaporated in vacuo, and purified by prep-HPLC to afford 12 as a solid (25 mg, 0.06 mmol). $^{1}$H NMR (500 MHz, CDL3), δ(ppm), 7.71 (1H, d, J=8 Hz), 7.58 (1H, d, J=9 Hz), 7.46 (1H, s), 7.46 (1H, t, J=5 Hz), 7.30 (1H, t, J=7 Hz), 3.41 (1H, t, J=9 Hz), 2.45-2.37 (1H, m) 1.27 (s, 3H), 0.69 (s, 3H). LCMS: rt=2.53 min, m/z=421.3 [M+H].

Example 14

Synthesis of Compound 13

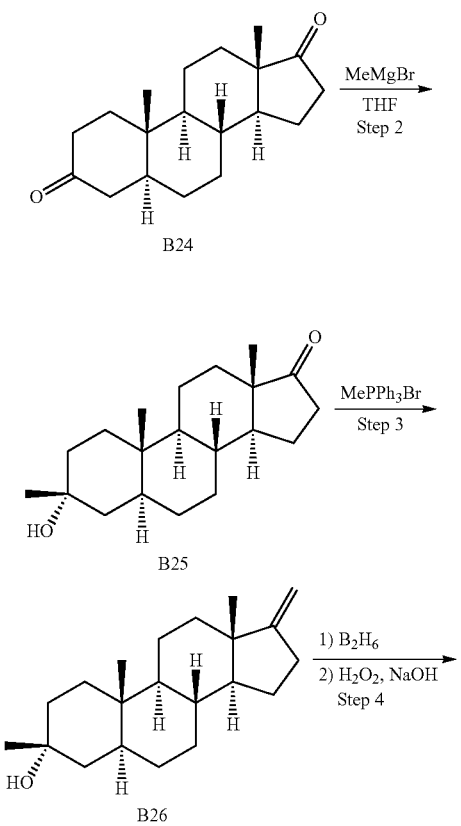

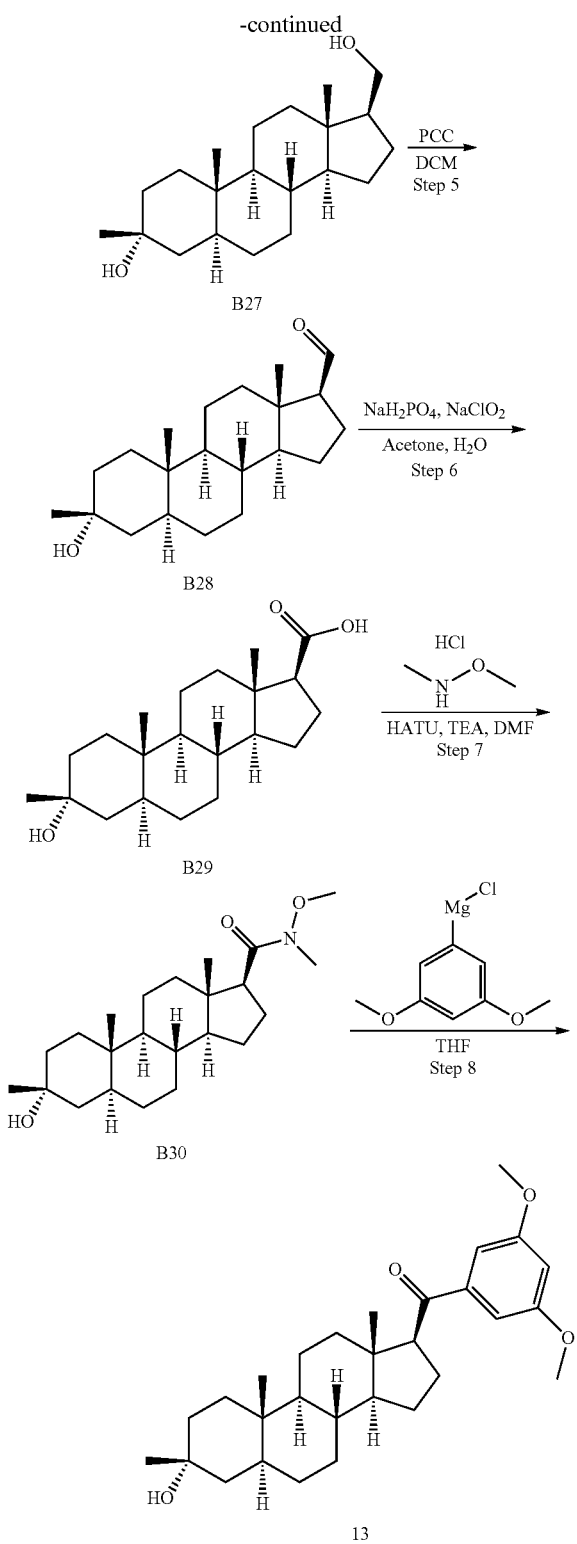

solution became clear and starch potassium iodide paper did not turn blue. The mixture was extracted with DCM (1 L×2). The combined organic phase was dried over $Na_2SO_4$ and concentrated to give crude B24 (60 g, crude) as solid.

Step 2. To a solution of B24 (60 g, 208 mmol) in THF (1000 mL) was added methylmagnesium bromide (624 mmol, 208 mL, 3M in ether) at −70° C. The mixture was stirred at −70° C. for 3 hours. TLC (PE:EA=3:1, PMA) indicated the reaction was finished. The reaction mixture was quenched with saturated $NH_4Cl$ solution (1500 mL) and then concentrated to give a residue, which was extracted with DCM (1000 mL×3). The organic phase was dried, concentrated to give crude B25 (50 g) as a solid.

Step 3. To a solution of $Ph_3PMeBr$ (280 g, 785 mmol) in THF (500 mL) was added a slurry of t-BuOK (87.9 g, 785 mmol) in THF (200 mL) under $N_2$. The mixture turned red and the mixture was stirred at 60° C. for 1 hour. A solution of B25 (48 g, 157 mmol) was added in one portion. The final reaction mixture was stirred at this temperature (60° C.) for 2 hours. TLC (PE:EA=3:1, PMA) indicated the reaction was finished. The reaction was worked up. To the combined reaction mixture was added saturated $NH_4Cl$ solution (1000 mL) and then extracted with EtOAc (1000 mL×2). The combined organic phase was dried, concentrated and purified on silicon gel column (PE:EA=50/1-20/1) to give B26 (15 g, 31.6%) as a solid.

$^1$H NMR (400 MHz. CDCl3) δ=4.65-4.57 (m, 2H), 2.53-2.42 (m, 1H), 2.27-2.16 (m, 1H), 1.85-1.10 (m, 21H), 1.05-0.78 (m, 2H), 0.77 (s, 7H)

Step 4. To a solution of B26 (15 g, 49.5 mmol) in THF (500 mL) was added dropwise a solution of BH3-Me2S (49.5 mL, 495 mmol) at 0° C. The solution was stirred at 15° C. for 3 h. TLC (PE/EtOAc=3/1) showed the reaction was completed. After cooling to 0° C., a solution of NaOH (250 mL, 3M) was added very slowly. After addition, $H_2O_2$ (67 g, 594 mmol, 30% in water) was added slowly and the inner temperature was maintained below 10° C. The resulting solution was stirred at 15° C. for 2 h. Then saturated aqueous $Na_2S_2O_3$ (500 mL) was added until the reaction solution became clear. The mixture was extracted with EtOAc (200× 3). The combined organic solution was washed with saturated aqueous $Na_2S_2O_3$ (100 mL×3), brine (200 mL), dried over $Na_2SO_4$ and concentrated in vacuum to give the crude product B27 (20 g) as a solid, which was used for the next step without further purification.

Step 5. To a solution of B27 (20 g, 62.4 mmol) in DCM (400 mL) was added PCC (26.7 g, 123 mmol) and $SiO_2$ (26.7 g). The final reaction mixture was stirred at 15° C. for 3 hours. After TLC (PE:EA=3:1) indicated the reaction was finished and one main spot was found, the mixture was concentrated and purified by combi-flash (PE:EA=100%-70%) to give B28 (10 g, 51.2%) as a solid.

Step 6. To a solution of B28 (10 g, 31.3 mmol) in acetone (150 mL) and 2-methyl-2-butene (35 mL) was added slowly drop wise aqueous $NaH_2PO_4$ (18.7 g, 156 mmol) and $NaClO_2$ (14.1 g, 156 mmol) in water (100 mL) at 0° C. The mixture was stirred at 15° C. for 2 h. TLC (PE/EA=1/1) showed the reaction was completed and two main spots were found. Then, the reaction was poured in to water (400 mL) and filtered. The filtered cake was washed with water (100 mL) and concentrated to afford a mixture (8 g) as a solid.

Step 7. To a solution of B29 (8 g, 23.9 mmol) in DMF (200 mL) was added HATU (18.1 g, 47.8 mmol), TEA (5.25 g, 47.8 mmol) and N,O-dimethylhydroxylamine (2.18 g, 35.8 mmol) at 15° C. The mixture was stirred at 15° C. for 16 hrs. TLC (PE/EA=1/1) showed the reaction was completed. The reaction was poured into water (500 mL) and Step 1. To a solution of B23 (55 g, 198 mmol) in DCM (2000 mL) was added Dess-Martin (167 g, 396 mmol) in portions at 15° C. After addition was completed, the mixture was stirred at 15° C. for 2 hours. TLC (PE:EA=3:1, PMA) indicated the reaction was finished and one main spot was found. To the mixture was added a saturated mixed solution of $NH_4Cl$ and $NaHCO_3$ (v:v=1:1) (1.5 L) until the reaction extracted with EtOAc (100 mL×2). The combined organic phase was washed with saturated brine (200 mL), dried with anhydrous $Na_2SO_4$, filtered and concentrated in vacuum. The residue was purified by silica gel chromatography (100-200 mesh silica gel, Petroleum ether/Ethyl acetate=4/1) to afford B30 (3 g) as a solid.

$^1$H NMR (400 MHz, CDCl3) δ=3.64 (s, 3H), 3.20 (s, 3H), 2.85-2.71 (m, 1H), 2.28-2.08 (m, 1H), 1.80-0.70 (m, 31H)

Step 8. To a solution of B30 (0.1 g, 0.264 mmol) in THF (2 mL) was added (3,5-dimethoxyphenyl)magnesium chloride (2.63 mL, 2.63 mmol, 1.0M in THF) under $N_2$. The reaction mixture was stirred at 15° C. for 1.5 hours. LCMS indicated the reaction was finished and desired MS peak was found. To the reaction mixture was added saturated $NH_4Cl$ solution (5 mL) and then extracted with EtOAc (2 mL×3). The combined organic phase was concentrated and purified by prep-HPLC to give 13 (47.8 mg) as a solid.

$^1$H NMR (400 MHz, CDCl3) δ 7.01 (d, J=2.3 Hz, 2H), 6.65-6.59 (m, 1H), 3.83 (s, 6H), 3.46-3.36 (m, 1H), 2.49-2.34 (m, 1H), 1.84-1.66 (m, 3H), 1.19 (s, 20H), 1.04-0.89 (m, 1H), 0.71 (s, 4H), 0.60 (s, 3H). LCMS Rt=1.489 min in 2 min chromatography, 10-80 AB, MS ESI calcd. for $C_{29}H_{43}O_4$ [M+H]$^+$ 455. found 455.

Example 15

Synthesis of Compound 14

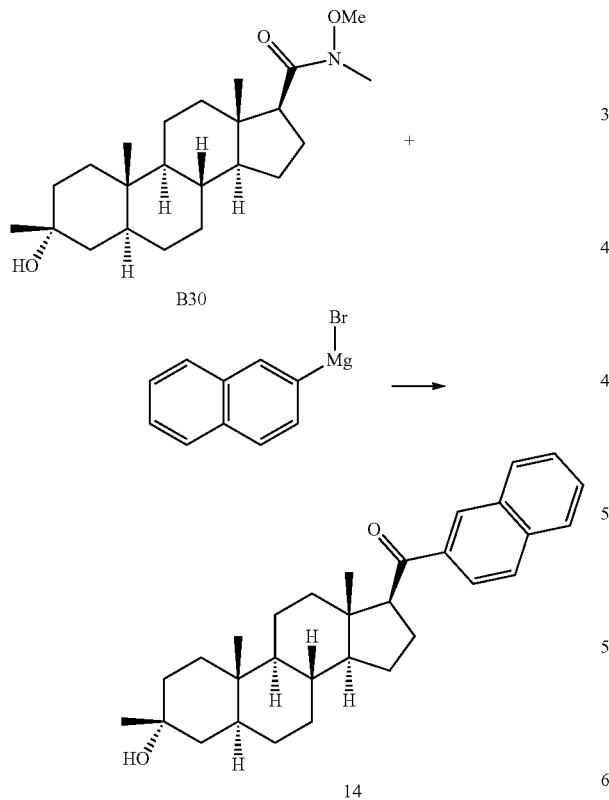

To a solution of B30 (0.1 g, 0.264 mmol) in THF (2 mL) was added naphthalen-2-yl magnesium bromide (5.26 mL, 2.63 mmol, 0.5M in THF) under $N_2$. The reaction mixture was stirred at 15° C. for 4 hours. LCMS indicated the reaction was finished and desired MS peak was found. To the reaction mixture was added saturated $NH_4Cl$ solution (5 mL) and then extracted with EtOAc (2 mL×3). The combined organic phase was concentrated and purified by prep-HPLC to give 14 (36.1 mg) as a solid.

$^1$H NMR (400 MHz. CDCl3) δ8.42-8.37 (m, 1H), 8.00-7.94 (m, 2H), 7.91-7.84 (m, 2H), 7.62-7.51 (m, 2H), 3.70-3.62 (m, 1H), 2.56-2.42 (m, 1H), 1.87-1.69 (m, 3H), 1.19 (s, 21H), 0.84-0.75 (m, 1H), 0.70 (s, 3H), 0.63 (s, 3H). LCMS Rt=1.553 min in 2 min chromatography, 10-80 AB, MS ESI calcd. for $C_{31}H_{41}O_2$[M+H]$^+$ 445. found 445.

Example 16

Synthesis of Compound 15

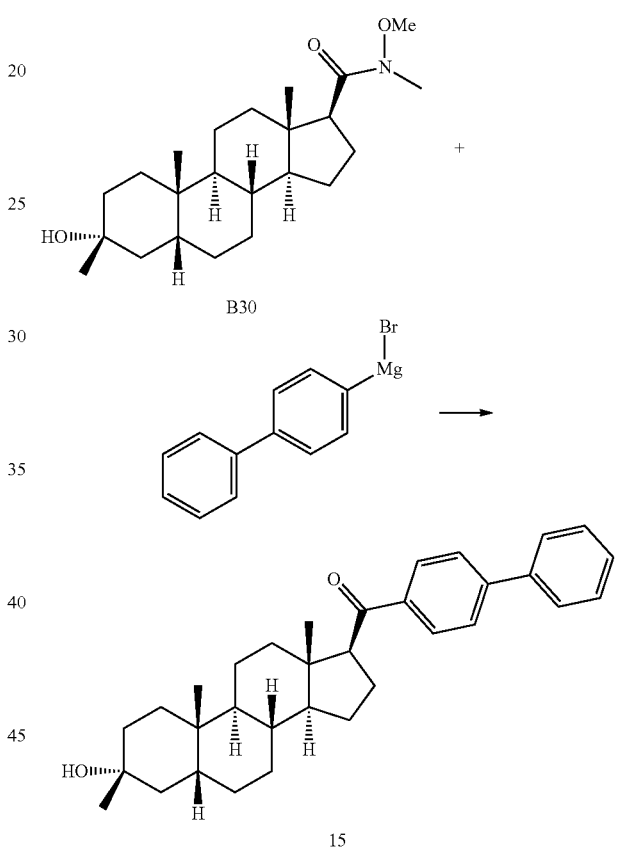

To a solution of B30 (0.1 g, 0.264 mmol) in THF (2 mL) was added [1,1'-biphenyl]-4-yl magnesium bromide (5.26 mL, 2.63 mmol, 0.5M in THF) under $N_2$. The reaction mixture was stirred at 15° C. for 4 hours. LCMS indicated the reaction was finished and desired MS peak was found. To the reaction mixture was added saturated $NH_4Cl$ solution (5 mL) and then extracted with EtOAc (2 mL×3). The combined organic phase was concentrated and purified by preparative HPLC to give 15 (41.4 mg) as a solid.

$^1$H NMR (400 MHz, CDCl3) δ 7.96 (d, J=8.3 Hz, 2H), 7.65 (dd, J=7.9, 11.9 Hz, 4H), 7.50-7.33 (m, 3H), 3.59-3.47 (m, 1H), 2.51-2.38 (m, 1H), 1.86-1.68 (m, 3H), 1.19 (s, 20H), 1.05-0.91 (m, 1H), 0.84-0.75 (m, 1H), 0.72 (s, 3H), 0.62 (s, 3H). LCMS Rt=1.645 min in 2 min chromatography, 10-80 AB, MS ESI calcd. for $C_{33}H_{43}O_2$ [M+H]$^+$ 471. found 471.

Example 17

Synthesis of Compound 16

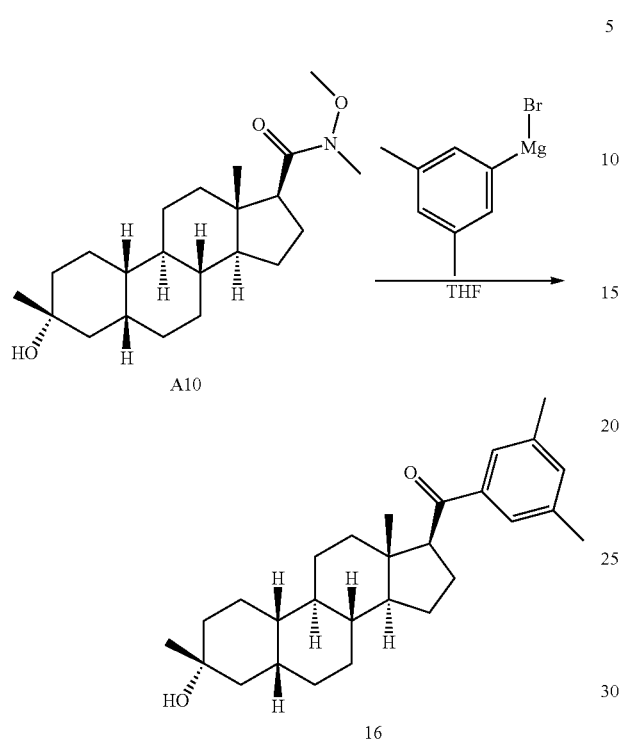

To a solution of A10 (100 mg, 0.275 mmol) in THF (3 mL) was added (3,5-dimethylphenyl)magnesium bromide (5.5 mL, 95%). The mixture was stirred at 20° C. for 3.5 h. When TLC showed starting material was consumed and new spot was produced, to the mixture was added sat. aq. NH$_4$HCl (5 mL). The organic phase was extracted with DCM (5 mL*2), washed with sat. aq. NaCl (8 mL*2), concentrated in vacuum. The residue was purified by prep. HPLC to give 16 (48.3 mg) as a solid.

$^1$H NMR (400 MHz, CDCl$_3$) δ7.47 (s, 2H), 7.16 (s, 1H), 3.47 (t, J=8.8 Hz, 1H), 2.36 (s, 7H), 1.84-1.70 (m, 5H), 1.66-1.58 (m, 2H), 1.49-1.24 (m, 16H), 1.17-1.04 (m, 2H), 0.98-0.85 (m, 1H), 0.60 (s, 3H). LCMS Rt=1.500 min in 2 min chromatography, 10-80 AB, MS ESI calcd. for C$_{28}$H$_{41}$O$_2$ [M+H]$^+$ 409. found 391 [M–H$_2$O].

Example 18

Synthesis of Compound 17

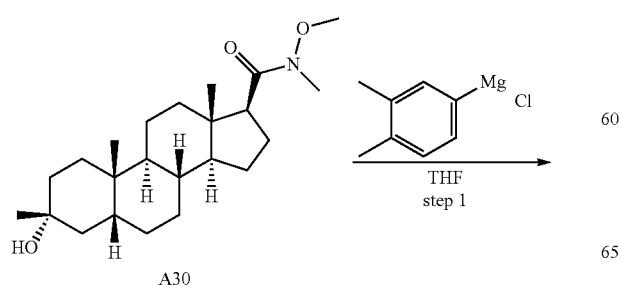

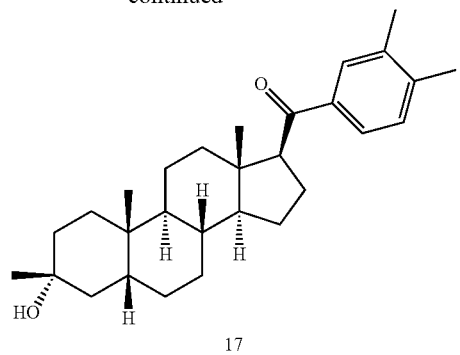

The synthesis of A30 can be found in Example 37, below.

To a solution of A30 (100 mg, 264 μmol) in anhydrous THF (2 mL) was added (3,4-dimethylphenyl)magnesium chloride (5.26 mL, 0.5 M, 2.63 mmol) at 25° C. The reaction mixture was stirred at 25° C. for 2 hours. LCMS showed the starting material was consumed completely. The reaction was quenched with saturated NH$_4$Cl aqueous (1 mL), concentrated under vacuum to give a residue, which was purified by Prep-HPLC (0.05% HCl-ACN) to afford 17 (61.8 mg) as a solid.

$^1$H NMR (400 MHz, CDCl$_3$) δ=7.67 (s, 1H), 7.61 (d, J=7.5 Hz, 1H), 7.18 (d, J=8.0 Hz, 1H), 3.47 (t, J=8.8 Hz, 1H), 2.48-2.36 (m, 1H), 2.31 (s, 6H), 2.04-1.92 (m, 1H), 1.90-1.80 (m, 1H), 1.79-1.63 (m, 3H), 1.54-0.97 (m, 21H), 0.91 (s, 3H), 0.58 (s, 3H)

LCMS R$_t$=1.475 min in 2 min chromatography, 10-80 AB, MS ESI calcd. for C$_{33}$H$_{42}$O$_2$ [M+H]$^+$ 423. found 423.3.

Example 19

Synthesis of Compound 18

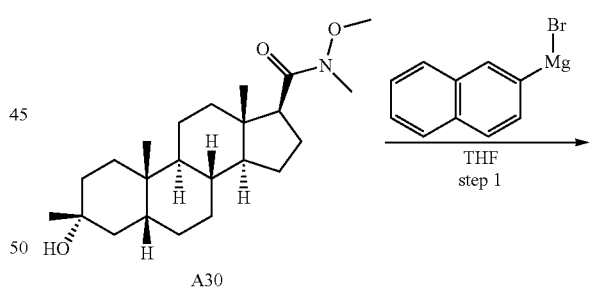

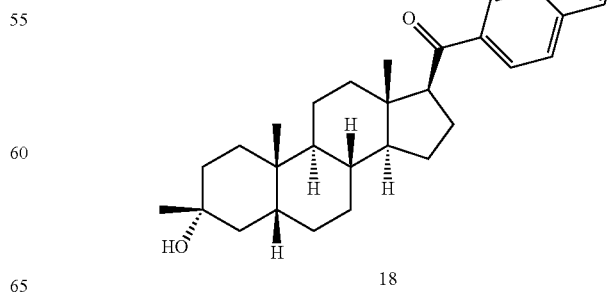

To a solution of A30 (100 mg, 264 µmol) in anhydrous THF (2 mL) was added naphthalen-2-yl magnesium bromide (5.26 mL, 0.5 M, 2.63 mmol) at 25° C. The reaction mixture was stirred at 25° C. for 2 hours. LCMS showed the starting material was consumed completely. The reaction was quenched with saturated NH₄Cl aqueous (1 mL), concentrated under vacuum to give a residue, which was purified by Prep-HPLC (0.05%/HCl-ACN) to afford 18 (8.4 mg) as a solid.

¹H NMR (400 MHz, CDCl₃) δ=8.39 (s, 1H), 8.02-7.92 (m, 2H), 7.88 (d, J=8.5 Hz, 2H), 7.65-7.51 (m, 2H), 3.67 (t, J=8.5 Hz, 1H), 2.55-2.43 (m, 1H), 2.07-1.75 (m, 5H), 1.66 (d, J=14.6 Hz, 2H), 1.58-1.23 (m, 19H), 1.21-0.97 (m, 3H), 0.90 (s, 3H), 0.63 (s, 3H)

LCMS $R_t$=1.496 min in 2 min chromatography, 10-80 AB, MS ESI calcd. for $C_{31}H_{41}O_2$ [M+H]⁺ 445. found 445.3.

Example 20

Synthesis of Compound 19

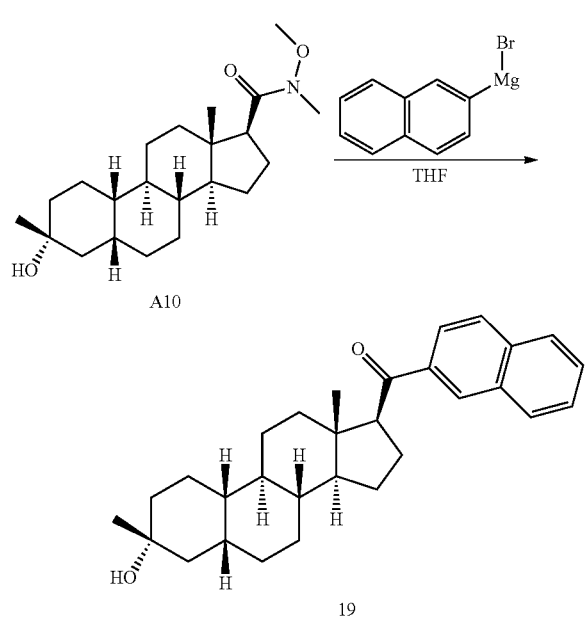

To a solution of A10 (100 mg, 0.275 mmol) in THF (3 mL) was added naphthalen-2-yl magnesium bromide (5.5 mL, 0.5 M in THF). The mixture was stirred at 20° C. for 3.5 h. When TLC showed starting material was consumed and new spot was produced, to the mixture was added sat. aq. NH₄Cl (5 mL). The organic phase was extracted with DCM (5 mL*2), washed with sat. aq. NaCl (8 mL*2), concentrated in vacuum. The residue was purified by preparative HPLC to give 19 (37 mg) as a solid.

¹H NMR (400 MHz, CDCl₃) δ 8.39 (s, 1H), 8.01-7.93 (m, 2H), 7.88 (d, J=8.8 Hz, 2H), 7.62-7.52 (m, 2H), 3.67 (t, J=8.7 Hz, 1H), 2.57-2.43 (m, 1H), 1.91-1.71 (m, 5H), 1.68-1.56 (m, 2H), 1.50-1.23 (m, 16H), 1.19-1.04 (m, 2H), 0.95-0.83 (m, 1H), 0.64 (s, 3H). LCMS Rt=1.495 min in 2 min chromatography, 10-80 AB, MS ESI calcd. for $C_{30}H_{39}O_2$ [M+H]⁺ 430. found 413 [M–H₂O].

Example 21

Synthesis of Compound 20

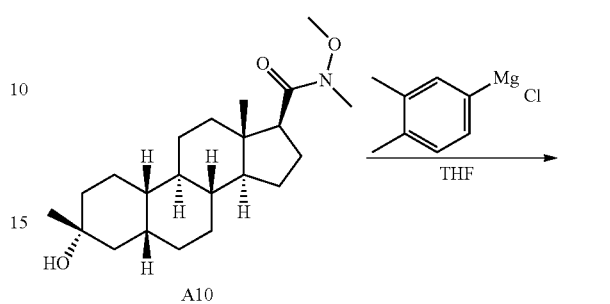

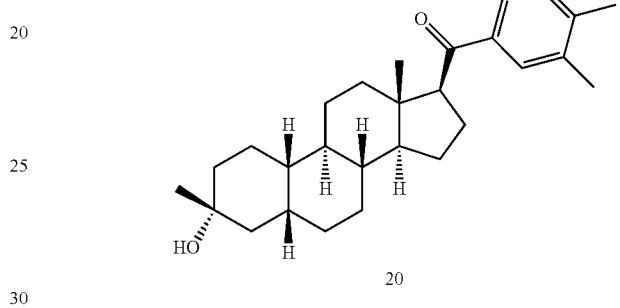

To a solution of A10 (100 mg, 0.275 mmol) in THF (3 mL) was added (3,4-dimethylphenyl)magnesium chloride (5.5 mL, 0.5 M in THF). The mixture was stirred at 20° C. for 3.5 h. When TLC showed starting material was consumed and new spot was produced. To the mixture was added Sat. NH₄Cl (5 mL). The aqueous layer was extracted with DCM (5 mL*2), washed with Sat. NaCl (8 mL*2), filtered and concentrated in vacuum. The residue was purified by prep-HPLC to give 20 (45 mg) as a solid.

¹H NMR (400 MHz, CDCl₃) δ7.66 (s, 1H), 7.61 (d, J=7.8 Hz, 1H), 7.18 (d, J=7.8 Hz, 1H), 3.47 (t, J=8.7 Hz, 1H), 2.48-2.36 (m, 1H), 2.31 (s, 6H), 1.82-1.60 (m, 6H), 1.51-1.23 (m, 17H), 1.19-1.02 (m, 2H), 0.98-0.85 (m, 1H), 0.60 (s, 3H). LCMS $t_R$=1.491 min in 2 min chromatography, 10-80 AB, MS ESI calcd. for $C_{28}H_{41}O_2$ [M+H]⁺ 409. found 391 [M–H₂O]⁺.

Example 22

Synthesis of Compound 21

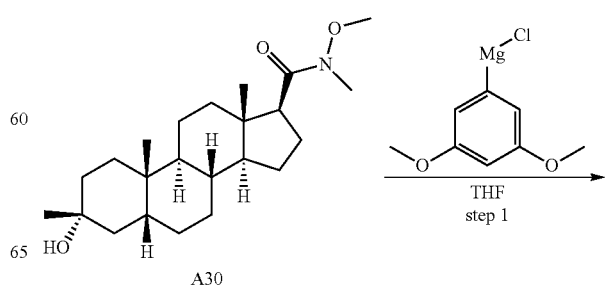

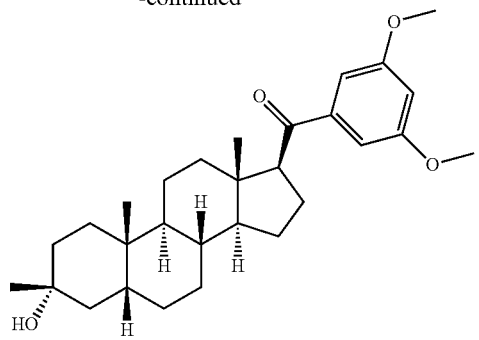

21

To a solution of A30 (100 mg, 264 μmol) in anhydrous THF (2 mL) was added (3,5-dimethoxyphenyl)magnesium chloride (2.63 mL, 1.0 M, 2.63 mmol) at 25° C. The reaction mixture was stirred at 25° C. for 2 hours. LCMS showed the starting material was consumed completely. The reaction was quenched with saturated NH₄Cl aqueous (1 mL), concentrated under vacuum to give a residue, which was purified by Prep-HPLC (0.05% HCl-ACN) to afford 21 (68.8 mg) as a solid.

$^1$H NMR (400 MHz, CDCl$_3$) δ=7.02 (d, J=2.0 Hz, 2H), 6.63 (s, 1H), 3.84 (s, 6H), 3.41 (t, J=8.8 Hz, 1H), 2.46-2.35 (m, 1H), 2.03-1.93 (m, 1H), 1.90-1.64 (m, 4H), 1.53-1.28 (m, 12H), 1.28-1.20 (m, 5H), 1.18-0.97 (m, 3H), 0.91 (s, 3H), 0.59 (s, 3H). LCMS R$_t$=1.474 min in 2 min chromatography, 10-80 AB, MS ESI calcd. for C$_{33}$H$_{43}$O$_2$ [M+H]$^+$ 455. found 437 ([M−H$_2$O]$^+$).

Example 23

Synthesis of Compound 22

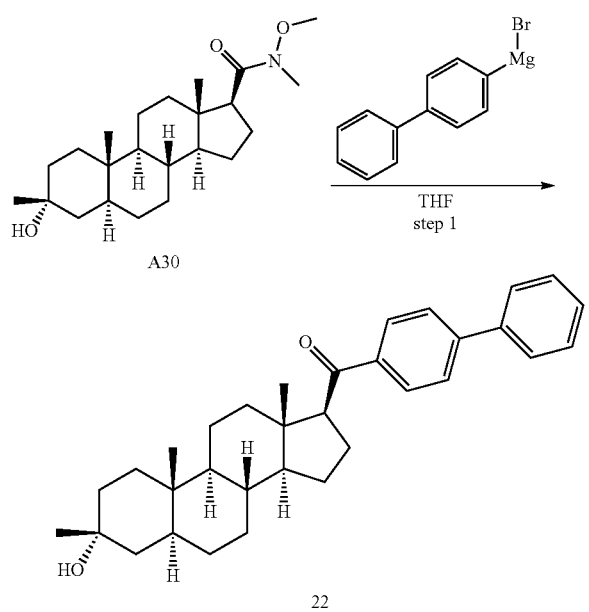

To a solution of A30 (100 mg, 264 μmol) in anhydrous THF (2 mL) was added [1,1'-biphenyl]-4-ylmagnesium bromide (5.26 mL, 0.5 M, 2.63 mmol) at 25° C. The reaction mixture was stirred at 25° C. for 2 hours. LCMS showed the starting material was consumed completely. The reaction was quenched with saturated NH₄Cl aqueous (1 mL), concentrated under vacuum to give a residue, which was purified by Prep-HPLC (0.05% HCl-ACN) to afford 22 (76 mg) as a solid.

$^1$H NMR (400 MHz, CDCl$_3$) δ=7.96 (d, J=80 Hz, 2H), 7.72-7.60 (m, 4H), 7.51-7.43 (m, 2H), 7.43-7.36 (m, 1H), 3.53 (t, J=8.5 Hz, 1H), 2.52-2.40 (m, 1H), 1.98 (t, J=13.3 Hz, 1H), 1.91-1.63 (m, 4H), 1.55-1.29 (m, 12H), 1.28-0.96 (m, 9H), 0.92 (s, 3H), 0.62 (s, 3H). LCMS R$_t$=1.556 min in 2 min chromatography, 10-80 AB, MS ESI calcd. for C$_{33}$H$_{43}$O$_2$ [M+H]$^+$ 471. found 471.3.

Example 24

Synthesis of Compound 23

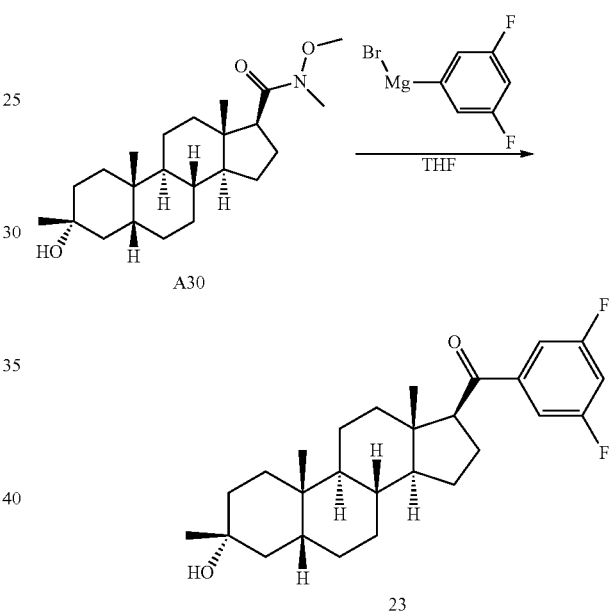

To a stirred solution of A30 (110 mg, 291 umol) in 3 mL of THF was added (3,5-difluorophenyl)magnesium bromide (0.5 M; 5.8 mL, 2.9 mmol) dropwise at 25° C. After stirring at 25° C. for 12 hrs, LCMS showed the reaction was complete. The reaction mixture was poured into ice-cold water and extracted with EtOAc (50 mL×2), washed with brine (30 mL×2), dried (Na2SO4), filtered, and evaporated in vacuo to give crude product. The reaction mixture was purified by HPLC separation (column: Phenomenex Synergi C18 150*25*10 um, gradient: 80-100% B (A=0.05% HCl-ACN, B=acetonitrile), flow rate: 25 mL/min) for further purification to obtain 23 (28.4 mg) as a solid.

$^1$HNMR (CDCl$_3$, 400 MHz): δ=7.38 (d, J=6.0 Hz, 2H), 6.99 (t, J=8.4 Hz, 1H), 3.35 (t, J=8.8 Hz, 1H), 2.35-2.45 (m, 1H), 1.96 (t, J=13.2 Hz, 1H), 1.73-1.90 (m, 3H), 1.69 (d, J=14.6 Hz, 1H), 1.33-1.54 (m, 12H), 1.21-1.28 (m, 5H), 1.10-1.19 (m, 2H), 1.01-1.08 (m, 1H), 0.92 (s, 3H), 0.59 (s, 3H) LCMS Rt=3.417 min in 4.0 min chromatography, 10-80 AB, MS ESI calcd. for C$_{27}$H$_{36}$F$_2$O$_2$ [M−+H]+ 430.3. found 413.0 [M−H$_2$O]$^+$.

Example 25

Synthesis of Compound 24

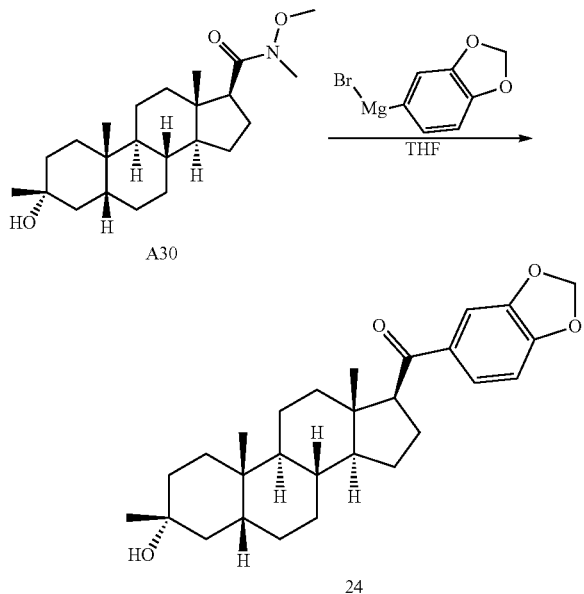

To a stirred solution of A30 (110 mg, 291 umol) in 3 mL of THF was added benzo[d][1,3]dioxol-5-ylmagnesium bromide (0.5 M; 5.8 mL, 2.9 mmol) dropwise at 25° C. After stirring at 25° C. for 12 hrs, LCMS showed the reaction was complete. The reaction mixture was poured into ice-cold water and extracted with EtOAc (50 mL×2), washed with brine (30 mL×2), dried (Na$_2$SO$_4$), filtered, and evaporated in vacuo to give crude product. The reaction mixture was purified by HPLC separation (column: Phenomenex Synergi C18 150*25*10 um, gradient: 80-100% B (A=0.05% HCl-ACN, B=acetonitrile), flow rate: 25 mL/min) for further purification to obtain 24 (21.1 mg) as a solid.

$^1$HNMR (CDCl$_3$, 400 MHz): δ=7.50 (d. J=8.0 Hz, 1H), 7.41 (s, 1H), 6.84 (d, J=8.0 Hz, 1H), 6.04 (s, 2H), 3.40 (t, J=8.6 Hz, 1H), 2.37-2.45 (m, 1H), 1.97 (t, J=13.6 Hz, 1H), 1.81-1.90 (m, 1H), 1.64-1.79 (m, 3H), 1.29-1.55 (m, 12H), 1.27 (s, 3H), 1.23 (br. s, 2H), 1.10-1.19 (m, 2H), 1.00-1.08 (m, 1H), 0.92 (s, 3H), 0.59 (s, 3H). LCMS Rt=3.309 min in 4.0 min chromatography, 10-80 AB, MS ESI calcd. for C$_2$H$_{39}$O$_4$[M+H]+ 439.3. found 439.1.

Example 26

Synthesis of Compound 25

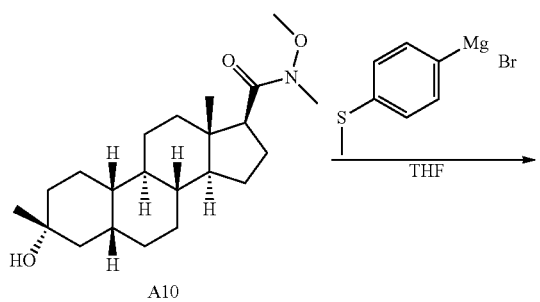

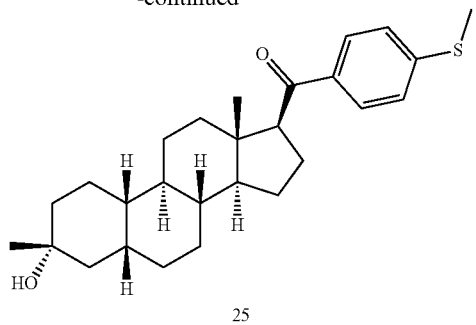

To a solution of A10 (100 mg, 0.275 mmol) in THF (3 mL) was added (4-(methylthio)phenyl)magnesium bromide (5.5 mL, 0.5 M in THF). The mixture was stirred at 20° C. for 3.5 h. To the mixture was added Sat. NH$_4$Cl (5 mL). The organic phase was extracted with DCM (5 mL*2), washed with Sat. NaCl (8 mL*2), concentrated in vacuum. The residue was purified by prep. HPLC$^1$ to give 25 (32 mg) as a solid.

$^1$H NMR (400 MHz, CDCl$_3$) δ7.81 (d, J=8.5 Hz, 2H), 7.25-7.22 (m, 2H), 3.45 (t, J=8.8 Hz, 1H), 2.56-2.35 (m, 4H), 1.84-1.72 (m, 5H), 1.53-1.25 (m, 18H), 1.20-0.84 (m, 3H), 0.59 (s, 3H).

LCMS Rt=1.476 min in 2 min chromatography, 10-80 AB, MS ESI calcd. for C$_{27}$H$_{39}$O$_2$S [M+H]$^+$ 427.3. found 409 [M−H$_2$O]$^+$.

Example 27

Synthesis of Compound 26

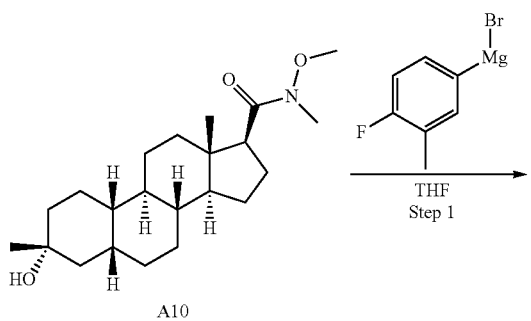

To a solution of A10 (100 mg, 0.275 mmol) in THF (3 mL) was added (4-fluoro-3-methylphenyl)magnesium bromide (2.75 mL) at 25° C. for 2 hours, at which point the reaction was complete as shown by LC-MS. An aqueous solution of NH$_4$Cl (5 mL) was added drop wise into the reaction mixture at 25° C., and extracted with EtOAc (10 mL×2). The combined organic solution was washed with brine (5 mL), dried over Na$_2$SO$_4$. The organic layer was filtered and concentrated under reduced pressure to give the crude mixture which was purified by HPLC to give 26 (47.5 mg) as a solid.

1H NMR (CDCl$_3$, 400 MHz) δ=7.83-7.70 (m, 2H), 7.06 (t, J=8.9 Hz, 1H), 3.46 (t, J=8.7 Hz, 1H), 2.48-2.31 (m, 4H), 1.89-1.73 (m, 5H), 1.71-1.60 (m, 2H), 1.61-1.60 (m, 1H), 1.54-1.45 (m, 3H), 1.43-1.33 (m, 7H), 1.33-1.24 (m, 6H), 1.22-1.05 (m, 2H), 1.03-0.88 (m, 1H), 0.62 (s, 3H). LCMS Rt=1.285 min in 2 min chromatography, 30-90 AB, MS ESI calcd. for C$_{27}$H$_{38}$FO$_2$ [M+H]$^+$ 413. found 413.

Example 28

Synthesis of Compound 27

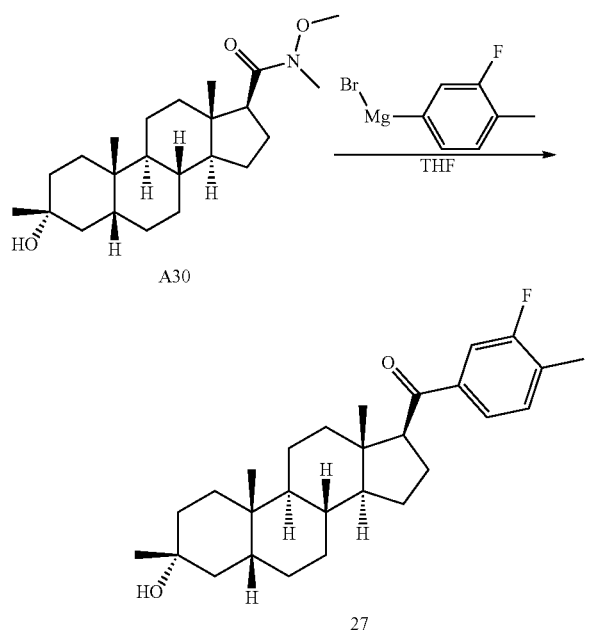

To a stirred solution of A30 (110 mg, 291 umol) in 3 mL of THF was added (3-fluoro-4-methylphenyl)magnesium bromide (0.5 M, 5.8 mL, 2.9 mmol) dropwise at 25° C. After stirring at 25° C. for 12 hrs, LCMS showed the reaction was complete. The reaction mixture was poured into ice-cold water and extracted with EtOAc (50 mL×2), washed with brine (30 mL×2), dried (Na$_2$SO$_4$), filtered, and evaporated in vacuo to give crude product. The reaction mixture was purified by HPLC separation (column: Phenomenex Synergi C18 150*25 10 um, gradient: 88-88% B (A=0.05% HCl-ACN, B=acetonitrile), flow rate: 25 mL/min) for further purification to obtain 27 (42.4 mg) as a solid.

$^1$HNMR (CDCl$_3$, 400 MHz): δ=7.48-7.61 (m, 2H), 7.20-7.26 (m, 1H), 3.41 (t, J=8.8 Hz, 1H), 2.37-2.44 (m, 1H), 2.33 (d, J=1.4 Hz, 3H), 1.97 (t, J=13.2 Hz, 1H), 1.87 (ddd, J=13.8, 9.3, 4.5 Hz, 1H), 1.65-1.80 (m, 3H), 1.33-1.56 (m, 12H), 1.22-1.29 (m, 5H), 0.99-1.18 (m, 3H), 0.92 (s, 3H), 0.58 (s, 3H). LCMS Rt=3.322 min in 4.0 min chromatography, 10-80 AB, MS ESI calcd. for C$_{28}$H$_{40}$FO$_2$ [M+H]+ 427.3. found 409.1 ([M−H$_2$O]$^+$.

Example 29

Synthesis of Compound 28

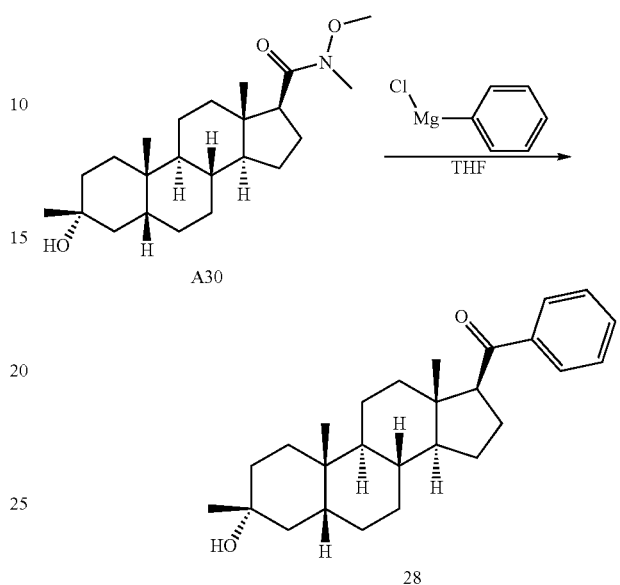

To a stirred solution of A30 (110 mg, 291 umol) in 3 mL of THF was added phenylmagnesium chloride (0.5 M; 5.8 mL, 2.9 mmol) dropwise at 25° C. After stirring at 25° C. for 12 hrs, LCMS showed the reaction was complete. The reaction mixture was poured into ice-cold water and extracted with EtOAc (50 mL×2), washed with brine (30 mL×2), dried (Na$_2$SO$_4$), filtered, and evaporated in vacuo to give crude product. The crude product was purified by HPLC separation (column: Gemini 150*25 5u, gradient: 69-94% B (A=0.05% HCl-ACN, B=acetonitrile), flow rate: 30 mL/min) for further purification to obtain 28 (48.4 mg, 291 μmol) as a solid.

$^1$HNMR (CDCl$_3$, 400 MHz): δ=7.88 (d, J=7.4 Hz, 1H), 7.50-7.58 (m, 1H), 7.39-7.48 (m, 2H), 3.50 (t, J=8.8 Hz, 1H), 2.36-2.52 (m, 1H), 1.98 (t, J=13.2 Hz, 1H), 1.85 (d, J=13.8 Hz, 1H), 1.74-1.81 (m, 2H), 1.68 (d, J=14.4 Hz, 1H), 1.32-1.55 (m, 13H), 1.21-1.29 (m, 5H), 0.99-1.17 (m, 3H), 0.91 (s, 3H), 0.60 (s, 3H). LCMS Rt=3.253 min in 4.0 min chromatography, 10-80 AB, MS ESI calcd. for C$_{27}$H$_{39}$O$_2$ [M+H]$^+$ 395.3. found 377.0 [M−H$_2$O]$^+$.

Example 30

Synthesis of Compound 29

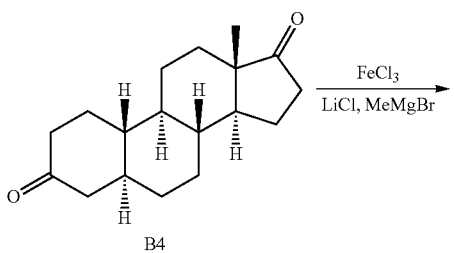

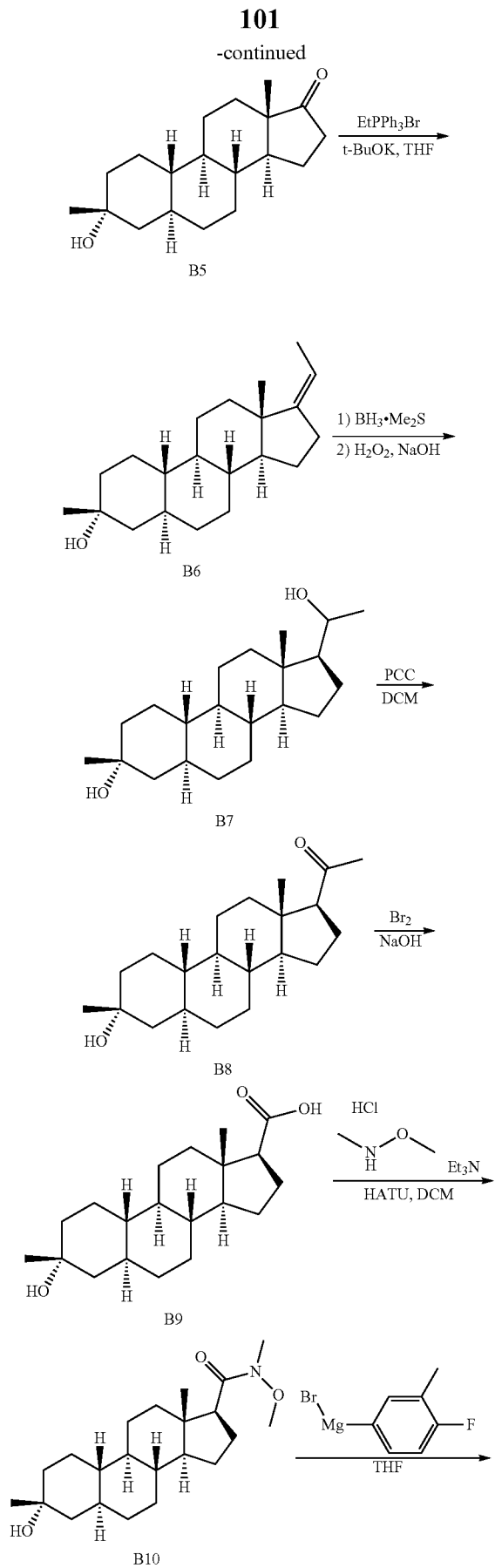

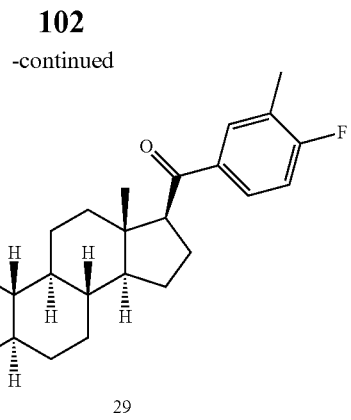

Step 1. Under nitrogen atmosphere, anhydrous THF (400 mL) was cooled to 10° C. and anhydrous LiCl (12.8 g, 304 mmol) was added in one portion. The mixture was stirred for 30 min after which a clear solution was obtained. To this mixture was added anhydrous $FeCl_3$ (25.7 g, 159 mmol) in one portion. The resulting mixture was stirred for additional 30 min. The reaction mixture was cooled to −35° C. and methyl magnesium bromide (3 M in diethyl ether, 193 mL, 580 mmol) was added dropwise maintaining the internal temperature between −35° C. and −30° C. The above mixture was stirred for 30 min at −30° C. B4 (40 g, 145 mmol) was added in one portion. The internal temperature was allowed to −20° C. and kept between −15° C. and −20° C. for 2 hours. TLC showed the reaction was completed. The reaction mixture was quenched with aqueous HCl (2 M, 200 mL), extracted with $CH_2Cl_2$ (500 mL×2). The combined organic layer was washed with aqueous NaOH (10%, 300 mL×2) and brine (300 mL), dried over anhydrous sodium sulfate, filtered and concentrated. The residue was triturated from EtOAc to give B5 (25.0 g, 59.3%) as a solid.

$^1$H NMR (400 MHz, $CDCl_3$) δ 2.44-2.40 (m, 1H), 2.09-2.00 (m, 1H), 1.89-1.57 (m, 7H), 1.54-1.03 (m, 16H), 0.87 (s, 3H), 0.73-0.70 (m, 2H).

Step 2. To a solution of ethyltriphenylphosphonium bromide (152 g, 412 mmol) in THF (600 mL), was added a solution of t-BuOK (46.1 g, 412 mmol) at 25° C. The mixture was heated to 60° C. and stirred for 1 h. B5 (30.0 g, 103 mmol) was added. The mixture was stirred at 60° C. for 2 hrs. TLC showed the reaction was completed. The mixture was poured into Sat.aq $NH_4Cl$ (500 mL), extracted with EtOAc (300 mL×2). The combined organic phase was washed with brine (300 mL), dried over anhydrous $Na_2SO_4$, filtered, concentrated. The residue was purified by silica gel column (PE/EtOAc=100/1) to afford B6 (30 g, 96.4%) as a solid.

$^1$H NMR (400 MHz, $CDCl_3$) δ 5.12-5.09 (m, 1H), 2.34-2.21 (m, 3H), 1.86-1.58 (m, 8H), 1.56-0.99 (m, 17H), 0.87 (s, 3H), 0.75-0.68 (m, 2H).

Step 3. To a solution of B6 (40 g, 132 mmol) in THF (300 mL) was added dimethylsulfide borane (132 mL, 1.32 mol) dropwise at 0° C. The mixture was stirred at 25° C. for 12 hrs. TLC showed the reaction was complete. After cooling to 0° C., a solution of NaOH (220 mL, 3M) was added very slowly. After the addition was complete, $H_2O_2$ (150 mL, 33%) was added slowly and the inner temperature was maintained below 10° C. The resulting solution was stirred at 25° C. for 2 hrs. The resulting solution was filtered, and the filtrate was extract with EtOAc (500 mL×3). The combined organic solution was washed with saturated aqueous $Na_2S_2O_3$ (500 mL×2), brine (500 mL), dried over $Na_2SO_4$ and concentrated in vacuum to give B7 (40 g, crude) as a solid. The crude product was used for the next step without further purification Step 4. To a solution of B7 (40 g, 124 mmol) and silica gel (44 g) in CH$_2$Cl$_2$ (400 mL) was added Pyridinium chlorochromate (53.4 g, 248 mmol) at 25° C. The mixture was stirred at 25° C. for 2 hrs. TLC showed the reaction was completed. The mixture was filtered and the filter cake was washed with CH$_2$Cl$_2$ (200 mL×2). The combined filtrate was concentrated in vacuum. The residue was purified by silica gel column (eluted with PE/EtOAc=10/1 to 1/1) to afford B8 (34 g, 86.2%) as a solid.

$^1$H NMR (400 MHz, CDCl$_3$) δ 2.55-2.51 (m, 1H), 2.20-2.10 (m, 4H), 2.00-1.64 (m, 4H), 1.60-0.99 (m, 20H), 0.75-0.69 (m, 3H), 0.60 (s, 3H).

Step 5. To a solution of B8 (10.0 g, 31.3 mmol) in dioxane/H$_2$O (400 mL/120 mL) at 0° C. was added sodium hypobromide (1500 mL) [prepared from NaOH (163 g), dibromine (54.1 mL), dioxane (600 mL) and H$_2$O (800 mL)]. The resulting mixture was stirred at 25° C. for 24 hours. After TLC showed the reaction was completed, sat. aq Na$_2$S$_2$O$_3$ (400 mL) was added followed by aq HCl (450 mL, 1M) was added into the mixture. The mixture was adjusted to pH=6 and the white solid was precipitated. The solid was filtered and the filter cake was washed with water (300 mL×2), dried in vacuum to give B9 (9.5, 95.0%) as a solid.

$^1$H NMR (400 MHz, DMSO-d$_6$) δ 11.89 (br, 1H), 3.87 (s, 1H), 2.29-2.26 (m, 1H), 2.00-1.93 (m, 2H), 1.65-1.15 (m, 9H), 1.13-0.91 (m, 13H), 0.85-0.75 (m, 5H).

Step 6. A mixture of B9 (12.2 g, 38.0 mmol), N,O-dimethylhydroxylamine hydrochloride (7.41 g, 76.0 mmol), HATU (17.3 g, 45.5 mmol) and Et$_3$N (21.0 mL, 152 mmol) in 300 mL of anhydrous CH$_2$Cl$_2$ was stirred for 18 hrs at 25° C. TLC showed the reaction was completed. The mixture was treated with water (200 mL), extracted with CH$_2$C$_2$ (300 mL×2). The combined organic phase was washed aq. HCl (200 mL, 1M), sat. aq NaHCO$_3$ (200 mL), and brine (300 mL), dried over anhydrous Na$_2$SO$_4$, filtered, concentrated in vacuum. The residue was purified by silica gel column (PE/EtOAc=5/1) to afford B10 (13.0 g, 94.2%) as a solid.

$^1$H NMR (CDCl$_3$, 400 MHz) δ 3.64 (s, 3H), 3.20 (s, 3H), 2.80 (br, 1H), 2.25-2.15 (m, 1H), 1.81-1.57 (m, 81H), 1.33-1.00 (m, 16H), 0.74 (s, 3H), 0.69-0.60 (m, 2H).

Step 7. To a solution of B10 (100 mg, 275 umol) in THF (3 mL) was added (4-fluoro-3-methylphenyl)magnesium bromide (2.74 mL, 1.37 mmol) dropwise at 25° C. The mixture was stirred at 25° C. for 3 h. LCMS showed the reaction was complete. Then, the reaction was concentrated in vacuum. The residue was purified by prep-HPLC separation (column: Phenomenex Synergi C18 150*30 mm*4 um, gradient: 80-95% B (A=0.05% HCl-acetonitrile, B=acetonitrile), flow rate: 25 mL/min) for further purification to obtain 29 (46.9 mg) as a solid.

$^1$HNMR (CDCl$_3$, CDCl3 400 MHz): δ=7.69-7.80 (m, 2H), 7.04 (t, J=8.8 Hz, 1H), 3.45 (t, J=8.6 Hz, 2H), 2.37-2.43 (m, 1H), 2.33 (s, 3H), 1.56-1.79 (m, 8H), 1.26-1.42 (m, 6H), 1.20 (s, 3H), 0.97-1.16 (m, 6H), 0.65-0.79 (m, 2H), 0.61 (s, 3H). LCMS Rt=3.457 min in 4.0 min chromatography, 10-80 AB, MS ESI calcd. for C$_{27}$H$_{38}$FO$_2$ [M+H]+ 413.28, found 413.2 [M+H]$^+$.

Example 31

Synthesis of Compound 30

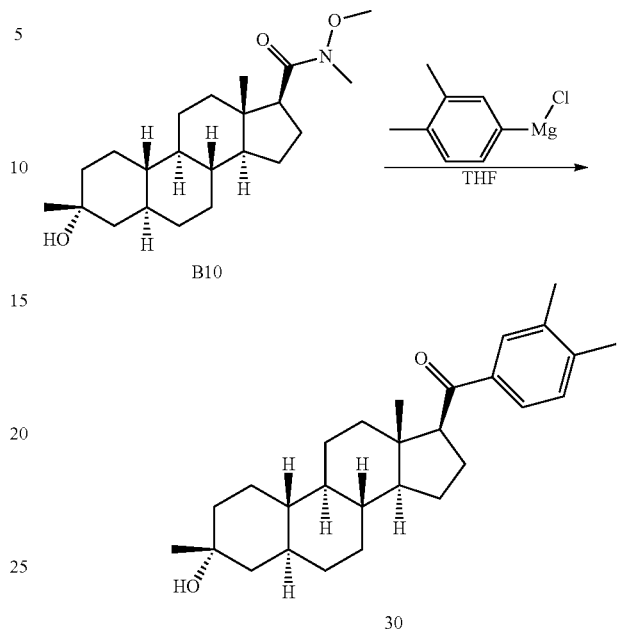

To a stirred solution of B10 (100 mg, 275 umol) in 3 mL of THF was added (3,4-dimethylphenyl)magnesium chloride (0.5 M; 2.74 mL, 1.37 mmol) dropwise at 25° C. After stirring at 25° C. for 12 hrs, LCMS showed the reaction was complete. The reaction mixture was poured into ice-cold water and extracted with EtOAc (50 mL×2), washed with brine (30 mL×2), dried (Na$_2$SO$_4$), filtered, and evaporated in vacuum to give crude product. The crude product was purified by HPLC separation (column: Phenomenex Synergi C18 150*30 mm*4 um, gradient: 80-93% B (A=0.05% HCl-ACN, B=acetonitrile), flow rate: 25 mL/min) for further purification to obtain 30 (28 mg) as a solid.

$^1$H NMR (CDCl$_3$, 400 MHz): δ=7.68 (s, 1H), 7.62 (d, J=8.0 Hz, 1H), 7.18 (d, J=7.6 Hz, 1H), 3.48 (t, J=8.6 Hz, 1H), 2.28-2.46 (m, 7H), 1.63-1.78 (m, 6H), 1.25-1.55 (m, 8H), 1.20 (s, 3H), 0.86-1.18 (m, 7H), 0.65-0.77 (m, 2H), 0.61 (s, 3H). LCMS Rt=3.488 min in 4.0 min chromatography, 10-80 AB, MS ESI calcd. for C$_{28}$H$_{41}$O$_2$[M+H]+ 409.3, found 409.1.

Example 32

Synthesis of Compound 31

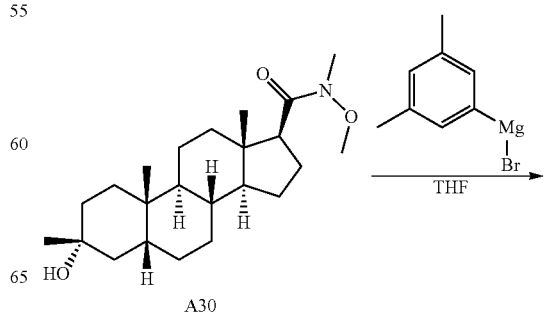

-continued

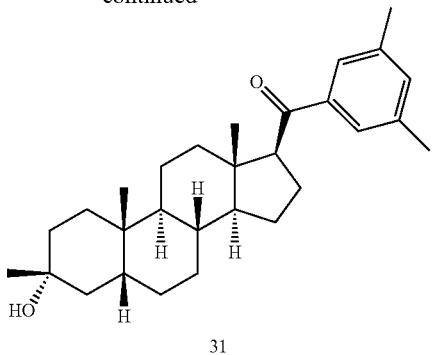

31

To a stirred solution of A30 (100 mg, 264 umol) in 3 mL of THF was added (3,5-dimethylphenyl)magnesium bromide (0.5 M, 2.62 mL, 1.31 mmol) dropwise at 25° C. After stirring at 25° C. for 12 hrs, LCMS showed the reaction was complete. The reaction mixture was poured into ice-cold water and extracted with EtOAc (50 mL×2), washed with brine (30 mL×2), dried (Na$_2$SO$_4$), filtered, and evaporated in vacuo to give crude product. The crude product was purified by HPLC separation (column: Phenomenex Synergi C18 150*30 mm*4 um, gradient: 80-100% B (A=0.05% HCl-ACN, B=acetonitrile), flow rate: 30 mL/min) to obtain 31 (15.3 mg) as a solid.

$^1$HNMR (CDCl$_3$, 400 MHz): δ=7.46 (s, 2H), 7.16 (s, 1H), 3.46 (t, J=8.8 Hz, 1H), 2.36 (s, 7H), 1.97 (t, J=13.2 Hz, 1H), 1.82-1.89 (m, 1H), 1.74 (br. s., 4H), 1.31-1.51 (m, 9H), 1.20-1.31 (m, 6H), 0.97-1.20 (m, 4H), 0.91 (s, 3H), 0.58 (s, 3H). LCMS Rt=3.478 min in 4.0 min chromatography, 10-80 AB, MS ESI calcd. for C$_{29}$H$_{43}$O$_2$ [M+H]$^+$ 423.3, found 405.1 [M–H$_2$O]$^+$.

Example 33

Synthesis of Compound 32

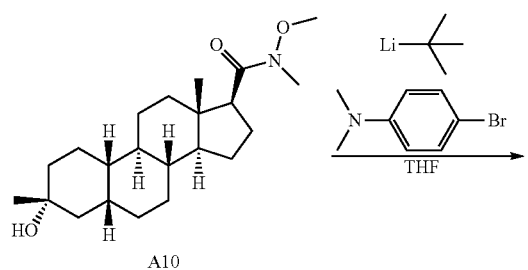

32

To a stirred solution of 4-bromo-N,N-dimethylaniline (1.3 M, 1.92 mL, 2.50 mmol) was added tert-butyllithium dropwise at –78° C. After stirring at –78° C. for 2 hrs, A10 (100 mg, 0.264 mmol was added. The mixture was stirred at –78° C. for 1 hour. LCMS showed the reaction was complete. The reaction mixture was quenched with NH$_4$Cl (30 mL). The mixture was extracted with EtOAc (20 mL×2), washed with brine (30 mL), dried over (Na$_2$SO$_4$), filtered, and evaporated in vacuo to give crude product. The crude product was purified by HPLC separation (column: Boston Green ODS 150*30 5u, gradient: 85-100% B (A=0.05% HCl-ACN, B=acetonitrile), flow rate: 25 ml/min) for further purification to afford 32 (11.9 mg) as a solid.

$^1$HNMR (CDCl$_3$, 400 MHz): δ=7.87 (d, J=9.0 Hz, 2H), 6.65 (d, J=9.0 Hz, 2H), 3.46 (t, J=8.6 Hz, 1H), 3.06 (s, 6H), 2.38-2.51 (m, 1H), 1.78-1.90 (m, 3H), 1.69-1.77 (m, 2H), 1.58-1.67 (m, 2H), 1.29-1.57 (m, 12H), 1.27 (s, 4H), 1.05-1.18 (m, 2H), 0.89-1.01 (m, 1H), 0.62 (s, 3H).

LCMS Rt=2.443 min in 4.0 min chromatography, 30-90 AB, MS ESI calcd. for C$_{28}$H$_{42}$NO$_2$ [M+H]+424.31, found 424.1.

Example 34

Synthesis of Compound 33

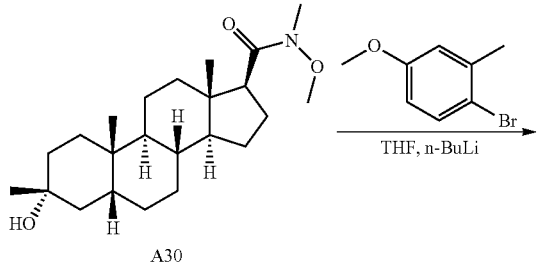

33

To a stirred solution of 1-bromo-4-methoxy-2-methylbenzene (2.5 M; 0.524 mL, 1.31 mmol) was added tert-butyllithium dropwise at –78° C. After stirring at –78° C. for 2 hrs, A30 (100 mg, 0.264 mmol was added. The mixture was stirred at –78° C. for 1 hour. LCMS showed the reaction was complete. The reaction mixture was quenched with NH$_4$Cl (30 mL). The mixture was extracted with EtOAc (20 mL×2), washed with brine (30 mL), dried over (Na$_2$SO$_4$), filtered, and evaporated under vacuo to give crude product. The crude product was purified by HPLC separation (column: Phenomenex Synergi C18 150*30 mm*4 um, gradient: 75-100% B (A=0.05% HCl-ACN, B=acetonitrile), flow rate: 30 mL/min) to afford 33 (13.5 mg) as a solid.

$^1$HNMR (CDCl$_3$, 400 MHz): δ=7.53 (d, J=8.0 Hz, 1H), 6.69-6.75 (m, 2H), 3.83 (s, 3H), 3.49 (d, J=5.6 Hz, 1H), 3.33

(t, J=8.8 Hz, 1H), 2.46 (s, 3H), 2.34-2.40 (m, 1H), 1.93-1.98 (m, 1H), 1.63-1.76 (m, 4H), 1.32-1.50 (m, 8H), 1.22-1.30 (m, 7H), 0.96-1.17 (m, 5H), 0.87-0.92 (m, 3H), 0.60 (s, 3H) LCMS Rt=3.478 min in 3.0 min chromatography, 30-90 CD. MS ESI calcd. for $C_{29}H_{43}O_3$ $[M+H]^+$ 439.31, found 439.3.

Example 35

Synthesis of Compound 34

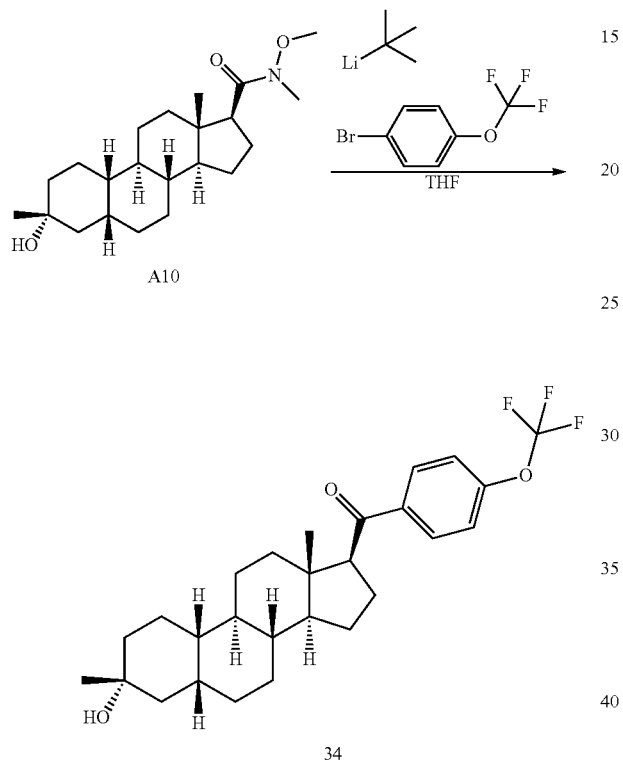

To a stirred solution of 1-bromo-4-(trifluoromethoxy) benzene (330 mg, 1.37 mmol) in 3 mL of THF was added tert-butyllithium (1.3 M; 2.0 mL, 2.61 mmol) dropwise at −78° C. After stirring at −78° C. for 2 hrs, A10 (100 mg, 0.275 mmol) was added. The mixture was stirred at −78° C. for 1 hour. LCMS showed the reaction was complete. The reaction mixture was quenched with $NH_4Cl$ (30 mL). The mixture was extracted with EtOAc (20 mL×2), washed with brine (30 mL), dried over $(Na_2SO_4)$, filtered, and evaporated in vacuo to give crude product. The crude product was purified by HPLC separation (column: Phenomenex Synergi C18 150*30 mm*4 um, gradient: 80-100% B (A=0.05% HCl-ACN, B=acetonitrile), flow rate: 30 mL/min) to obtain 34 (57 mg) as a solid.

$^1$H NMR (CDCl$_3$, 400 MHz): δ=7.93 (d, J=8.6 Hz, 2H), 7.26-7.29 (m, 2H), 3.45 (t, J=8.8 Hz, 1H), 2.37-2.46 (m, 1H), 1.73-1.86 (m, 5H), 1.58-1.65 (m, 2H), 1.41-1.50 (m, 3H), 1.37 (d, J=12.6 Hz, 6H), 1.24-1.33 (m, 7H), 1.06-1.17 (m, 2H), 0.87-0.97 (m, 1H), 0.60 (s, 3H). LCMS Rt=3.467 min in 4.0 min chromatography, 10-80 AB, MS ESI calcd. for $C_{27}H_{36}F_3O_3$ $[M+H]^+$ 465.26, found 447.2 $[M-H_2O]^+$.

Example 36

Synthesis of Compound 35

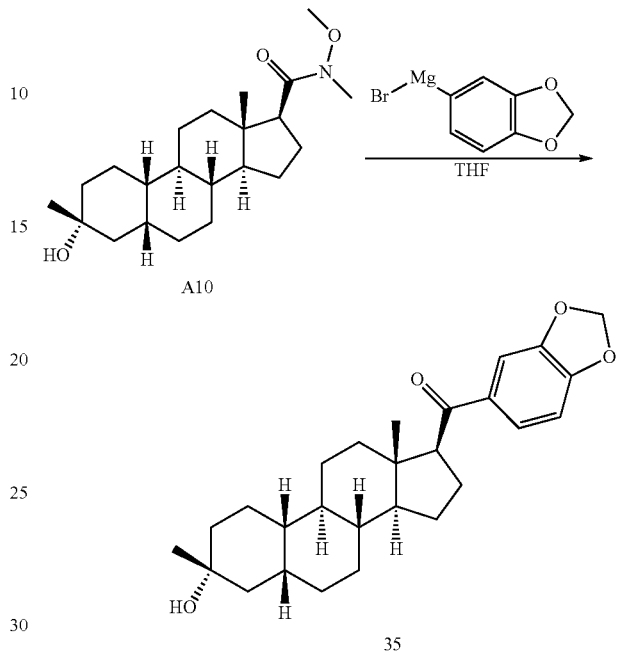

To a solution of A10 (100 mg, 0.275 mmol) in THF (3 mL) was added benzo[d][1,3]dioxol-5-yl magnesium bromide (5.5 mL, 95%). The mixture was stirred at 20° C. for 3.5 h. When TLC showed starting material was consumed and new spot was produced, to the mixture was added sat. aq. $NH_4Cl$ (5 mL). The organic phase was extracted with DCM (5 mL*2), washed with sat. aq. NaCl (8 mL×2), concentrated in vacuum. The residue was purified by preparative HPLC to give 35 (30 mg) as a solid.

$^1$H NMR (400 MHz, CDCl$_3$) δ7.49 (dd, J=1.6, 8.2 Hz, 1H), 7.40 (d, J=1.5 Hz, 1H), 6.83 (d, J=8.0 Hz, 1H), 6.03 (s, 2H), 3.40 (t, J=8.5 Hz, 1H), 2.47-2.35 (m, 1H), 1.82-1.73 (m, 4H), 1.66-1.58 (m, 2H), 1.50-1.25 (m, 17H), 1.19-0.87 (m, 3H), 0.60 (s, 3H). LCMS Rt=1.391 min in 2 min chromatography, 10-80 AB, MS ESI calcd. for $C_{27}H_{37}O_4$ $[M+H]^+$ 425.26, found 407 $[M-H_2O]^+$.

Example 37

Synthesis of Compound 36

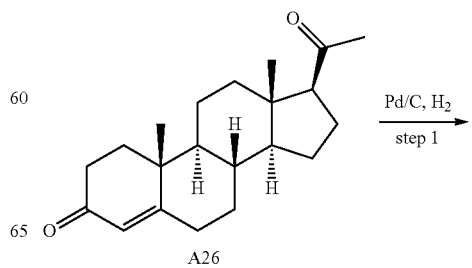

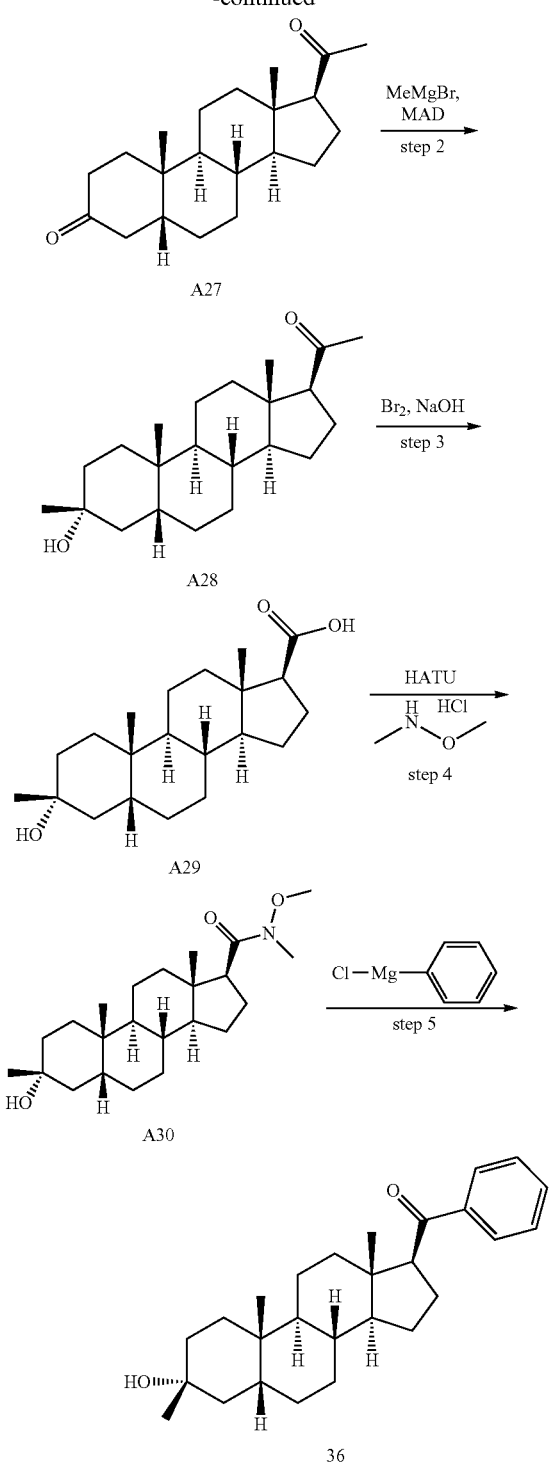

Step 1. The mixture of A26 (40 g, 127 mmol) and Pd/C (4 g) in ethyl acetate (200 mL) and THF (200 mL) was stirred at 25° C. under H (15 psi) for 4 hours. TLC (PE:EA=5:1) showed the starting material was consumed completely. The reaction mixture was filtered, and the filtered cake was washed with ethyl acetate (40 mL×5). The combined organic phase was concentrated under vacuum to give A27 (41 g, crude) as a solid $^1$H NMR (400 MHz, CDCl$_3$) δ=2.69 (t, J=14.1 Hz, 1H), 2.61-2.48 (m, 1H), 2.43-2.25 (m, 1H), 2.24-1.96 (m, 8H), 1.95-1.78 (m, 2H), 1.75-1.07 (m, 15H), 1.03 (s, 3H), 0.64 (s, 3H)

Step 2. To a solution of 2,6-di-tert-butyl-4-methylphenol (170 g, 774 mmol) in toluene (150 mL) was added trimethylaluminum (193 mL, 387 mmol, 2.0 M in toluene) dropwise blew 25° C. under N$_2$ atmosphere. The resulting mixture was stirred at 25° C. for 1 hour. A27 (41 g, 129 mmol) in toluene (50 mL) was added at −78° C. The mixture was stirred at −78° C. for 1 hour. Methylmagnesium bromide (129 mL, 387 mmol, 3.0 M in diethyl ether) was added at −78° C. The reaction mixture was stirred at −78° C. for 4 hours. TLC (PE:EA=2:1) showed the starting material was consumed completely. The mixture was quenched by saturated aqueous NH$_4$Cl (20 mL), extracted with ethyl acetate (150 mL×2). The combined organic phase was washed with brine (150 mL), dried over anhydrous Na$_2$SO$_4$. The ethyl acetate solvent was evaporated to afford crude solid, which was purified by chromatography on silica gel (PE/EtOAc=7/1) to afford desired product A28 (36 g) as light solid.

$^1$H NMR (400 MHz, CDCl$_3$) δ=2.58-2.46 (m, 1H), 2.22-2.09 (m, 4H), 2.06-1.79 (m, 3H), 1.78-0.99 (m, 25H), 0.94 (s, 3H), 0.59 (s, 3H).

Step 3. Liquid bromine (5.76 g, 36.0 mmol) was added slowly to a vigorously stirred sodium hydroxide aqueous (48.0 mL, 3 M, 144 mmol) at 0° C. When all the bromine was dissolved, the mixture was diluted with cold dioxane (10 mL) and was added slowly to a stirred solution of 1 A28 (4 g, 12.0 mmol) in dioxane (15 mL) and water (10 mL). The homogeneous yellow solution became colorless slowly and a white precipitate was formed. The reaction mixture was stirred at 25° C. for 16 hours. The remaining oxidizing reagent was quenched by Na$_2$S$_2$O$_3$ aqueous (30 mL) and the mixture was then heated at 80° C. until the solid material was dissolved. Acidification of the solution with hydrochloride acid (3 N) furnished a white precipitate. The solid was filtered and washed with water (100 mL×3) to give a white solid, which was dried under vacuum to afford A29 (4.01 g, 100%) as a solid.

$^1$H NMR (400 MHz, CDCl$_3$) δ=11.90 (br. s, 1H), 4.24 (s, 1H), 2.28 (t, J=9.0 Hz, 1H), 2.01-1.54 (m, 8H), 1.50-1.28 (m, 6H), 1.26-0.92 (m, 13H), 0.91 (s, 3H), 0.61 (s, 3H)

Step 4. To a suspension of A29 (4.01 g, 11.9 mmol) and N,O-dimethylhydroxylamine hydrochloride (4.64 g, 47.6 mmol) in DMF (40 mL) was added HATU (9.04 g, 23.8 mmol) at 25° C. DIPEA (15.3 g, 119 mmol) was added to the resulting mixture. The reaction mixture was stirred at 25° C. for 2 hours. TLC (PE:EA=2:1) showed the starting material was consumed completely. H$_2$O (500 mL) was added to the reaction mixture at 25° C. A precipitate in the mixture was filtrated to give a light solid, which was washed with water (40 mL×3), dried under vacuum to afford A30 (4.31 g, 95.9%) as a solid.

$^1$H NMR (400 MHz, CDCl$_3$) δ=11.90 (br. s., 1H), 4.24 (s, 1H), 2.28 (t, J=9.0 Hz, 1H), 2.01-1.54 (m, 8H), 1.50-1.28 (m, 6H), 1.26-0.92 (m, 13H), 0.91 (s, 3H), 0.61 (s, 3H)

Step 5. To a solution of B30 (0.1 g, 0.264 mmol) in THF (2 mL) was added phenylmagnesium chloride (5.26 mL, 2.63 mmol, 0.5M in THF) under N$_2$. The reaction mixture was stirred at 15° C. for 16 hours. LCMS indicated the reaction was finished and desired MS peak was found. To the reaction mixture was added saturated NH$_4$Cl solution (5 mL) and then extracted with EtOAc (2 mL×3). The combined organic phase was concentrated and purified by prep-HPLC to give 36 (20.6 mg) as a solid.

¹H NMR (400 MHz, CDCl₃) δ7.88-7.86 (m, 2H), 7.54-7.51 (m, 1H), 7.45-7.41 (m, 2H), 3.50-3.46 (m, 1H), 2.45-2.38 (m, 1H), 1.80-0.72 (m, 25H), 0.70 (s, 3H), 0.59 (s, 3H). LCMS Rt=1.466 min in 2 min chromatography, 10-80 AB, MS ESI calcd. for $C_{27}H_{39}O_2[M+H]^+$ 395.29, found 377 $[M-H_2O]^+$.

Example 38

Synthesis of Compound 37

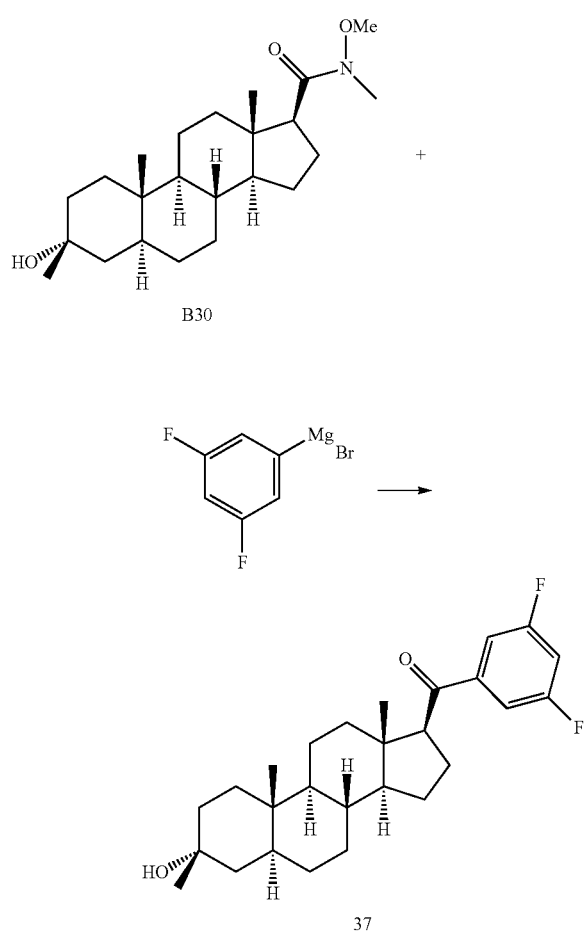

To a solution of B30 (0.1 g, 0.264 mmol) in THF (2 mL) was added (3,5-difluorophenyl)magnesium bromide (5.26 mL, 2.63 mmol, 0.5M in THF) under N₂. The reaction mixture was stirred at 15° C. for 16 hours. LCMS indicated the reaction was finished and desired MS peak was found. To the reaction mixture was added saturated NH₄Cl solution (5 mL) and then extracted with EtOAc (2 mL×3). The combined organic phase was concentrated and purified by prep-HPLC to give 37 (14.2 mg) as a solid.

¹H NMR (400 MHz, CDCl3) δ7.37 (d, J=6.0 Hz, 2H), 7.04-6.89 (m, 1H), 3.40-3.28 (m, 1H), 2.47-2.30 (m, 1H), 1.87-1.65 (m, 3H), 1.19 (s, 19H), 0.72 (s, 4H), 0.59 (s, 3H). LCMS Rt=1.540 min in 2 min chromatography, 10-80 AB, MS ESI calcd. for $C_{27}H_{37}F_2O_2$ $[M+H]^+$ 431.27, found 413 $[M-H_2O]^+$, Example 39

Synthesis of Compound 38

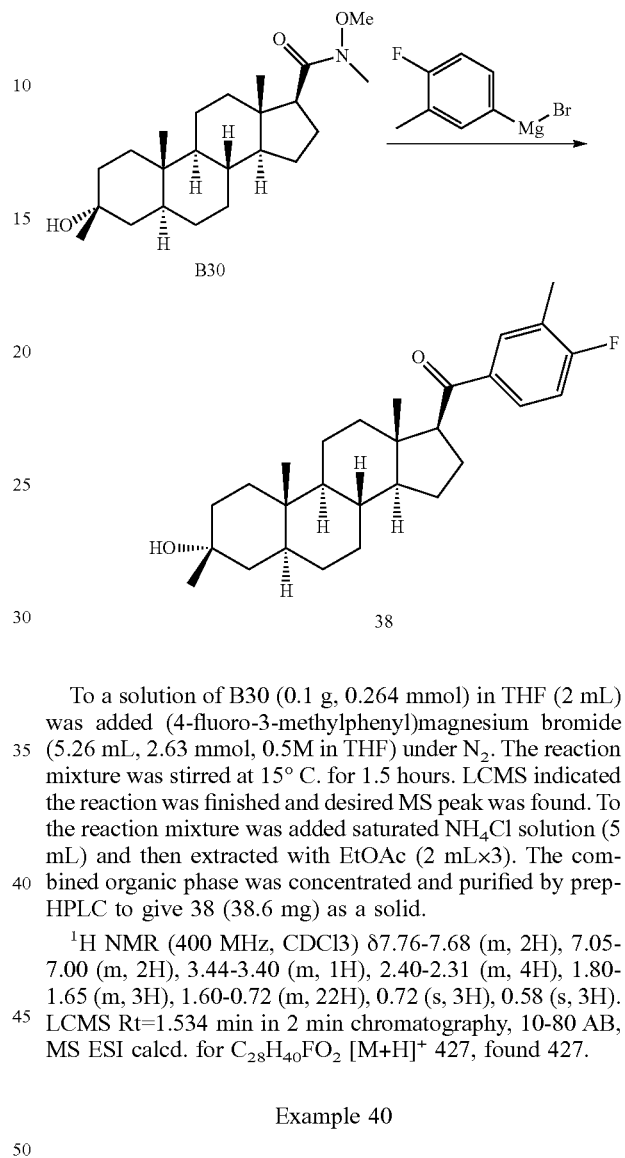

To a solution of B30 (0.1 g, 0.264 mmol) in THF (2 mL) was added (4-fluoro-3-methylphenyl)magnesium bromide (5.26 mL, 2.63 mmol, 0.5M in THF) under N₂. The reaction mixture was stirred at 15° C. for 1.5 hours. LCMS indicated the reaction was finished and desired MS peak was found. To the reaction mixture was added saturated NH₄Cl solution (5 mL) and then extracted with EtOAc (2 mL×3). The combined organic phase was concentrated and purified by prep-HPLC to give 38 (38.6 mg) as a solid.

¹H NMR (400 MHz, CDCl3) δ7.76-7.68 (m, 2H), 7.05-7.00 (m, 2H), 3.44-3.40 (m, 1H), 2.40-2.31 (m, 4H), 1.80-1.65 (m, 3H), 1.60-0.72 (m, 22H), 0.72 (s, 3H), 0.58 (s, 3H). LCMS Rt=1.534 min in 2 min chromatography, 10-80 AB, MS ESI calcd. for $C_{28}H_{40}FO_2$ $[M+H]^+$ 427, found 427.

Example 40

Synthesis of Compound 39

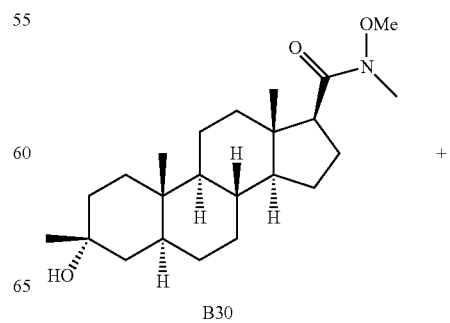

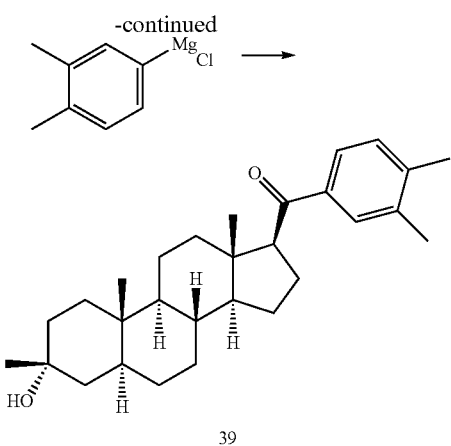

To a solution of B30 (0.1 g, 0.264 mmol) in THF (2 mL) was added (3,4-dimethylphenyl)magnesium chloride (5.26 mL, 2.63 mmol, 0.5M in THF) under $N_2$. The reaction mixture was stirred at 15° C. for 4 hours. LCMS indicated the reaction was finished and desired MS peak was found. To the reaction mixture was added saturated $NH_4Cl$ solution (5 mL) and then extracted with EtOAc (2 mL×3). The combined organic phase was concentrated and purified by prep-HPLC to give 39 (27.8 mg) as a solid.

$^1$H NMR (400 MHz, CDCl3) δ7.69-7.65 (m, 1H), 7.64-7.58 (m, 1H), 7.22-7.15 (m, 1H), 3.50-3.41 (m, 1H), 2.46-2.35 (m, 1H), 2.31 (s, 6H), 1.81-1.66 (m, 3H), 1.61-1.05 (m, 20H), 1.04-0.89 (m, 1H), 0.82-0.73 (m, 1H), 0.71 (s, 3H), 0.59 (s, 3H). LCMS Rt=1.536 min in 2 min chromatography, 10-80 AB, MS ESI calcd. for $C_{29}H_{43}O_2[M+H]^+$ 423, found 423.

Example 41

Synthesis of Compound 40

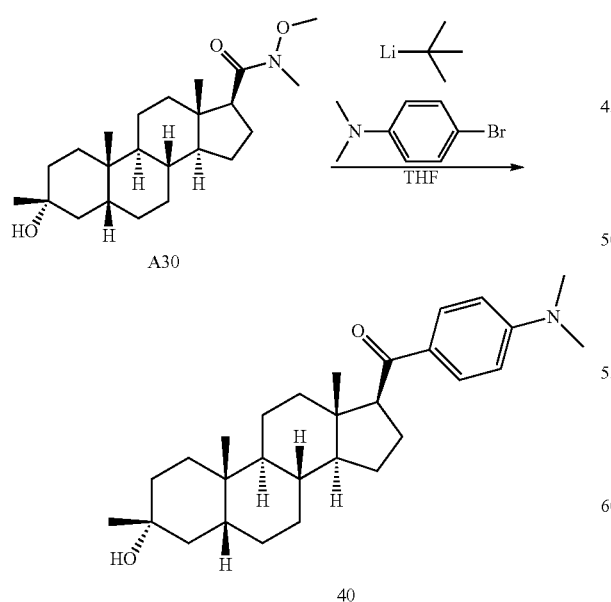

To a stirred solution of 4-bromo-N,N-dimethylaniline (262 mg, 1.31 mmol) in 3 mL of THF was added tert-butyllithium (1.3 M; 1.92 mL, 2.50 mmol) dropwise at −78° C. After stirring at −78° C. for 2 hrs, A30 (100 mg, 0.264 mmol was added. The mixture was stirred at −78° C. for 1 hour. LCMS showed the reaction was complete. The reaction mixture was quenched with $NH_4Cl$ (30 mL). The mixture was extracted with EtOAc (20 mL×2), washed with brine (30 mL), dried over ($Na_2SO_4$), filtered, and evaporated in vacuo to give crude product. The crude product was purified by HPLC separation (column: Phenomenex Synergi C18 150*30 mm*4 um, gradient: 75-100% B (A=0.05% HCl-ACN, B=acetonitrile), flow rate: 30 mL/min) for further purification to obtain 40 (11.2 mg) as a solid.

$^1$HNMR (CDCl$_3$, 400 MHz): δ=7.86 (d, J=9.0 Hz, 2H), 6.64 (d, J=9.0 Hz, 2H), 3.44 (t, J=8.6 Hz, 1H), 3.05 (s, 6H), 2.39-2.45 (m, 1H), 1.99 (d, J=12.0 Hz, 1H), 1.84 (d, J=13.6 Hz, 2H), 1.63-1.77 (m, 4H), 1.35-1.51 (m, 9H), 1.20-1.29 (m, 6H), 1.10-1.18 (m, 2H), 1.04 (dd, J=14.6 Hz, 1H), 0.91 (s, 3H), 0.59 (s, 3H). LCMS Rt=2.511 min in 4.0 min chromatography, 30-30 AB, MS ESI calcd. for $C_{29}H_{44}NO_2$ [M+H]+ 438.33, found 438.1.

Example 42

Synthesis of Compound 41

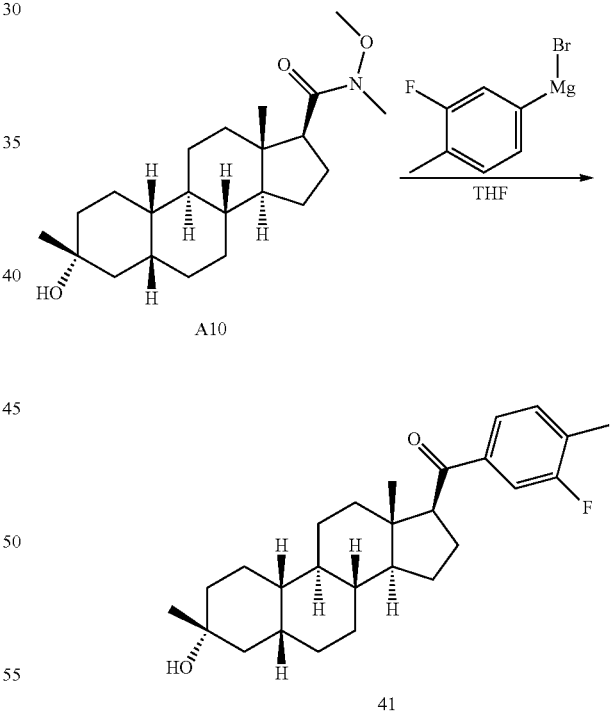

To a solution of A10 (100 mg, 0.275 mmol) in THF (3 mL) was added (3-fluoro-4-methylphenyl)magnesium bromide (5.5 mL, 95%). The mixture was stirred at 20° C. for 3.5 h. When TLC showed starting material was consumed and new spot was produced, to the mixture was added sat. aq. $NH_4Cl$ (5 mL). The organic phase was extracted with DCM (5 mL×2), washed with sat. aq. NaCl (8 mL×2), concentrated in vacuum. The residue was purified by preparative. HPLC twice to give 41 (58 mg) as a solid.

$^1$H NMR (400 MHz, CDCl$_3$) δ 7.59-7.49 (m, 2H), 7.25-7.20 (m, 1H), 3.41 (t, J=8.8 Hz, 1H), 2.47-2.36 (m, 1H), 2.32 (d, J=1.5 Hz, 3H), 1.82-1.75 (m, 4H), 1.69-1.57 (m, 2H), 1.50-1.25 (m, 17H), 1.18-1.04 (m, 2H), 1.00-0.84 (m, 1H), 0.60 (s, 3H). LCMS Rt=1.476 min in 2 min chromatography, 10-80 AB, MS ESI calcd. for C$_{27}$H$_{37}$F$_2$O [M+H]$^+$ 413.28, found 395 [M−H$_2$O]$^+$.

Example 43

Synthesis of Compound 42

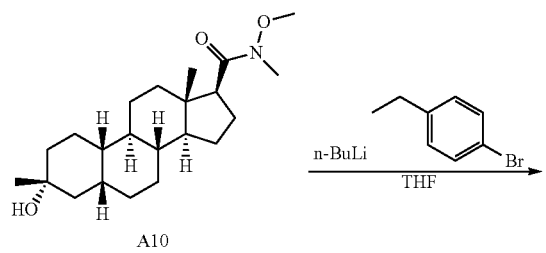

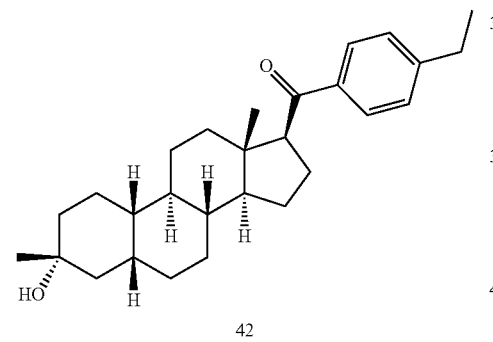

42

To a solution of 1-bromo-4-ethylbenzene (305 mg, 1.65 mmol) in THF (3 mL) was added butyllithium (0.66 mL, 0.825 mmol) dropwise at −68° C. The mixture was stirred at −68 OC for 2 h. A10 (120 mg, 0.33 mmol) in 1 mL THF was added dropwise at −68° C. The reaction was stirred at −68 OC for 2 hours. LCMS showed the reaction was complete. The reaction was quenched with NH$_4$Cl (20 mL), extracted with EtOAc (20 mL×2). The combined organic layers were washed with brine (10 mL). The organic layer was dried over Na$_2$SO$_4$, filtered and evaporated to afford crude product. The crude product was purified by prep-HPLC to give 42 (46.4 mg, 0.113 mmol) as a solid.

$^1$H NMR (400 MHz, CDCl$_3$) δ=7.82 (d, J=8.0 Hz, 2H), 7.25 (s, 1H), 3.49 (t, J=8.8 Hz, 1H), 2.70 (q, J=7.7 Hz, 2H), 2.48-2.38 (m, 1H), 1.87-1.69 (m, 5H), 1.69-1.55 (m, 2H), 1.54-1.41 (m, 4H), 1.41-1.34 (m, 5H), 1.34-1.21 (m, 11H), 1.20-1.01 (m, 2H), 1.00-0.84 (m, 1H), 0.61 (s, 3H). LCMS t$_R$=1.299 min in 2 min chromatography, 30-90 AB, MS ESI calcd. for C$_{28}$H$_{40}$O$_2$ [M]$^+$ 408, found 408.

Example 44

Synthesis of Compound 43

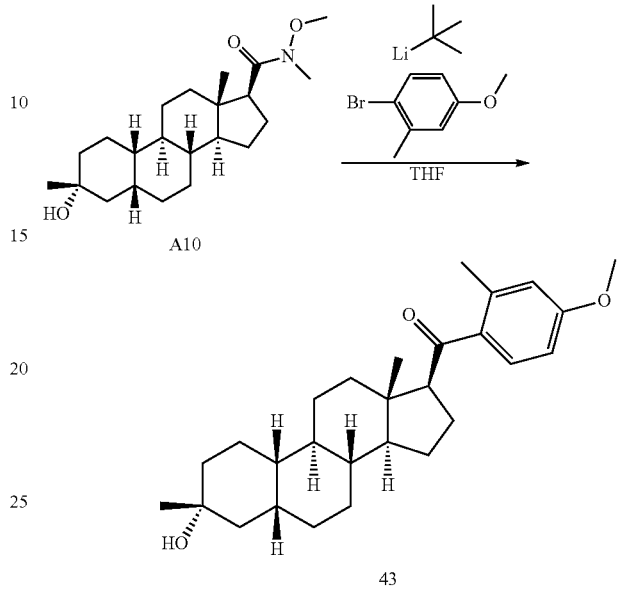

43

To a stirred solution of 1-bromo-4-methoxy-2-methylbenzene (275 mg, 1.37 mmol) in 3 mL of THF was added tert-butyllithium (1.3 M, 2.00 mL, 2.61 mmol) dropwise at −78° C. After stirring at −78° C. for 2 hrs, A10 (100 mg, 0.275 mmol was added. The mixture was stirred at −78° C. for 1 hour. LCMS showed the reaction was complete. The reaction mixture was quenched with NH$_4$Cl (30 mL). The mixture was extracted with EtOAc (20 mL×2), washed with brine (30 mL), dried over (Na$_2$SO$_4$), filtered, and evaporated in vacuum to give crude product. The crude product was purified by HPLC separation (column: Phenomenex Synergi C18 150*30 mm*4 um, gradient: 70-100% B (A=0.05% HCl-ACN, B=acetonitrile), flow rate: 30 mL/min) for further purification to obtain 42 (20 mg) as a solid.

$^1$HNMR (CDCl3, 400 MHz): δ=7.54 (d, J=8.6 Hz, 1H), 6.68-6.77 (m, 2H), 3.83 (s, 3H), 3.34 (t, J=8.8 Hz, 1H), 2.47 (s, 3H), 2.34-2.42 (m, 1H), 1.69-1.85 (m, 5H), 1.57-1.68 (m, 2H), 1.22-1.50 (m, 14H), 0.97-1.22 (m, 4H), 0.86-0.93 (m, 1H), 0.62 (s, 3H). LCMS Rt=2.600 min in 4.0 min chromatography, 30-90 AB, MS ESI calcd. for C$_{28}$H$_{41}$O$_3$[M+H]+ 425.3, found 425.2.

Example 45

Synthesis of Compound 44

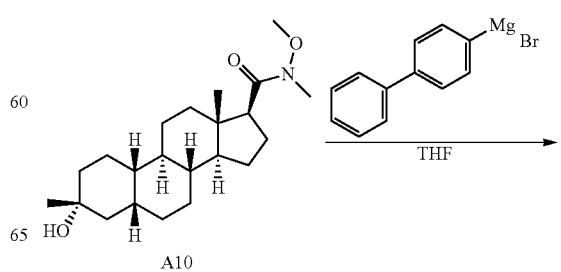

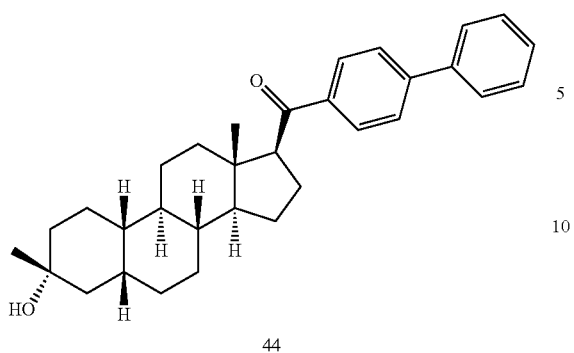

44

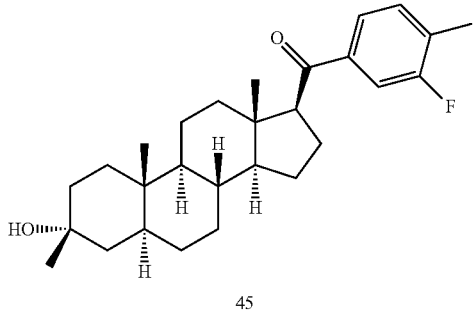

45

To a solution of A10 (150 mg, 0.412 mmol) in THF (3 mL) was added [1,1'-biphenyl]-4-yl magnesium bromide (8.22 mL, 0.5 M in THF). The mixture was stirred at 20° C. for 3.5 h. When TLC showed starting material was consumed and new spot was produced, to the mixture was added sat. aq. NH$_4$Cl (5 mL). The organic phase was extracted with DCM (5 mL*2), washed with sat. aq. NaCl (8 mL*2), concentrated in vacuum. The residue was purified by prep. HPLC to give 44 (113 mg) as a solid.

$^1$H NMR (400 MHz, CDCl$_3$) δ7.96 (d, J=8.3 Hz, 2H), 7.69-7.61 (m, 4H), 7.50-7.44 (m, 2H), 7.42-7.36 (m, 1H), 3.53 (t, J=8.7 Hz, 1H), 2.52-2.37 (m, 1H), 1.79 (d, J=10.3 Hz, 5H), 1.68-1.61 (m, 1H), 1.51-0.88 (m, 20H), 0.63 (s, 3H). LCMS Rt=1.081 min in 1.5 min chromatography, 5-95 AB, MS ESI calcd. for C$_{32}$H$_{41}$O$_2$[M+H]$^+$ 457.3, found 439[M–H$_2$O]$^+$.

To a solution of B30 (0.1 g, 0.264 mmol) in THF (2 mL) was added (3-fluoro-4-methylphenyl)magnesium bromide (5.26 mL, 2.63 mmol, 0.5M in THF) under N$_2$. The reaction mixture was stirred at 15° C. for 16 hours. LCMS indicated the reaction was finished and desired MS peak was found. To the reaction mixture was added saturated NH$_4$Cl solution (5 mL) and then extracted with EtOAc (2 mL×3). The combined organic phase was concentrated and purified by prep-HPLC to give 45 (22.7 mg) as a solid.

$^1$H NMR (400 MHz, CDCl3) δ7.64-7.47 (m, 2H), 7.25-7.17 (m, 1H), 3.47-3.36 (m, 1H), 3.10-2.91 (m, 2H), 2.32 (s, 4H), 1.87-1.06 (m, 21H), 1.04-0.90 (m, 1H), 0.71 (s, 4H), 0.58 (s, 3H). LCMS Rt=1.541 min in 2 min chromatography, 10-80 AB, MS ESI calcd. for C$_{28}$H$_{40}$FO$_2$ [M+H]$^+$ 427, found 409 [M–H$_2$O]$^+$.

Example 46

Synthesis of Compound 45

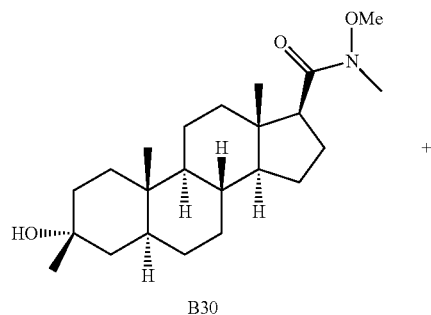

B30

+

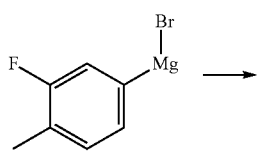

Example 47

Synthesis of Compound 46

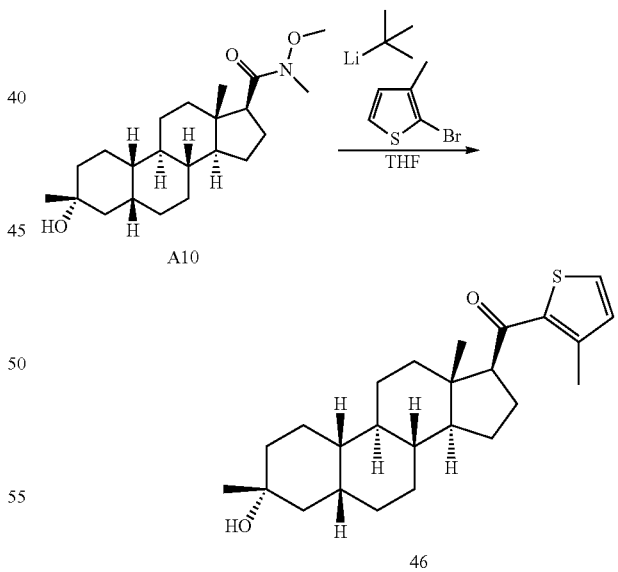

To a stirred solution of 2-bromo-3-methylthiophene (242 mg, 1.37 mmol) in 3 mL of THF was added tert-butyllithium (1.3 M: 2.00 mL, 2.61 mmol) dropwise at –78° C. After stirring at –78° C. for 2 hrs. A10 (100 mg, 0.275 mmol was added. The mixture was stirred at –78° C. for 1 hour. LCMS showed the reaction was complete. The reaction mixture was quenched with NH$_4$Cl (30 mL). The mixture was extracted with EtOAc (20 mL×2), washed with brine (30 mL), dried over (Na2SO4), filtered, and evaporated in vacuum to give crude product. The crude product was purified by HPLC separation (column: Phenomenex Synergi C18 150*30 mm*4 um, gradient: 80-100% B (A=0.05% HCl-ACN, B=acetonitrile), flow rate: 30 mL/min) for further purification to obtain 46 (10 mg) as a solid.

$^1$HNMR (CDCl3, 400 MHz): δ=7.37 (d, J=5.0 Hz, 1H), 6.97 (d, 1=5.0 Hz, 1H), 3.16 (t, J=8.8 Hz, 1H), 2.57 (s, 3H), 2.31-2.42 (m, 1H), 1.72-1.87 (m, 5H), 1.65 (d, J=13.6 Hz, 2H), 1.32-1.56 (m, 12H), 1.28 (s, 4H), 1.08-1.21 (m, 2H), 0.93-1.06 (m, 1H), 0.71 (s, 3H). LCMS Rt=2.591 min in 4.0 min chromatography, 30-90 AB, MS ESI calcd. for $C_{25}H_{37}O_2S$ [M+H]+ 401.24, found 401.1.

Example 48

Synthesis of Compound 47

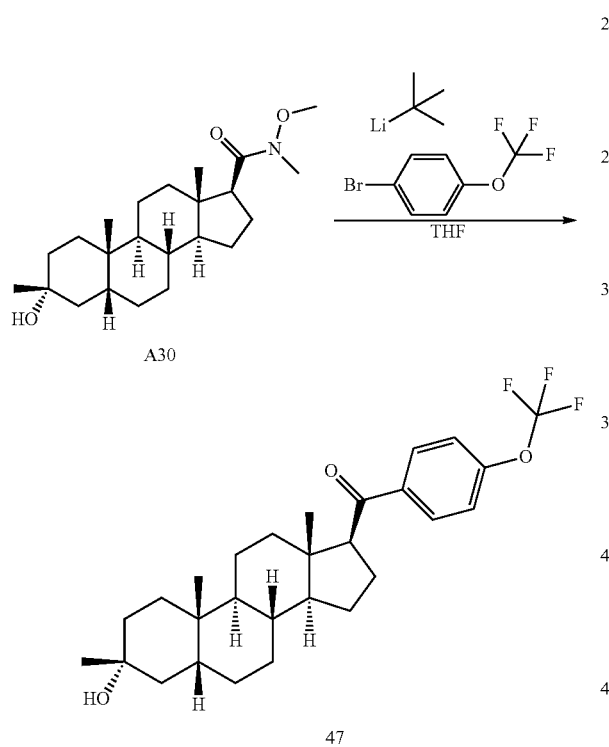

47

To a stirred solution of 1-bromo-4-(trifluoromethoxy) benzene (315 mg, 1.31 mmol) in 3 mL of THF was added tert-butyllithium (1.3 M; 1.92 mL, 2.5 mmol) dropwise at −78° C. After stirring at −78° C. for 2 hrs, A30 (100 mg, 0.264 mmol was added. The mixture was stirred at −78° C. for 1 hour. LCMS showed the reaction was complete. The reaction mixture was quenched with NH4Cl (30 mL). The mixture was extracted with EtOAc (20 mL×2), washed with brine (30 mL), dried over (Na₂SO₄), filtered, and evaporated in vacuo to give crude product. The crude product was purified by HPLC separation (column: Phenomenex Synergi C18 150*30 mm*4 um, gradient: 80-100% B (A=0.05% HCl-ACN, B=acetonitrile), flow rate: 30 mL/min) for further purification to obtain 47 (19.3 mg) as a solid.

$^1$HNMR (CDCl₃, 400 MHz): δ=7.92 (d, J=8.0 Hz, 1H), 7.25 (d, J=7.0 Hz, 2H), 3.43 (br s, 1H), 2.31-2.47 (m, 1H), 1.62-2.01 (m, 6H), 1.32-1.53 (m, 11H), 1.19-1.30 (m, 6H), 0.97-1.17 (m, 3H), 0.90 (br. s., 3H), 0.57 (br. s., 3H). LCMS Rt=2.907 min in 4.0 min chromatography, 30-90 AB, MS ESI calcd. for $C_{28}H_{38}F_3O_3$ [M+H]⁺ 479.3, found 461.2 [M−H₂O]⁺.

Example 49

Synthesis of Compound 48

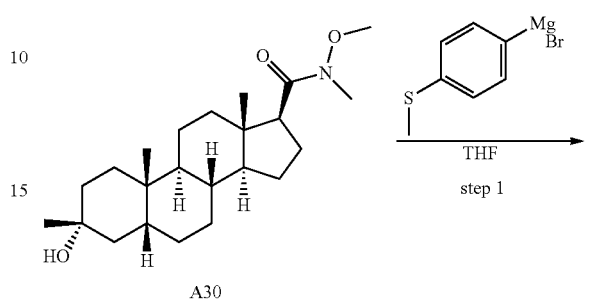

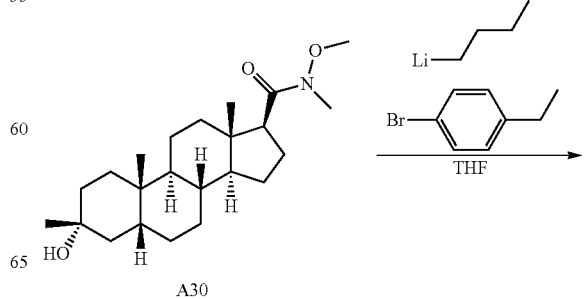

48

To a solution of A30 (100 mg, 264 μmol) in anhydrous THF (2 mL) was added (4-(methylthio)phenyl)magnesium bromide (5.26 mL, 0.5 M, 2.63 mmol) at 25° C. The reaction mixture was stirred at 25° C. for 2 hours. LCMS showed the starting material was consumed completely. The reaction was quenched with saturated NH₄Cl aqueous (1 mL), concentrated under vacuum to give a residue, which was purified by Prep-HPLC (0.05% HCl-ACN) to afford 48 (65.4 mg) as a solid.

$^1$H NMR (400 MHz, CDCl₃) δ=7.81 (d, J=8.0 Hz, 2H), 7.24 (s, 1H), 3.44 (t, J=8.8 Hz, 1H), 2.52 (s, 3H), 2.48-237 (m, 1H), 2.04-1.92 (m, 1H), 1.91-1.81 (m, 1H), 1.79-1.64 (m, 3H), 1.54-1.19 (m, 17H), 1.18-0.97 (m, 3H), 0.91 (s, 3H), 0.58 (s, 3H). LCMS $R_t$=1.441 min in 2 min chromatography, 10-80 AB, MS ESI calcd for $C_{28}H_{41}O_2S$ [M+H]⁺ 441.3, found 441.3 [M+H]⁺.

Example 50

Synthesis of Compound 49

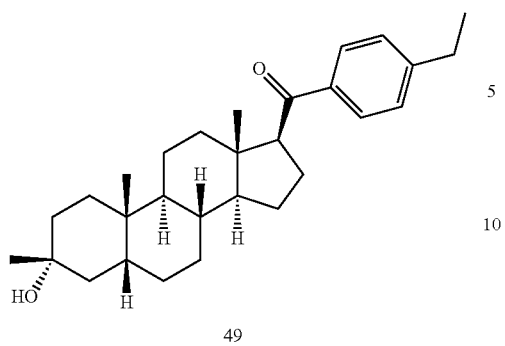

49

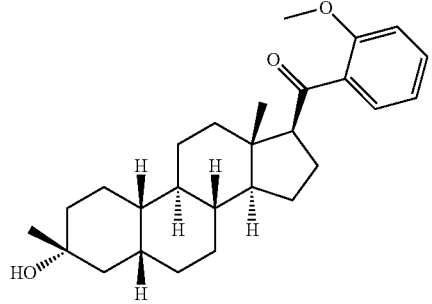

50

A solution of 1-bromo-4-ethylbenzene (366 mg, 1.98 mmol) in THF (3 mL) was added butyllithium (0.792 mL, 1.98 mmol) dropwise at −78° C. The mixture was stirred at −78° C. for 2 h. A30 in 1 mL THF was added dropwise at −78° C. The reaction was stirred at −78° C. for 2 hours. LCMS showed the reaction was complete. Then, the reaction was quenched with NH$_4$Cl (20 mL). Extracted with EtOAc (20 mL×2) The combined organic layers were washed with brine (10 mL). The organic layer was dried over Na$_2$SO$_4$, filtered and evaporated to afford crude product. The crude product was purified by prep-HPLC separation (column: Phenomenex Synergi C18 150*30 mm*4 um, gradient: 85-100% B (A=0.05% HCl-ACN, B=acetonitrile), flow rate: 30 mL/min) for further purification to obtain 49 (69.9 mg) as a solid.

$^1$HNMR (CDCl$_3$, 400 MHz): δ=7.82 (d, J=8.0 Hz, 2H), 7.25 (br s, 1H), 3.48 (t, J=8.8 Hz, 1H), 2.70 (q, J=7.6 Hz, 2H), 2.37-2.48 (m, 1H), 1.93-2.03 (m, 1H), 1.81-1.91 (m, 1H), 1.64-1.79 (m, 3H), 1.31-1.55 (m, 11H), 1.18-1.30 (m, 8H), 0.92-1.18 (m, 4H), 0.91 (s, 3H), 0.59 (s, 3H). LCMS Rt=3.492 min in 4.0 min chromatography, 10-80 AB, MS ESI calcd. for C$_{29}$H$_{43}$O$_2$ [M+H]$^+$423.32, found 405.1 [M−H$_2$O]$^+$.

Example 51

Synthesis of Compound 50

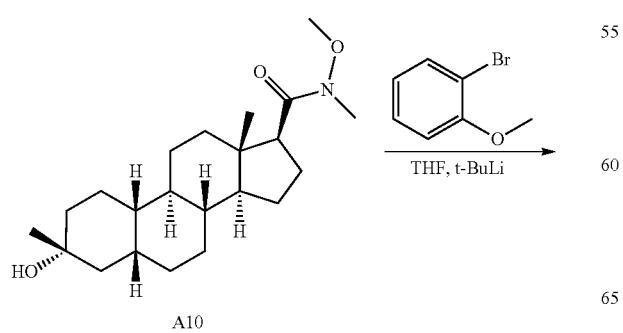

A solution of 1-bromo-2-methoxybenzene (514 mg, 2.75 mmol) in THF (3 mL) was added t-butyllithium (3.80 mL, 4.94 mmol) dropwise at −78° C. The mixture was stirred at −78° C. for 2 h. A10 (100 mg, 2.75 mmol) in THF (1 mL) was added dropwise at −78° C. The reaction was stirred at 15° C. for 2 hours. TLC showed the reaction was complete. The reaction was quenched with Sat. NH$_4$Cl (20 mL) and extracted with EtOAc (20 mL×2). The combined organic layers were washed with brine (10 mL). The organic layer was dried over Na$_2$SO$_4$, filtered and evaporated to afford crude product, which was purified by prep-HPLC to afford 50 (68 mg) as a solid.

$^1$H NMR (400 MHz, CDCl$_3$) δ 7.30-7.44 (m, 2 H) 6.88-7.00 (m, 2 H) 3.85 (s, 3 H) 3.54 (t, J=8.91 Hz, 1 H) 2.27-2.42 (m, 1 H) 1.53-1.89 (m, 8 H) 0.96-1.52 (m, 20 H) 0.79-0.92 (m, 1 H) 0.61 (s, 3 H). LCMS Rt=1.593 min in 2.0 min chromatography, 50-100 AB, MS ESI calcd. for C$_{27}$H$_{39}$O$_3$ [M+H]$^+$ 411, found 411.

Example 52

Synthesis of Compound 51

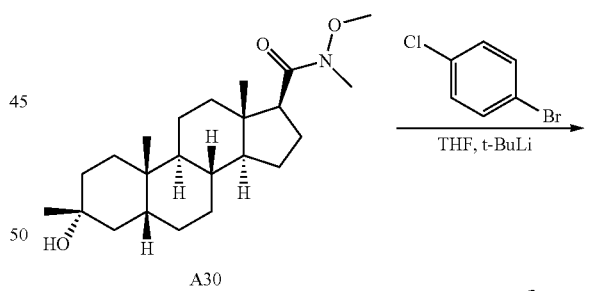

51

A solution of 1-bromo-4-chlorobenzene (503 mg, 2.63 mmol) in THF (3 mL) was added t-butyllithium (3.65 mL, 4.75 mmol) dropwise at −78° C. The mixture was stirred at −78° C. for 2 h. A30 (100 mg, 2.75 mmol) in THF (1 mL) was added dropwise at 15° C. The reaction was stirred at 15° C. for 2 hours. TLC showed the reaction was complete. The reaction was quenched with Sat. NH$_4$Cl (20 mL) and extracted with EtOAc (20 mL×2). The combined organic layers were washed with brine (10 mL), dried over Na$_2$SO$_4$, filtered and evaporated to afford crude product, which was purified by prep-HPLC to afford 51 (38 mg) as a solid.

$^1$H NMR (400 MHz, CDCl$_3$) δ 7.82 (d, J=8.53 Hz, 2 H) 7.41 (d, J=8.53 Hz, 2 H) 3.43 (t, J=8.78 Hz, 1 H) 2.33-2.49 (m, 1 H) 1.91-2.05 (m, 1 H) 1.63-1.91 (m, 4 H) 1.28-1.60 (m, 15 H) 0.98-1.28 (m, 10 H) 0.91 (s, 3 H) 0.58 (s, 3 H). LCMS Rt=0.976 min in 2.0 min chromatography, 50-100 AB, MS ESI calcd. for C$_{27}$H$_{38}$ClO$_2$ [M]$^+$ 430, found 429 [M]$^+$.

Example 53

Synthesis of Compound 52

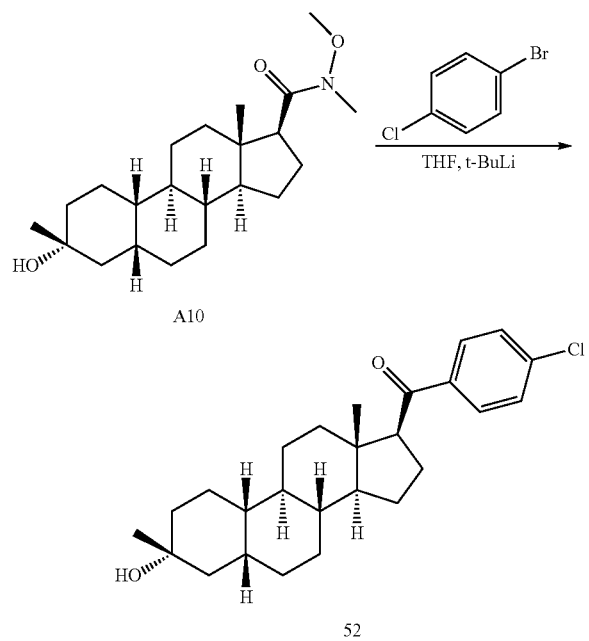

A solution of 1-bromo-4-chlorobenzene (526 mg, 2.75 mmol) in THF (3 mL) was added t-butyllithium (3.80 mL, 4.94 mmol) dropwise at −78° C. The mixture was stirred at −78° C. for 2 hrs. A10 (100 mg, 2.75 mmol) in THF (1 mL) was added dropwise at 15° C. The reaction was stirred at 15° C. for 2 hours. TLC showed the reaction was complete. The reaction was quenched with Sat. NH$_4$Cl (20 mL) and extracted with EtOAc (20 mL×2). The combined organic layers were washed with brine (10 mL), dried over Na$_2$SO$_4$, filtered and evaporated to afford crude product, which was purified by prep-HPLC separation to afford 52 (60 mg) as a solid.

$^1$H NMR (400 MHz, CDCl$_3$) δ 7.82 (d, J=8.53 Hz, 2 H) 7.41 (d, J=8.53 Hz, 2 H) 3.44 (t, J=8.66 Hz, 1 H) 2.35-2.48 (m, 1 H) 1.71-1.87 (m, 5 H) 1.22-1.70 (m, 21 H) 1.02-1.21 (m, 2 H) 0.85-0.99 (m, 1 H) 0.60 (s, 3 H). LCMS Rt=0.994 min in 2.0 min chromatography, 50-100 AB, MS ESI calcd. for C$_{26}$H$_{35}$ClO$_2$ [M+H]$^+$ 416.3, found 415 [M]$^+$.

Example 54

Synthesis of Compound 53

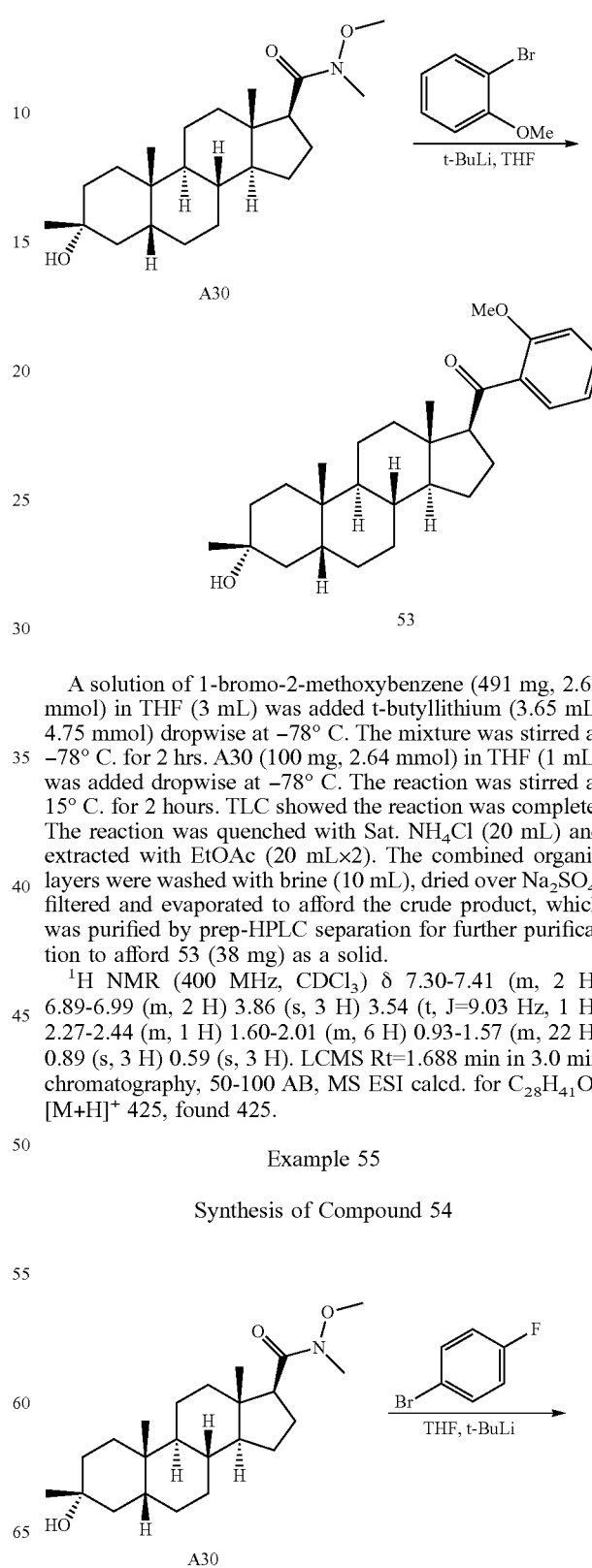

A solution of 1-bromo-2-methoxybenzene (491 mg, 2.63 mmol) in THF (3 mL) was added t-butyllithium (3.65 mL, 4.75 mmol) dropwise at −78° C. The mixture was stirred at −78° C. for 2 hrs. A30 (100 mg, 2.64 mmol) in THF (1 mL) was added dropwise at −78° C. The reaction was stirred at 15° C. for 2 hours. TLC showed the reaction was complete. The reaction was quenched with Sat. NH$_4$Cl (20 mL) and extracted with EtOAc (20 mL×2). The combined organic layers were washed with brine (10 mL), dried over Na$_2$SO$_4$, filtered and evaporated to afford the crude product, which was purified by prep-HPLC separation for further purification to afford 53 (38 mg) as a solid.

$^1$H NMR (400 MHz, CDCl$_3$) δ 7.30-7.41 (m, 2 H) 6.89-6.99 (m, 2 H) 3.86 (s, 3 H) 3.54 (t, J=9.03 Hz, 1 H) 2.27-2.44 (m, 1 H) 1.60-2.01 (m, 6 H) 0.93-1.57 (m, 22 H) 0.89 (s, 3 H) 0.59 (s, 3 H). LCMS Rt=1.688 min in 3.0 min chromatography, 50-100 AB, MS ESI calcd. for C$_{28}$H$_{41}$O$_3$ [M+H]$^+$ 425, found 425.

Example 55

Synthesis of Compound 54

-continued

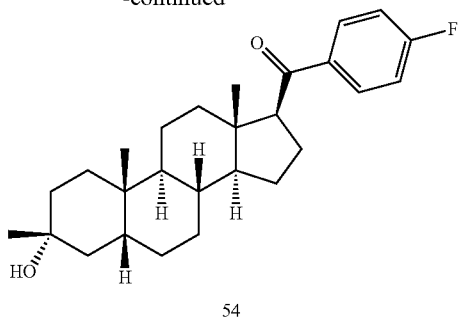

54

A solution of 1-bromo-4-fluorobenzene (460 mg, 2.63 mmol) in THF (3 mL) was added t-butyllithium (3.65 mL, 4.75 mmol) dropwise at −78° C. The mixture was stirred at −78° C. for 2 hrs. A30 (100 mg, 2.64 mmol) in THF (1 mL) was added dropwise at −78° C. The reaction was stirred at 15° C. for 2 hours. TLC showed the reaction was complete. The reaction was quenched with Sat. NH$_4$Cl (20 mL) and extracted with EtOAc (20 mL×2). The combined organic layers were washed with brine (10 mL). The organic layer was dried over Na$_2$SO$_4$, filtered and evaporated to afford crude product, which was purified by prep-HPLC to afford 54 (33 mg) as a solid.

$^1$H NMR (400 MHz, CDCl$_3$) δ 7.91 (dd, J=8.78, 5.52 Hz, 2 H), 7.11 (t, J=8.53 Hz, 2 H), 3.44 (t. J=8.78 Hz, 1 H), 2.33-2.48 (m, 1 H), 1.62-2.05 (m, 5 H), 1.56 (s, 4 H), 0.98-1.53 (m, 20 H), 0.86-0.95 (m, 3 H), 0.58 (s, 3 H). LCMS Rt=0.885 min in 2.0 min chromatography, 50-100 AB, MS ESI calcd. for C$_{27}$H$_{38}$FO$_2$ [M+H]$^+$ 413.3, found 395[M−H$_2$O]$^+$.

Example 56

Synthesis of Compound 55

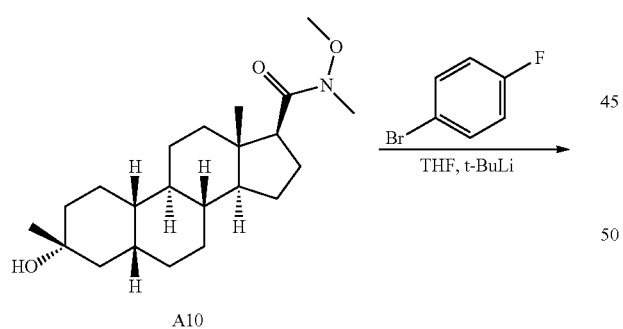

A solution of 1-bromo-4-fluorobenzene (359 mg, 2.75 mmol) in THF (3 mL) was added t-butyllithium (3.8 mL, 4.94 mmol) dropwise at −78° C. The mixture was stirred at −78° C. for 2 h. A10 (100 mg, 2.75 mmol) in THF (1 mL) was added dropwise at −78° C. The reaction was stirred at −78° C. for 2 hours. TLC showed the reaction was completed. The reaction was quenched with Sat NH$_4$Cl (20 mL) and extracted with EtOAc (20 mL×2). The combined organic layers were washed with brine (10 mL), dried over Na$_2$SO$_4$, filtered and evaporated to afford crude product, which was purified by prep-HPLC separation to afford 55 (101 mg) as a solid.

$^1$H NMR (400 MHz, CDCl$_3$) δ 7.91 (dd, J=8.78, 5.52 Hz, 2 H), 7.11-7.11 (m, 1 H), 7.11-7.11 (m, 1H), 7.10-7.11 (m, 1H), 7.11 (t, J=8.66 Hz, 2H), 3.45 (t, J=8.66 Hz, 1 H), 2.36-2.49 (m, 1 H), 1.70-1.89 (m, 5 H), 1.53-1.69 (m, 8 H), 1.03-1.52 (m, 19 H), 0.84-1.00 (m, 1 H), 0.60 (s, 3 H). LCMS Rt=0.857 min in 2.0 min chromatography, 50-100 AB, MS ESI calcd. for C$_{26}$H$_{36}$FO$_2$ [M+H]$^+$ 399.3, found 381 [M−H$_2$O]$^+$.

Example 57

Synthesis of Compound 56

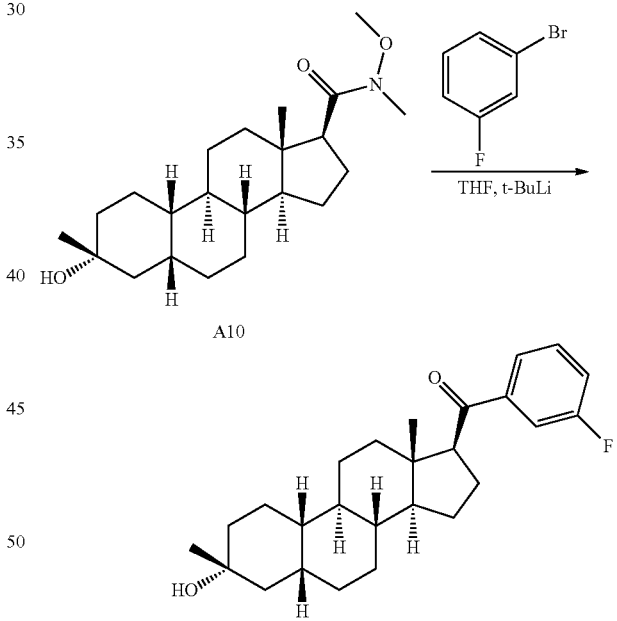

To a solution of 1-bromo-3-fluorobenzene (239 mg, 1.37 mmol) in THF (5 mL) was added n-butyllithium (1.90 mL, 2.47 mmol) dropwise at −68° C. The mixture was stirred at −68° C. for 2 hrs. A10 (100 mg, 275 μmol) in THF (3 mL) was added dropwise at −68° C. The reaction was stirred at 25° C. for 2 hours. LCMS showed the reaction was complete. The reaction was quenched with NH$_4$Cl (20 mL), extracted with EtOAc (20 mL×2). The combined organic layers were washed with brine (10 mL), dried over Na$_2$SO$_4$, filtered and evaporated to afford crude product, which was purified by prep-HPLC to give 56 (28.2 mg) as a solid.

¹H NMR (400 MHz, DMSO) δ 7.78-7.42 (m, 4H), 4.25 (s, 1H), 3.67 (t, J=8.4 Hz, 1H), 2.28-2.15 (m, 1H), 1.79-1.63 (m, 5H), 1.62-1.48 (m, 2H), 1.47-1.34 (m, 4H), 1.32-1.17 (m, 7H), 1.16-0.96 (m, 8H), 0.84 (d, J=12.0 Hz, 1H), 0.50 (s, 3H). LCMS Rt=1.223 min in 2 min chromatography, 30-90 AB, MS ESI calcd. for $C_{26}H_{36}FO_2$ $[M+H]^+$ 381, found 381 $[M-H_2O]^+$.

Example 58

Synthesis of Compound 57

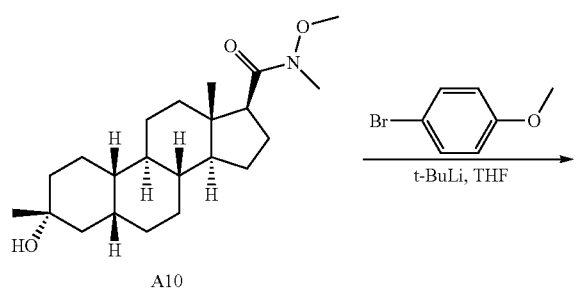

To a stirred solution of 1-bromo-4-methoxybenzene (256 mg, 1.37 mmol) in 3 mL of THF was added tert-butyllithium (1.3 M; 2 mL, 2.61 mmol) dropwise at −78° C. under $N_2$. After stirring at −78° C. for 2 hrs, A10 (100 mg, 0.275 mmol) was added. The mixture was stirred at 25° C. for 1 hour. LCMS showed the reaction was completed. The reaction mixture was quenched with $NH_4Cl$ (30 mL), extracted with EtOAc (20 mL×2), washed with brine (30 mL), dried over $Na_2SO_4$, filtered and evaporated in vacuum. The crude product was purified by preparative HPLC (column: Phenomenex Synergi C18 150*30 mm*4 um, gradient 90-98% B (A=0.05% HCl-ACN, B=acetonitrile), flow rate: 30 mL/min) to obtain 57 (41.0 mg) as a solid.

¹H NMR (CDCl₃, 400 MHz): δ 7.90 (d, J=8.6 Hz, 2H), 6.92 (d, J=9.0 Hz, 2H), 3.87 (s, 3H), 3.46 (t, J=8.6 Hz, 1H), 2.36-2.49 (m, 1H), 1.70-1.85 (m, 5H), 1.53-1.69 (m, 3H), 1.25-1.50 (m, 15H), 1.03-1.19 (m, 2H), 0.86-1.00 (m, 1H), 0.61 (s, 3H). LCMS Rt=2.415 min in 4.0 min chromatography, 30-90 CD, MS EST calcd. for $C_{27}H_{39}O_3$ $[M+H]^+$ 411, found 411.

Example 59

Synthesis of Compound 58

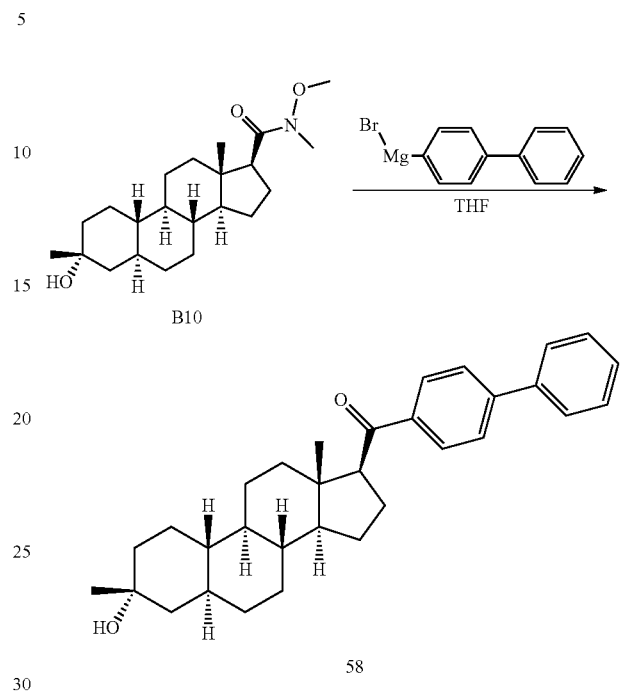

To a solution of B10 (100 mg, 0.275 mmol) in THF (3 mL) was added naphthalen-2-yl magnesium bromide (2.74 mL) at 25° C. for 2 hours TLC showed the reaction was complete. Aqueous solution of $NH_4Cl$ (5 mL) was added dropwise at 25° C., and extracted with EtOAc (10 mL×2). The combined organic solution was washed with brine (5 mL), dried over $Na_2SO_4$. The organic layer was filtered and concentrated under reduced pressure to get the mixture, which was purified by HPLC to give 58 (18.5 mg, 40.5 μmol) as a solid.

¹H NMR (400 MHz, CDCl₃) δ 8.03-7.93 (m, 2H), 7.72-7.61 (m, 4H), 7.53-7.45 (m, 2H), 7.44-7.37 (m, 1H), 3.60-3.51 (m, 1H), 2.54-2.42 (m, 1H), 1.85-1.62 (m, 7H), 1.37 (br. s., 7H), 1.24-0.93 (m, 10H), 0.66 (s, 5H). LCMS Rt=1.392 min in 2 min chromatography, 30-90 AB, MS ESI calcd for $C_{32}H_{41}O_2$ $[M+H]^+$ 457, found 457.

Example 60

Synthesis of Compound 59

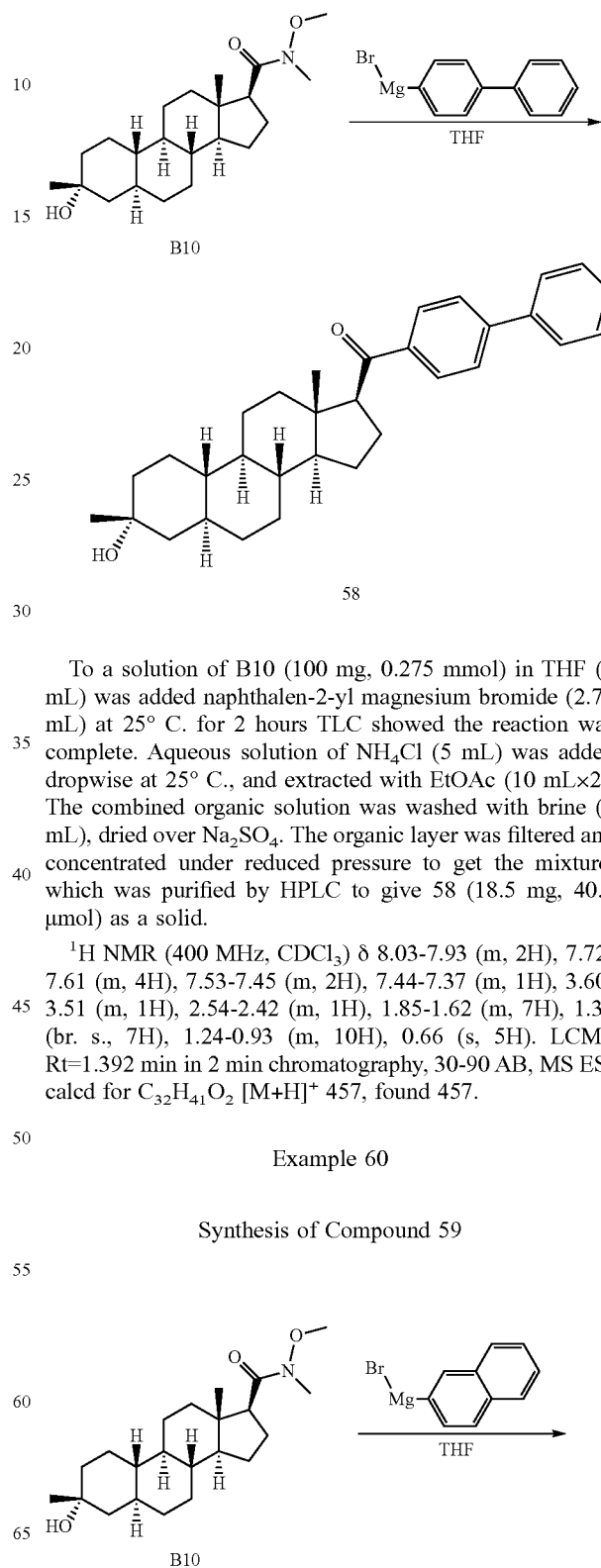

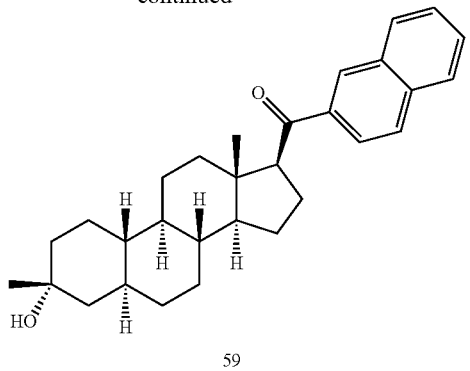

59

To a solution of B10 (100 mg, 0.275 mmol) in THF (3 mL) was added naphthalen-2-yl magnesium bromide (550 μL) at 25° C. for 2 hours. TLC showed the reaction was complete. An aqueous solution of NH₄Cl (5 mL) was added dropwise into the reaction mixture at 25° C., and extracted with EtOAc (10 mL×2). The combined organic solution was washed with brine (5 mL), dried over Na₂SO₄. The organic layer was filtered and concentrated under reduced pressure to get the mixture, which was purified by HPLC to give 59 (7.8 mg) as a solid.

¹H NMR (400 MHz, CDCl₃) δ 8.41 (s, 1H), 8.03-7.97 (m, 2H), 7.93-7.87 (m, 2H), 7.64-7.54 (m, 2H), 3.74-3.66 (m, 1H), 2.59-2.46 (m, 1H), 1.88-1.76 (m, 2H), 1.76-1.60 (m, 5H), 1.56-1.53 (m, 1H), 1.40 (br. s., 6H), 1.21 (s, 10H), 0.81-0.70 (m, 1H), 0.67 (s, 4H). LCMS Rt=1.346 min in 2 min chromatography, 30-90 AB, MS ESI calcd. for C₃₀H₃₉O₂[M+H]⁺ 431. found 431.

Example 61

Synthesis of Compound 60

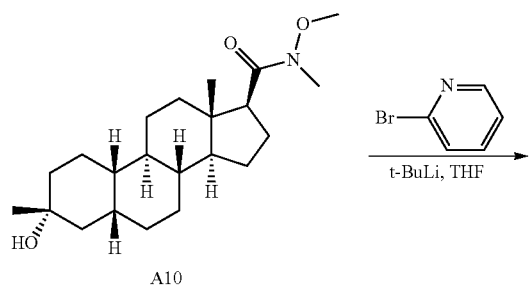

A10

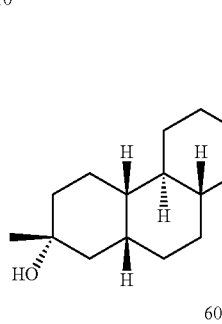

60

To a stirred solution of 2-bromopyridine (216 mg, 1.37 mmol) in 3 mL of THF was added tert-butyllithium (1.3 M; 2 mL, 2.61 mmol) drop-wise at −78° C. under N₂. After stirring at −78° C. for 2 hrs, A10 (100 mg, 0.275 mmol) was added. The mixture was stirred at 25° C. for 1 hour. LCMS showed the reaction was complete. The reaction mixture was quenched with Sat NH₄Cl (30 mL). The mixture was extracted with EtOAc (20 mL×2), washed with brine (30 mL), dried over (Na₂SO₄), filtered and evaporated in vacuum to give crude product. The crude product was purified by per-HPLC separation (column: Phenomenex Synergi C18 150*30 mm*4 um, gradient: 70-80% B (A=0.05% HCl-ACN, B=acetonitrile), flow rate: 30 mL/min) to obtain 60 (49.9 mg) as a solid.

¹H NMR (CDCl₃, 400 MHz): δ 8.66 (d, J=4.6 Hz, 1H), 7.94 (d, J=8.0 Hz, 1H), 7.78-7.85 (m, 1H), 7.40-7.46 (m, 1H), 4.22 (t, J=8.8 Hz, 1H), 2.24-2.41 (m, 1H), 1.74-1.87 (m, 5H), 1.23-1.56 (m, 17H), 1.04-1.20 (m, 3H), 0.83-0.95 (m, 1H), 0.63 (s, 3H). LCMS Rt=2.154 min in 4.0 min chromatography, 30-90 AB, MS ESI calcd. for C₂₅H₃₆NO₂ [M+H]⁺ 382, found 382.

Example 62

Synthesis of Compound 61

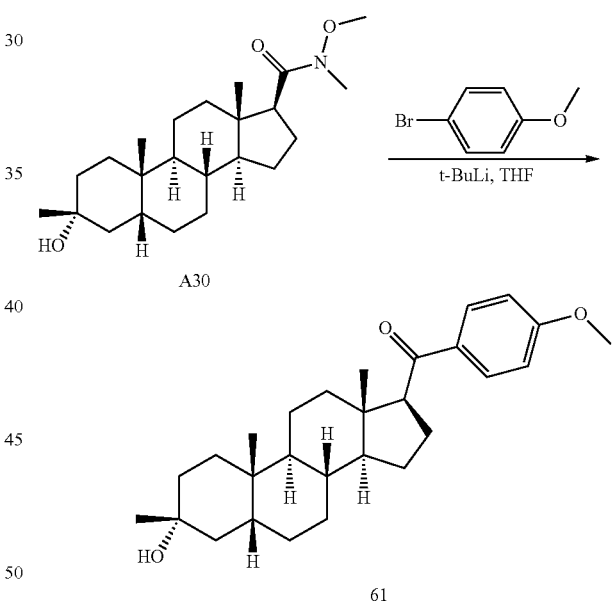

To a stirred solution of 1-bromo-4-methoxybenzene (245 mg, 1.31 mmol) in 3 mL of THF was added tert-butyllithium (1.3 M; 1.92 mL, 2.50 mmol) drop-wise at −78° C. under N₂. After stirring at −78° C. for 2 hrs, A30 (100 mg, 0.264 mmol) was added. The mixture was stirred at 25° C. for 1 hour. LCMS showed the reaction was complete. The reaction mixture was quenched with Sat NH₄Cl (30 mL). The mixture was extracted with EtOAc (20 mL×2), washed with brine (30 mL), dried over Na₂SO₄, filtered, and evaporated in vacuum to give crude product. The crude product was purified by HPLC separation (column: Phenomenex Synergi C18 150*30 mm*4 um, gradient: 75-100% B (A=0.05% HCl-ACN, B=acetonitrile), flow rate: 30 mL/min) to give 61 (13.3 mg) as a solid.

$^1$H NMR (CDCl$_3$, 400 MHz): δ 7.89 (d, J=8.6 Hz, 2H), 6.91 (d, J=9.0 Hz, 2H), 3.86 (s, 3H), 3.45 (t, J=8.8 Hz, 1H), 2.37-2.47 (m, 1H), 1.97 (t, J=13.2 Hz, 1H), 1.63-1.91 (m, 5H), 1.31-1.54 (m, 11H), 1.19-1.27 (m, 5H), 1.09-1.18 (m, 2H), 1.03 (td, J=14.4, 3.3 Hz, 1H), 0.91 (s, 3H), 0.58 (s, 3H). LCMS Rt=1.230 min in 2.0 min chromatography, 30-90 AB, MS ESI calcd. for C$_{28}$H$_{41}$O$_3$[M+H]$^+$ 425.3, found 407 [M−H$_2$O]$^+$.

Example 63

Synthesis of Compound 62

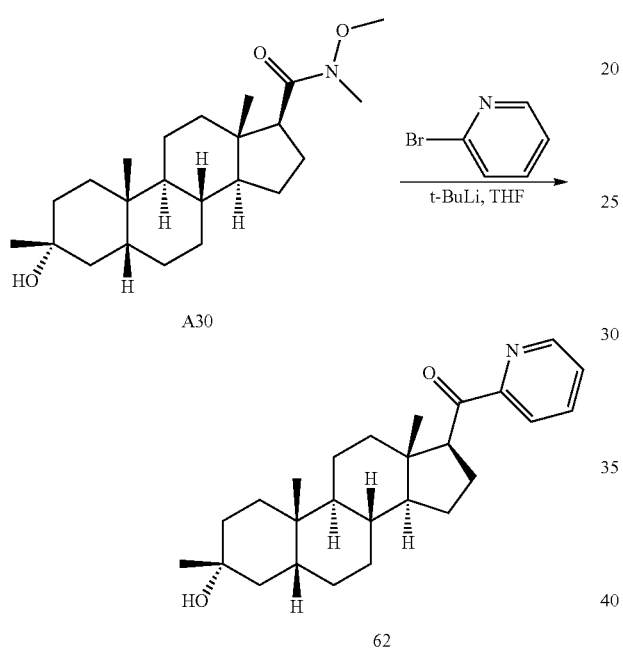

To a stirred solution of 2-bromopyridine (206 mg, 1.31 mmol) in 3 mL of THF was added tert-butyllithium (1.3 M: 1.92 mL, 2.50 mmol) drop-wise at −78° C. under N$_2$. After stirring at −78° C. for 2 hrs, A30 (100 mg, 0.264 mmol) was added. The mixture was stirred at 25° C. for 1 hour. LCMS showed the reaction was complete. The reaction mixture was quenched with Sat NH$_4$Cl (30 mL). The mixture was extracted with EtOAc (20 mL×2), washed with brine (30 mL), dried over (Na$_2$SO$_4$), filtered, and evaporated in vacuum to give crude product. The crude product was purified by per-HPLC separation (column: Phenomenex Synergi C18 150*30 mm*60, gradient: 84-84% B (A=0.05% HCl-ACN, B=acetonitrile), flow rate: 30 mL/min) to give 62 (20.3 mg) as a solid.

$^1$H NMR (MeOD, 400 MHz): δ 8.81 (d, J=4.8 Hz, 1H), 8.33-8.39 (m, 1H), 8.26-8.32 (m, 1H), 7.87-7.94 (m, 1H), 4.03 (t, J=8.8 Hz, 1H), 2.30-2.46 (m, 1H), 1.79-2.09 (m, 5H), 1.71 (d, J=14.4 Hz, 1H), 1.34-1.60 (m, 10H), 1.21-1.31 (m, 7H), 1.03-1.20 (m, 2H), 0.96 (s, 3H), 0.65 (s, 3H). LCMS Rt=2.257 min in 4.0 min chromatography, 30-90 AB, MS ESI calcd. for C$_{26}$H$_{38}$NO$_2$ [M+H]$^+$ 396, found 396.

Example 64

Synthesis of Compound 63

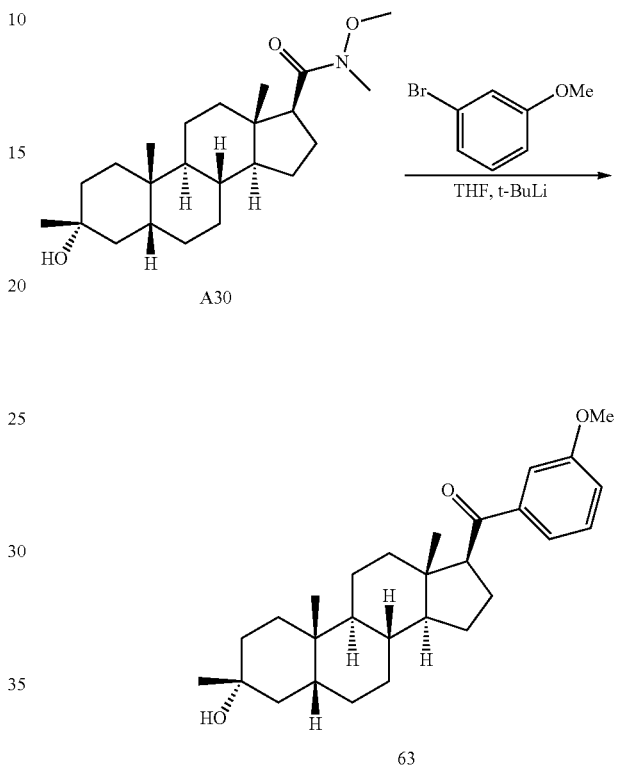

To a stirred solution of 1-bromo-3-methoxybenzene (245 mg, 1.31 mmol) in 3 mL of THF was added tert-butyllithium (1.3 M, 1.92 mL, 2.50 mmol) dropwise at −78° C. under N$_2$. After stirring at −78° C. for 2 hrs, A30 (100 mg, 0.264 mmol) was added. The mixture was stirred at 25° C. for 1 hour. LCMS showed the reaction was complete. The reaction mixture was quenched with Sat. NH$_4$Cl (30 mL). The mixture was extracted with EtOAc (20 mL×2). The combined organic layer was washed with brine (30 mL), dried over Na$_2$SO$_4$, filtered, and evaporated in vacuo to give crude product, which was purified by prep-HPLC separation (column: Phenomenex Synergi C18 150*30 mm*4 um, gradient: 75-100% B (A=0.05% HCl-ACN, B=acetonitrile), flow rate: 30 mL/min) for further purification to afford 63 (19.4 mg) as a solid.

$^1$H NMR (CDCl3, 400 MHz): δ 7.45 (d, J=7.6 Hz, 1H), 7.40 (s, 1H), 7.34 (t, J=8.0 Hz, 1H), 7.08 (dd, J=8.0, 2.3 Hz, 1H), 3.86 (s, 3H), 3.45 (t, J=8.8 Hz, 1H), 2.37-2.47 (m, 1H), 1.65-2.00 (m, 6H), 1.33-1.53 (m, 10H), 1.22-1.28 (m, 5H), 1.08-1.18 (m, 2H), 0.98-1.05 (m, 1H), 0.89-0.89 (m, 1H), 0.91 (s, 3H), 0.59 (s, 3H). LCMS Rt=3.246 min in 4.0 min chromatography, 30-90 CD, MS ESI calcd. for C$_{28}$H$_{41}$O$_3$ [M+H]$^+$ 425.3, found 407.3 [M−H$_2$O]$^+$.

Example 65

Synthesis of Compound 64

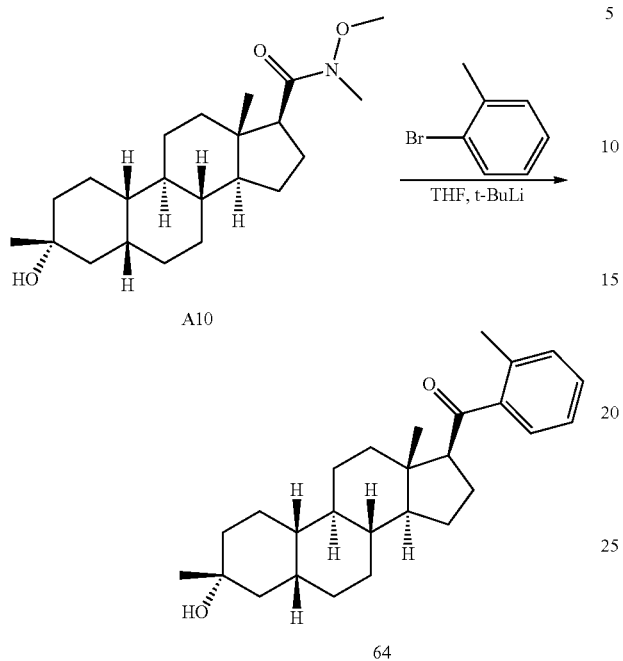

To a stirred solution of 1-bromo-2-methylbenzene (234 mg, 1.37 mmol) in 3 mL of THF was added tert-butyllithium (1.3 M; 2 mL, 2.61 mmol) dropwise at −78° C. under $N_2$. After stirring at −78° C. for 2 hrs, A10 (100 mg, 0.275 mmol was added. The mixture was stirred at 25° C. for 1 hour. LCMS showed the reaction was complete. The reaction mixture was quenched with Sat. $NH_4Cl$ (30 mL). The mixture was extracted with EtOAc (20 mL×2), washed with brine (30 mL), dried over ($Na_2SO_4$), filtered, and evaporated in vacuum to give crude product, which was purified by prep-HPLC separation (column: Phenomenex Synergi C18 150*30 mm*4 um, gradient: 70-95% B (A=0.05% HCl-ACN, B=acetonitrile), flow rate: 25 mL/min) for further purification to give 64 (23.4 mg) as a solid.

$^1$H NMR (CDCl$_3$, 400 MHz): δ 7.47 (d, J=7.4 Hz, 1H), 7.30-7.34 (m, 1H), 7.22 (d, J=7.4 Hz, 2H), 3.31 (t, J=8.8 Hz, 1H), 2.31-2.46 (m, 4H), 1.69-1.83 (m, 5H), 1.19-1.51 (m, 16H), 0.97-1.19 (m, 4H), 0.82-0.90 (m, 1H), 0.66 (s, 3H). LCMS Rt=2.592 min in 4.0 min chromatography, 30-90 CD, MS ESI calcd. for $C_{27}H_{39}O_2[M+H]^+$ 395.3, found 377.29 $[M-H_2O]^+$.

Example 66

Synthesis of Compound 65

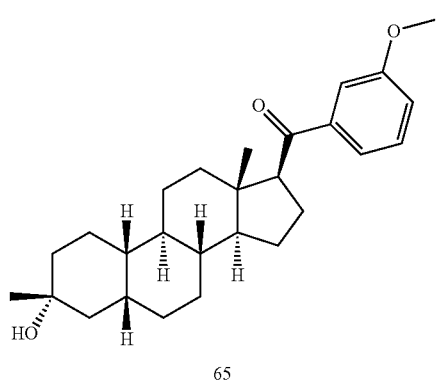

To a stirred solution of 1-bromo-3-methoxybenzene (256 mg, 1.37 mmol) in 3 mL of THF was added tert-butyllithium (1.3 M; 2 mL, 2.61 mmol) dropwised at −78° C. under $N_2$. After stirring at −78° C. for 1 hrs, A10 (100 mg, 0.275 mmol) was added. The mixture was stirred at 25° C. for 20 min. LCMS showed the reaction was completed. The reaction mixture was quenched with $NH_4Cl$ (30 mL), extracted with EtOAc (20 mL×2), washed with brine (30 mL), dried over $Na_2SO_4$, filtered and evaporated in vacuum. The crude product was purified by HPLC separation (column: Phenomenex Synergi C18 150*30 mm*4 um, gradient: 75-100% B (A=0.05% HCl-ACN, B=acetonitrile), flow rate: 30 mL/min) to obtain 65 (63.3 mg) as a solid.

$^1$H NMR (CDCl$_3$, 400 MHz): 7.45 (d, J=7.6 Hz, 1H), 7.40 (s, 1H), 7.34 (t, J=7.8 Hz, 1H), 7.08 (dd, J=8.2, 2.1 Hz, 1H), 3.86 (s, 3H), 3.46 (t, J=8.8 Hz, 1H), 2.38-2.46 (m, 1H), 1.70-1.87 (m, 5H), 1.58-1.68 (m, 2H), 1.11-1.52 (m, 17H), 1.03-1.10 (m, 1H), 0.84-0.99 (m, 1H), 0.61 (s, 3H). LCMS Rt=3.153 min in 4.0 min chromatography, 10-80 CD, MS ESI calcd for $C_{27}H_{38}O_3$ $[M-H_2O+H]^+$ 393, found 393.

Example 67

Synthesis of Compound 66

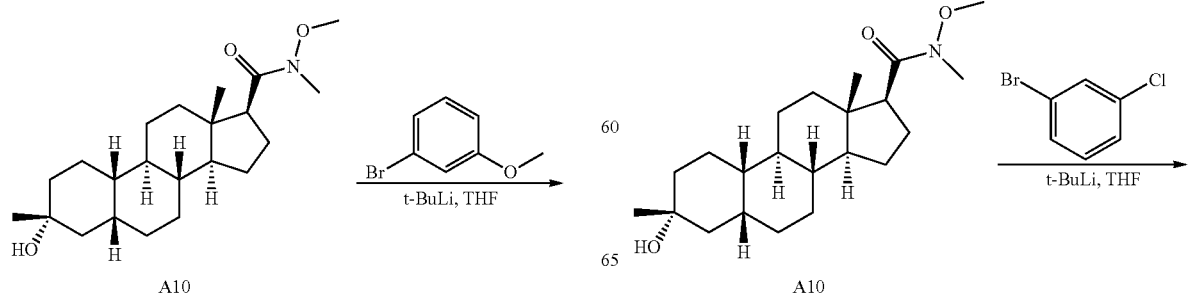

-continued

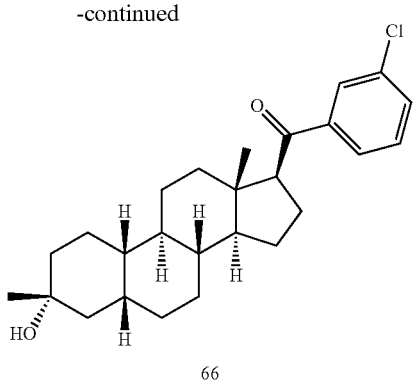

66

To a stirred solution of 1-bromo-3-chlorobenzene (262 mg, 1.37 mmol) in 3 mL of THF was added tert-butyllithium (1.3 M; 2 mL, 2.61 mmol) dropwise at −78° C. under $N_2$. After stirring at −78° C. for 2 hrs, A10 (100 mg, 0.275 mmol was added. The mixture was stirred at 25° C. for 1 hour. LCMS showed the reaction was completed. The reaction mixture was quenched with $NH_4Cl$ (30 mL), extracted with EtOAc (20 mL×2), washed with brine (30 mL), dried over $Na_2SO_4$, filtered and evaporated in vacuum. The crude product was purified by HPLC separation (column: Phenomenex Synergi C18 150*30 mm*4 um, gradient: 75-100%/B (A=0.05% HCl-ACN, B=acetonitrile), flow rate: 30 mL/min) to obtain 66 (67.6 mg) as a solid.

$^1$H NMR (CDCl$_3$, 400 MHz): δ 7.84 (s, 1H), 7.73 (d, J=7.6 Hz, 1H), 7.50 (d, J=8.6 Hz, 1H), 7.34-7.43 (m, 1H), 3.43 (t, J=8.6 Hz, 1H), 2.36-2.45 (m, 1H), 1.70-1.86 (m, 5H), 1.57-1.67 (m, 2H), 1.41-1.54 (m, 3H), 1.21-1.41 (m, 13H), 1.04-1.17 (m, 2H), 0.88-0.99 (m, 1H), 0.60 (s, 3H). LCMS Rt=2.722 min in 4.0 min chromatography, 30-90 CD, MS ESI calcd. for $C_{26}H_{36}ClO_2$ [M+H]$^+$ 415.3, found 397.0 [M−H$_2$O]$^+$.

Example 68

Synthesis of Compound 67

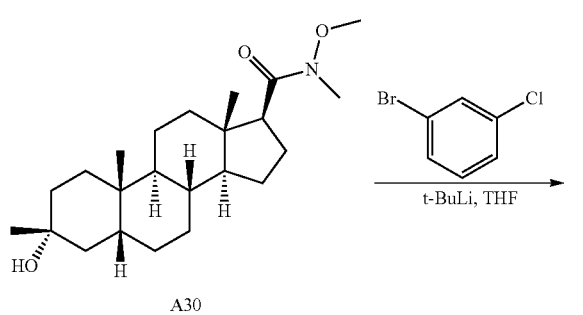

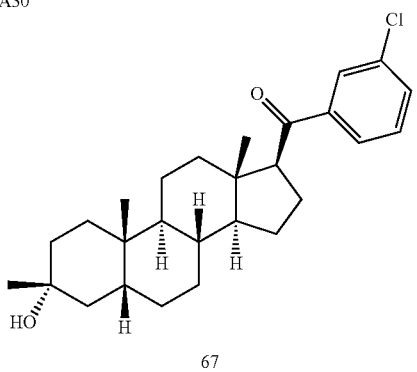

67

To a stirred solution of 1-bromo-3-chlorobenzene (250 mg, 1.31 mmol) in 3 mL of THF was added tert-butyllithium (1.3 M; 1.92 mL, 2.50 mmol) dropwise at −78° C. After stirring at −78° C. for 2 hrs, A30 (100 mg, 0.264 mmol) was added. The mixture was stirred at −78° C. for 1 hour. LCMS showed the reaction was completed. The reaction mixture was quenched with $NH_4Cl$ (30 mL), extracted with EtOAc (20 mL×2), washed with brine (30 mL), dried over $Na_2SO_4$, filtered and evaporated in vacuum. The crude product was purified by HPLC separation (column: Phenomenex Synergi C18 150*30 mm*4 um, gradient: 80-100% B (A=0.05% HCl-ACN, B=acetonitrile), flow rate: 30 mL/min) for to obtain 67 (22.3 mg) as a solid.

$^1$H NMR (CDCl$_3$, 400 MHz): δ 7.84 (s, 1H), 7.73 (d, J=7.6 Hz, 1H), 7.50 (d, J=8.0 Hz, 1H), 7.33-7.43 (m, 1H), 3.41 (t, J=8.6 Hz, 1H), 2.34-2.45 (m, 1H), 1.96 (t, J=13.2 Hz, 1H), 1.59-1.87 (m, 5H), 1.20-1.53 (m, 17H), 1.09-1.16 (m, 1H), 0.98-1.07 (m, 1H), 0.90 (s, 3H), 0.58 (s, 3H). LCMS Rt=2.800 min in 4.0 min chromatography, 30-90 CD, MS ESI calcd. for $C_{27}H_{38}ClO_2$ [M+H]$^+$ 429.3, found 411.0 [M−H$_2$O]$^+$.

Example 69

Synthesis of Compound 68

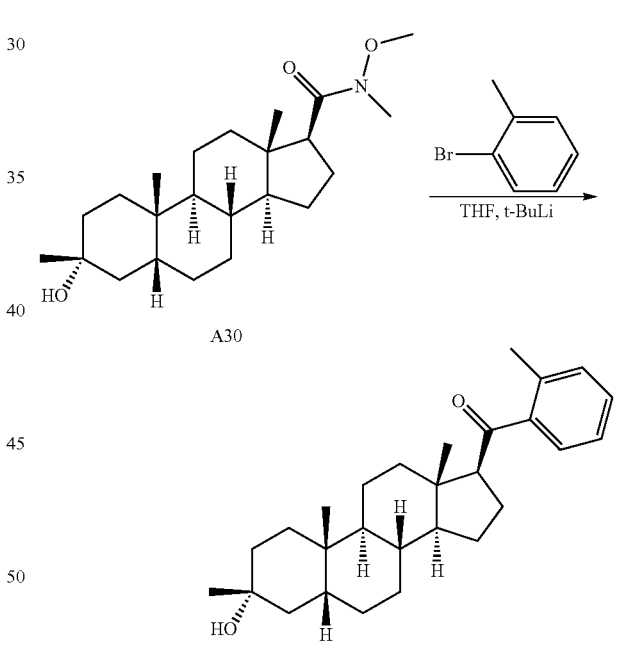

To a stirred solution of 1-bromo-2-methylbenzene (224 mg, 1.31 mmol) in 3 mL of THF was added tert-butyllithium (1.3 M; 1.92 mL, 2.50 mmol) dropwise at −78° C. under $N_2$. After stirring at −78° C. for 2 hrs, A30 (100 mg, 0.264 mmol was added. The mixture was stirred at 25° C. for 1 hour. LCMS showed the reaction was complete. The reaction mixture was quenched with Sat. $NH_4Cl$ (30 mL). The mixture was extracted with EtOAc (20 mL×2), washed with brine (30 mL), dried over $Na_2SO_4$, filtered, and evaporated in vacuo to give crude product, which was purified by prep-HPLC separation (column: Phenomenex Synergi C18 150*30 mm*4 um, gradient: 70-95% B (A=0.05% HCl- ACN, B=acetonitrile), flow rate: 25 mL/min) for further purification to obtain 68 (15.6 mg) as a solid.

$^1$H NMR (CDCl3, 400 MHz): δ 7.47 (d, J=7.4 Hz, 1H), 7.30-7.34 (m, 1H), 7.18-7.25 (m, 2H), 3.30 (t, J=8.8 Hz, 1H), 2.31-2.46 (m, 4H), 1.93 (t, J=13.4 Hz, 1H), 1.83 (dt, J=9.2, 4.5 Hz, 1H), 1.74 (d, J=3.4 Hz, 1H), 1.61-1.67 (m, 2H), 1.20-1.47 (m, 16H), 0.95-1.16 (m, 4H), 0.89 (s, 3H), 0.64 (s, 3H). LCMS Rt=2.672 min in 4.0 min chromatography, 30-90 CD, MS ESI calcd. for $C_{28}H_{40}O_2$ [M−H$_2$O+H]$^+$ 391.1, found 391.3.

Example 70

Synthesis of Compound 69

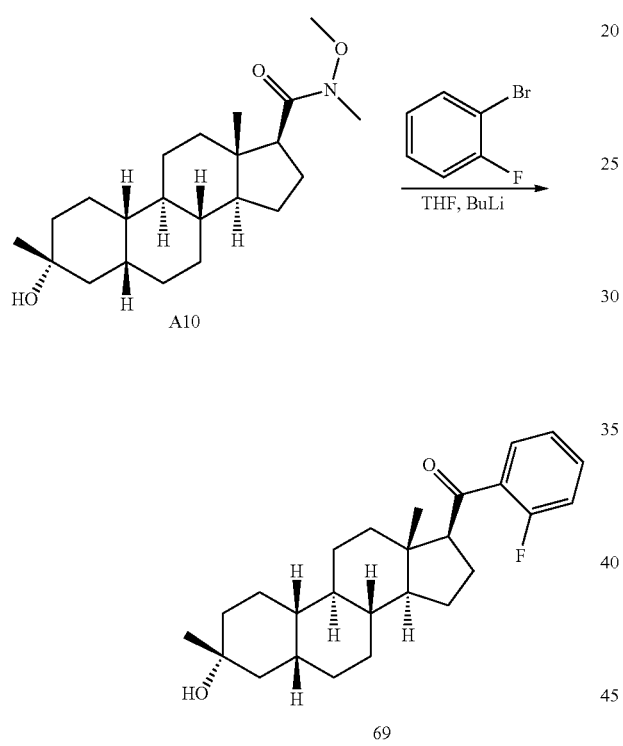

To a solution of 1-bromo-2-fluorobenzene (239 mg, 1.37 mmol) in THF (5 mL) was added n-butyllithium (1.90 mL, 2.47 mmol) dropwise at −68° C. The mixture was stirred at −68 OC for 2 hrs. A10 (100 mg, 275 mol) in THF (3 mL) was added dropwise at −68° C. The reaction was stirred at 25° C. for 2 hours. LCMS showed the reaction was complete. The reaction was quenched with Sat. NH$_4$Cl (20 mL), extracted with EtOAc (20 mL×2). The combined organic layers were washed with brine (10 mL), dried over Na$_2$SO$_4$, filtered and evaporated to afford crude product, which was purified by prep-HPLC to give 69 (21.6 mg) as a solid.

$^1$H NMR (400 MHz, DMSO) δ 7.68-7.54 (m, 2H), 7.34-7.28 (m, 2H), 4.21 (s, 1H), 3.40 (t, J=8.4 Hz, 1H), 2.30-2.17 (m, 1H), 1.77-1.51 (m, 6H), 1.49-1.12 (m, 12H), 1.12-0.90 (m, 7H), 0.89-0.74 (m, 1H), 0.58-0.50 (m, 3H). LCMS Rt=1.187 min in 2 min chromatography, 30-90 AB, MS ESI calcd. for $C_{26}H_{36}FO_2$ [M+H]$^+$ 399.3, found 381 [M−H$_2$O]$^+$.

Example 71

Synthesis of Compound 70

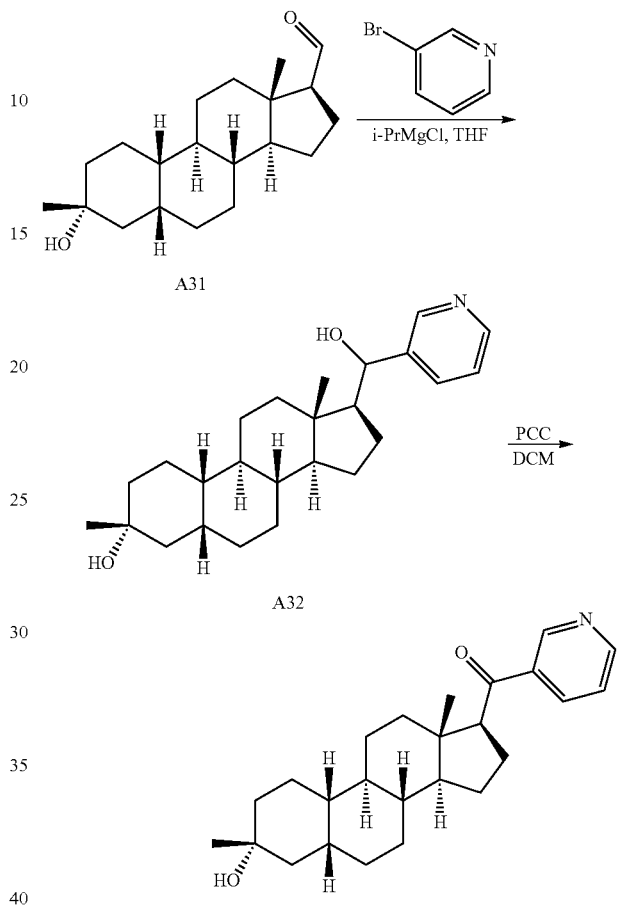

Step 1. To a solution of 3-bromopyridine (51.8 mg, 328 umol) in 3 mL of THF was added isopropylmagnesium chloride (2 M, 164 uL, 328 umol) drop-wise at 15° C. under N$_2$. After stirring at 15° C. for 1 hour, A31 (50 mg, 0.164 mmol) was added. The mixture was stirred at 15° C. for 1 hour. LCMS showed the reaction was complete. The reaction mixture was quenched with saturated sat NH$_4$Cl (30 mL). The mixture was extracted with EtOAc (20 mL×2). The combined organic layer washed with brine (30 mL), dried over Na$_2$SO$_4$, filtered and evaporated m vacuum to give 60 mg of crude product.

Step 2. To a solution of A32 (60 mg, 156 umol) in DCM (3 mL) was added PCC (50.3 mg, 234 umol) at 15° C. The mixture was stirred at 15° C. for 1 hr. LCMS showed the reaction was complete. The solution was filtered and the filter cake was washed with DCM (50 mL×2). The combined filtrate was concentrated in vacuum. The residue was purified by silica gel column eluted with PE/EtOAc (10/1) to afford a crude product, which was then purified by perp-HPLC (column: Phenomenex Gemini 150*25 mm*10 um, gradient: 45-70% B (A=0.05% HCl-ACN, B=acetonitrile), flow rate: 30 mL/min) to give 70 (1.6 mg) as a solid.

$^1$H NMR (CDCl$_3$, 400 MHz) δ=9.15-9.05 (m, 1H), 8.80-8.70 (m, 1H), 8.20-8.10 (m, 1H), 7.47-7.35 (m, 1H), 3.46 (t,

J=8.6 Hz, 1H), 3.08 (br. s., 1H), 2.52-2.34 (m, 1H), 1.90-1.72 (m, 5H), 1.68-1.61 (m, 2H), 1.52-1.44 (m, 3H), 1.43-1.33 (m, 7H), 1.31-1.24 (m, 5H), 1.20-1.04 (m, 2H), 1.00-0.85 (m, 1H), 0.62 (s, 3H). LCMS Rt=1.206 min in 2.0 min chromatography, 10-80 AB. MS ESI calcd. for $C_{25}H_{36}NO_2$ [M+H]$^+$ 382, found 382.

Example 72

Synthesis of Compound 71

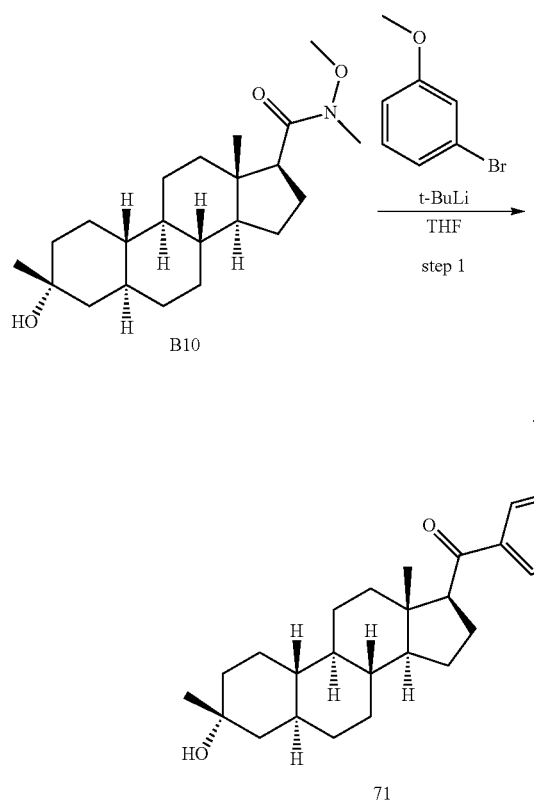

To a solution of 1-bromo-4-methylbenzene (203 mg, 1.09 mmol) in THF (0.3 mL) was added tert-butyllithium (1.68 mL, 1.3 M) at −60° C. The mixture was stirred at −60° C. for 1 hr. A solution of B10 (40 mg, 110 µmol) in THF (0.1 mL) was added into the mixture at −60° C. The reaction mixture was stirred at 25° C. for 2 hrs. TLC showed the reaction was complete. Saturated NH$_4$Cl (1 mL) was added. The mixture was extracted with EtOAc (1.5 mL×3). The combined organic layers were dried over Na$_2$SO$_4$. The mixture was filtered. The filtrate was concentrated in vacuum. The residue was purified by prep-HPLC (column: Phenomenex Synergi C18 150*30 mm*4 um, gradient 80-95% B (A=0.05% HCl-ACN, B=acetonitrile), flow rate: 25 mL/min) to give 71 (6.5 mg) as a solid.

$^1$H NMR (400 MHz, CDCl$_3$) δ 7.56-7.43 (m, 2H), 7.41-7.29 (m, 1H), 7.11-7.06 (m, 1H), 3.86 (s, 3H), 3.48-3.39 (m, 1H), 2.47-2.36 (m, 1H), 1.81-1.46 (m, 10H), 1.53-0.91 (m, 20H), 0.72-0.58 (m, 5H). LCMS t$_R$=1.039 min in 1.5 min chromatography, 5-95 AB, MS ESI calcd. for $C_{27}H_{39}O$ [M+H]$^+$ 411, found 411.

Example 73

Synthesis of Compound 72

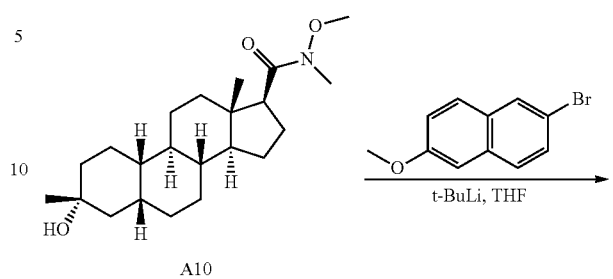

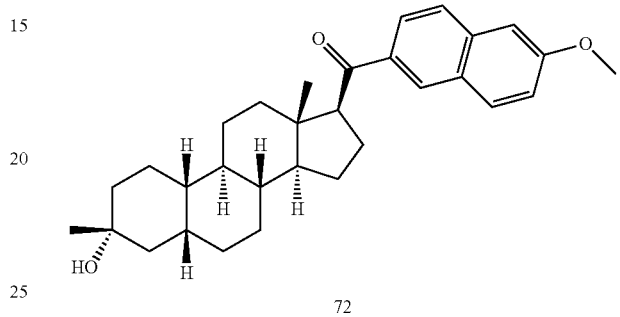

To a stirred solution of 2-bromo-6-methoxynaphthalene (258 mg, 1.09 mmol) in 3 mL of THF was added tert-butyllithium (1.3 M, 1.6 mL, 2.09 mmol) drop-wise at −78° C. under N$_2$. After stirring at −78° C. for 1 hour, A10 (80 mg, 0.220 mmol) was added. The mixture was stirred at 25° C. for 1 hour. LCMS showed the reaction was complete. The reaction mixture was quenched with saturated NH$_4$Cl (30 mL). The mixture was extracted with EtOAc (20 mL×2). The combined organic layer washed with brine (30 mL), dried over Na$_2$SO$_4$, filtered, and evaporated in vacuum to give crude product, which was purified by prep-HPLC separation (column: Phenomenex Synergi C18 150*30 mm*4 um, gradient: 80-100% B (A=0.05% HCl-ACN, B=acetonitrile), flow rate: 30 mL/min) to afford 72 (58.3 mg) as a solid.

$^1$H NMR (CDCl$_3$, 400 MHz): δ 8.33 (s, 1H), 7.93-7.99 (m, 1H), 7.85 (d, J=8.6 Hz, 1H), 7.75 (d, J=8.6 Hz, 1H), 7.20 (dd, J=9.0, 2.5 Hz, 1H), 7.15 (d, J=2.0 Hz, 1H), 3.95 (s, 3H), 3.64 (t, J=8.6 Hz, 1H), 2.55-2.42 (m, 1H), 1.88-1.73 (m, 5H), 1.69-1.59 (m, 1H), 1.55-1.20 (m, 17H), 1.19-1.04 (m, 2H), 0.97-0.83 (m, 1H), 0.64 (s, 3H). LCMS Rt=1.242 min in 2.0 min chromatography, 30-90 AB, MS EST calcd. for $C_{31}H_{41}O_3$ [M+H]$^+$ 461, found 461.

Example 74

Synthesis of Compound 73

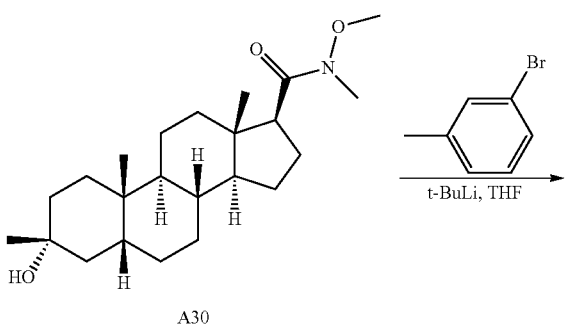

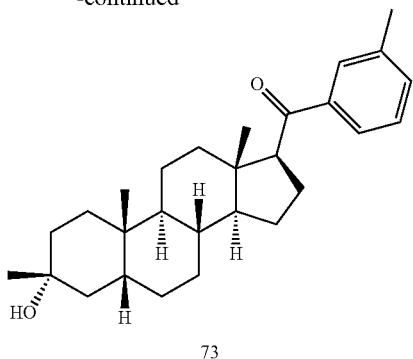

73

To a stirred solution of 1-bromo-3-methylbenzene (224 mg, 1.31 mmol) in 3 mL of THF was added tert-butyllithium (1.3 M; 1.6 mL, 2.5 mmol) drop-wise at −78° C. under N$_2$. After stirring at −78° C. for 2 hours, A30 (100 mg, 0.264 mmol) was added. The mixture was stirred at 25° C. for 1 hour. LCMS showed the reaction was complete. The reaction mixture was quenched with Sat NH$_4$Cl (30 mL). The mixture was extracted with EtOAc (20 mL×2), washed with brine (30 mL), dried over Na$_2$SO$_4$, filtered, and evaporated in vacuum to give crude product. The crude product was purified by prep-HPLC separation (column: Phenomenex Synergi C18 150*30 mm*4 um, gradient: 80-100% B (A=0.05% HCl-ACN, B=acetonitrile), flow rate: 30 mL/min) to afford 73 (12.2 mg) as a solid.

$^1$H NMR (CDCl$_3$, 400 MHz): δ 7.62-7.70 (m, 2H), 7.28-7.36 (m, 2H), 3.47 (t J=8.8 Hz, 1H), 2.34-2.47 (m, 4H), 1.97 (t, J=13.2 Hz, 1H), 1.59-1.92 (m, 5H), 1.28-1.51 (m, 10H), 1.20-1.27 (m, 5H), 0.96-1.18 (m, 4H), 0.90 (s, 3H), 0.59 (s, 3H). LCMS Rt=1.261 min in 2.0 min chromatography, 30-90 AB, MS ESI calcd. for C$_{28}$H$_{41}$O$_2$[M+H]$^+$ 409, found 409.

Example 75

Synthesis of Compound 74

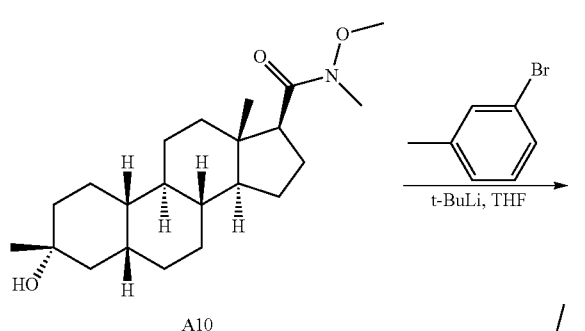

74

To a stirred solution of 1-bromo-3-methoxybenzene (186 mg, 1.09 mmol) in 3 mL of THF was added tert-butyllithium (1.3 M; 1.6 mL, 2.09 mmol) drop-wise at −78° C. under N$_2$. After stirring at −78° C. for 2 hrs, A10 (80 mg, 0.22 mmol) was added. The mixture was stirred at 25° C. for 1 hour. LCMS showed the reaction was complete. The reaction mixture was quenched with Sat NH$_4$Cl (30 mL). The mixture was extracted with EtOAc (20 mL×2), washed with brine (30 mL), dried over Na$_2$SO$_4$, filtered, and evaporated in vacuum to give crude product. The crude product was purified by perp-HPLC separation (column: Phenomenex Synergi C18 150*30 mm*4 um, gradient: 85-85% B (A=0.05% HCl-ACN, B=acetonitrile), flow rate: 30 mL/min) to give 74 (18.8 mg) as a solid.

$^1$H NMR (CDCl$_3$, 400 MHz): δ 7.60-7.74 (m, 2H), 7.29-7.39 (m, 2H), 3.48 (t, J=8.6 Hz, 1H), 2.33-2.48 (m, 4H), 1.69-1.85 (m, 5H), 1.55-1.69 (m, 3H), 1.41-1.51 (m, 3H), 1.20-1.41 (m, 12H), 1.02-1.16 (m, 2H), 0.82-0.97 (m, 1H), 0.60 (s, 3H). LCMS Rt=1.232 min in 2.0 min chromatography, 30-90 AB, MS ESI calcd. for C$_{27}$H$_{39}$O$_2$[M+H]$^+$ 395.3, found 377 [M−H$_2$O]$^+$.

Example 76

Synthesis of Compound 75

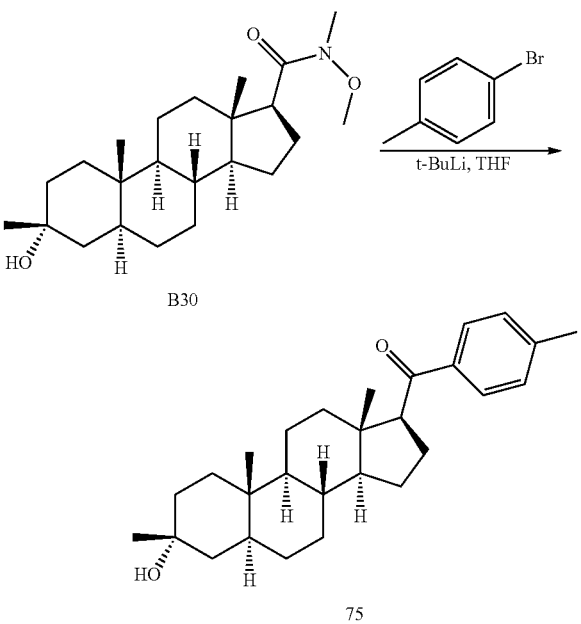

To a stirred solution of 1-bromo-4-methylbenzene (51.5 mg, 0.264 mmol) in 3 mL of THF was added tert-butyllithium (1.3 M in hexane, 0.4 mL, 0.52 mmol) dropwise at −65° C. under N$_2$. After stirring at −65° C. for 2 hrs, B30 (50 mg, 0.132 mmol) was added. The mixture was stirred at 15° C. for 1 hour. LCMS showed the reaction was complete. The reaction mixture was quenched with Sat. NH$_4$Cl (30 mL). The mixture was extracted with EtOAc (20 mL×2), washed with brine (30 mL), dried over Na$_2$SO$_4$, filtered, and evaporated in vacuum to give crude product. The crude product was purified by HPLC separation (column: Phenomenex Synergi C18 150*25*10 um, gradient: 69-74% B (A=0.1% TFA-ACN, B=acetonitrile), flow rate: 30 mL/min) for further purification to obtain 75 (21.9 mg) as a solid.

$^1$H NMR (CDCl$_3$, 400 MHz) δ 7.79 (d, J=8.6 Hz, 2H), 7.23 (d, J=8.0 Hz, 2H), 3.47 (t, J=8.6 Hz, 1H), 2.47-2.36 (m, 4H), 1.78-1.69 (m, 3H), 1.50-1.17 (m, 19H), 1.17-1.08 (m, 1H), 1.03-0.92 (m, 1H), 0.83-0.74 (m, 1H), 0.72 (s, 3H), 0.60 (s, 3H). LCMS Rt=1.277 min in 2.0 min chromatography, 30-90 AB, MS ESI calcd. for C$_{28}$H$_{41}$NO$_2$ [M+H]$^+$ 409, found 409.

Example 77

Synthesis of Compound 76

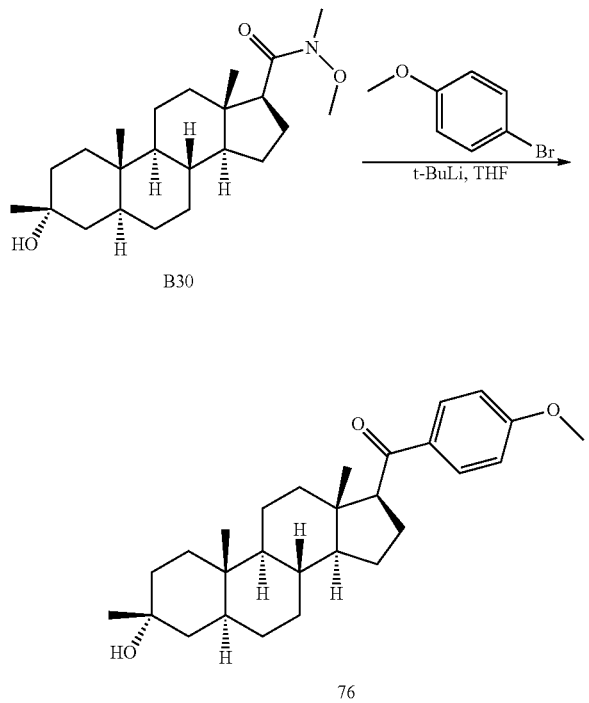

To a stirred solution of 1-bromo-4-methoxybenzene (49.3 mg, 0.264 mmol) in 3 mL of THF was added tert-butyl-lithium (1.3 M: 406 μL, 0.528 mmol) drop-wise at −65° C. under N$_2$. After stirring at −65° C. for 2 hrs, B30 (50 mg, 0.132 mmol) was added. The mixture was stirred at 15° C. for 1 hour. LCMS showed the reaction was complete. The reaction mixture was quenched with Sat. NH$_4$Cl (30 mL). The mixture was extracted with EtOAc (20 mL×2), washed with brine (30 mL), dried over Na$_2$SO$_4$, filtered, and evaporated in vacuum to give the crude product. The crude product was purified by HPLC separation (column: Phenomenex Synergi C18 150*30 mm*4 um, gradient: 90-95% B (A=0.05% HCl-ACN, B=acetonitrile), flow rate: 25 mL/min) for further purification to obtain 76 (26.1 mg) as a solid.

$^1$H NMR (CDCl$_3$, 400 MHz) δ 7.89 (d, J=8.6 Hz, 2H), 6.91 (d, J=9.0 Hz, 2H), 3.86 (s, 3H), 3.45 (t, J=8.6 Hz, 1H), 2.45-2.36 (m, 1H), 1.78-1.68 (m, 3H), 1.53-1.12 (m, 20H), 1.03-0.92 (m, 1H), 0.82-0.75 (m, 1H), 0.71 (s, 3H), 0.59 (s, 3H). LCMS Rt=1.302 min in 2.0 min chromatography, 30-90 AB, MS ESI calcd. for C$_{28}$H$_{41}$O$_3$ [M+H]$^+$ 425, found 425.

Example 78

Synthesis of Compound 77

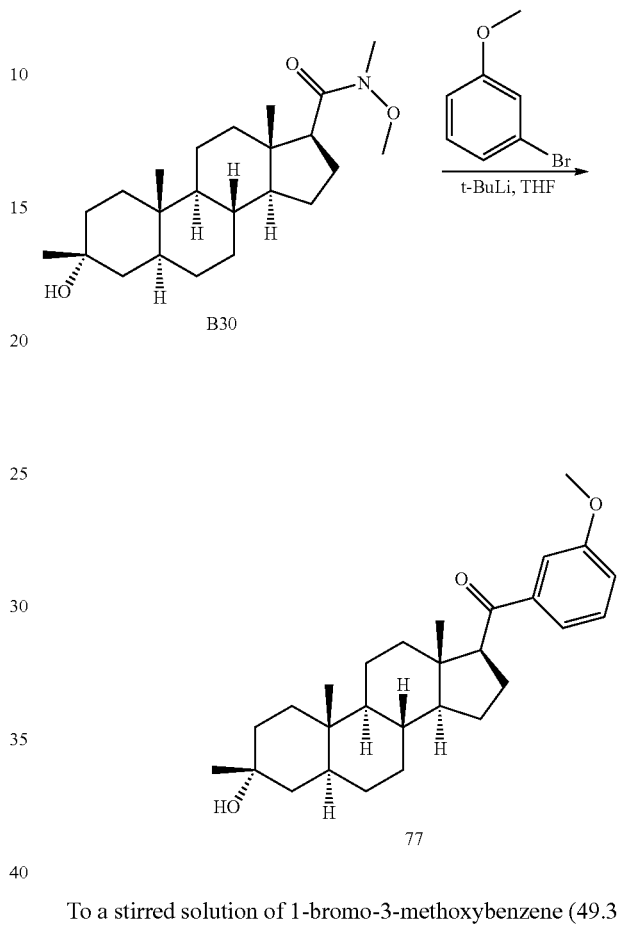

To a stirred solution of 1-bromo-3-methoxybenzene (49.3 mg, 0.264 mmol) in 3 mL of THF was added tert-butyl-lithium (1.3 M, 406 uL, 0.528 mmol) drop-wise at −65° C. under N$_2$. After stirring at −65° C. for 2 hrs, B30 (50 mg, 0.132 mmol) was added. The mixture was stirred at 15° C. for 1 hour. LCMS showed the reaction was complete. The reaction mixture was quenched with Sat. NH$_4$Cl (30 mL). The mixture was extracted with EtOAc (20 mL×2), washed with brine (30 mL), dried over Na$_2$SO$_4$, filtered, and evaporated in vacuum to give crude product. The crude product was purified by HPLC separation (column: Phenomenex Synergi C18 150*30 mm*4 um, gradient: 90-95% B (A=0.05% HCl-ACN, B=acetonitrile), flow rate: 25 mL/min) for further purification to obtain 77 (19.9 mg) as a solid.

$^1$H NMR (CDCl$_3$, 400 MHz) δ 7.50-7.30 (m, 3H), 7.07 (dd, J=2.0, 8.0 Hz, 1H), 3.85 (s, 3H), 3.45 (t, J=8.8 Hz, 1H), 2.46-2.34 (m, 1H), 1.81-1.67 (m, 3H), 1.53-1.26 (m, 12H), 1.25-1.09 (m, 8H), 1.03-0.92 (m, 1H), 0.81-0.74 (m, 1H), 0.71 (s, 3H), 0.60 (s, 3H). LCMS Rt=1.315 min in 2.0 min chromatography, 30-90 AB, MS ESI calcd. for C$_{28}$H$_{41}$O$_3$ [M+H]$^+$ 425, found 425.

Example 79

Synthesis of Compound 78

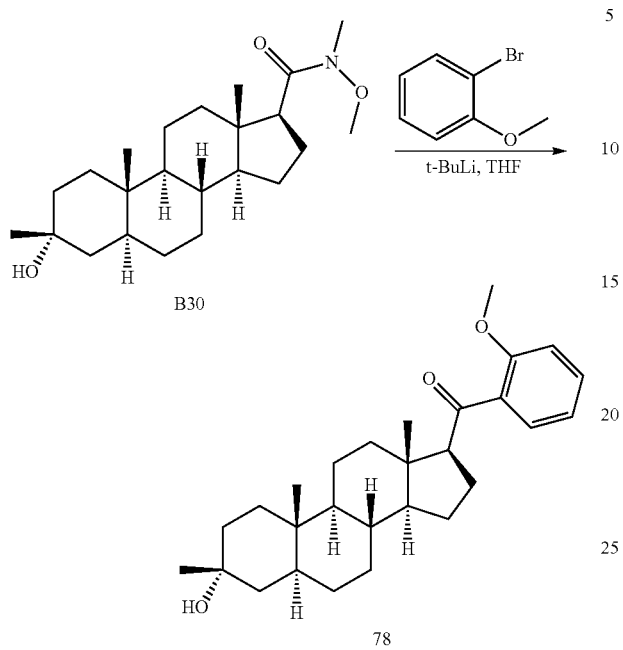

To a stirred solution of 1-bromo-2-methoxybenzene (49.3 mg, 0.264 mmol) in 3 mL of THF was added tert-butyllithium (1.3 M, 406 µL, 0.528 mmol) dropwise at −65° C. under $N_2$. After stirring at −65° C. for 2 hrs, B30 (50 mg, 0.132 mmol) was added. The mixture was stirred at 15° C. for 1 hour. LCMS showed the reaction was complete. The reaction mixture was quenched with Sat $NH_4Cl$ (30 mL) The mixture was extracted with EtOAc (20 mL×2), washed with brine (30 mL), dried over $Na_2SO_4$, filtered, and evaporated in vacuum to give crude product. The crude product was purified by HPLC separation (column: Phenomenex Synergi C18 150*30 mm*4 um, gradient: 95-95% B (A=0.05% HCl-ACN, B=acetonitrile), flow rate: 25 mL/min) for further purification to obtain 78 (19.6 mg) as a solid.

$^1$H NMR (CDCl$_3$, 400 MHz) δ 7.43-7.28 (m, 2H), 7.02-6.82 (m, 2H), 3.84 (s, 3H), 3.55-3.45 (m, 1H), 2.43-2.25 (m, 1H), 1.79-1.63 (m, 5H), 1.48-1.33 (m, 6H), 1.25-1.16 (m, 10H), 1.12-1.04 (m, 2H), 1.00-0.85 (m, 1H), 0.77-0.70 (m, 1H), 0.69 (s, 3H), 0.60 (s, 3H). LCMS Rt=1.277 min in 2.0 min chromatography, 30-90 AB, MS ESI calcd. for $C_{28}H_{41}O_3[M+H]^+$ 425, found 425.

Example 80

Synthesis of Compound 79

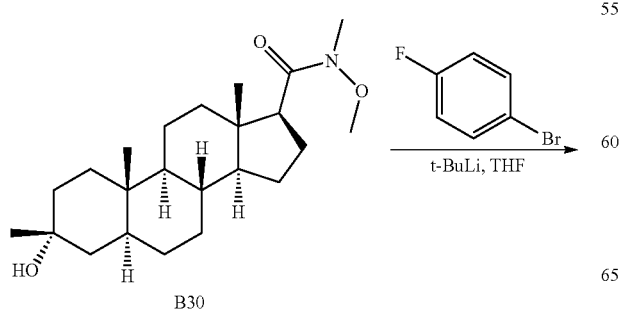

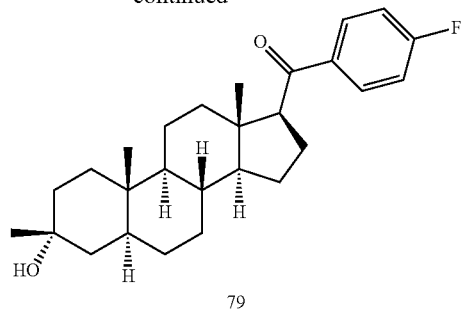

To a stirred solution of 1-bromo-4-fluorobenzene (46.1 mg, 0.264 mmol) in 3 mL of THF was added tert-butyllithium (1.3 M, 406 µL, 0.528 mmol) dropwise at −65° C. under $N_2$. After stirring at −65° C. for 2 hrs, B30 (50 mg, 0.132 mmol) was added. The mixture was stirred at 15° C. for 1 hour. LCMS showed the reaction was complete. The reaction mixture was quenched with Sat $NH_4Cl$ (30 mL). The mixture was extracted with EtOAc (20 mL×2), washed with brine (30 mL), dried over $Na_2SO_4$, filtered, and evaporated in vacuum to give crude product. The crude product was purified by HPLC separation (column-Phenomenex Synergi C18 150*30 mm*4 um, gradient: 85-95% B (A=0.05% HCl-ACN, B=acetonitrile), flow rate: 30 mL/min) to obtain 79 (22.1 mg) as a solid.

$^1$H NMR (CDCl$_3$, 400 MHz) δ 7.91 (dd, J=5.6, 8.5 Hz, 2H), 7.10 (t, J=8.6 Hz, 2H), 3.44 (t, J=8.6 Hz, 1H), 2.45-2.35 (m, 1H), 1.83-1.64 (m, 4H), 1.54-1.42 (m, 6H), 1.38 (d, J=13.4 Hz, 2H), 1.32-1.14 (m, 11H), 1.02-0.92 (m, 1H), 0.83-0.74 (m, 1H), 0.71 (s, 3H), 0.59 (s, 3H). LCMS Rt=1.240 min in 2.0 min chromatography, 30-90 AB, MS ESI calcd. for $C_{27}H_{38}FO_2$ $[M+H]^+$ 413, found 413.

Example 81

Synthesis of Compound 80

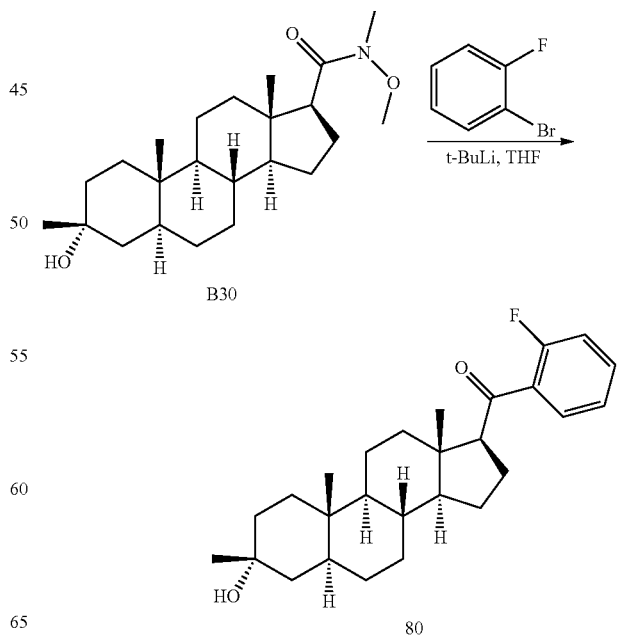

To a stirred solution of i-bromo-2-fluorobenzene (46.1 mg, 0.264 mmol) in 3 mL of THF was added tert-butyllithium (1.3 M in hexane, 406 μL, 0.528 mmol) drop-wise at −65° C. under $N_2$. After stirring at −65° C. for 2 hrs, B30 (50 mg, 0.132 mmol) was added. The mixture was stirred at 15° C. for 1 hour. LCMS showed the reaction was complete. The reaction mixture was quenched with Sat $NH_4Cl$ (30 mL). The mixture was extracted with EtOAc (20 mL×2), washed with brine (30 mL), dried over $Na_2SO_4$, filtered, and evaporated in vacuum to give crude product. The crude product was purified by HPLC separation (column: Phenomenex Synergi C18 150*30 mm*4 um, gradient: 84-84% B (A=0.05% HCl-ACN, B=acetonitrile), flow rate: 30 mL/imin) for further purification to obtain 80 (19.9 mg) as a solid.

$^1$H NMR (CDCl$_3$, 400 MHz) δ 7.57-7.48 (m, 1H), 7.47-7.39 (m, 1H), 7.19 (t, J=7.6 Hz, 1H), 7.12-7.05 (m, 1H), 3.39 (t, J=8.6 Hz, 1H), 2.43-2.32 (m, 1H), 1.79-1.66 (m, 3H), 1.49-1.31 (m, 7H), 1.28-1.13 (m, 12H), 1.13-1.04 (m, 1H), 0.96 (dq, J=5.4, 12.1 Hz, 1H), 0.79-0.73 (m, 1H), 0.70 (s, 3H), 0.60 (s, 3H). LCMS Rt=1.217 min in 2.0 min chromatography, 30-90 AB, MS ESI calcd. for $C_{27}H_{39}FO_2$ [M+H]$^+$ 413, found 395 [M−H$_2$O]$^+$.

Example 82

Synthesis of Compound 81

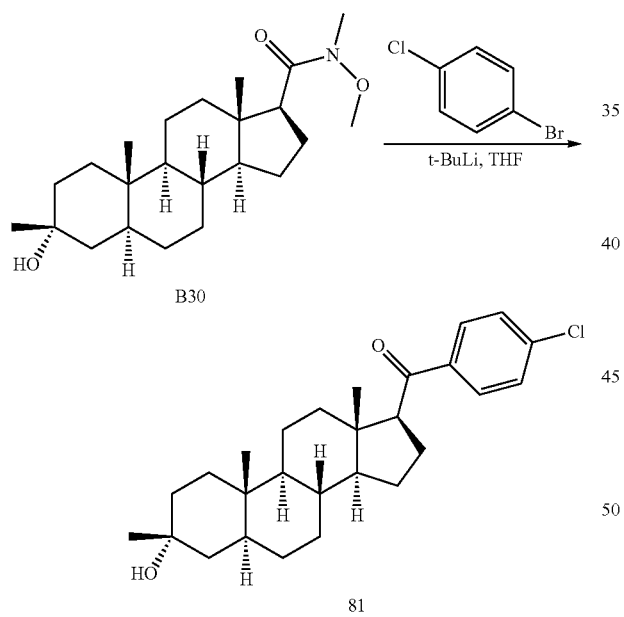

To a stirred solution of 1-bromo-4-chlorobenzene (50.5 mg, 0.264 mmol) in 3 mL of THF was added tert-butyllithium (1.3 M; 406 μL, 0.528 mmol) drop-wise at −65° C. under $N_2$. After stirring at −65° C. for 2 hrs, B30 (50 mg, 0.132 mmol) was added. The mixture was stirred at 15° C. for 1 hour. LCMS showed the reaction was complete. The reaction mixture was quenched with Sat. $NH_4Cl$ (30 mL). The mixture was extracted with EtOAc (20 mL×2), washed with brine (30 mL), dried over $Na_2SO_4$, filtered, and evaporated in vacuum to give crude product. The crude product was purified by HPLC separation (column: Phenomenex Synergi C18 150*30 mm*4 um, gradient: 88-88% B (A=0.05% HCl-ACN, B=acetonitrile), flow rate: 30 mL/min) for further purification to obtain 81 (11.8 mg) as a solid.

$^1$H NMR (CDCl$_3$, 400 MHz) δ 7.85 (d, J=8.4 Hz, 2H), 7.43 (d, J=8.6 Hz, 2H), 3.45 (t, J=8.6 Hz, 1H), 2.48-2.38 (m, 1H), 1.87-1.66 (m, 4H), 1.56-1.46 (m, 5H), 1.42-1.25 (m, 9H), 1.24-1.16 (m, 5H), 1.05-0.95 (m, 1H), 0.84-0.76 (m, 1H), 0.74 (s, 3H), 0.60 (s, 3H). LCMS Rt=1.318 min in 2.0 min chromatography, 30-90 AB, MS ESI calcd. for $C_{27}H_{37}ClO_2$ [M+H]$^+$ 429.3, found 411 [M−H$_2$O]$^+$.

Example 83

Synthesis of Compound 82

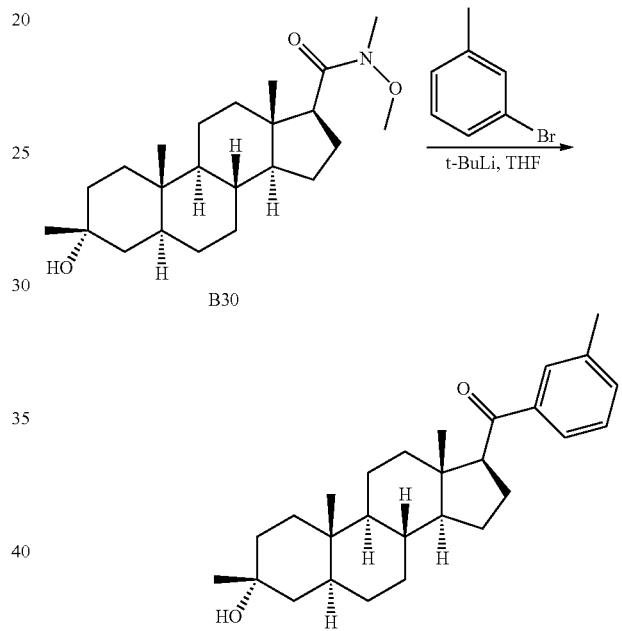

To a stirred solution of 1-bromo-3-methylbenzene (45.1 mg, 0.264 mmol) in 3 mL of THF was added tert-butyllithium (1.3 M; 406 μL, 0.528 mmol) drop-wise at −65° C. under $N_2$. After stirring at −65° C. for 2 hrs. B30 (50 mg, 0.132 mmol) was added. The mixture was stirred at 15° C. for 1 hour. LCMS showed the reaction was complete. The reaction mixture was quenched with Sat $NH_4Cl$ (30 mL) The mixture was extracted with EtOAc (20 mL×2), washed with brine (30 mL), dried over $Na_2SO_4$, filtered, and evaporated in vacuum to give crude product. The crude product was purified by HPLC separation (column: Phenomenex Synergi C18 150*25*10 um, gradient: 69-94% B (A=0.1% TFA-ACN, B=acetonitrile), flow rate: 30 mL/min) for further purification to obtain 82 (24.6 mg) as a solid.

$^1$H NMR (CDCl$_3$, 400 MHz) δ 7.70-7.60 (m, 2H), 7.36-7.29 (m, 2H), 3.47 (t, J=8.6 Hz, 1H), 2.48-2.33 (m, 4H), 1.80-1.67 (m, 3H), 1.52-1.41 (m, 6H), 1.41-1.22 (m, 9H), 1.19 (s, 4H), 1.16-1.07 (m, 1H), 1.03-0.92 (m, 1H), 0.82-0.74 (m, 1H), 0.71 (s, 3H), 0.60 (s, 3H). LCMS Rt=1.273 min in 2.0 min chromatography, 30-90 AB, MS ESI calcd. for $C_{28}H_{41}O_2$ [M+H]$^+$ 409, found 409.

Example 84

Synthesis of Compound 83

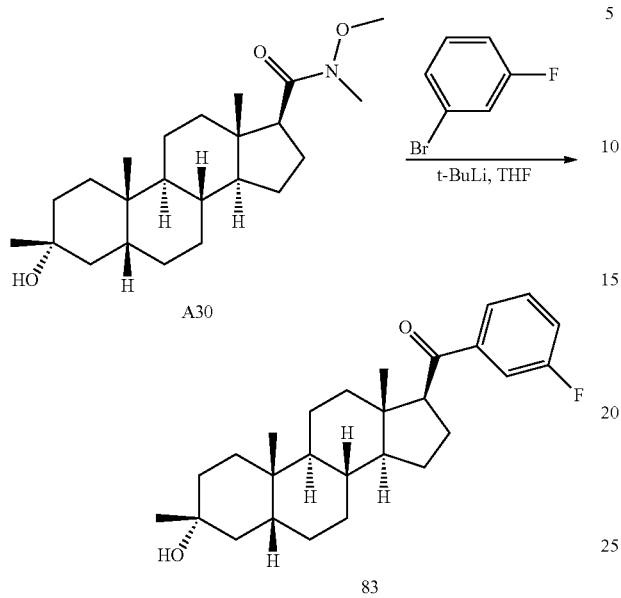

To a solution of 1-bromo-3-fluorobenzene (460 mg, 2.63 mmol) in THF (3 mL) was added t-butyllithium (4.75 mL, 4.75 mmol) dropwise at −78° C. After stirring at −78° C. for 2 h a solution of A30 (100 mg, 0.264 mmol) in THF (1 mL) was added dropwise at 15° C. The reaction was stirred at 15° C. for 2 hours. TLC showed the reaction was completed. The reaction was quenched with sat. NH$_4$Cl (20 mL) and extracted with EtOAc (20 mL×2). The combined organic layers were washed with brine (10 mL), dried over Na$_2$SO$_4$, filtered and evaporated. The crude residue was purified by prep-HPLC separation (column: Phenomenex Synergi C18 150*30 mm*4 um, gradient: 85-90% B (A=0.05% HCl-ACN, B=acetonitrile), flow rate: 30 mL/min) to obtain 83 (16.0 mg) as a solid.

$^1$H NMR (400 MHz, CDCl$_3$) δ 7.65 (d, 1 H) 7.56 (dt, 1 H) 7.42 (td, 1 H) 7.19-7.25 (m, 1 H) 3.42 (t, 1 H) 2.36-2.47 (m, 1 H) 1.92-2.04 (m, 1 H) 1.62-1.91 (m, 4 H) 0.97-1.58 (m, 23 H) 0.86-0.93 (m, 3 H) 0.54-0.61 (m, 3 H). LCMS Rt=0.893 min in 2.0 min chromatography, 10-80 AB, MS ESI calcd. for C$_{27}$H$_{38}$FO$_2$ 413 [M+H]$^+$, found 395.2 [M−H$_2$O]$^+$.

Example 85

Synthesis of Compound 84

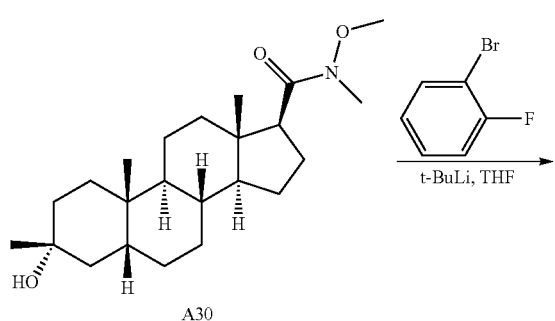

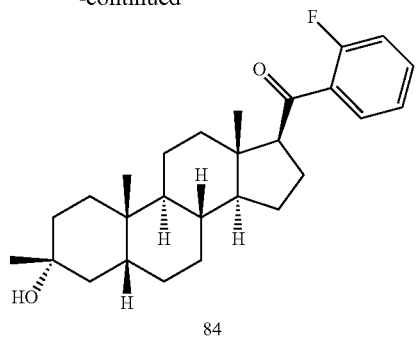

To a stirred solution of 1-bromo-2-fluorobenzene (229 mg, 1.31 mmol) in 3 mL of THF was added tert-butyllithium (1.3 M, 1.92 mL, 2.50 mmol) drop-wise at −78° C. under N$_2$. After stirring at −78° C. for 1 hour, A30 (100 mg, 0.264 mmol) was added. The mixture was stirred at 25° C. for 1 hour. LCMS showed the reaction was complete. The reaction mixture was quenched with saturated NH$_4$Cl (30 mL). The mixture was extracted with EtOAc (20 mL×2). The combined organic layer washed with brine (30 mL), dried over Na$_2$SO$_4$, filtered, and evaporated in vacuum to give crude product, which was purified by prep-HPLC separation (column: Phenomenex Synergi C18 150*30 mm*4 um, gradient: 81-81% B (A=0.05% HCl-ACN, B=acetonitrile), flow rate: 30 mL/min) to give 84 (18.7 mg) as a solid.

$^1$H NMR (CDCl$_3$, 400 MHz): δ 7.53 (t, J=6.8 Hz, 1H), 7.40-7.48 (m, 1H), 7.19 (t, J=7.4 Hz, 1H), 7.12-7.05 (m, 1H), 3.40 (t, J=8.8 Hz, 1H), 2.32-2.44 (m, 1H), 1.94 (t, J=13.4 Hz, 1H), 1.88-1.61 (m, 5H), 1.52-1.27 (m, 10H), 1.26-1.18 (m, 6H), 1.16-0.96 (m, 3H), 0.89 (s, 3H), 0.59 (s, 3H). LCMS Rt=1.205 mm in 2.0 min chromatography, 30-90 AB, MS ESI calcd. for C$_{27}$H$_{38}$FO$_2$ 413 [M+H]$^+$, found 395.2 [M−H$_2$O]$^+$.

Example 86

Synthesis of Compound 85

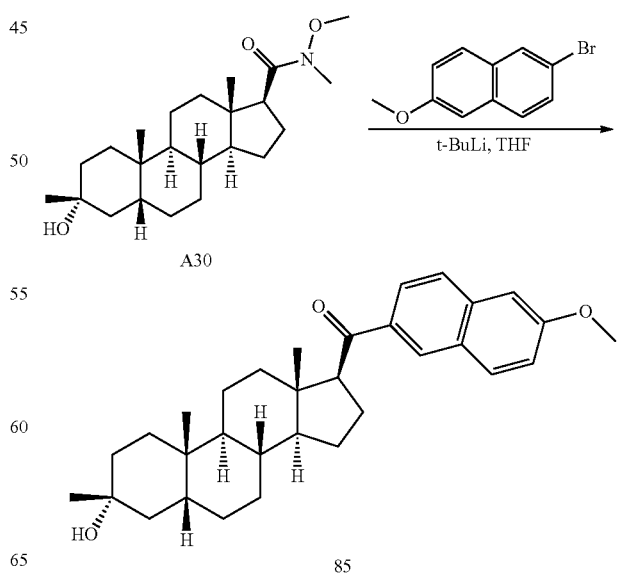

To a stirred solution of 2-bromo-6-methoxynaphthalene (310 mg, 1.31 mmol) in 3 mL of THF was added tert-butyllithium (1.3 M, 1.92 mL, 2.50 mmol) drop-wise at −78° C. under $N_2$. After stirring at −78° C. for 1 hour, A30 (100 mg, 0.264 mmol) was added. The mixture was stirred at 25° C. for 1 hour. LCMS showed the reaction was complete. The reaction mixture was quenched with saturated $NH_4Cl$ (30 mL). The mixture was extracted with EtOAc (20 mL×2). The combined organic layer washed with brine (30 mL), dried over $Na_2SO_4$, filtered and evaporated in vacuum to give crude product, which was purified by prep-HPLC separation (column: Phenomenex Synergi C18 150*30 mm*4 um, gradient: 85-90% B (A=0.05% HCl-ACN, B=acetonitrile), flow rate: 30 mL/min) to afford 85 (29.3 mg) as a solid.

$^1$H NMR (CDCl$_3$, 400 MHz): δ 8.33 (s, 1H), 7.96 (d, J=8.6 Hz, 1H), 7.85 (d, J=9.0 Hz, 1H), 7.75 (d, J=8.6 Hz, 1H), 7.20 (dd, J=8.8, 2.4 Hz, 1H), 7.15 (s, 1H), 3.95 (s, 3H), 3.64 (t, J=8.8 Hz, 1H), 2.44-2.52 (m, 1H), 1.94-2.02 (m, 1H), 1.76-1.91 (m, 3H), 1.66 (d, J=14.4 Hz, 1H), 1.29-1.54 (m, 12H), 1.21-1.28 (m, 5H), 0.97-1.19 (m, 3H), 0.90 (s, 3H), 0.62 (s, 3H). LCMS Rt=1.267 min in 2.0 min chromatography, 30-90 AB, MS ESI calcd. for $C_{32}H_{43}O_3$ [M+H]$^+$ 475.3, found 457 [M−H$_2$O]$^+$.

Example 87

Synthesis of Compound 86

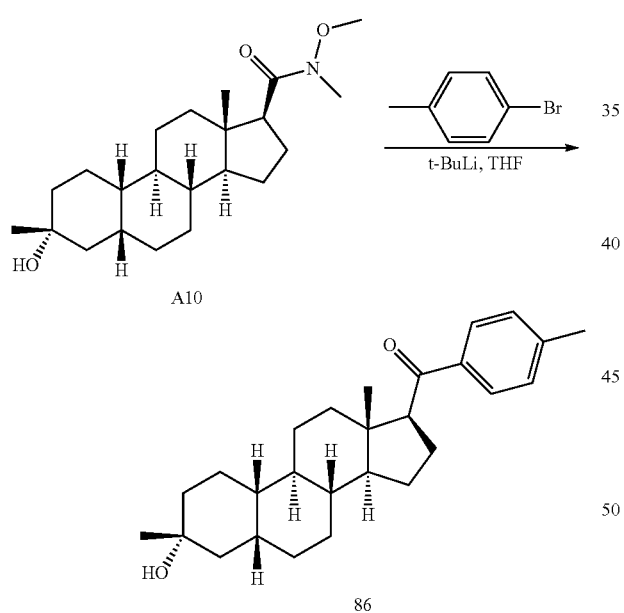

To a stirred solution of 1-bromo-4-methylbenzene (186 mg, 1.09 mmol) in 3 mL of THF was added tert-butyllithium (1.3 M; 1.6 mL, 2.09 mmol) drop-wise at −78° C. under $N_2$. After stirring at −78° C. for 2 hour, A10 (80 mg, 0.22 mmol) was added. The mixture was stirred at 25° C. for 1 hour. LCMS showed the reaction was complete. The reaction mixture was quenched with saturated $NH_4Cl$ (30 mL). The mixture was extracted with EtOAc (20 mL×2), washed with brine (30 mL), dried over $Na_2SO_4$, filtered, and evaporated in vacuum to give crude product. The crude product was purified by prep-HPLC separation (column: Phenomenex Synergi C18 150*30 mm*4 um, gradient: 80-100% B (A=0.05% HCl-ACN, B=acetonitrile), flow rate: 30 mL/min) to obtain 86 (23.7 mg) as a solid.

$^1$H NMR (CDCl$_3$, 400 MHz): δ 7.79 (d, J=8.0 Hz, 2H), 7.24 (d, J=8.0 Hz, 2H), 3.48 (t, J=8.6 Hz, 1H), 2.37-2.48 (m, 4H), 1.72-1.84 (m, 5H), 1.59-1.67 (m, 2H), 1.25-1.49 (m, 15H), 1.06-1.17 (m, 2H), 0.82-0.99 (m, 2H), 0.60 (s, 3H). LCMS Rt=1.233 min in 2.0 min chromatography, 30-90 AB, MS ESI calcd. for $C_{27}H_{39}O_2$ [M+H]$^+$ 395.3, found 377 [M−H$_2$O]$^+$.

Example 88

Synthesis of Compound 87

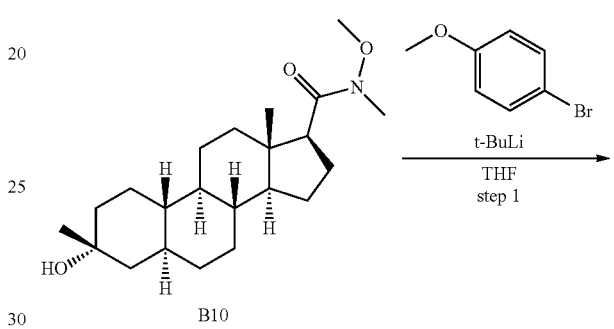

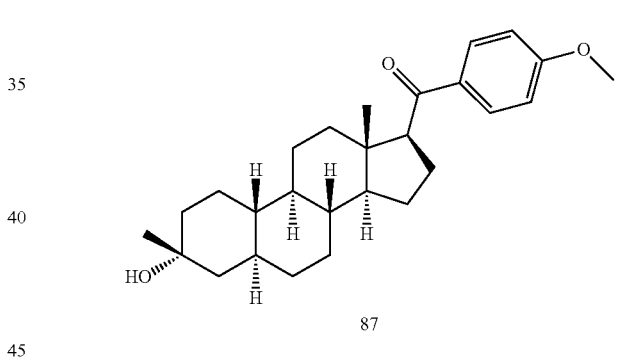

To a solution of 1-bromo-4-methylbenzene (203 mg, 1.09 mmol) in THF (0.3 mL) was added tert-butyllithium (1.68 mL, 1.3 M) at −60° C. The mixture was stirred at −60° C. for 1 hr. A solution of B10 (40 mg, 110 μmol) in THF (0.1 mL) was added into the mixture at −60° C. The reaction mixture was stirred at 25° C. for 2 hrs. TLC showed the reaction was complete. Saturation $NH_4Cl$ (1 mL) was added. The mixture was extracted with EtOAc (1.5 mL×3). The combined organic layers were dried over $Na_2SO_4$. The mixture was filtered. The filtrate was concentrated in vacuum. The residue was purified by purified by prep-HPLC (column: Phenomenex Synergi C18 150*30 mm*4 um, gradient 95-100% B (A=0.05% HCl-ACN, B=acetonitrile), flow rate: 25 mL/min) to give 87 (5 mg) as a solid.

$^1$H NMR (400 MHz. CDCl$_3$) δ 7.90 (d, J=8.8 Hz, 2H), 6.92 (d, J=8.8 Hz, 2H), 3.86 (s, 3H), 3.50-3.43 (m, 1H), 2.46-239 (m, 1H), 1.79-1.44 (m, 9H), 1.53-0.93 (m, 17H), 0.71-0.57 (m, 5H). LCMS t$_R$=0.991 min in 1.5 min chromatography, 5-95 AB, MS ESI calcd. for $C_{27}H_{39}O_3$ [M+H]$^+$ 411, found 411.

Example 89

Synthesis of Compound 88

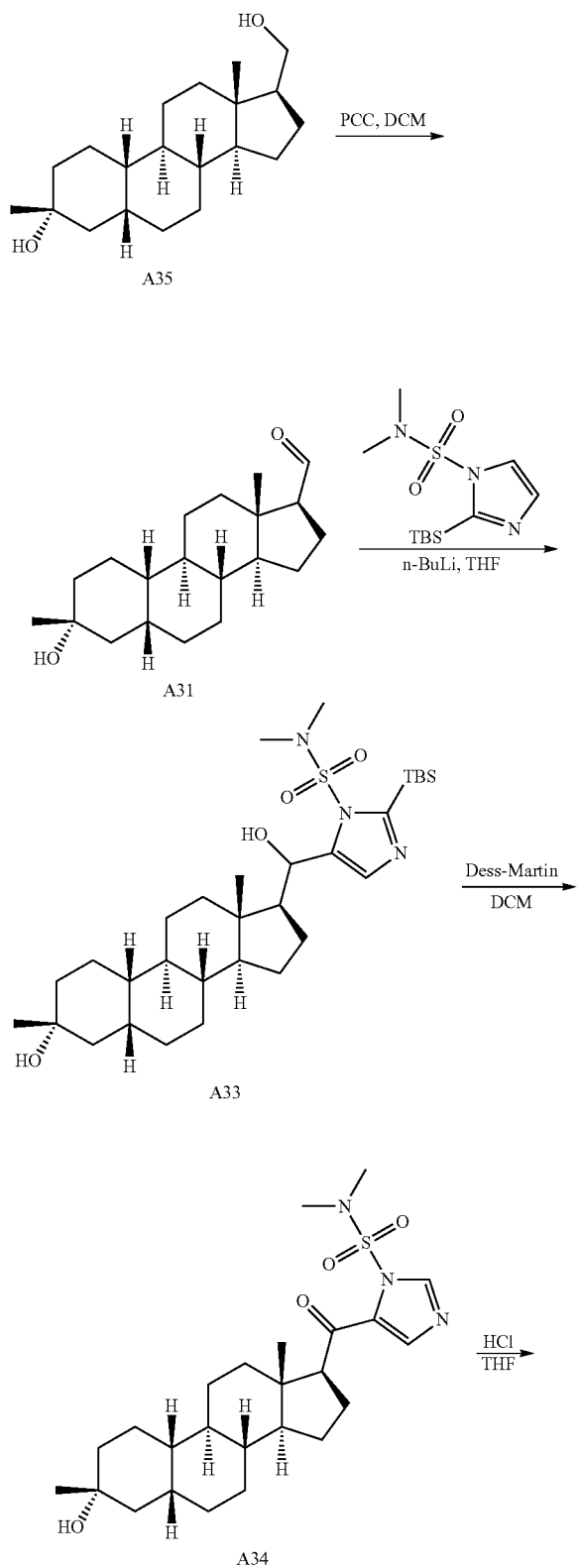

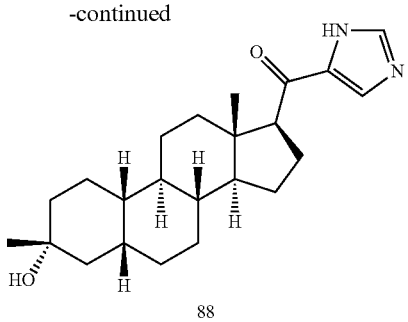

Step 1. To a solution of A35 (1 g, 3.26 mmol) in DCM (5 mL) was added PCC (1.05 g, 4.89 mmol) at 15° C. The mixture was stirred at 15° C. for 1 hr. TLC showed the reaction was complete. The solution was filtered and the filter cake was washed with DCM (50 mL×2). The combined filtrate was concentrated in vacuum. The residue was purified by silica gel column eluted with (PE/EtOAc=10/1) to afford A31 (300 mg) as a solid.

$^1$H NMR (CDCl$_3$, 400 MHz) δ 9.85-9.70 (m, 1H), 2.34-2.26 (m, 1H), 2.16-2.06 (m, 1H), 2.01-1.95 (m, 1H), 1.89-1.60 (m, 8H), 1.49-1.18 (m, 16H), 1.13-1.00 (m, 3H), 0.69 (s, 3H)

Step 2. To a stirring solution of 2-(tert-butyldimethylsilyl)-N,N-dimethyl-1H-imidazole-1-sulfonamide (189 mg, 656 umol) in 2 mL of THF was added drop wise n-BuLi (2.5 M; 196 uL, 492 umol) at −65° C. After stirring at −65° C. for 40 min, a solution of A31 (100 mg, 328 umol) in 2 mL of THF was added drop wise at −65° C. After stirring at 15° C. for 2 h, TLC showed the reaction was complete. The reaction mixture was poured into ice-cold water and extracted with EtOAc (20 mL×2), washed with brine (50 mL), dried over Na$_2$SO$_4$, filtered and evaporated in vacuum to afford A33 (140 mg, crude) as a solid.

Step 3. To a stirring solution of A33 (140 mg, 235 umol) in 5 mL of DCM was added Dess-Martin (199 mg, 470 umol) at 15° C. The mixture was stirring at 15° C. for 2 hours. TLC showed the reaction was complete. The reaction mixture was poured into sat. Na$_2$S$_2$O$_3$ (20 mL) and extracted with EtOAc (20 mL×2), washed with brine (50 mL), dried over Na$_2$SO$_4$, filtered and evaporated in vacuum. The residue was purified by silica gel chromatography (PE/EA=10/1~3/1) to afford A34 (70 mg) as a solid.

$^1$H NMR (CDCl$_3$, 400 MHz) δ 8.17 (s, 1H), 7.66 (s, 1H), 3.13-3.02 (m, 7H), 2.86 (s, 1H), 2.40-2.30 (m, 1H), 1.85-1.78 (m, 3H), 1.77-1.70 (m, 2H), 1.68-1.57 (m, 4H), 1.52-1.22 (m, 17H), 1.17-1.07 (m, 2H), 1.04-0.93 (m, 1H), 0.67 (s, 3H).

Step 4. To a solution of A34 (30 mg, 62.8 umol) in THF (3 mL) was added hydrogen chloride (1 M, 125 uL, 125 umol) at 15° C. The mixture was stirred at 15° C. for 1 hr. and then the reaction mixture was quenched with saturated sat. NaHCO$_3$ (30 mL). The mixture was extracted with EtOAc (20 mL×2). The combined organic layer washed with brine (30 mL), dried over Na$_2$SO$_4$, filtered and evaporated in vacuum to give crude product which was purified by prep-HPLC separation (column: Phenomenex Synergi C18 150*25*10 um, gradient: 29-54% B (A=0.225% FA-ACN, B=acetonitrile), flow rate: 30 mL/min) and then triturated with n-hexane (5 mL) to give 88 (8.8 mg) as a solid.

155

¹H NMR (CDCl₃, 400 MHz): δ 7.77 (s, 1H), 7.68 (s, 1H), 3.25-3.05 (m, 1H), 2.39-2.31 (m, 1H), 1.87-1.80 (m, 3H), 1.78-1.60 (m, 8H), 1.51-1.30 (m, 10H), 1.27 (s, 3H), 1.17-1.06 (m, 2H), 1.04-0.96 (m, 1H), 0.65 (s, 3H). LCMS Rt=1.000 min in 2.0 min chromatography, 10-80 AB, MS ESI calcd. for C₂₃H₃₅N₂O₂[M+H]⁺ 371, found 371.

Example 90

Synthesis of Compound 89

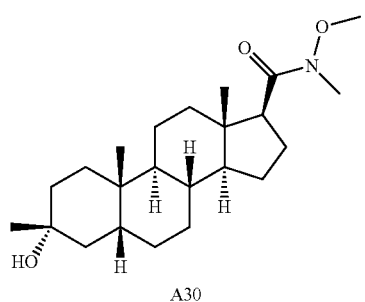

To a stirred solution of 1-bromo-4-methylbenzene (224 mg, 1.31 mmol) in 3 mL of THF was added tert-butyllithium (1.3 M, 1.92 mL, 2.5 mmol) drop-wise at −78° C. under N₂. After stirring at −78° C. for 1 hour, A30 (100 mg, 0.264 mmol) was added. The mixture was stirred at 25° C. for 1 hour. LCMS showed the reaction was complete. The reaction mixture was quenched with saturated NH₄Cl (30 mL). The mixture was extracted with EtOAc (20 mL×2), washed with brine (30 mL), dried over Na₂SO₄, filtered, and evaporated in vacuum to give crude product, which was purified by prep-HPLC separation (column: Phenomenex Synergi C18 150*30 mm*4 um, gradient: 85-85% B (A=0.05% HCl-ACN, B=acetonitrile), flow rate: 30 mL/min) to give 89 (18.1 mg) as a solid.

¹H NMR (CDCl₃, 400 MHz): δ 7.79 (d, J=8.0 Hz, 2H), 7.23 (d, J=8.0 Hz, 2H), 3.47 (t, J=8.8 Hz, 1H), 2.38-2.48 (m, 4H), 1.97 (t, J=13.2 Hz, 1H), 1.62-1.90 (m, 5H), 1.32-1.51 (m, 10H), 1.20-1.30 (m, 6H), 1.08-1.18 (m, 2H), 1.04 (dd, J=14.1, 3.6 Hz, 1H), 0.91 (s, 3H), 0.58 (s, 3H). LCMS Rt=1.267 min in 2.0 min chromatography, 30-90 AB, MS ESI calcd. for C₂₅H₄₁O₂[M+H]⁺ 409, found 409.

156

Example 91

Synthesis of Compound 90

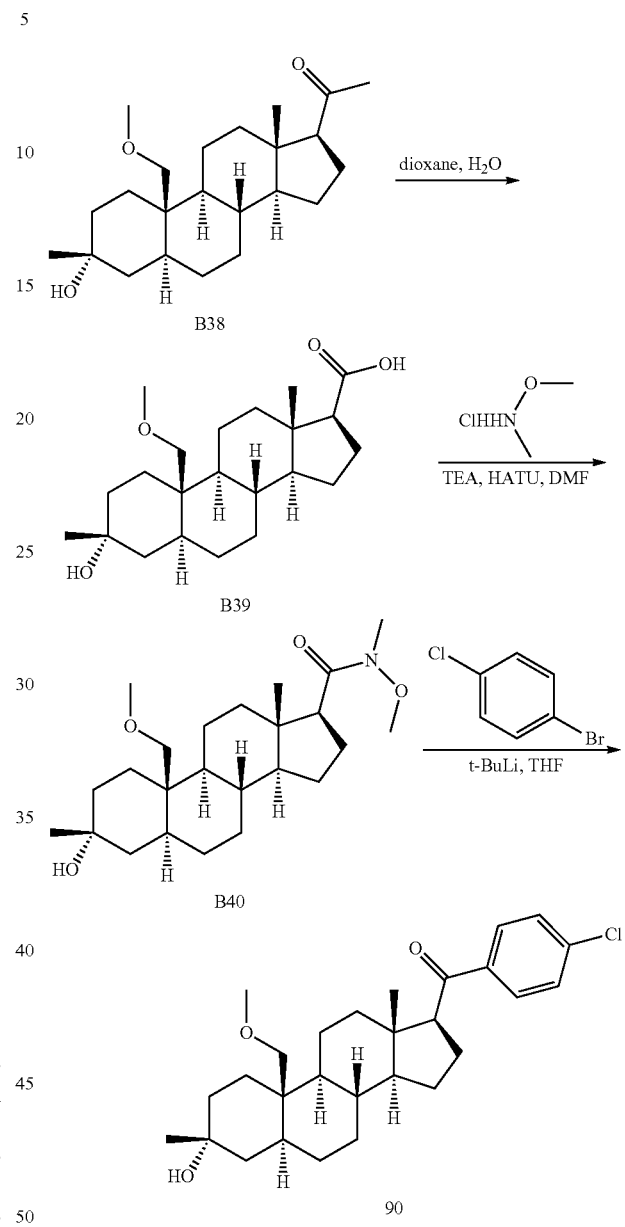

Step 1. To a solution of B38 (10 g, 27.5 mmol) in dioxane/H₂O (374 mL/110 mL) at 0° C. was added sodium hypobromide [prepared from NaOH (145 g), bromine (47.7 mL), dioxane (798 mL) and H₂O (1230 mL)]. The resulting mixture was stirred at 25° C. for 24 hours and was cooled to 0° C. Saturated aqueous sodium sulfite solution (1000 mL) and aqueous HCl solution (1 M, 500 mL) were sequentially added. The mixture was extracted with ethyl acetate (1000 mL×2). The organic phase was washed with water (1000 mL×3), brine (1000 mL), dried over anhydrous Na₂SO₄, filtered and evaporated to afford B39 (8 g) as a solid.

¹H NMR (DMSO-d₆, 400 MHz) δ=11.90 (br. s., 1H), 3.89 (s, 1H), 3.67-3.61 (m, 1H), 3.43 (d, J=10.0 Hz, 1H), 3.31 (br. s., 1H), 3.20 (s, 3H), 2.25 (t, J=9.0 Hz, 1H), 2.00-1.77 (m, 3H), 1.72-1.28 (m, 11H), 1.22-0.99 (m, 11H), 0.95-0.81 (m, 1H), 0.76-0.67 (m, 1H), 0.63 (s, 3H).

Step 2. To a solution of B39 (7.8 g, 21.3 mmol) in DMF (100 mL) was added HATU (9.69 g, 25.5 mmol), TEA (14.6 mL, 106 mmol) and N,O-dimethylhydroxylamine hydrochloride (7.26 g, 74.5 mmol) at 15° C. The mixture was stirred at 15° C. for 2 hrs. TLC (PE/EA=1/1) showed the reaction was complete. The mixture was poured into water (200 mL) and extracted with EtOAc (2×200 mL). The combined organic layer was washed with brine (100 mL), dried over anhydrous $Na_2SO_4$, filtered and concentrated. The residue was purified by column chromatography on silica (petroleum ether/ethyl acetate=10:1) to afford B40 (8 g) as a solid.

$^1$H NMR (CDCl$_3$, 400 MHz) δ=3.64 (s, 3H), 3.49-3.44 (m, 1H), 3.39-3.35 (m, 1H), 3.28 (s, 3H), 3.19 (s, 3H), 2.78 (br. s., 1H), 2.25-2.11 (m, 1H), 2.02 (td, J=3.4, 13.2 Hz, 1H), 1.84-1.62 (m, 5H), 1.59-1.41 (m, 6H), 1.34-1.04 (m, 11H), 0.96 (dd, J=4.8, 12.0 Hz, 1H), 0.85-0.72 (m, 4H). LCMS Rt=3.497 min in 7.0 min chromatography, 10-80 AB, MS ESI calcd. for $C_{24}H_{42}NO_4$ [M+H]$^+$ 408, found 408.

Step 3. To a stirred solution of 1-bromo-4-chlorobenzene (75 mg, 0.392 mmol) in 3 mL of THF was added tert-butyllithium (1.3 M; 587 uL, 0.764 mmol) dropwise at −65° C. under N$_2$. After stirring at −65° C. for 2 hrs, B40 (80 mg, 0.196 mmol) in THF (1 mL) was added dropwise. The mixture was stirred at 15° C. for 1 hour. LCMS showed the reaction was complete. The reaction mixture was quenched with Sat. NH$_4$Cl (30 mL). The mixture was extracted with EtOAc (20 mL×2), washed with brine (30 mL), dried over Na$_2$SO$_4$, filtered, and evaporated in vacuum to give crude product. The crude product was purified by HPLC separation (column: Phenomenex Synergi Max-RP 250*50 mm*10 urn, gradient: 88-93% B (A=0.05% HCl-ACN, B=acetonitrile), flow rate: 30 mL/min) to obtain 90 (19.7 mg) as a solid.

$^1$H NMR (CDCl$_3$, 400 MHz) δ 7.82 (d. J=8.6 Hz, 2H), 7.41 (d, J=8.6 Hz, 2H), 3.47-3.39 (m, 2H), 3.37-3.30 (m, 1H), 3.23 (s, 3H), 2.48-2.35 (m, 1H), 2.00-1.93 (m, 1H), 1.81-1.69 (m, 3H), 1.65-1.59 (m, 2H), 1.56-1.44 (m, 5H), 1.39-1.28 (m, 5H), 1.27-1.14 (m, 7H), 1.13-0.97 (m, 2H), 0.86-077 (m, 1H), 0.61 (s, 3H). LCMS Rt=3.085 min in 4.0 min chromatography, 30-90 AB, MS ESI calcd. for $C_{28}H_{40}ClO_3$ [M+H]$^+$ 460.3, found 441 [M−H$_2$O]$^+$.

Example 92

Synthesis of Compound 91

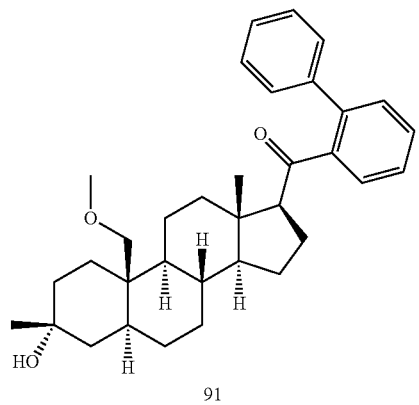

91

To a stirring solution of 2-bromo-1,1'-biphenyl (91.3 mg, 0.392 mmol) in 3 mL of THF was added tert-butyllithium (1.3 M, 587 μL, 0.764 mmol) dropwise at −65° C. under N$_2$. After stirring at −65° C. for 2 hrs, a solution of B40 (80 mg, 0.196 mmol) in THF (1 mL) was added dropwise. The mixture was stirred at 15° C. for 1 hour. LCMS showed the reaction was complete. The reaction mixture was quenched with sat. NH$_4$Cl (30 mL). The mixture was extracted with EtOAc (20 mL×2), washed with brine (30 mL), dried over Na$_2$SO$_4$, filtered, and evaporated in vacuum to give crude product. The crude product was purified by HPLC separation (column: Boston Green ODS 150*30 5u, gradient: 92-98% B (A=0.05% HCl-ACN, B=acetonitrile), flow rate: 25 mL/min) for further purification to obtain 91 (17.8 mg) as a solid.

$^1$H NMR (CDCl$_3$, 400 MHz) δ 7.51-7.30 (m, 9H), 3.38-3.34 (m, 1H), 3.30-3.25 (m, 1H), 3.22 (s, 3H), 2.31-2.25 (m, 1H), 2.23-2.14 (m, 1H), 1.93-1.86 (m, 1H), 1.51-1.32 (m, 8H), 1.31-1.16 (m, 6H), 1.15-0.69 (m, 8H), 0.64-0.54 (m, 5H). LCMS Rt=3.112 min in 4.0 min chromatography, 30-90 AB, MS ESI calcd. for $C_{34}H_{45}O_3$ [M+H]$^+$ 501, found 501.

Example 93

Synthesis of Compound 92

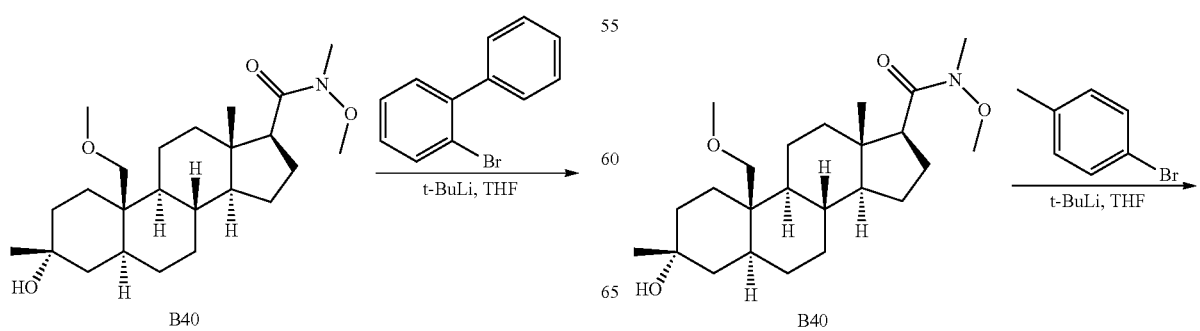

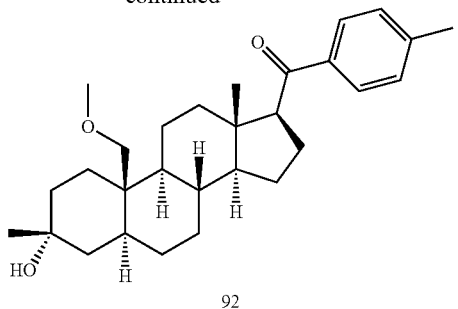

92

To a stirring solution of 1-bromo-4-methylbenzene (67 mg, 0.392 mmol) in 3 mL of THF was added tert-butyllithium (1.3 M: 587 μL, 0.764 mmol) dropwise at −65° C. under N$_2$. After stirring at −65° C. for 2 hrs, a solution of B40 (80 mg, 0.196 mmol) in THF (1 mL) was added dropwise. The mixture was stirred at 15° C. for 1 hour. LCMS showed the reaction was completed. The reaction mixture was quenched with sat. NH$_4$Cl (30 mL). The mixture was extracted with EtOAc (20 mL×2), washed with brine (30 mL), dried over Na$_2$SO$_4$, filtered, and evaporated in vacuum to give crude product. The crude product was purified by HPLC separation (column: Boston Green ODS 150*30 5u, gradient: 82-98% B (A=0.05% HCl-ACN, B=acetonitrile), flow rate: 25 mL/min) for further purification to obtain 92 (24.9 mg) as a solid.

$^1$H NMR (CDCl$_3$, 400 MHz) δ 7.78 (d, J=8.0 Hz, 2H), 7.22 (d, J=8.0 Hz, 2H), 3.50-3.39 (m, 2H), 3.37-3.31 (m, 1H), 3.23 (s, 3H), 2.48-2.37 (m, 4H), 2.00-1.93 (m, 1H), 1.79-1.69 (m, 3H), 1.62-1.54 (m, 3H), 1.50-1.44 (m, 3H), 1.42-1.25 (m, 6H), 1.25-1.15 (m, 5H), 1.15-0.92 (m, 3H), 0.86-0.76 (m, 1H), 0.61 (s, 3H). LCMS Rt=2.954 min in 2.0 min chromatography, 30-90 AB, MS ESI calcd. for C$_{29}$H$_{43}$O$_3$ [M+H]$^+$ 439, found 421 [M−H$_2$O]$^+$.

Example 94

Synthesis of Compound 93

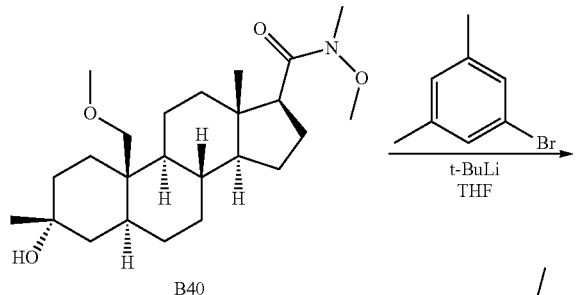

B40

93

To a stirring solution of 1-bromo-3,5-dimethylbenzene (72.5 mg, 0.392 mmol) in 3 mL of THF was added tert-butyllithium (1.3 M; 587 uL, 0.764 mmol) dropwise at −65° C. under N$_2$. After stirring at −65° C. for 2 hrs, a solution of B40 (80 mg, 0.196 mmol) in THF (1 mL) was added dropwise. The mixture was stirred at 15° C. for 1 hour. LCMS showed the reaction was complete. The reaction mixture was quenched with sat. NH$_4$Cl (30 mL). The mixture was extracted with EtOAc (20 mL×2), washed with brine (30 mL), dried over Na$_2$SO$_4$, filtered, and evaporated in vacuum to give crude product. The crude product was purified by HPLC separation (column: Phenomenex Synergi Max-RP 250*50 mm*10 um, gradient: 88-93% B (A=0.05% HCl-ACN, B=acetonitrile), flow rate: 30 mL/min) for further purification to obtain 93 (47.4 mg) as a solid.

$^1$H NMR (CDCl$_3$, 400 MHz) δ 745 (s, 2H), 7.16 (s, 1H), 3.49-3.40 (m, 2H), 3.37-3.32 (m, 1H), 3.23 (s, 3H), 2.45-2.33 (m, 7H), 2.00-1.95 (m, 1H), 1.80-1.70 (m, 3H), 1.56-1.44 (m, 6H), 1.43-1.25 (m, 6H), 1.24-1.17 (m, 5H), 1.16-0.95 (m, 3H), 0.87-0.75 (m, 1H), 0.62 (s, 3H). LCMS Rt=3.124 min in 4.0 min chromatography, 30-90 AB, MS ESI calcd. for C$_{30}$H$_{45}$O$_3$ [M+H]$^+$ 453, found 453.

Example 95

Synthesis of Compound 94

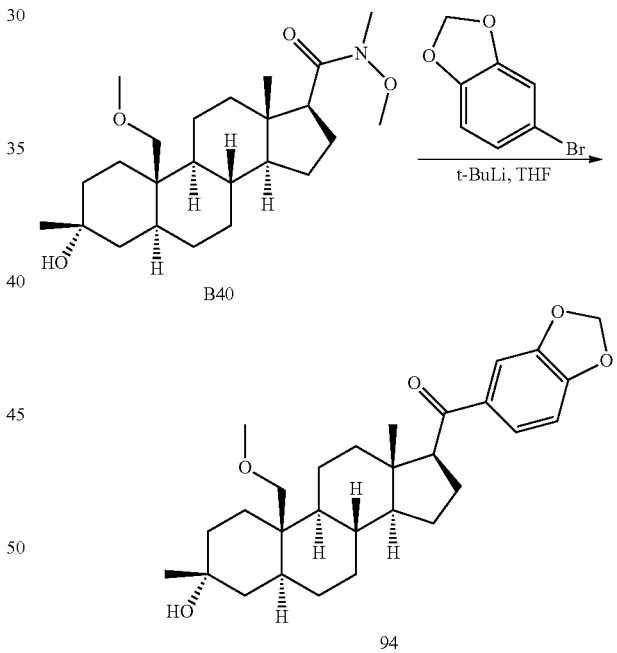

B40

94

To a stirring solution of 5-bromobenzo[d][1,3]dioxole (78.7 mg, 0.392 mmol) in 3 mL of THF was added tert-butyllithium (1.3 M; 587 uL, 0.764 mmol) dropwise at −65° C. under N$_2$. After stirring at −65° C. for 2 hrs, a solution of B40 (80 mg, 0.196 mmol) in THF (1 mL) was added dropwise. The mixture was stirred at 15° C. for 1 hour. LCMS showed the reaction was completed. The reaction mixture was quenched with sat. NH$_4$Cl (30 mL). The mixture was extracted with EtOAc (20 mL×2), washed with brine (30 mL), dried over Na$_2$SO$_4$, filtered, and evaporated in vacuum to give crude product. The crude product was purified by HPLC separation (column Phenomenex Synergi Max-RP 250*50 mm*10 um, gradient: 88-93% B (A=0.05% HCl-ACN, B=acetonitrile), flow rate: 30 mL/min) to obtain 94 (28.2 mg) as a solid.

¹H NMR (CDCl₃, 400 MHz) δ 7.49 (dd, 1H), 7.39 (d, 1H), 6.83 (d, 1H), 6.03 (s, 2H), 3.45-3.33 (m, 3H), 3.24 (s, 3H), 2.45-2.36 (m, 1H), 2.01-1.95 (m, 1H), 1.77-1.68 (m, 3H), 1.60-1.50 (m, 2H), 1.53-1.42 (m, 5H), 1.42-1.18 (m, 10H), 1.15-0.96 (m, 3H), 0.86-0.77 (m, 1H), 0.61 (s, 3H). LCMS Rt=3.401 min in 4.0 min chromatography, 10-10 AB, MS ESI calcd. for $C_{29}H_{41}O_5$ [M+H]⁺ 469.3, found 451 [M−H₂O]⁺.

Example 96

Synthesis of Compound 95

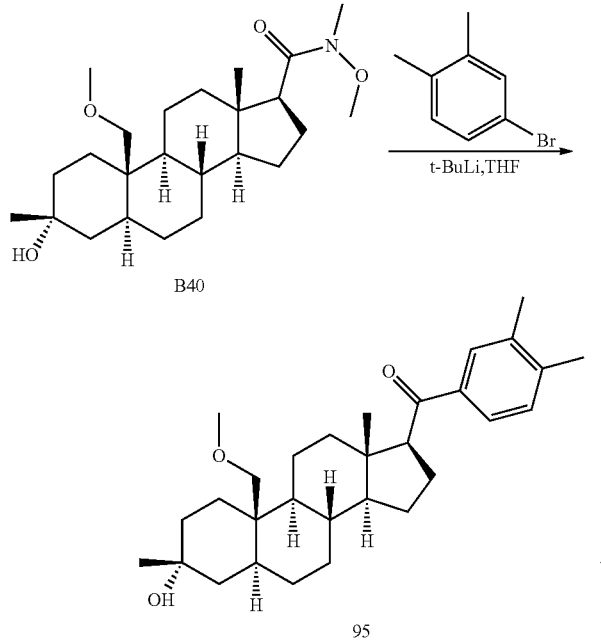

To a stirring solution of 4-bromo-1,2-dimethylbenzene (72.5 mg, 0.392 mmol) in 3 mL of THF was added tert-butyllithium (1.3 M; 587 uL 0.764 mmol) dropwise at −65° C. under N₂. After stirring at −65° C. for 2 hrs, a solution of B40 (80 mg, 0.196 mmol) in THF (1 mL) was added dropwise. The mixture was stirred at 15° C. for 1 hour. LCMS showed the reaction was complete. The reaction mixture was quenched with Sat. NH₄Cl (30 mL). The mixture was extracted with EtOAc (20 mL×2), washed with brine (30 mL), dried over Na₂SO₄, filtered, and evaporated in vacuum to give crude product. The crude product was purified by HPLC separation (column: Phenomenex Synergi Max-RP 250*50 mm*10 um, gradient: 88-93% B (A=0.05% HCl-ACN, B=acetonitrile), flow rate: 30 mL/min) for further purification to obtain 95 (12 mg) as a solid.

¹H NMR (CDCl₃, 400 MHz) δ 7.65 (s, 1H), 7.60 (d, J=7.8 Hz, 1H), 7.17 (d, J=7.8 Hz, 1H), 3.49-3.39 (m, 2H), 3.37-3.31 (m, 1H), 3.23 (s, 3H), 2.47-2.36 (m, 1H), 2.30 (s, 6H), 2.00-1.95 (m, 1H), 1.78-1.68 (m, 3H), 1.54-1.44 (m, 6H), 1.42-1.17 (m, 11H), 1.16-0.92 (m, 3H), 0.86-0.75 (m, 1H), 0.61 (s, 3H). LCMS Rt=3.079 min in 4.0 min chromatography, 30-90 AB, MS ESI calcd. for $C_{30}H_{45}O_3$ [M+H]⁺ 453, found 453.

Example 97

Synthesis of Compound 96

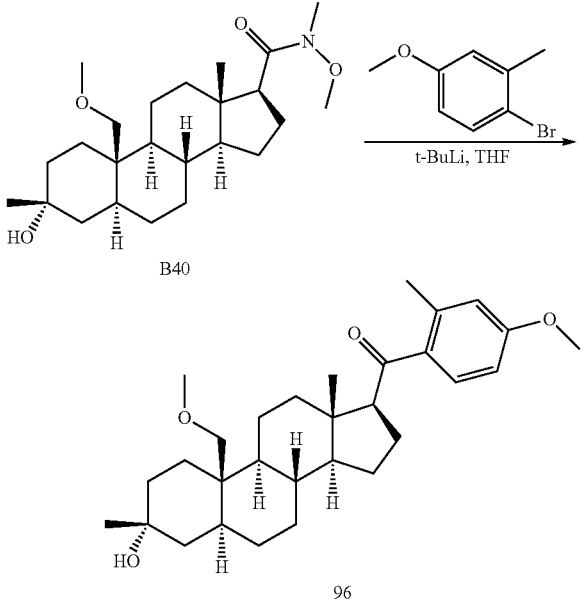

To a stirring solution of 1-bromo-4-methoxy-2-methyl-benzene (78.8 mg, 0.392 mmol) in 3 mL of THF was added tert-butyllithium (1.3 M; 587 uL, 0.764 mmol) dropwise at −65° C. under N₂. After stirring at −65° C. for 2 hrs, a solution of B40 (80 mg, 0.196 mmol) in THF (1 mL) was added dropwise. The mixture was stirred at 15° C. for 1 hour. LCMS showed the reaction was complete. The reaction mixture was quenched with sat. NH₄Cl (30 mL). The mixture was extracted with EtOAc (20 mL×2), washed with brine (30 mL), dried over Na₂SO₄, filtered, and evaporated in vacuum to give crude product. The crude product was purified by HPLC separation (column: Boston Green ODS 150*30 5u, gradient: 92-98% B (A=0.05% HCl-ACN, B=acetonitrile), flow rate: 25 mL/min) for further purification to obtain 96 (14.3 mg) as a solid.

¹H NMR (CDCl₃, 400 MHz) δ 7.53 (d, J=8.6 Hz, 1H), 6.76-6.68 (m, 2H), 3.83 (s, 3H), 3.44-3.40 (m, 1H), 3.36-3.29 (m, 2H), 3.23 (s, 3H), 2.47 (s, 3H), 2.44-2.34 (m, 1H), 1.99-1.90 (m, 1H), 1.77-1.67 (m, 3H), 1.51-1.41 (m, 6H), 1.39-1.12 (m, 11H), 1.11-0.94 (m, 3H), 0.81-0.72 (m, 1H), 0.64 (s, 3H). LCMS Rt=2.925 min in 4.0 min chromatography, 30-90 AB, MS ESI calcd. for $C_{30}H_{45}O_4$ [M+H]⁺ 469, found 469.

Example 98

Synthesis of Compound 97

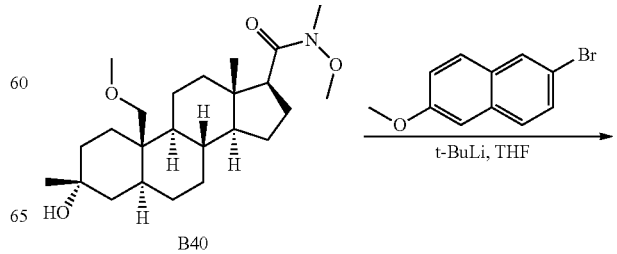

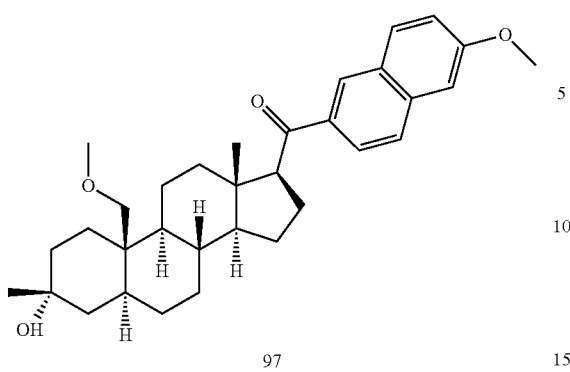

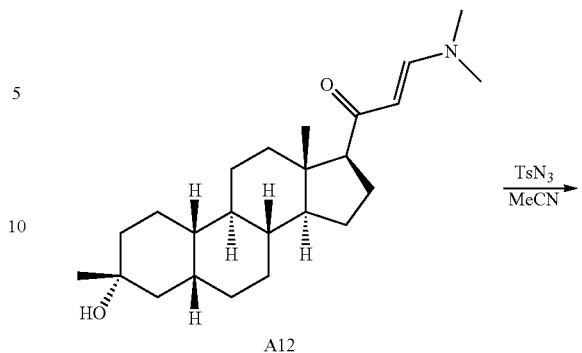

To a stirring solution of 2-bromo-6-methoxynaphthalene (92.9 mg, 0.392 mmol) in 3 mL of THF was added tert-butyllithium (1.3 M; 587 uL, 0.764 mmol) dropwise at −65° C. under $N_2$. After stirring at −65° C. for 2 hrs, a solution of B40 (80 mg, 0.196 mmol) in THF (1 mL) was added dropwise. The mixture was stirred at 15° C. for 1 hour. LCMS showed the reaction was completed. The reaction mixture was quenched with sat. $NH_4Cl$ (30 mL). The mixture was extracted with EtOAc (20 mL×2), washed with brine (30 mL), dried over $Na_2SO_4$, filtered, and evaporated in vacuum to give crude product. The crude product was purified by HPLC separation (column: Phenomenex Synergi Max-RP 250*50 mm*10 um, gradient: 84-84% B (A=0.05% HCl-ACN, B=acetonitrile), flow rate: 30 mL/min) for further purification to obtain 97 (36.5 mg) as a solid.

$^1$H NMR (CDCl$_3$, 400 MHz) δ 8.33 (s, 1H), 7.96 (dd, J=1.4, 8.7 Hz, 1H), 7.85 (d, J=9.0 Hz, 1H), 7.75 (d, J=8.6 Hz, 1H), 7.20 (dd, J=2.4, 8.9 Hz, 1H), 7.15 (d, J=2.4 Hz, 1H), 3.95 (s, 3H), 3.63 (t, J=8.8 Hz, 1H), 3.46-3.40 (m, 1H), 3.36-3.30 (m, 1H), 3.22 (s, 3H), 2.55-2.42 (m, 18H), 2.00-1.90 (m, 1H), 1.82-1.71 (m, 3H), 1.53-1.44 (m, 6H), 1.43-1.31 (m, 6H), 1.25-1.20 (m, 5H), 1.17-0.99 (m, 3H), 0.87-0.80 (m, 1H), 0.66 (s, 3H). LCMS Rt=1.278 min in 2.0 min chromatography, 30-90 AB. MS ESI calcd. for $C_{33}H_{45}O_4$ $[M+H]^+$ 505.3, found 487 $[M-H_2O]^+$.

Example 99

Synthesis of Compound 98

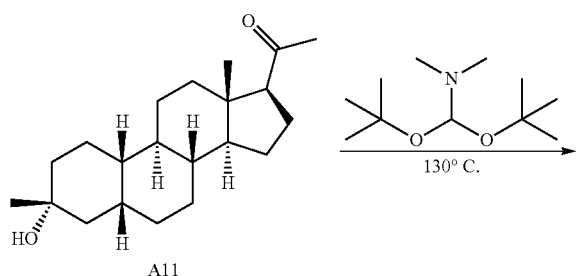

Step 1. To a solution of A11 (1.0 g, 3.13 mmol) in 1,1-di-tert-butoxy-N,N-dimethylmethanamine (10 mL) was refluxed at 130° C. for 18 hours. The mixture was concentrated to give 8.4 g of crude product A12 which was used for next step directly.

LCMS Rt=1.754 min in 3.0 min chromatography, 10-80 AB, MS ESI calcd. for $C_{24}H_{40}NO_2$ $[M+H]^+$ 374, found 374.

Step 2. To a solution of crude A12 (1.16 g, 3.10 mmol, 8.4 g crude) in $CH_3CN$ (20 mL) was added 4-methylbenzenesulfonyl azide (3.05 g, 15.5 mmol). The mixture was stirred at 15° C. for 25 hours. LCMS showed the starting material was consumed, and the desired compound was determined by LCMS. The solution was quenched with Sat. $Na_2S_2O_3$ (50 mL). The mixture was extracted with EA (50 mL×2). The combined organic phase was washed with brine (30 mL), dried over $Na_2SO_4$, filtered and concentrated in vacuum to give the crude product (3.6 g). The crude product was purified by silica gel chromatography (PE:EA=1:1) to give product as solid (450 mg, crude), which was purified by prep-HPLC (column: Phenomenex Synergi C18 150*25*10 um, gradient: 38-63%/B (A=water (0.1% TFA), B=acetonitrile), flow rate: 30 ml/min) to afford 110 mg of 98.

$^1$H NMR (400 MHz, CDCl3) δ 8.17 (s, 1H), 3.63 (t. J=8.5 Hz, 1H), 2.43-229 (m, 1H), 1.95-0.90 (m, 29H), 0.66 (s, 3H). LCMS Rt=1.860 min in 3.0 min chromatography, 10-80 AB, MS ESI calcd. for $C_{22}H_{34}N_3O_2$ $[M+H]^+$ 372, found 372.

Example 100

Synthesis of Compounds 99 and 100

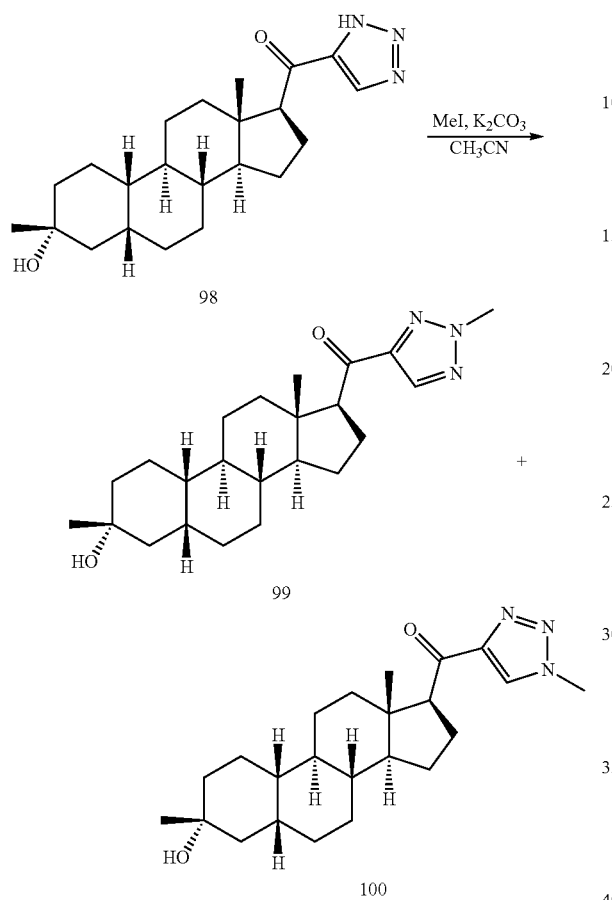

To a solution of 98 (88 mg, 236 μmol) in CH$_3$CN (1 mL) was added K$_2$CO$_3$ (97.7 mg, 708 mol) and MeI (0.650, 4.58 mmol). The reaction mixture was stirred at 15° C. for another 15 hrs. The starting material was consumed completely which was determined by LCMS. The reaction was quenched with aqueous sodium hypochlorite (5%, 20 mL). The mixture was extracted with EA (50 mL×3). The combined organic phase was washed with brine (40 mL), dried over anhydrous Na$_2$SO$_4$, filtered and concentrated in vacuum to give the crude product. The crude product was purified by silica gel chromatography (PE:EA=1:1) to give the crude 99 (25 mg) and 100 (13 mg). 99 was purified by prep-HPLC (column: Boston Green ODS 150*30 5u, gradient: 68-98% B (A=water (0.05% HCl), B=acetonitrile), flow rate: 25 mL/min) to give purified 99 (5 mg), the structure of 99 was randomly assigned. 100 was purified by prep-HPLC (column: Boston Green ODS 150*30 5u, gradient 65-95% B (A=water (0.05% HCl), B=acetonitrile), flow rate: 25 mL/min) to give 100 (4.2 mg).

99: $^1$H NMR (400 MHz, CDCl3) δ 7.99 (s, 1H), 4.24 (s, 3H), 3.53 (t, J=8.5 Hz, 1H), 2.42-2.25 (m, 1H), 2.09-0.84 (m, 32H), 0.65 (s, 3H). LCMS Rt=1.228 min in 2.0 min chromatography, 30-90 AB, MS ESI calcd for C$_{23}$H$_{36}$N$_3$O$_2$ [M+H]$^+$ 386, found 368 [M−H$_2$O]$^+$.

100: $^1$H NMR (400 MHz, CDCl3) δ 8.01 (s, 1H), 4.14 (s, 3H), 3.83 (t, J=8.9 Hz, 1H), 2.38-2.25 (m, 1H), 1.88-0.81 (m, 35H), 0.65 (s, 3H). LCMS Rt=1.085 min in 2.0 min chromatography, 30-90 AB, MS ESI calcd. for C$_{23}$H$_{36}$N$_3$O$_2$ [M+H]$^+$ 386, found 386.

Example 101

Synthesis of Compound 101

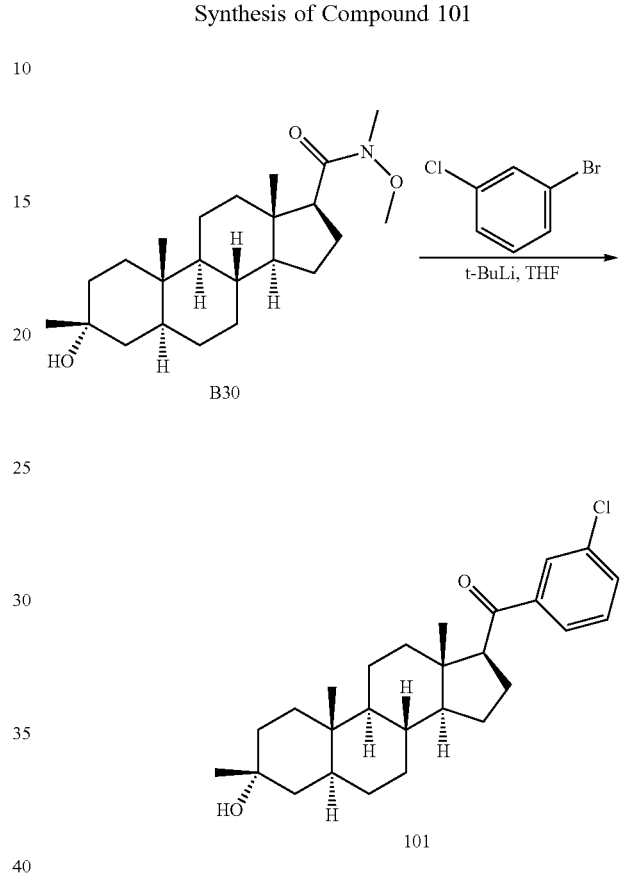

To a stirred solution of 1-bromo-3-chlorobenzene (50.5 mg, 0.264 mmol) in 3 mL of THF was added tert-butyllithium (1.3 M, 406 uL, 0.528 mmol) dropwise at −65° C. under N$_2$. After stirring at −65° C. for 2 hrs, B30 (50 mg, 0.132 mmol) was added. The mixture was stirred at 15° C. for 1 hour. LCMS showed the reaction was complete. The reaction mixture was quenched with Sat. NH$_4$Cl (30 mL). The mixture was extracted with EtOAc (20 mL×2), washed with brine (30 mL), dried over Na$_2$SO$_4$, filtered, and evaporated in vacuum to give crude product. The crude product was purified by HPLC separation (column: Phenomenex Synergi C18 150*25*10 um, gradient: 72-97% B (A=0.225% FA-ACN, B=acetonitrile), flow rate: 30 mL/min) to obtain 30 mg of impure material. Additional HPLC separation (column: Phenomenex Synergi C18 250*21.2 mm*4 um, gradient: 95-95% B (A=0.05% HCl-ACN, B=acetonitrile), flow rate: 25 mL/min) gave 101 as (8.2 mg) a white solid.

$^1$H NMR (CDCl$_3$, 400 MHz) δ 7.84 (s, 1H), 7.74 (d, J=8.0 Hz, 1H), 7.50 (d, J=8.6 Hz, 1H), 7.41-7.35 (m, 1H), 3.41 (t, J=8.8 Hz, 1H), 2.43-2.35 (m, 1H), 1.84-1.65 (m, 4H), 1.53-1.44 (m, 5H), 1.38-1.22 (m, 9H), 1.21-1.11 (m, 5H), 1.03-0.92 (m, 1H), 0.82-0.75 (m, 1H), 0.71 (s, 3H), 0.59 (s, 3H). LCMS Rt=1.326 min in 2.0 min chromatography, 30-90 AB, MS ESI calcd. for C$_{27}$H$_{38}$ClO$_2$[M+H]$^+$ 429.2, found 411 [M−H$_2$O]$^+$.

Example 102

Synthesis of Compound 102

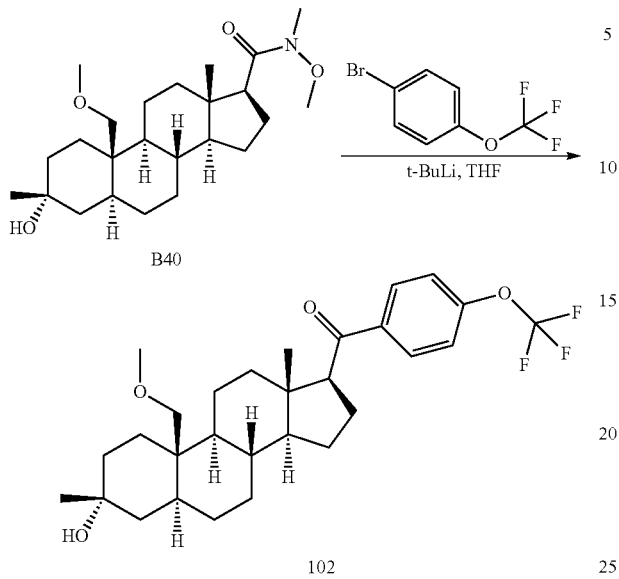

To a stirring solution of 1-bromo-4-(trifluoromethoxy)benzene (94.4 mg, 0.392 mmol) in 3 mL of THF was added tert-butyllithium (1.3 M; 587 uL, 0.764 mmol) dropwise at −65° C. under $N_2$. After stirring at −65° C. for 2 hrs, a solution of B40 (80 mg, 0.196 mmol) in THF (1 mL) was added dropwise. The mixture was stirred at 15° C. for 1 hour. LCMS showed the reaction was completed. The reaction mixture was quenched with sat. $NH_4Cl$ (30 mL). The mixture was extracted with EtOAc (20 mL×2), washed with brine (30 mL), dried over $Na_2SO_4$, filtered, and evaporated in vacuum to give crude product. The crude product was purified by HPLC separation (column: Boston Green ODS 150*30 5u, gradient: 90-100% B (A=0.05% HCl-ACN, B=acetonitrile), flow rate: 30 mL/min) for further purification to obtain 102 (45.8 mg) as a solid.

$^1$H NMR (CDCl$_3$, 400 MHz) δ 7.92 (d, J=8.8 Hz, 2H), 7.25 (d, J=8.8 Hz, 2H), 3.47-3.40 (m, 2H), 3.36-3.32 (m, 1H), 3.23 (s, 3H), 2.47-2.35 (m, 1H), 2.00-1.94 (m, 1H), 1.79-1.70 (m, 3H), 1.53-1.43 (m, 6H), 1.41-1.27 (m, 6H), 1.26-1.18 (m, 5H), 1.16-0.96 (m, 3H), 0.86-0.78 (m, 1H), 0.62 (s, 3H). LCMS Rt=3.164 min in 4.0 min chromatography, 30-90 AB, MS ESI calcd. for $C_{29}H_{40}F_3O_4$[M+H]$^+$ 509.3, found 491 [M−H$_2$O]$^+$.

Example 103

Synthesis of Compound 103

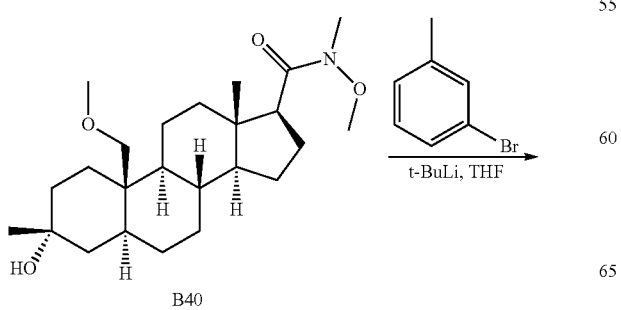

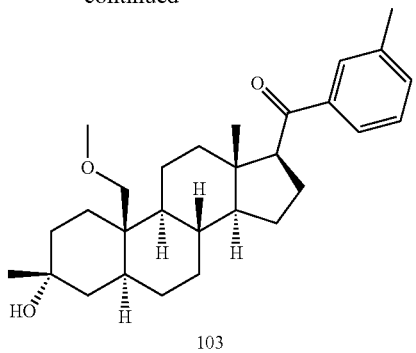

To a stirring solution of 1-bromo-3-methylbenzene (67 mg, 0.392 mmol) in 3 mL of THF was added tert-butyllithium (1.3 M; 587-μL, 0.764 mmol) dropwise at −65° C. under $N_2$. After stirring at −65° C. for 2 hrs, a solution of B40 (80 mg, 0.196 mmol) in THF (1 mL) was added dropwise. The mixture was stirred at 15° C. for 1 hour. LCMS showed the reaction was completed. The reaction mixture was quenched with Sat. $NH_4Cl$ (30 mL). The mixture was extracted with EtOAc (20 mL×2), washed with brine (30 mL), dried over $Na_2SO_4$, filtered, and evaporated in vacuum to give crude product. The crude product was purified by HPLC separation (column: Boston Green ODS 150*30 5u, gradient 82-98% B (A=0.05% HCl-ACN, B=acetonitrile), flow rate: 25 mL/min) for further purification to obtain 103 (40.3 mg) as a solid.

$^1$H NMR (CDCl$_3$, 400 MHz) δ 7.69-7.62 (m, 2H), 7.36-7.28 (m, 2H), 3.50-3.40 (m, 2H), 3.37-3.31 (m, 1H), 3.23 (s, 3H), 2.48-2.37 (m, 4H), 2.00-1.93 (m, 1H), 1.80-1.70 (m, 3H), 1.65-1.50 (m, 4H), 1.48-1.44 (m, 2H), 1.38-1.25 (m, 6H), 1.25-1.18 (m, 5H), 1.16-0.93 (m, 3H), 0.86-0.78 (m, 1H), 0.62 (s, 3H). LCMS Rt=2.960 min in 4.0 min chromatography, 30-90 AB, MS ESI calcd. for $C_{29}H_{43}O_3$ [M+H]$^+$ 439.3, found 421 [M−H$_2$O]$^+$.

Example 104

Synthesis of Compound 104

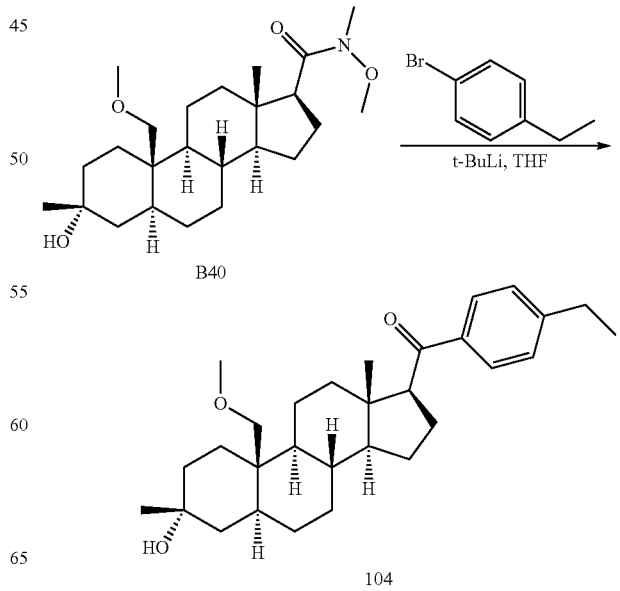

To a stirring solution of 1-bromo-4-ethylbenzene (72.5 mg, 0.392 mmol) in 3 mL of THF was added tert-butyllithium (1.3 M; 587 uL, 0.764 mmol) dropwise at −65° C. under N$_2$. After stirring at −65° C. for 2 hrs, a solution of B40 (80 mg, 0.196 mmol) in THF (1 mL) was added dropwise. The mixture was stirred at 15° C. for 1 hour. LCMS showed the reaction was completed. The reaction mixture was quenched with sat. NH$_4$Cl (30 mL). The mixture was extracted with EtOAc (20 mL×2), washed with brine (30 mL), dried over Na$_2$SO$_4$, filtered, and evaporated in vacuum to give crude product. The crude product was purified by HPLC separation (column: Phenomenex Synergi Max-RP 250*50 mm*10 um, gradient: 88-93% B (A=0.05% HCl-ACN, B=acetonitrile), flow rate: 30 mL/min) for further purification to obtain 104 (22.6 mg) as a solid.

$^1$H NMR (CDCl$_3$, 400 MHz) δ 7.80 (d, J=8.4 Hz, 2H), 7.24 (d, J=8.4 Hz, 2H), 3.49-3.40 (m, 2H), 3.36-3.31 (m, 1H), 3.23 (s, 3H), 2.69 (q, J=7.6 Hz, 2H), 2.49-2.36 (m, 1H), 2.01-1.93 (m, 1H), 1.77-1.68 (m, 3H), 1.54-1.44 (m, 6H), 1.41-1.34 (m, 2H), 1.33-1.16 (m, 12H), 1.16-0.95 (m, 3H), 0.86-0.77 (m, 1H), 0.62 (s, 3H). LCMS Rt=3.113 min in 4.0 min chromatography, 30-90 AB, MS EST calcd. for C$_{30}$H$_{45}$O$_3$ [M+H]$^+$ 453, found 453.

Example 105

Synthesis of Compound 105

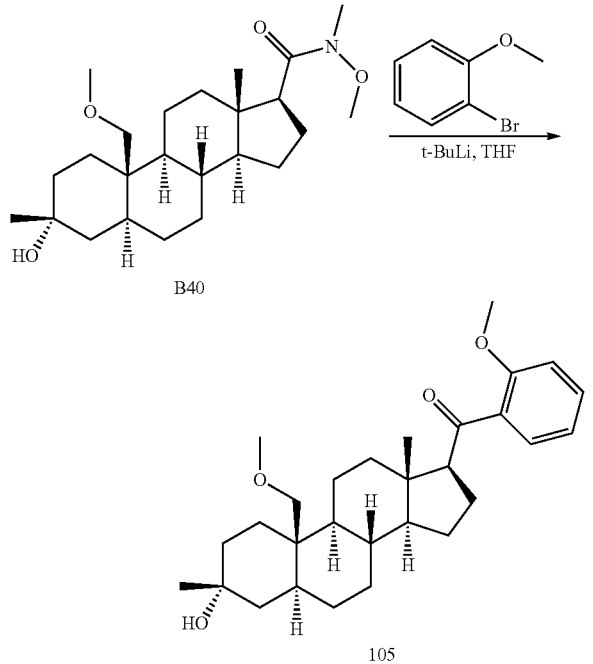

To a stirring solution of 1-bromo-2-methoxybenzene (228 mg, 1.22 mmol) in 3 mL of THF was added tert-butyllithium (1.3 M; 1.69 mL, 2.2 mmol) dropwise at −65° C. under N$_2$. After stirring at −65° C. for 2 hrs, a solution of B40 (100 mg, 0.245 mmol) in THF (1 mL) was added dropwise. The mixture was stirred at 15° C. for 1 hour. LCMS showed the reaction was completed. The reaction mixture was quenched with sat. NH$_4$Cl (30 mL). The mixture was extracted with EtOAc (20 mL×2), washed with brine (30 mL), dried over Na$_2$SO$_4$, filtered, and evaporated in vacuum to give crude product. The crude product was purified by HPLC separation (column: Phenomenex Synergi Max-RP 250*50 mm*10 um, gradient: 83-88% B (A=0.05% HCl-ACN, B=acetonitrile), flow rate: 30 mL/min) to obtain 105 (11.4 mg) as a solid.

$^1$H NMR (CDCl$_3$, 400 MHz) δ 7.40-7.34 (m, 1H), 7.31 (dd, J=1.6, 7.7 Hz, 1H), 6.96 (t, I=7.2 Hz, 1H), 6.90 (d, J=8.4 Hz, 1H), 3.84 (s, 3H), 3.51 (t, J=9.0 Hz, 1H), 3.44-3.38 (m, 1H), 3.35-3.29 (m, 1H), 3.23 (s, 3H), 2.41-2.30 (m, 1H), 2.00-1.90 (m, 1H), 1.78-1.67 (m, 4H), 1.53-1.40 (m, 7H), 1.33-1.26 (m, 2H), 1.25-1.20 (m, 5H), 1.18-0.87 (m, 5H), 0.80-0.70 (m, 1H), 0.63 (s, 3H). LCMS Rt=2.730 min in 4.0 min chromatography, 30-90 AB, MS ESI calcd. for C$_{29}$H$_{43}$O$_4$ [M+H]$^+$ 455, found 455.

Example 106

Synthesis of Compound 106

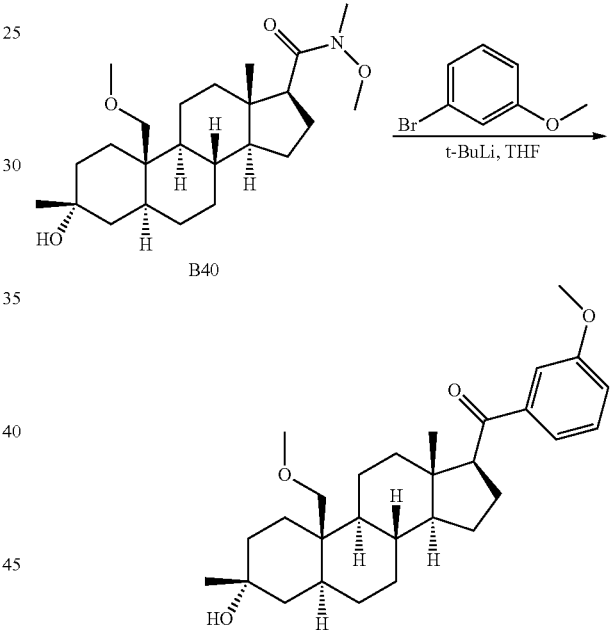

To a stirring solution of 1-bromo-3-methoxybenzene (183 mg, 0.980 mmol) in 3 mL of THF was added tert-butyllithium (1.3 M, 1.35 mL, 1.76 mmol) dropwise at −65° C. under N$_2$. After stirring at −65° C. for 2 hrs, a solution of B40 (80 mg, 0.196 mmol) in THF (1 mL) was added dropwise. The mixture was stirred at 15° C. for 1 hour. LCMS showed the reaction was completed. The reaction mixture was quenched with sat NH$_4$Cl (30 mL). The mixture was extracted with EtOAc (20 mL×2), washed with brine (30 mL), dried over Na$_2$SO$_4$, filtered, and evaporated in vacuum to give crude product. The crude product was purified by HPLC separation (column: Phenomenex Synergi Max-RP 250*50 mm*10 um, gradient: 85-95% B (A=0.05% HCl-ACN, B=acetonitrile), flow rate: 30 mL/min) for further purification to obtain 106 (15.4 mg) as a solid.

$^1$H NMR (CDCl$_3$, 400 MHz) δ 7.45 (d, J=7.8 Hz, 1H), 7.39 (s, 1H), 7.33 (t, J=8.0 Hz, 1H), 7.07 (dd, J=2.0, 8.3 Hz, 1H), 3.85 (s, 3H), 3.48-3.39 (m, 2H), 3.36-3.31 (m, 1H), 3.23 (s, 3H), 2.47-2.35 (m, 1H), 1.97 (d, J=13.2 Hz, 1H), 1.81-1.69 (m, 3H), 1.52-1.17 (m, 17H), 1.16-0.92 (m, 3H), 0.85-0.75 (m, 1H), 0.62 (s, 3H). LCMS Rt=2.821 min in 2.0 min chromatography, 30-90 AB, MS ESI calcd. for C$_{29}$H$_{43}$O$_4$[M+H]$^+$ 455, found 455.

Example 107

Synthesis of Compound 107

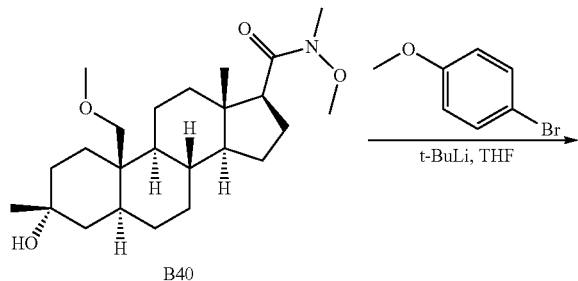

To a stirred solution of 1-bromo-4-methoxybenzene (91.6 mg, 0.490 mmol) in 3 mL of THF was added tert-butyllithium (1.3 M; 753 uL, 0.98 mmol) dropwise at −65° C. under N$_2$. After stirring at −65° C. for 2 hrs, B40 (100 mg, 0.245 mmol) in THF (1 mL) was added dropwise. The mixture was stirred at 15° C. for 1 hour. LCMS showed the reaction was complete. The reaction mixture was quenched with Sat. NH$_4$Cl (30 mL). The mixture was extracted with EtOAc (20 mL×2), washed with brine (30 mL), dried over Na$_2$SO$_4$, filtered, and evaporated in vacuum to give crude product. The crude product was purified by HPLC separation (column: Phenomenex Synergi C18 250*21.2 mm*4 um, gradient: 75-95% B (A=0.05% HCl-ACN, B=acetonitrile), flow rate: 25 mL/min) to obtain 107 (25.6 mg) as a solid.

$^1$H NMR (CDCl$_3$, 400 MHz) δ 7.89 (d, J=8.8 Hz, 2H), 6.91 (d, J=8.8 Hz, 2H), 3.86 (s, 3H), 3.49-3.39 (m, 2H), 3.37-3.30 (m, 1H), 3.23 (s, 3H), 2.49-2.35 (m, 1H), 2.01-1.93 (m, 1H), 1.78-1.68 (m, 3H), 1.54-1.39 (m, 7H), 1.38-1.17 (m, 10H), 1.16-0.92 (m, 3H), 0.85-0.75 (m, 1H), 0.61 (s, 3H). LCMS Rt=2.790 min in 4.0 min chromatography, 30-90 AB, MS ESI calcd, for C$_{29}$H$_{43}$O$_4$ [M+H]$^+$ 455, found 455.

Example 108

Synthesis of Compound 108

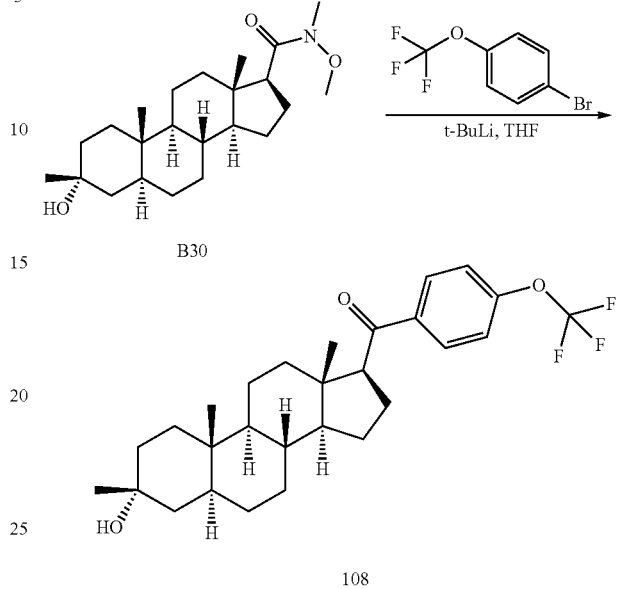

To a stirred solution of 1-bromo-4-(trifluoromethoxy)benzene (127 mg, 0.528 mmol) in 3 mL of THF was added tert-butyllithium (1.3 M; 807 uL, 1.05 mmol) dropwise at −65° C. under N$_2$. After stirring at −65° C. for 2 hrs, a solution of B30 (50 mg, 0.132 mmol) in THF (1 mL) was added dropwise. The mixture was stirred at 15° C. for 1 hour. LCMS showed the reaction was completed. The reaction mixture was quenched with Sat NH$_4$Cl (30 mL). The mixture was extracted with EtOAc (20 mL×2), washed with brine (30 mL), dried over Na$_2$SO$_4$, filtered, and evaporated in vacuum to give crude product, which was purified by prep-HPLC separation (column Phenomenex Synergi C18 150*30 mm*4 um, gradient: 90-95% B (A=0.05% HCl-ACN, B=acetonitrile), flow rate: 25 mL/min) for further purification to obtain 108 (49.1 mg) as a solid.

$^1$H NMR (CDCl$_3$, 400 MHz) 7.93 (d, J=8.8 Hz, 2H), 7.26-7.23 (m, 2H), 3.44 (t, J=8.8 Hz, 1H), 2.47-2.34 (m, 1H), 1.80-1.67 (m, 3H), 1.55-1.41 (m, 6H), 1.40-1.22 (m, 9H), 1.20-1.13 (m, 5H), 1.04-0.91 (m, 1H), 0.83-0.74 (m, 1H), 0.71 (s, 3H), 0.59 (s, 3H). LCMS Rt=1.342 min in 2.0 min chromatography, 30-90 AB, MS ESI calcd. for C$_{28}$H$_{38}$F$_3$O$_3$ [M+H]$^+$ 479.3, found 461 [M−H$_2$O]$^+$.

Example 109

Synthesis of Compound 109

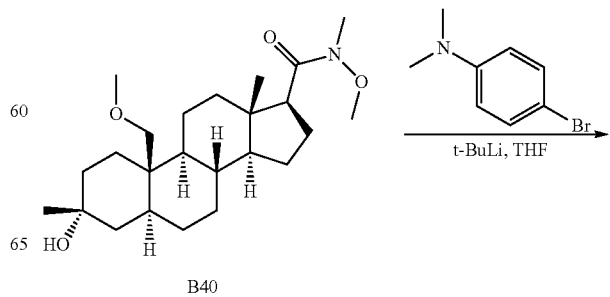

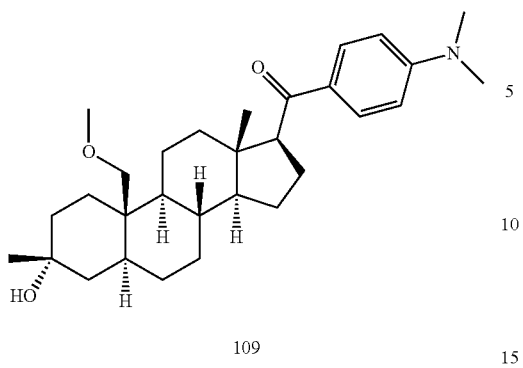

109

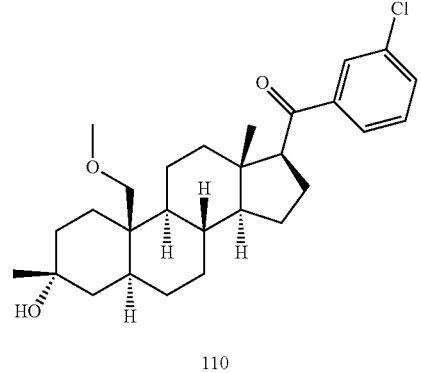

110

To a stirring solution of 4-bromo-N,N-dimethylaniline (78.4 mg, 0.392 mmol) in 3 mL of THF was added tert-butyllithium (1.3 M; 587 uL, 0.764 mmol) dropwise at −65° C. under $N_2$. After stirring at −65° C. for 2 hrs, a solution of B40 (80 mg, 0.196 mmol) in THF (1 mL) was added dropwise. The mixture was stirred at 15° C. for 1 hour. LCMS showed the reaction was completed. The reaction mixture was quenched with sat. $NH_4Cl$ (30 mL). The mixture was extracted with EtOAc (20 mL×2), washed with brine (30 mL), dried over $Na_2SO_4$, filtered, and evaporated in vacuum to give crude product. The crude product was purified by HPLC separation (column: Phenomenex Synergi Max-RP 250*50 mm*10 um, gradient: 83-88% B (A=0.05% HCl-ACN, B=acetonitrile), flow rate: 30 mL/min) for further purification to obtain 109 (26.3 mg) as a solid.

$^1$H NMR (CDCl$_3$, 400 MHz) δ 7.87 (d, J=8.8 Hz, 2H), 6.71 (d, J=8.0 Hz, 2H), 3.46-3.40 (m, 2H), 3.38-3.32 (m, 1H), 3.23 (s, 3H), 3.06 (s, 6H), 2.49-2.37 (m, 1H), 2.00-1.95 (m, 1H), 1.77-1.68 (m, 3H), 1.54-1.44 (m, 7H), 1.42-1.27 (m, 5H), 1.27-1.16 (m, 5H), 1.15-0.93 (m, 3H), 0.86-0.78 (m, 1H), 0.62 (s, 3H). LCMS Rt=2.113 min in 3.0 min chromatography, 30-90 AB, MS ESI calcd. for $C_{30}H_{46}NO_3$ [M+H]$^+$ 468, found 468.

Example 110

Synthesis of Compound 110

To a stirring solution of 1-bromo-3-chlorobenzene (75 mg, 0.392 mmol) in 3 mL of THF was added tert-butyllithium (1.3 M; 587 uL, 0.764 mmol) dropwise at −65° C. under $N_2$. After stirring at −65° C. for 2 hrs, B40 (80 mg, 0.196 mmol) in THF (1 mL) was added dropwise. The mixture was stirred at 15° C. for 1 hour. LCMS showed the reaction was completed. The reaction mixture was quenched with sat. $NH_4Cl$ (30 mL). The mixture was extracted with EtOAc (20 mL×2), washed with brine (30 mL), dried over $Na_2SO_4$, filtered, and evaporated in vacuum to give crude product. The crude product was purified by HPLC separation (column: Phenomenex Synergi Max-RP 250*50 mm*10 um, gradient: 88-93% B (A=0.05% HCl-ACN, B=acetonitrile), flow rate: 30 mL/min) for further purification to obtain 110 (10.3 mg) as a solid.

$^1$H NMR (CDCl$_3$, 400 MHz) δ 7.83 (t, J=1.8 Hz, 1H), 7.72 (d, J=7.8 Hz, 1H), 7.52-7.47 (m, 1H), 7.41-7.34 (m, 1H), 3.45-3.39 (m, 2H), 3.36-3.31 (m, 1H), 3.23 (s, 3H), 2.46-2.35 (m, 1H), 2.00-1.92 (m, 1H), 1.80-1.68 (m, 4H), 1.52-1.42 (m, 5H), 1.38-1.25 (m, 6H), 1.25-1.21 (m, 5H), 1.15-0.98 (m, 3H), 0.85-0.75 (m, 1H), 0.61 (s, 3H). LCMS Rt=3.113 min in 4.0 min chromatography, 30-90 AB, MS ESI calcd. for $C_{28}H_{40}ClO_3$ [M+H]$^+$ 459.3, found 441 [M−H$_2$O]$^+$.

Example 111

Synthesis of Compound 111

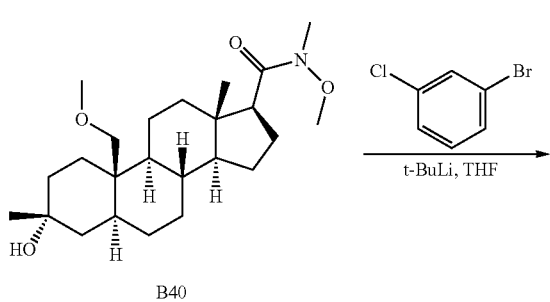

B40

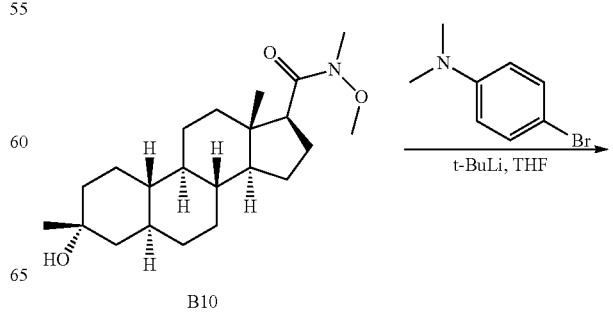

B10

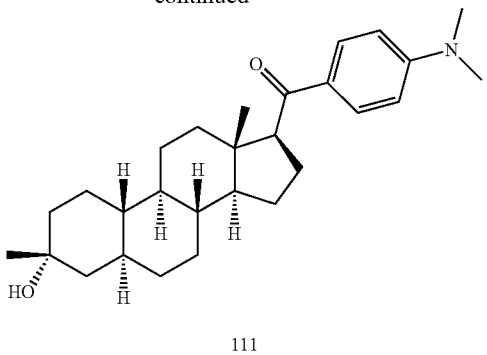

111

To a stirred solution of 4-bromo-N,N-dimethylaniline (110 mg, 0.550 mmol) in 3 mL of THF was added tert-butyllithium (1.3 M; 838 uL, 1.09 mmol) dropwise at −65° C. under $N_2$. After stirring at −65° C. for 2 hrs, a solution of B10 (100 mg, 0.275 mmol) in THF (1 mL) was added dropwise. The mixture was stirred at 15° C. for 1 hour. LCMS showed the reaction was complete. The reaction mixture was quenched with Sat. $NH_4Cl$ (30 mL). The mixture was extracted with EtOAc (20 mL×2), washed with brine (30 mL), dried over $Na_2SO_4$, filtered, and evaporated in vacuum to give crude product, which was purified by HPLC separation (column: Phenomenex Synergi C18 150*25*10 um, gradient: 59-84% B (A=0.1% TFA-ACN, B=acetonitrile), flow rate: 30 mL/min) for further purification to obtain 111 (20 mg) as a solid.

$^1$H NMR (CDCl$_3$, 400 MHz) δ 7.87 (d, J=9.0 Hz, 2H), 6.66 (d, J=8.8 Hz, 2H), 3.45 (t, J=8.8 Hz, 1H), 3.05 (s, 6H), 2.45-2.38 (m, 1H), 1.71-1.48 (m, 9H), 1.45-1.24 (m, 6H), 1.20 (s, 3H), 1.15-0.93 (m, 6H), 0.78-0.64 (m, 2H), 0.61 (s, 3H). LCMS Rt=1.189 min in 2.0 min chromatography, 30-90 AB, MS ESI calcd. for $C_{28}H_{42}NO_2$ [M+H]$^+$ 424.,424.

Example 112

Synthesis of Compound 112

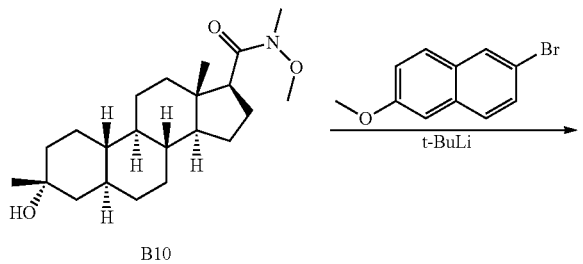

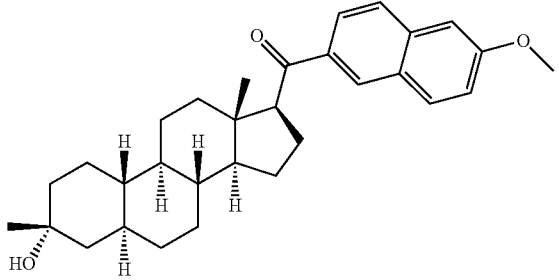

112

To a solution of 2-bromo-6-methoxynaphthalene (488 mg, 2.06 mmol) in THF (3 mL) was added tert-butyllithium (2.85 mL, 1.3 M in) at −70° C. The mixture was stirred at −70° C. for 1 h. A solution of B10 (150 mg, 0.4126 mmol) in THF (1 mL) was added at −70° C. The mixture was stirred at 25° C. for 1 hrs. The mixture was quenched with Sat. $NH_4Cl$ (10 mL), extracted with EtOAc (10 mL×3), washed with brine (30 mL×3), dried over $Na_2SO_4$, filtered, concentrated in vacuum to give a crude product, which was purified with prep. HPLC (Column: Phenomenex Synergi C18 150*30 mm*4 um; Condition: water (0.05%/HCl)-ACN; Gradient 90%-95% B; Gradient Time (min): 10; FlowRate (ml/min): 25) to give 112 (64.2 mg) as a solid.

$^1$H NMR (400 MHz, CDCl$_3$) δ 8.35-8.31 (m, 1H), 7.98-7.94 (m, 1H), 7.85 (d, J=9.0 Hz, 1H), 7.75 (d, J=8.8 Hz, 1H), 7.22-7.17 (m, 1H), 7.16-7.14 (m, 1H), 3.95 (s, 3H), 3.64 (t, J=8.7 Hz, 1H), 2.57-2.39 (m, 1H), 1.84-1.59 (m, 7H), 1.45-1.24 (m, 7H), 1.20-0.93 (m, 10H), 0.82-0.57 (m, 5H). LCMS t$_R$=1.096 min in 1.5 min chromatography, 5-95 AB, MS ESI calcd. for $C_{31}H_{41}O_3$ [M+H]$^+$ 461, found 461.

Example 113

Synthesis of Compound 113

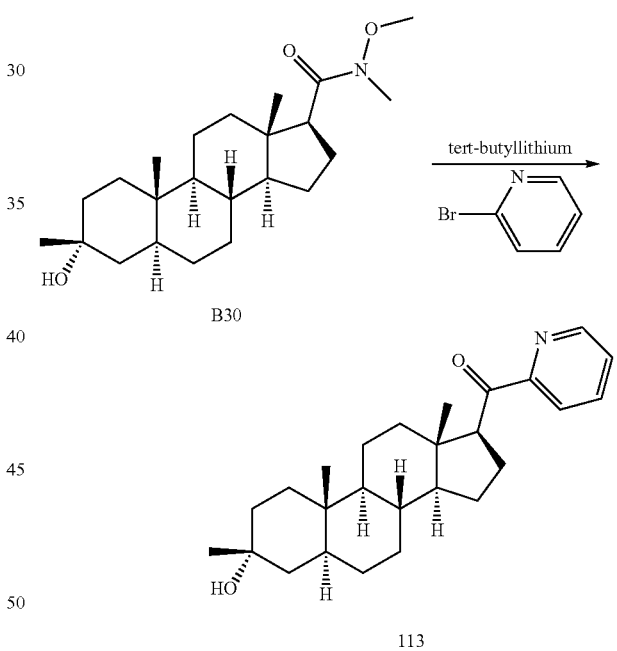

To a solution of 2-bromopyridine (165 mg, 1.05 mmol) in THF (5 mL) was added tert-butyllithium (1.45 mL) at −68° C. The mixture was stirred at −68° C. for 1 hrs. B30 (80 mg, 211 μmol) in THF (5 mL) was added dropwise at −68° C. The reaction was stirred at 25° C. for 1 hrs. LCMS showed the reaction was completed. The reaction was quenched with $NH_4Cl$ (10 mL), extracted with EtOAc (10 mL×2). The combined organic layers were washed with brine (10 mL). The organic layer was dried over $Na_2SO_4$, filtered and concentrated under reduced pressure to give crude product, which was purified by HPLC separation (column: Boston Green ODS 150*30 5u, gradient: 91-100% condition: (water (0.05% HCl)-ACN), flow rate: 25 mL/min) to give 113 (15 mg) as a solid.

$^1$H NMR (400 MHz, CDCl$_3$) δ 8.67-8.66 (m, 1H), 7.95-7.93 (m, 1H), 7.82-7.81 (m, 1H), 7.44-7.41 (m, 1H), 4.21-4.17 (m, 1H), 2.36-2.31 (m, 1H), 1.78-1.69 (m, 3H), 1.47-1.18 (m, 22H), 1.12-0.92 (m, 1H), 0.78-0.75 (m, 1H), 0.71 (s, 3H), 0.62 (s, 3H). LCMS Rt=1.299 min in 2 min chromatography, 30-90 AB, MS ESI calcd. for C$_{26}$H$_{38}$NO$_2$ [M+H]$^+$ 396, found 396.

Example 114

Synthesis of Compound 114

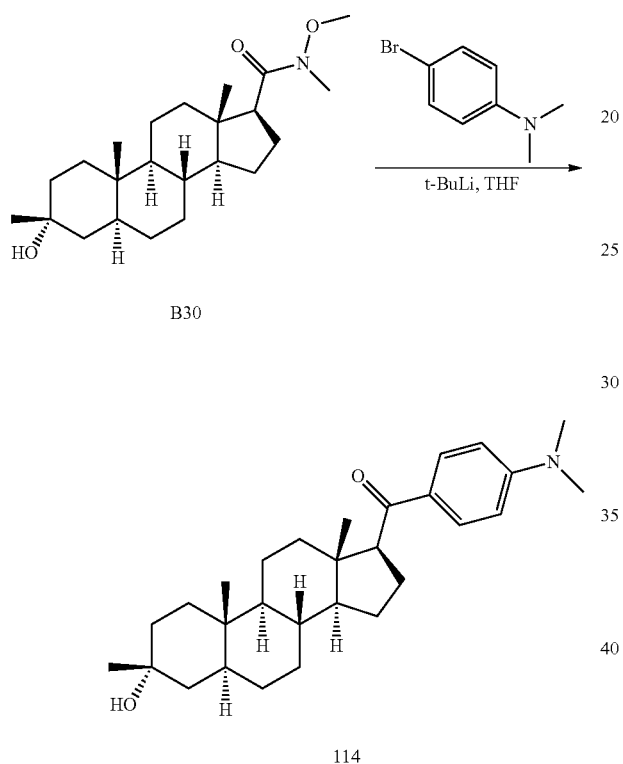

To a solution of 4-bromo-N,N-dimethylaniline (210 mg, 1.05 mmol) in THF (5 mL) was added tert-butyllithium (1.45 mL) at −68° C. The mixture was stirred at −68° C. for 1 hrs. A solution of B30 (80 mg, 211 μmol) in THF (5 mL) was added dropwise at −68° C. The reaction was stirred at 25° C. for 1 hrs. LCMS showed the reaction was completed. The reaction was quenched with NH$_4$Cl (10 mL), extracted with EtOAc (10 mL×2). The combined organic layers were washed with brine (10 mL). The organic layer was dried over Na$_2$SO$_4$, filtered and concentrated under reduced pressure to give crude product, which was purified by HPLC separation (column: Boston Green ODS 150*30 5u, gradient: 92-98% condition: (water (0.05% HCl)-ACN), flow rate: 25 mL/min) to give 114 (57.2 mg) as a solid.

$^1$H NMR (400 MHz, CDCl$_3$) δ 7.87 (d, J=9.0 Hz, 2H), 6.65 (d, J=9.0 Hz, 2H), 3.44 (t, J=8.8 Hz, 1H), 3.05 (s, 6H), 2.48-2.36 (m, 1H), 1.79-1.66 (m, 4H), 1.51-109 (m, 19H), 1.07-0.69 (m, 5H), 0.60 (s, 3H). LCMS Rt=1.032 min in 1.5 min chromatography, 5-95 AB, MS ESI calcd for C$_{29}$H$_{44}$NO$_2$ [M+H]$^+$ 438, found 438.

Example 115

Synthesis of Compound 115

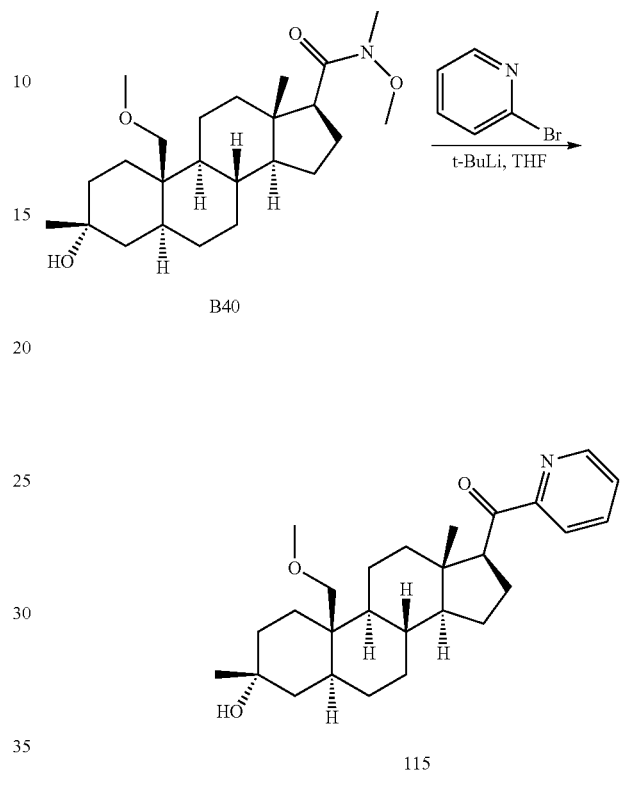

To a stirring solution of 2-bromopyridine (61.9 mg, 0.392 mmol) in 3 mL of THF was added tert-butyllithium (1.3 M; 587 uL, 0.764 mmol) dropwise at −65° C. under N$_2$. After stirring at −65° C. for 2 hrs, a solution of B40 (80 mg, 0.196 mmol) in THF (1 mL) was added dropwise. The mixture was stirred at 15° C. for 1 hour. and then the reaction mixture was quenched with sat. NH$_4$Cl (30 mL). The mixture was extracted with EtOAc (20 mL×2), washed with brine (30 mL), dried over Na$_2$SO$_4$, filtered, and evaporated in vacuum to give crude product. The crude product was purified by HPLC separation (column: Phenomenex Synergi Max-RP 250*50 mm*10 um, gradient 83-88% B (A=0.05% HCl-ACN, B=acetonitrile), flow rate: 30 ml/min) for further purification to obtain 115 (36.3 mg) as a solid.

$^1$H NMR (CDCl$_3$, 400 MHz) δ 8.67 (d, J=4.6 Hz, 1H), 7.93 (d, J=7.8 Hz, 1H), 7.82 (t, J=7.2 Hz, 1H), 7.47-7.41 (m, 1H), 4.19 (t, J=9.0 Hz, 1H), 3.46-3.41 (m, 1H), 3.36-3.31 (m, 1H), 3.23 (s, 3H), 2.40-2.27 (m, 1H), 2.00-1.92 (m, 1H), 1.85-1.68 (m, 4H), 1.54-1.44 (m, 5H), 1.44-1.26 (m, 6H), 1.25-1.13 (m, 5H), 1.12-0.96 (m, 3H), 0.85-0.75 (m, 1H), 0.64 (s, 3H). LCMS Rt=3.208 min in 4.0 min chromatography, 10-80 AB, MS ESI calcd. for C$_{27}$H$_{40}$NO$_3$ [M+H]$^+$ 426, found 426.

Example 116

Synthesis of Compound 116

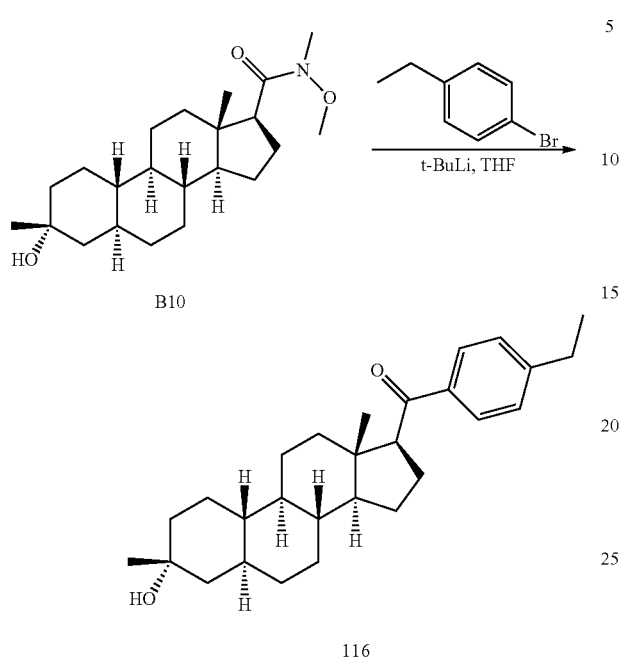

To a solution of 1-bromo-4-ethylbenzene (381 mg, 2.06 mmol) in THF (3 mL) was added tert-butyllithium (2.85 mL, 1.3 M in THF) at −70° C. The mixture was stirred at −70° C. for 1 h. A solution of B10 (150 mg, 0.4126 mmol) in THF (1 mL) was added at −70° C. and the mixture was stirred at 25° C. for 1 hr. The mixture was quenched with Sat. NH$_4$Cl (10 mL), extracted with EtOAc (10 mL×3), washed with brine (30 mL×3), dried over Na$_2$SO$_4$, filtered, concentrated in vacuum to give a crude product which was purified with prep. HPLC (Column: Phenomenex Synergi C18 150*30 mm*4 um; Condition: water (0.05% HCl)-ACN: Gradient 90%-95% B; Gradient Time (min): 10; FlowRate (ml/min): 25) to give 116 (84.4 mg) as a solid.

$^1$HNMR (400 MHz, CDCl$_3$) δ 7.82 (d, J=8.3 Hz, 2H), 7.25 (d, J=8.3 Hz, 2H), 3.48 (t, J=8.7 Hz, 1H), 2.70 (q, J=7.7 Hz, 2H), 2.50-2.26 (m, 1H), 1.77-1.59 (m, 6H), 1.55-1.50 (m, 1H), 1.45-0.85 (m, 20H), 0.77-0.57 (m, 5H). LCMS t$_R$=1.090 min in 1.5 min chromatography, 5-95 AB, MS ESI calcd. for C$_{28}$H$_{41}$O$_2$ [M+H]$^+$ 409, found 409.

Example 117

Synthesis of Compound 117

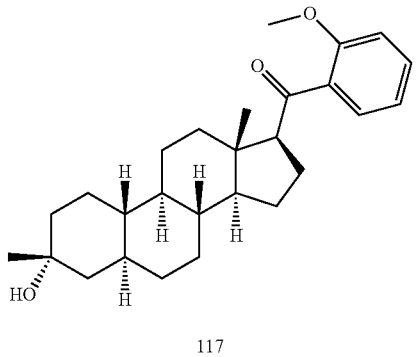

To a solution of 1-bromo-2-methoxybenzene (256 mg, 1.37 mmol) in THF (5 mL) was added tert-butyllithium (1.90 mL, 2.47 mmol) at −68° C. The mixture was stirred at −68° C. for 1 hour. B10 (100 mg, 275 μmol) in THF (5 mL) was added dropwise at −68° C. The reaction was stirred at 25° C. for 2 hours. The reaction was quenched with NH$_4$Cl (10 mL), extracted with EtOAc (10 mL×2). The combined organic layers were washed with brine (10 mL). The organic layer was dried over Na$_2$SO$_4$, filtered and concentrated under reduced pressure to give crude product which was purified by HPLC separation (Phenomenex Synergi C18 150*30 mm*4 um, gradient: 90-98% condition: (water (0.05% HCl)-ACN), flow rate: 25 mL/min) to give 117 (27.7 mg) as a solid.

$^1$H NMR (400 MHz, CDCl$_3$) δ 7.42-7.36 (m, 1H), 7.32 (dd, J=1.8, 7.5 Hz, 1H), 7.01-6.89 (m, 2H), 3.85 (s, 3H), 3.56-3.49 (m, 1H), 2.40-2.29 (m, 1H), 1.83-1.74 (m, 1H), 1.69-1.49 (m, 7H), 1.36-1.21 (m, 5H), 1.19 (s, 3H), 1.16-0.83 (m, 7H), 0.70-0.56 (m, 5H). LCMS Rt=1.283 min in 2 min chromatography, 30-90 AB, MS ESI calcd. for C$_{27}$H$_{39}$O$_3$ [M+H]$^+$ 411. found 411.

Example 118

Synthesis of Compound 118

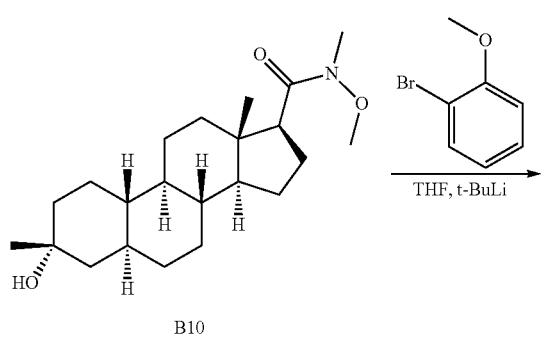

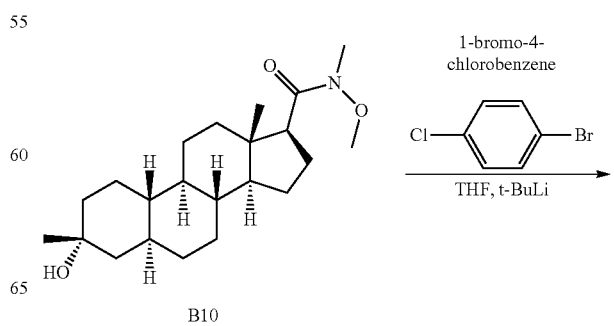

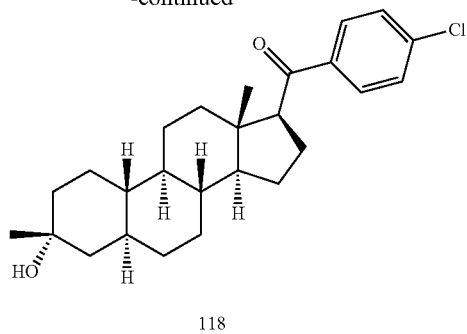

118

To a solution of 1-bromo-4-chlorobenzene (275 mg, 1.37 mmol) in THF (5 mL) was added tert-butyllithium (1.90 mL, 2.47 mmol) at −68° C. The mixture was stirred at −68° C. for 1 hour. B10 (100 mg, 275 μmol) in THF (5 mL) was added dropwise at −68° C. The reaction was stirred at 25° C. for 2 hours. The reaction was quenched with NH$_4$Cl (10 mL), extracted with EtOAc (10 mL×2) The combined organic layers were washed with brine (10 mL). The organic layer was dried over Na$_2$SO$_4$, filtered and concentrated under reduced pressure to give crude product which was purified by HPLC separation (Phenomenex Synergi C18 150*30 mm*4 um, gradient: 90-98%0/condition: (water (0.05% HCl)-ACN), flow rate: 25 mL/min) to give 118 (27.4 mg) as a solid.

$^1$H NMR (400 MHz, CDCl3) δ 7.82 (d, J=8.4 Hz, 2H), 7.41 (d, J=8.4 Hz, 2H), 3.44 (t, J=8.7 Hz, 1H), 2.47-2.36 (m, 1H), 1.82-1.65 (m, 5H), 1.64-1.61 (m, 1H), 1.55-1.56 (m, 1H), 1.55-1.50 (m, 1H), 1.35-1.32 (m, 6H), 1.22-0.85 (m, 10H), 0.78-0.57 (m, 5H). LCMS Rt=1.411 min in 2 min chromatography, 30-90 AB, MS ESI calcd. for C$_{26}$H$_{36}$ClO$_2$ [M+H]$^+$ 415, found 415.

Example 119

Synthesis of Compound 119

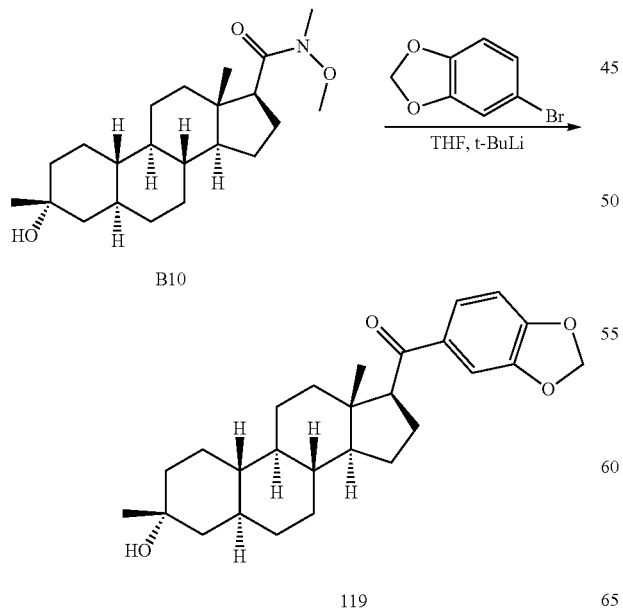

119

To a solution of 6-bromobenzo[d][1,3]dioxole (275 mg, 1.37 mmol) in THF (5 mL) was added tert-butyllithium (1.90 mL, 2.47 mmol) at −68° C. The mixture was stirred at −68° C. for 1 hrs. B10 (100 mg, 275 μmol) in THF (5 mL) was added dropwise at −68° C. The reaction was stirred at 25° C. for 2 hours. The reaction was quenched with NH$_4$Cl (10 mL), extracted with EtOAc (10 mL×2). The combined organic layers were washed with brine (10 mL). The organic layer was dried over Na$_2$SO$_4$, filtered and concentrated under reduced pressure to give crude product which was purified by HPLC separation (Phenomenex Synergi C18 150*30 mm*4 um, gradient: 90-98% condition: (water (0.05% HCl)-ACN), flow rate: 25 mL/min) to give 119 (41.2 mg) as a solid.

$^1$H NMR (400 MHz, CDCl3) δ 7.50 (dd, J=1.6, 8.2 Hz, 1H), 7.40 (d, J=1.5 Hz, 1H), 6.83 (d, J=8.3 Hz, 1H), 6.04 (s, 2H), 3.40 (t, J=8.5 Hz, 1H), 2.46-2.35 (m, 1H), 1.79-1.61 (m, 6H), 1.52-1.54 (m, 1H), 1.44-1.48 (m, 1H), 1.40-1.24 (m, 5H), 1.22-1.16 (m, 4H), 1.16-0.92 (m, 6H), 0.60 (m, 5H). LCMS Rt=1.293 min in 2 min chromatography, 30-90 AB, MS ESI calcd. for C$_{27}$H$_{37}$O$_4$ [M+H]$^+$ 425, found 425.

Example 120

Synthesis of Compound 120

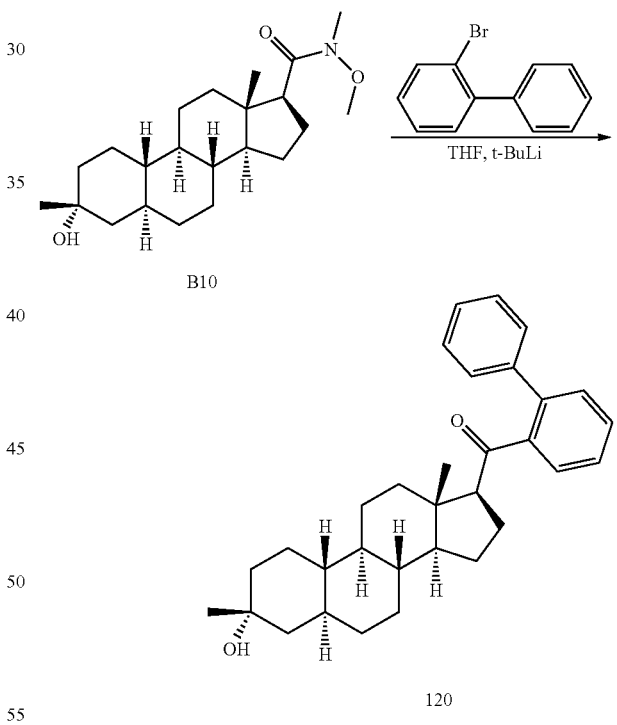

120

To a solution of 2-bromo-1,1'-biphenyl (319 mg, 1.37 mmol) in THF (5 mL) was added tert-butyllithium (1.90 mL, 2.47 mmol) at −68° C. The mixture was stirred at −68° C. for 1 hour. B10 (100 mg, 275 μmol) in THF (5 mL) was added dropwise at −68° C. The reaction was stirred at 25° C. for 2 hours. The reaction was quenched with NH$_4$Cl (10 mL), extracted with EtOAc (10 mL×2). The combined organic layers were washed with brine (10 mL). The organic layer was dried over Na$_2$SO$_4$, filtered and concentrated under reduced pressure to give crude product which was purified by HPLC separation (Phenomenex Synergi C18

150*30 mm*4 um, gradient: 90-98% condition: (water (0.05% HCl)-ACN), flow rate: 25 mL/min) to give 120 (30.7 mg) as a solid.

$^1$H NMR (400 MHz, CDCl3) δ 7.53-7.30 (m, 9H), 2.36-2.27 (m, 1H), 2.23-2.10 (m, 1H), 1.54-1.39 (m, 6H), 1.34-1.19 (m, 3H), 1.17 (s, 3H), 1.15-0.63 (m, 13H), 0.62-0.44 (m, 5H). LCMS Rt=1.099 min in 2 min chromatography, 5-95 AB, MS ESI calcd. for $C_{32}H_{41}O_2$ [M+H]$^+$ 457, found 457.

Example 121

Synthesis of Compound 121

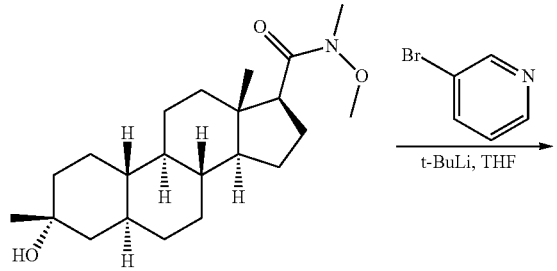

To a solution of 3-bromopyridine (325 mg, 2.06 mmol) in THF (3 mL) was added tert-butyllithium (2.85 mL, 1.3 M in THF) at −70° C. The mixture was stirred at −70° C. for 1 h. A solution of B10 (150 mg, 0.4126 mmol) in THF (1 mL) was added at −70° C. The mixture was stirred at 25° C. for 1 hrs. The mixture was quenched with Sat. NH$_4$Cl (10 mL), extracted with EtOAc (10 mL×3), washed with brine (30 mL×3), dried over Na$_2$SO$_4$, filtered, concentrated in vacuum to give a crude product, which was purified with prep. HPLC (Column: Boston Green ODS 150*30 5u; Condition: water (0.05% HCl)-CAN; Gradient: 60%-90% B; Gradient Time (min): 10; 100% B Hold Time (min): 4; FlowRate (ml/min): 25) to give 121 (68 mg) as a solid.

$^1$H NMR (400 MHz, CD$_3$OD) δ 9.08 (s, 1H), 8.78 (d, J=3.5 Hz, 1H), 8.44 (d, J=8.3 Hz, 1H), 7.68 (dd, J=5.0, 8.0 Hz, 1H), 3.66 (t, J=8.5 Hz, 1H), 2.48-2.36 (m, 1H), 1.87-1.61 (m, 7H), 1.55-1.44 (m, 3H), 1.37-0.98 (m, 13H), 0.83-0.59 (m, 5H). LCMS tR=0.881 min in 1.5 min chromatography, 5-95 AB, MS ESI calcd. for $C_{25}H_{36}NO_2$ [M+H]$^+$ 382, found 382.

Example 122

Synthesis of Compound 122

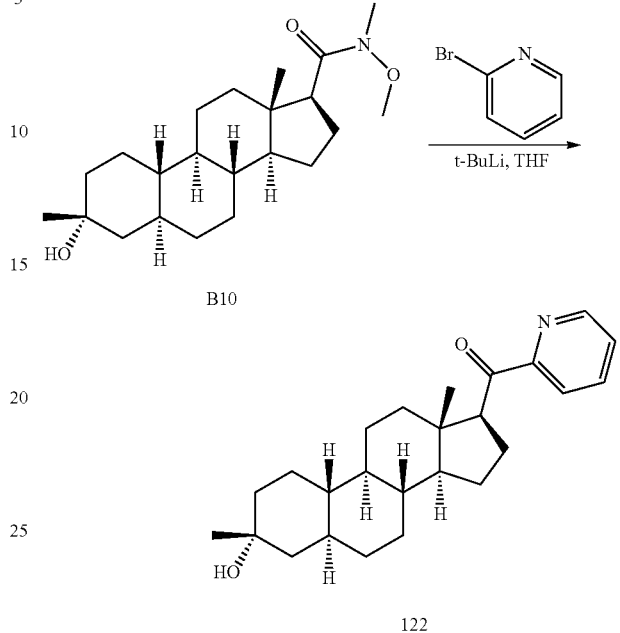

To a solution of 2-bromopyridine (325 mg, 2.06 mmol) in THF (3 mL) was added tert-butyllithium (2.85 mL, 1.3 M in THF) at −70° C. The mixture was stirred at −70° C. for 1 h. A solution of B10 (150 mg, 0.4126 mmol) in THF (1 mL) was added at −70° C. The mixture was stirred at 25° C. for 1 hrs. The mixture was quenched with Sat. NH$_4$Cl (10 mL), extracted with EtOAc (10 mL×3), washed with brine (30 mL×3), dried over Na$_2$SO$_4$, filtered, concentrated in vacuum to give a crude product, which was purified with prep. HPLC (Column: Phenomenex Synergi C18 150*30 mm*4 um; Condition: water (0.05% HCl)-ACN; Gradient 90%-95% B; Gradient Time (min): 10; FlowRate (ml/min): 25) to give 122 (17.7 mg,) as a solid.

$^1$H NMR (400 MHz, CDCl$_3$) δ 8.68-8.64 (m, 1H), 7.96-7.92 (m, 1H), 7.84-7.77 (m, 1H), 7.45-7.40 (m, 1H), 4.20 (t, J=9.0 Hz, 1H), 2.39-2.24 (m, 1H), 1.85-1.60 (m, 7H), 1.52-1.25 (m, 6H), 1.21-0.85 (m, 11H), 0.78-0.56 (m, 5H). LCMS t$_R$=0.998 min in 1.5 min chromatography, 5-95 AB, MS ESI calcd. for $C_{25}H_{35}NO_2$ [M+H]$^+$ 382, found 382.

Example 123

Synthesis of Compound 123

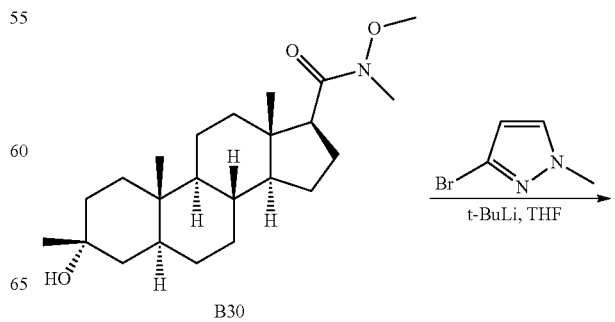

-continued

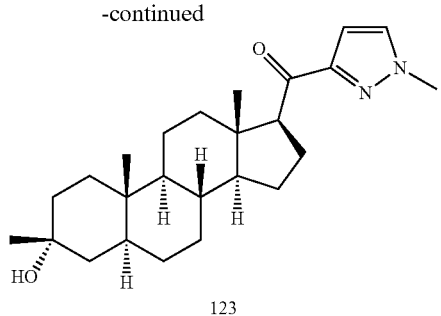

123

To a solution of 3-bromo-1-methyl-1H-pyrazole (169 mg, 1.05 mmol) in THF (5 mL) was added tert-butyllithium (1.45 mL) at −68° C. The mixture was stirred at −68° C. for 1 hrs. B30 (80 mg, 211 μmol) in THF (5 mL) was added dropwise at −68° C. The reaction was stirred at 25° C. for 1 hour. LCMS showed the reaction was completed. The reaction mixture was quenched with NH$_4$Cl (10 mL), extracted with EtOAc (10 mL×2). The combined organic layers were washed with brine (10 mL). The organic layer was dried over Na$_2$SO$_4$, filtered and concentrated under reduced pressure to give crude product, which was purified by HPLC separation (column: Boston Green ODS 150*30 5u, gradient: 92-98% condition: (water (0.05% HCl)-ACN), flow rate: 25 mL/min) to give 123 (6.4 mg) as a solid.

$^1$H NMR (400 MHz, CDCl3) δ 7.35-7.34 (m, 1H), 6.75-6.74 (m, 1H), 3.96 (s, 3H), 3.62 (t, J=8.7 Hz, 1H), 2.38-2.26 (m, 1H), 1.83-1.67 (m, 3H), 1.56-1.09 (m, 19H), 1.07-0.91 (m, 1H), 0.89-0.69 (m, 4H), 0.65 (s, 3H). LCMS Rt=0.956 min in 1.5 min chromatography, 5-95 AB, MS ESI calcd. for C$_{25}$H$_{39}$N$_2$O$_2$ [M+H]$^+$ 399, found 399.

Example 124

Synthesis of Compound 124

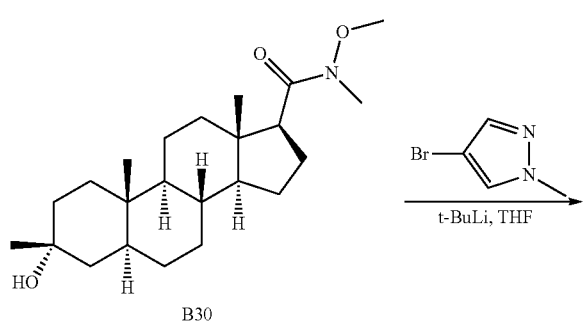

124

To a solution of 4-bromo-1-methyl-1H-pyrazole (169 mg, 1.05 mmol) in THF (5 mL) was added tert-butyllithium (1.45 mL) at −68° C. The mixture was stirred at −68° C. for 1 hr. B30 (80 mg, 211 umol) in THF (5 mL) was added dropwise at −68° C. The reaction mixture was stirred at 25° C. for 1 hour. LCMS showed the reaction was completed. The reaction was quenched with NH$_4$Cl (10 mL), extracted with EtOAc (10 mL×2). The combined organic layers were washed with brine (10 mL). The organic layer was dried over Na$_2$SO$_4$, filtered and concentrated under reduced pressure to give crude product, which was purified by HPLC separation (column: Boston Green ODS 150*30 5u, gradient: 92-98% condition: (water (0.05% HCl)-ACN), flow rate: 25 mL/min) to give 124 (23 mg) as a solid.

$^1$H NMR (400 MHz, CDCl3) δ 7.87 (s, 1H), 7.83 (s, 1H), 3.93 (s, 3H), 3.04-2.97 (m, 1H), 2.42-2.29 (m, 1H), 1.78-1.62 (m, 5H), 1.55-1.11 (m, 21H), 1.06-0.91 (m, 1H), 0.85-0.69 (m, 4H), 0.62 (s, 3H). LCMS Rt=1.124 min in 2 min chromatography, 30-90 AB, MS ESI calcd. for C$_{25}$H$_{39}$N$_2$O$_2$[M+H]$^+$ 399, found 399.

Example 125

Synthesis of Compound 125

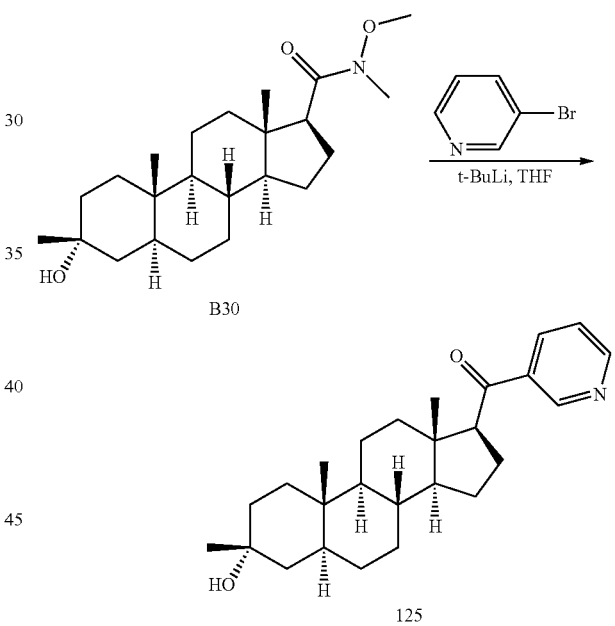

125

To a solution of 3-bromopyridine (206 mg, 1.31 mmol) in THF (5 mL) was added tert-butyllithium (1.82 mL) at −68° C. The mixture was stirred at −68° C. for 1 hour. B30 (100 mg, 264 μmol) in THF (5 mL) was added dropwise at −68° C. The reaction was stirred at 25° C. for 1 hour. LCMS showed the reaction was completed. The reaction mixture was quenched with NH$_4$Cl (10 mL), extracted with EtOAc (10 mL×2) The combined organic layers were washed with brine (10 mL). The organic layer was dried over Na$_2$SO$_4$, filtered and concentrated under reduced pressure to give crude product, which was purified by HPLC separation (column: Boston Green ODS 150*30 5u, gradient: 92-98% condition: (water (0.05% HCl)-ACN), flow rate: 25 mL/min) to give 125 (7.4 mg) as a solid.

$^1$H NMR (400 MHz, CDCl$_3$) δ 9.25-9.15 (m, 1H), 8.85-8.70 (m, 1H), 8.25-2.15 (m, 1H), 7.55-7.40 (m, 1H), 3.50-3.40 (m, 1H), 2.51-2.36 (m, 1H), 1.93-1.62 (m, 11H), 1.56-1.08 (m, 26H), 1.07-0.65 (m, 7H), 0.60 (s, 3H). LCMS Rt=0.903 min in 1.5 min chromatography, 5-95 AB, MS ESI calcd. for $C_{26}H_{38}NO_2$ [M+H]$^+$ 396, found 396.

Example 126

Synthesis of Compound 126

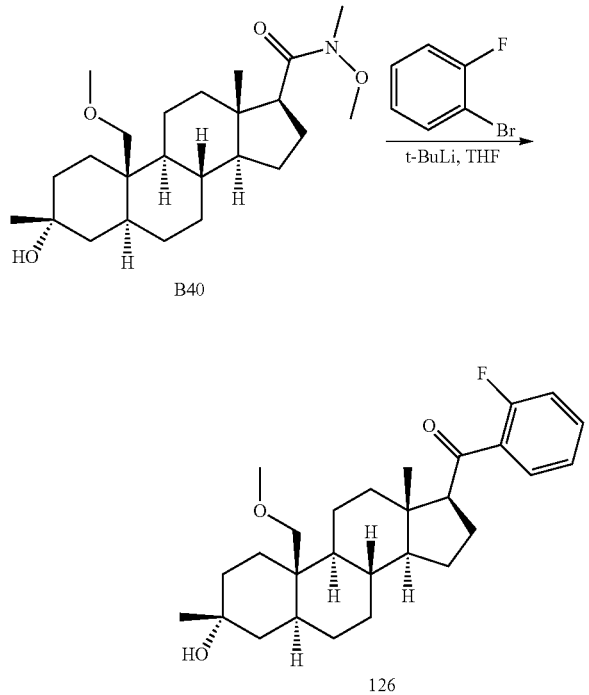

To a stirred solution of 1-bromo-2-fluorobenzene (68.5 mg, 0.392 mmol) in 3 mL of THF was added tert-butyllithium (1.3 M; 587 uL, 0.764 mmol) dropwise at −65° C. under $N_2$. After stirring at −65° C. for 2 hrs, B40 (80 mg, 0.196 mmol) in THF (1 mL) was added dropwise. The mixture was stirred at 15° C. for 1 hour. LCMS showed the reaction was complete. The reaction mixture was quenched with Sat. NH$_4$Cl (30 mL). The mixture was extracted with EtOAc (20 mL×2), washed with brine (30 mL), dried over Na$_2$SO$_4$, filtered, and evaporated in vacuum to give crude product. The crude product was purified by HPLC separation (column: Phenomenex Synergi Max-RP 250*50 mm*10 um, gradient: 85-90% B (A=0.05% HCl-ACN, B=acetonitrile), flow rate: 30 mL/min) to obtain 126 (19.4 mg) as a solid.

$^1$H NMR (CDCl$_1$, 400 MHz) δ 7.51 (dt, J=1.8, 7.6 Hz, 1H), 7.48-7.39 (m, 1H), 7.22-7.14 (m, 1H), 7.08 (dd, J=8.3, 10.8 Hz, 1H), 3.43-3.36 (m, 2H), 3.34-3.29 (m, 1H), 3.23 (s, 3H), 2.45-2.32 (m, 1H), 1.94 (td, J=3.5, 13.1 Hz, 1H), 1.83-1.66 (m, 4H), 1.51-1.41 (m, 6H), 1.34-1.16 (m, 10H), 1.15-0.90 (m, 3H), 0.82-0.71 (m, 1H), 0.62 (s, 3H). LCMS Rt=2.809 min in 4.0 min chromatography, 30-90 AB, MS ESI calcd. for $C_{28}H_{40}FO_3$ [M+H]$^+$ 443.3, found 425 [M−H$_2$O]$^+$.

Example 127

Synthesis of Compound 127

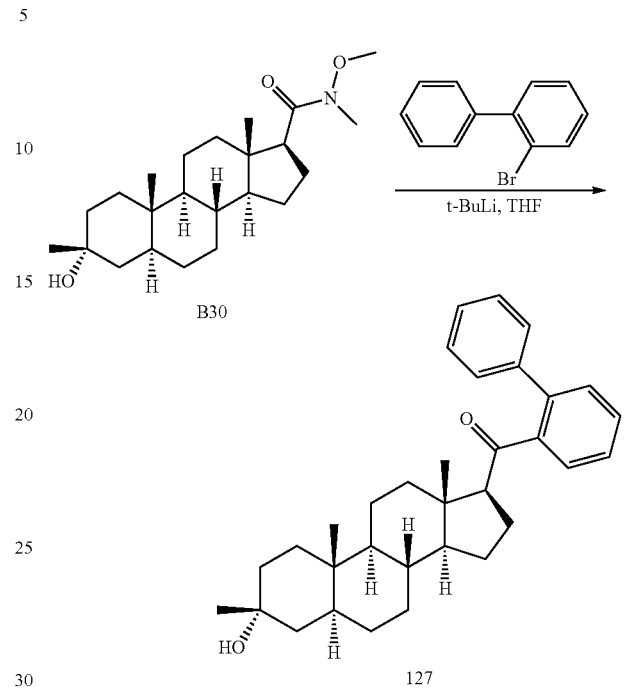

To a solution of 2-bromo-1,1'-biphenyl (244 mg, 1.05 mmol) in THF (5 mL) was added tert-butyllithium (1.45 mL) at −68° C. The mixture was stirred at −68° C. for 1 hrs. A solution of B30 (80 mg, 211 μmol) in THF (5 mL) was added dropwise at −68° C. The reaction was stirred at 25° C. for 1 hour. LCMS showed the reaction was completed. The reaction was quenched with NH$_4$Cl (10 mL), extracted with EtOAc (10 mL×2). The combined organic layers were washed with brine (10 mL). The organic layer was dried over Na$_2$SO$_4$, filtered and concentrated under reduced pressure to give crude product, which was purified by HPLC separation (column: Boston Green ODS 150*30 5u, gradient: 91-100% condition: (water (0.05% HCl)-ACN), flow rate: 25 mL/min) to give 127 (27.3 mg) as a solid.

$^1$H NMR (400 MHz, CDCl$_3$) δ 7.53-7.30 (m, 9H), 2.33-2.26 (m, 1H), 2.22-2.09 (m, 1H), 1.50-0.62 (m, 27H), 0.56 (m, 4H). LCMS Rt=1.473 min in 2 min chromatography, 30-90 AB, MS ESI calcd. for $C_{33}H_{43}O_2$[M+H]$^+$ 471, found 471.

Example 128

Synthesis of Compound 128

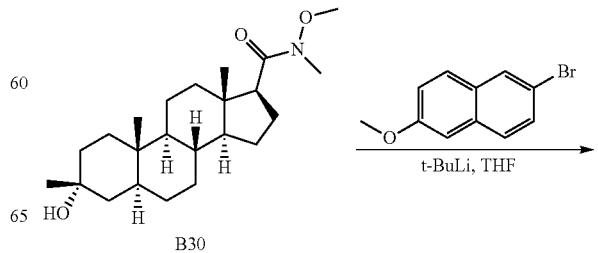

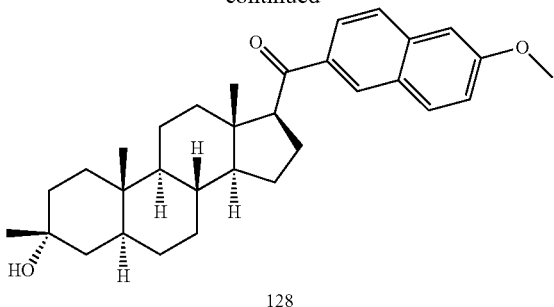

128

To a solution of 2-bromo-6-methoxynaphthalene (248 mg, 1.05 mmol) in THF (5 mL) was added tert-butyllithium (1.45 mL) at −68° C. The mixture was stirred at −68° C. for 1 hrs. A solution of B30 (80 mg, 211 µmol) in THF (5 mL) was added dropwise at −68° C. The reaction was stirred at 25° C. for 1 hour. LCMS showed the reaction was completed. The reaction was quenched with NH$_4$Cl (10 mL), extracted with EtOAc (10 mL×2). The combined organic layers were washed with brine (10 mL). The organic layer was dried over Na$_2$SO$_4$, filtered and concentrated under reduced pressure to give crude product, which was purified by HPLC separation (column: Boston Green ODS 150*30 5u, gradient: 92-98% condition: (water (0.05% HCl)-ACN), flow rate: 25 mL/min) to give 128 (42.9 mg) as a solid.

$^1$H NMR (400 MHz, CDCl$_3$) δ 8.34 (s, 1H), 7.97 (dd, J=1.5, 8.5 Hz, 1H), 7.86 (d, J=8.8 Hz, 1H), 7.76 (d, J=8.5 Hz, 1H), 7.23-7.14 (m, 2H), 3.95 (s, 3H), 3.64 (t, J=8.7 Hz, 1H), 2.53-2.43 (m, 1H), 1.85-1.69 (m, 3H), 1.50-1.17 (m, 19H), 1.16-0.93 (m, 2H), 0.85-0.76 (m, 1H), 0.71 (s, 3H), 0.63 (s, 3H). LCMS Rt=1.100 min in 1.5 min chromatography, 5-95 AB, MS ESI calcd. for C$_{32}$H$_{43}$O$_3$[M+H]$^+$ 475, found 475.

Example 129

Synthesis of Compound 129

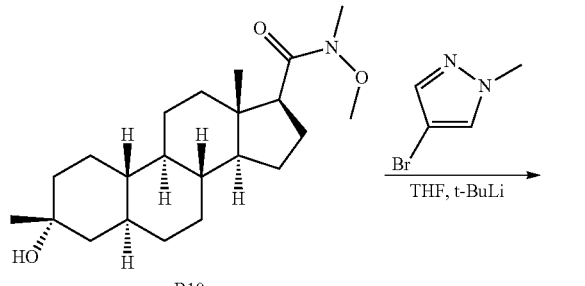

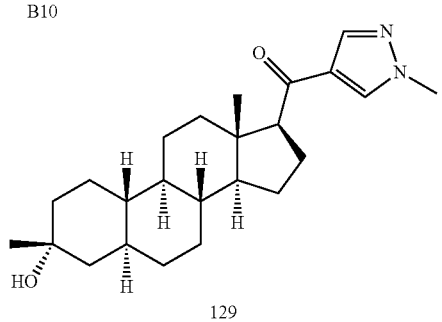

129

To a solution of (220 mg, 1.37 mmol) in THF (5 mL) was added tert-butyllithium (1.90 mL, 2.47 mmol) at −68° C. The mixture was stirred at −68° C. for 1 hour. B10 (100 mg, 275 µmol) in THF (5 mL) was added dropwise at −68° C. The reaction was stirred at 25° C. for 2 hours. The reaction was quenched with NH$_4$Cl (10 mL), extracted with EtOAc (10 mL×2). The combined organic layers were washed with brine (10 mL). The organic layer was dried over Na$_2$SO$_4$, filtered and concentrated under reduced pressure to give crude product which was purified by HPLC separation (Phenomenex Synergi C18 150*30 mm*4 um, gradient: 90-98% condition: (water (0.05% HCl)-ACN), flow rate: 25 mL/min) to give 129 (25.9 mg) as a solid.

$^1$H NMR (400 MHz, CDCl$_3$) δ 7.87 (s, 1H), 7.83 (s, 1H), 3.93 (s, 3H), 3.02 (t, J=8.9 Hz, 1H), 2.42-2.32 (m, 1H), 1.81-1.62 (m, 8H), 1.61-1.55 (m, 2H), 1.43-1.24 (m, 5H), 1.20 (s, 3H), 1.18-0.95 (m, 6H), 0.80-0.60 (m, 5H). LCMS Rt=1.058 min in 2 min chromatography, 30-90 AB, MS ESI calcd. for C$_{24}$H$_{37}$N$_2$O$_2$[M+H]$^+$ 385, found 385.

Example 130

Synthesis of Compound 130

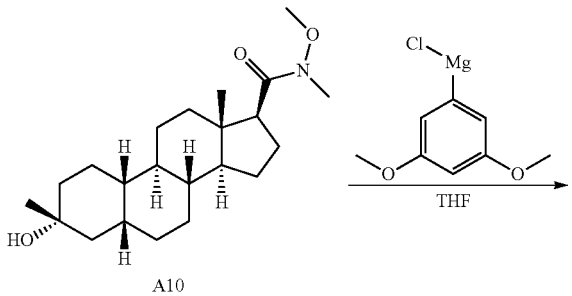

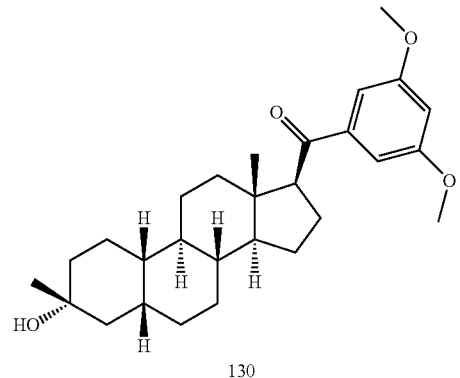

130

To a solution of A10 (100 mg, 0.275 mmol) in THF (3 mL) was added (3,5-dimethoxyphenyl)magnesium chloride (2.75 mL, 1 M in THF). The mixture was stirred at 20° C. for 3.5h and then to the mixture was added sat. aq. NH$_4$Cl (5 mL). The organic phase was extracted with DCM (5 mL*2), washed with sat. aq. NaCl (8 mL*2), concentrated in vacuum. The residue was purified by prep. HPLC to give 130 (19 mg) as a solid.

$^1$H NMR (400 MHz, CDCl$_3$) δ 7.01 (d, J=2.5 Hz, 2H), 6.62 (t, J=2.3 Hz, 1H), 3.83 (s, 6H), 3.42 (t, J=8.7 Hz, 1H), 2.49-2.33 (m, 1H), 1.86-1.58 (m, 7H), 1.52-1.27 (m, 13H), 1.26 (s, 3H), 1.20-0.85 (m, 3H), 0.61 (s, 3H). LCMS Rt=1.427 min in 2 min chromatography, 10-80 AB, MS ESI calcd. for C$_{28}$H$_{41}$O$_4$ [M+H]$^+$ 441.3, found 423 [M−H$_2$O]$^+$.

Example 131

Synthesis of Compound 131

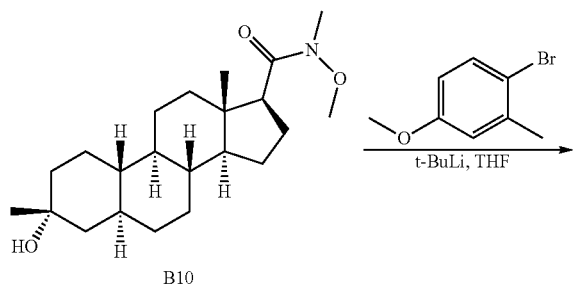

B10

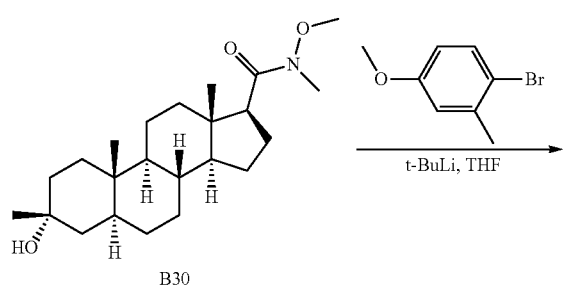

131

To a solution of 1-bromo-4-methoxy-2-methylbenzene (414 mg, 2.06 mmol) in THF (3 mL) was added tert-butyllithium (2.85 mL, 1.3 M in THF) at −70° C. The mixture was stirred at −70° C. for 1 h. A solution of B10 (150 mg, 0.4126 mmol) in THF (1 mL) was added at −70° C. The mixture was stirred at 25° C. for 1 hrs. TLC showed starting material was consumed and new spots were produced. The mixture was quenched with Sat. NH$_4$Cl (10 mL), extracted with EtOAc (10 mL×3), washed with brine (30 mL×3), dried over Na$_2$SO$_4$, filtered, concentrated in vacuum to give a crude product which was purified with prep. HPLC (Column: Phenomenex Synergi C18 150*30 mm*4 um; Condition: water (0.05% HCl)-ACN; Gradient 90%-95% B; Gradient Time (min): 10; FlowRate (ml/min): 25) to give 131 (26 mg) as a solid.

$^1$H NMR (400 MHz: CDCl$_3$) δ 7.54 (d, J=8.5 Hz, 1H), 6.75-6.68 (m, 2H), 3.83 (s, 3H), 3.34 (t, J=8.7 Hz, 1H), 2.50-2.33 (m, 4H), 1.80-1.45 (m, 8H), 1.36-1.22 (m, 5H), 1.20-0.89 (m, 11H), 0.72-0.54 (m, 5H). LCMS t$_R$=1.058 min in 1.5 min chromatography, 5-95 AB, MS ESI calcd. for C$_{21}$H$_{41}$O$_3$[M+H]$^+$ 425, found 425.

Example 132

Synthesis of Compound 132

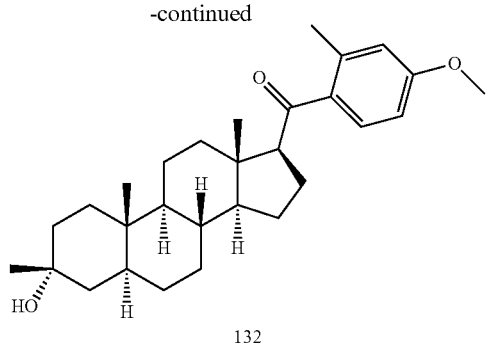

B30

132

To a solution of 1-bromo-4-methoxy-2-methylbenzene (211 mg, 1.05 mmol) in THF (5 mL) was added tert-butyllithium (1.45 mL) at −68° C. The mixture was stirred at −68° C. for 1 hrs. A solution of B30 (80 mg, 211 μmol) in THF (5 mL) was added dropwise at −68° C. The reaction was stirred at 25° C. for 1 hour. LCMS showed the reaction was completed. The reaction was quenched with NH$_4$Cl (10 mL), extracted with EtOAc (10 mL×2). The combined organic layers were washed with brine (10 mL). The organic layer was dried over Na$_2$SO$_4$, filtered and concentrated under reduced pressure to give crude product, which was purified by HPLC separation (column: Boston Green ODS 150*30 5u, gradient: 91-100% condition: (water (0.05% HCl)-ACN), flow rate: 25 mL/min) to give 132 (29.3 mg) as a solid.

$^1$H NMR (400 MHz, CDCl$_3$) δ 7.55 (d, J=8.3 Hz, 1H), 6.77-6.68 (m, 2H), 3.83 (s, 3H), 3.33 (t, J=8.5 Hz, 1H), 2.47 (s, 3H), 2.43-2.32 (m, 1H), 1.78-1.65 (m, 4H), 1.52-1.31 (m, 9H), 1.30-1.06 (m, 14H), 1.04-0.87 (m, 1H), 0.79-0.67 (m, 4H), 0.61 (s, 3H). LCMS Rt=1.066 min in 2 min chromatography, 5-95 AB, MS ESI calcd. for C$_{29}$H$_{43}$O$_3$ [M+H]$^+$ 439, found 439.

Example 133

Synthesis of Compound 133

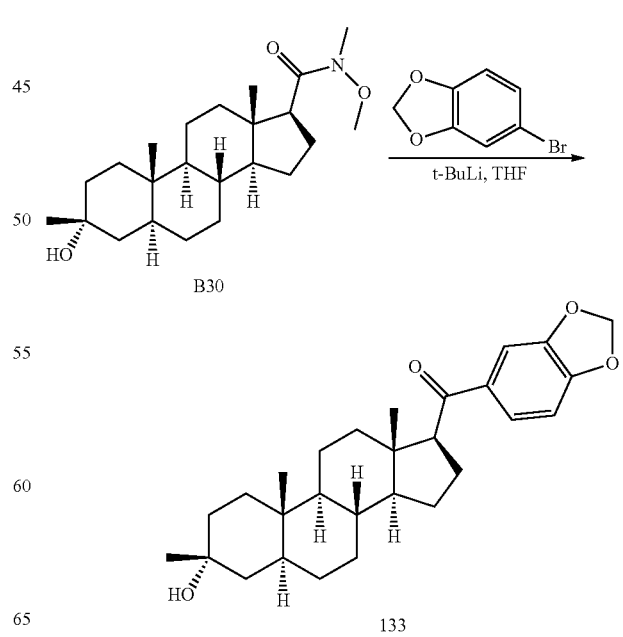

B30

133

To a solution of 6-bromobenzo[d][1,3]dioxole (158 mg, 789 μmol) in THF (5 mL) was added tert-butyllithium (1.09 mL) at −68° C. After stirring at −68° C. for 1 hr, a solution of B30 (60 mg, 158 μmol) in THF (5 mL) was added dropwise at −68° C. The reaction was stirred at 25° C. for 2 hours. TLC showed the reaction was completed. The reaction was quenched with Sat. NH$_4$Cl (10 mL), extracted with EtOAc (10 mL×2). The combined organic layers were washed with brine (10 mL). The organic layers were dried over Na$_2$SO$_4$, filtered and concentrated under reduced pressure to give a crude product, which was purified by HPLC separation (column: Boston Green ODS 150*30 5u, gradient 80-95% B (A=0.05% HCl-ACN, B=acetonitrile), flow rate: 25 ml/min) and lyophilized to give 133 (14.9 mg) as a solid $^1$H NMR (400 MHz, CDCl$_3$) δ 7.55 (dd, J=8.2, 1.4 Hz, 1H), 7.40 (d, J=1.3 Hz, 1H), 7.01 (d, J=8.0 Hz, 1H), 6.13 (d, J=1.0 Hz, 2H), 3.87 (s, 1H), 3.58 (t, J=8.3 Hz, 1H), 2.29-2.17 (m, 1H), 1.74-1.58 (m, 3H), 1.55-1.39 (m, 3H), 1.36-1.00 (m, 17H), 0.98-0.84 (m, 1H), 0.78-0.61 (m, 4H), 0.47 (s, 3H). LCMS Rt=1.033 min in 1.5 min chromatography, 5-95 AB, MS ESI calcd for C$_{28}$H$_{40}$O$_4$ [M+H]$^+$ 439, found 439.

Example 134

Synthesis of Compound 134

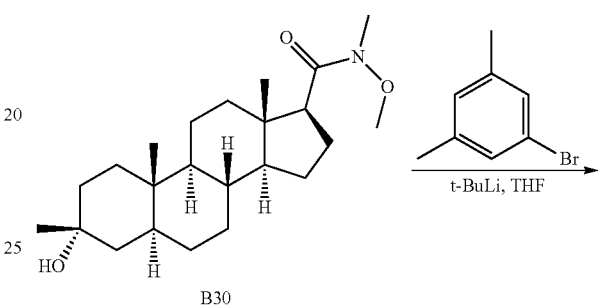

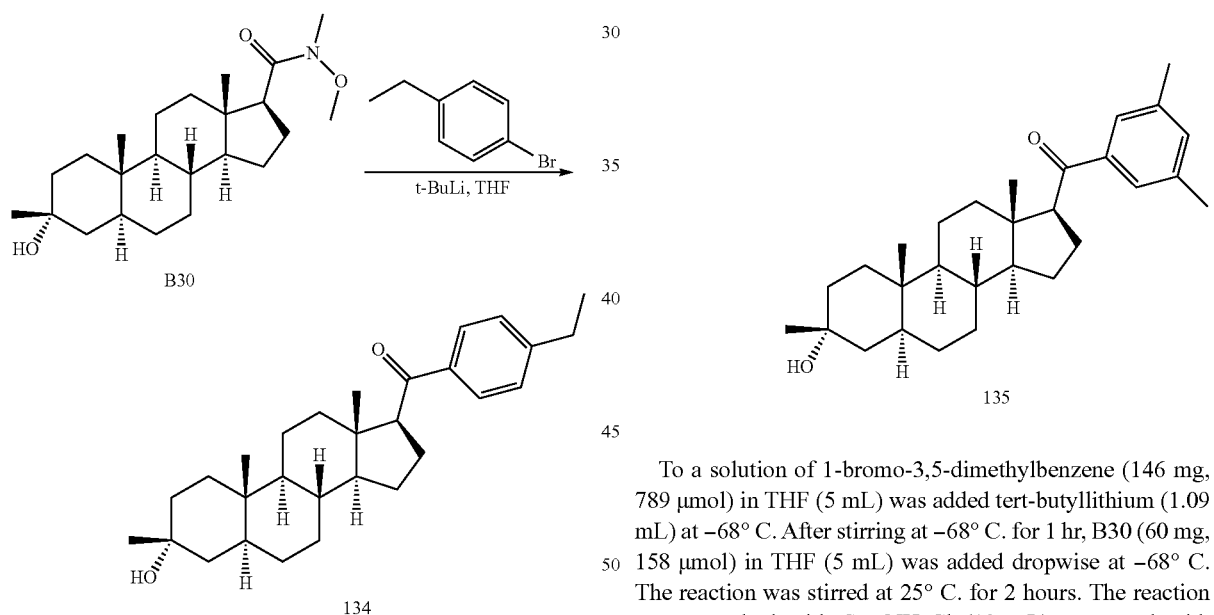

To a solution of 1-bromo-4-ethylbenzene (146 mg, 789 μmol) in THF (5 mL) was added tert-butyllithium (1.09 mL) at −68° C. After stirring at −68° C. for 1 hr, a solution of B30 (60 mg, 158 μmol) in THF (5 mL) was added dropwise at −68° C. The reaction was stirred at 25° C. for 2 hours. TLC showed the reaction was completed. The reaction was quenched with Sat. NH$_4$Cl (10 mL), extracted with EtOAc (10 mL×2). The combined organic layers were washed with brine (10 mL). The organic layer was dried over Na$_2$SO$_4$, filtered and concentrated under reduced pressure to give a crude product, which was purified by HPLC separation (column: Boston Green ODS 150*30 5u, gradient: 95-100% B (A=0.05% HCl-ACN, B=acetonitrile), flow rate: 25 mL/min) and lyophilized to give 134 (23.3 mg) as a solid.

$^1$H NMR (400 MHz, DMSO-d$_6$) δ 7.83 (d, J=8.0 Hz, 2H), 7.33 (d, J=8.0 Hz, 2H), 3.86 (s, 1H), 3.63 (t, J=8.5 Hz, 1H), 2.67 (q, J=7.5 Hz, 2H), 2.32-2.20 (m, 1H), 1.76-1.60 (m, 3H), 1.52-1.31 (m, 7H), 1.27-1.10 (m, 11H), 1.08-0.88 (m, 5H), 0.76-0.60 (m, 4H), 0.48 (s, 3H). LCMS Rt=1.115 min in 1.5 min chromatography, 5-95 AB, MS ESI calcd. for C$_{29}$H$_{44}$O$_2$ [M+H]$^+$ 423, found 423.

Example 135

Synthesis of Compound 135

To a solution of 1-bromo-3,5-dimethylbenzene (146 mg, 789 μmol) in THF (5 mL) was added tert-butyllithium (1.09 mL) at −68° C. After stirring at −68° C. for 1 hr, B30 (60 mg, 158 μmol) in THF (5 mL) was added dropwise at −68° C. The reaction was stirred at 25° C. for 2 hours. The reaction was quenched with Sat NH$_4$Cl (10 mL), extracted with EtOAc (10 mL×2). The combined organic layers were washed with brine (10 mL). The organic layer was dried over Na$_2$SO$_4$, filtered and concentrated under reduced pressure to give a product, which was purified by prep-HPLC (column: Boston Green ODS 150*30 5u, gradient: 95-100% condition: (0.05% HCl-ACN), flow rate: 25 mL/min) and lyophilized to give 135 (27.6 mg) as a solid.

$^1$H NMR (400 MHz. DMSO-d$_6$) δ 7.48 (s, 2H), 7.23 (s, 1H), 3.86 (s, 1H), 3.61 (t, J=8.4 Hz, 1H), 2.33 (s, 6H), 2.30-2.18 (m, 1H), 1.75-1.60 (m, 3H), 1.55-0.80 (m, 21H), 0.77-0.61 (m, 4H), 0.48 (s, 3H). LCMS Rt=1.113 min in 1.5 min chromatography, 5-95 AB, ESI calcd. for C$_{29}$H$_{43}$O$_2$ [M+H]$^+$ 423, found 423.

Example 136

Synthesis of Compound 136

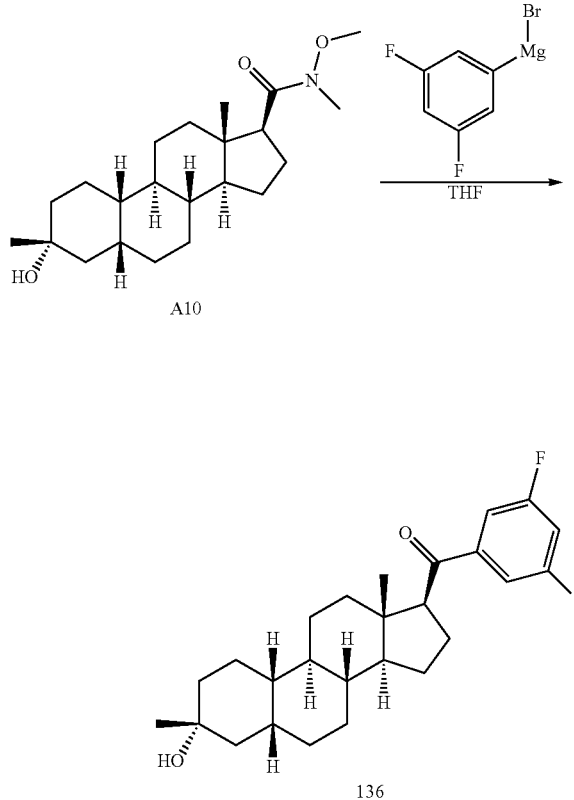

To a stirred solution of A10 (110 mg, 302 umol) in 3 mL of THF was added (4-(trifluoromethoxy)phenyl)magnesium bromide (0.5 M, 6.02 mL, 3.01 mmol) dropwise at 25° C. After stirring at 25° C. for 12 hrs, LCMS showed the reaction was complete. The reaction mixture was poured into ice-cold water and extracted with EtOAc (50 mL×2), washed with brine (30 mL×2), dried (Na₂SO₄), filtered, and evaporated in vacuo to give crude product, which was purified by prep-HPLC separation (column: Boston Green ODS 150*30 5u, gradient: 90-100% B (A=0.05% HCl-ACN, B=acetonitrile), flow rate: 25 mL/min) for further purification to obtain to (3,5-difluorophenyl)((3R,5R,8R,9R,10S,13S,14S,17S)-3-hydroxy-3,13-dimethylhexadeca-hydro-1H-cyclopenta[a]phenanthren-17-yl)methanone (67 mg, 53%) as a solid.

¹HNMR (CDCl₃, 400 MHz): δ 7.38 (d, J=6.0 Hz, 2H), 6.99 (t, J=8.6 Hz, 1H), 3.36 (t, J=8.6 Hz, 1H), 2.36-2.42 (m, 1H), 1.73-1.85 (m, 5H), 1.63 (d, J=13.6 Hz, 2H), 1.26-1.50 (m, 15H), 1.04-1.15 (m, 2H), 0.85-1.02 (m, 2H), 0.61 (s, 3H)

LCMS Rt=3.219 min in 4.0 min chromatography, 10-80 AB, purity 100%, MS ESI calcd. for $C_{26}H_{35}F_2O_2$ [M+H]+ 417.3, found 399.0 [M−H₂O]+.

Example 137

Synthesis of Compound 137

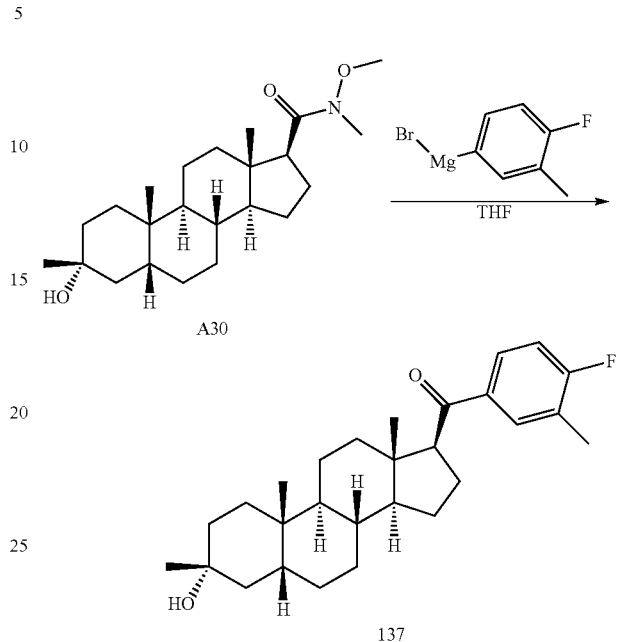

To a stirred solution of A30 (110 mg, 291 umol) in 3 mL of THF was added (4-fluoro-3-methylphenyl)magnesium bromide (0.5 M, 5.8 mL, 2.9 mmol) dropwise at 25° C. After stirring at 25° C. for 12 hrs, LCMS showed the reaction was complete. The reaction mixture was poured into ice-cold water and extracted with EtOAc (50 mL×2), washed with brine (30 mL×2), dried (Na2SO4), filtered, and evaporated in vacuo to give crude product. The reaction mixture was purified by HPLC separation (column: Phenomenex Synergi C18 150*25*10 um, gradient 80-100% B (A=0.05% HCl-ACN, B=acetonitrile), flow rate: 25 mL/min) for further purification to obtain (4-fluoro-3-methylphenyl)((3R,5R,8R,9S,10S,13S,14S,17S)-3-hydroxy-3,10,13-trimethyl-hexadecahydro-1H-cyclopenta[a]phenanthren-17-yl)methanone (52.1 mg, 40.2%) as a solid.

¹HNMR (CDCl₃, 400 MHz): δ=7.76 (d, J=7.6 Hz, 1H), 7.71 (br. s., 1H), 7.04 (t, J=9.0 Hz, 1H), 3.44 (t, J=8.8 Hz, 1H), 2.36-2.43 (m, 1H), 2.33 (s, 3H), 1.92-2.05 (m, 2H), 1.81-1.88 (m, 1H), 1.67-1.78 (m, 3H), 1.32-1.51 (m, 10H), 1.26 (s, 3H), 1.23 (br. s., 2H), 1.09-1.18 (m, 2H), 0.98-1.08 (m, 2H), 0.91 (s, 3H), 0.58 (s, 3H)

LCMS Rt=3.430 min in 4.0 min chromatography, 10-80 AB, purity 95.9%, MS ESI calcd. for $C_{28}H_{40}FO_2$ [M+H]+ 426.6, found 409.0 [M−H₂O]+.

Assay Methods

Compounds provided herein can be evaluated using various assays; examples of which are described below.

Steroid Inhibition of TBPS Binding

TBPS binding assays using rat brain cortical membranes in the presence of 5 μM GABA has been described (Gee et al, *J. Pharmacol. Exp. Ther.* 1987, 241, 346-353; Hawkinson et al, *Mol. Pharmacol.* 1994, 46, 977-985; Lewin, A. H et al., *Mol. Pharmacol.* 1989, 35, 189-194).

Briefly, cortices are rapidly removed following decapitation of carbon dioxide-anesthetized Sprague-Dawley rats (200-250 g). The cortices are homogenized in 10 volumes of ice-cold 0.32 M sucrose using a glass/teflon homogenizer and centrifuged at 1500×g for 10 min at 4° C. The resultant supernatants are centrifuged at 10,000×g for 20 min at 4° C. to obtain the P2 pellets. The P2 pellets are resuspended in 200 mM NaCl/50 mM Na—K phosphate pH 7.4 buffer and centrifuged at 10,000×g for 10 min at 4° C. This washing procedure is repeated twice and the pellets are resuspended in 10 volumes of buffer. Aliquots (100 µL) of the membrane suspensions are incubated with 3 nM [$^{35}$S]-TBPS and 5 µL aliquots of test drug dissolved in dimethyl sulfoxide (DMSO) (final 0.5%) in the presence of 5 µM GABA. The incubation is brought to a final volume of 1.0 mL with buffer. Nonspecific binding is determined in the presence of 2 µM unlabeled TBPS and ranged from 15 to 25%. Following a 90 min incubation at room temp, the assays are terminated by filtration through glass fiber filters (Schleicher and Schuell No. 32) using a cell harvester (Brandel) and rinsed three times with ice-cold buffer. Filter bound radioactivity is measured by liquid scintillation spectrometry. Non-linear curve fitting of the overall data for each drug averaged for each concentration is done using Prism (GraphPad). The data are fit to a partial instead of a full inhibition model if the sum of squares is significantly lower by F-test. Similarly, the data are fit to a two component instead of a one component inhibition model if the sum of squares is significantly lower by F-test. The concentration of test compound producing 50% inhibition (IC$_{50}$) of specific binding and the maximal extent of inhibition (I$_{max}$) are determined for the individual experiments with the same model used for the overall data and then the means±SEM.s of the individual experiments are calculated. Picrotoxin serves as the positive control for these studies as it has been demonstrated to robustly inhibit TBPS binding.

Various compounds are or can be screened to determine their potential as modulators of [$^{35}$S]-TBPS binding in vitro. These assays are or can be performed in accordance with the above discussed procedures.

For Table 1, "A" indicates an IC$_{50}$<20 nM, "B" indicates an IC$_{50}$ of 20 nM to 50 nM, "C" indicates an IC$_{50}$>50 nM to 100 nM, and "D" indicates IC$_{50}$>100 nM.

TABLE 1

| Compound | 35S-TBPS Radioligand Displacement (IC50) |
| --- | --- |
| 1 | A |
| 2 | D |
| 3 | D |
| 4 | B |
| 5 | B |
| 6 | D |
| 7 | C |
| 8 | D |
| 9 | B |
| 10 | A |
| 11 | B |
| 12 | B |
| 130 | B |
| 24 | A |
| 23 | C |
| 28 | B |
| 27 | B |
| 26 | B |
| 48 | B |
| 15 | B |
| 18 | C |
| 21 | D |
| 17 | C |
| 20 | C |
| 25 | B |
| 19 | C |
| 16 | A |
| 13 | D |
| 22 | C |
| 14 | C |
| 39 | C |
| 38 | C |
| 37 | C |
| 36 | C |
| 45 | D |
| 35 | A |
| 41 | B |
| 44 | C |
| 49 | A |
| 29 | D |
| 34 | A |
| 47 | B |
| 33 | D |
| 32 | B |
| 31 | C |
| 30 | D |
| 43 | B |
| 46 | D |
| 40 | B |
| 42 | A |
| 59 | C |
| 58 | C |
| 56 | B |
| 55 | B |
| 54 | C |
| 53 | D |
| 52 | B |
| 51 | C |
| 50 | D |
| 64 | D |
| 68 | D |
| 63 | C |
| 60 | D |
| 62 | D |
| 61 | D |
| 74 | B |
| 73 | C |
| 86 | B |
| 89 | C |
| 72 | B |
| 85 | D |
| 84 | D |
| 83 | B |
| 88 | D |
| 70 | C |
| 71 | D |
| 87 | D |
| 75 | D |
| 82 | D |
| 81 | D |
| 80 | D |
| 79 | D |
| 78 | D |
| 77 | D |
| 76 | D |
| 101 | D |
| 133 | D |
| 134 | D |
| 135 | D |
| 98 | D |
| 108 | D |
| 111 | D |
| 99 | D |
| 100 | D |
| 107 | C |
| 106 | D |
| 105 | D |
| 110 | C |
| 102 | C |
| 104 | D |

TABLE 1-continued

| Compound | 35S-TBPS Radioligand Displacement (IC50) |
|---|---|
| 109 | D |
| 92 | D |
| 103 | D |
| 97 | D |
| 91 | D |
| 96 | D |
| 95 | D |
| 94 | C |
| 93 | C |
| 115 | D |
| 114 | D |
| 128 | D |
| 127 | D |
| 132 | D |
| 113 | D |
| 125 | B |
| 124 | C |
| 123 | D |
| 136 | B |
| 137 | B |

Patch Clamp Electrophysiology of Recombinant $\alpha_1\beta_2\gamma_2$ and $\alpha_4\beta_3\delta$ GABA$_A$ Receptors Cellular electrophysiology is used to measure the pharmacological properties of our GABA$_A$ receptor modulators in heterologous cell systems. Each compound is tested for its ability to affect GABA mediated currents at a submaximal agonist dose (GABA EC$_{20}$=2 µM). LTK cells are stably transfected with the $\alpha_1\beta_2\gamma_2$ subunits of the GABA receptor and CHO cells are transiently transfected with the $\alpha_4\beta_3\delta$ subunits via the Lipofecatamine method. Cells were passaged at a confluence of about 50-80% and then seeded onto 35 mm sterile culture dishes containing 2 ml culture complete medium without antibiotics or antimycotics. Confluent clusters of cells are electrically coupled (Pritchett et al., Science, 1988, 242, 1306-1308.). Because responses in distant cells are not adequately voltage clamped and because of uncertainties about the extent of coupling (Verdoorn et al., Neuron 1990, 4, 919-928), cells were cultivated at a density that enables the recording of single cells (without visible connections to other cells).

Whole cell currents were measured with HEKA EPC-10 amplifiers using PatchMaster software or by using the high throughput QPatch platform (Sophion). Bath solution for all experiments contained (in mM): NaCl 137 mM, KCl 4 mM, CaCl$_2$ 1.8 mM, MgCl$_2$ 1 mM, HEPES 10 mM, D-Glucose 10 mM, pH (NaOH) 7.4. In some cases 0.005% cremophor was also added. Intracellular (pipette) solution contained: KCl 130 mM, MgCl$_2$ 1 mM, Mg-ATP 5 mM, HEPES 10 mM, EGTA 5 mM, pH 7.2. During experiments, cells and solutions were maintained at room temperature (19° C.-30° C.). For manual patch clamp recordings, cell culture dishes were placed on the dish holder of the microscope and continuously perfused (1 ml/mm) with bath solution. After formation of a Gigaohm seal between the patch electrodes and the cell (pipette resistance range: 2.5 MΩ-6.0 MΩ; seal resistance range: >1 GΩ) the cell membrane across the pipette tip was ruptured to assure electrical access to the cell interior (whole-cell patch-configuration). For experiments using the QPatch system, cells were transferred as suspension to the QPatch system in the bath solution and automated whole cell recordings were performed.

Cells were voltage clamped at a holding potential of −80 mV. For the analysis of test articles, GABA receptors were stimulated by 2 µM GABA after sequential pre-incubation of increasing concentrations of the test article. Pre-incubation duration was 30 s and the duration of the GABA stimulus was 2 s. Test articles were dissolved in DMSO to form stock solutions (10 mM). Test articles were diluted to 0.01, 0.1, 1, and 10 µM in bath solution. All concentrations of test articles were tested on each cell. The relative percentage potentiation was defined as the peak amplitude in response to GABA EC$_{20}$ in the presence of the test article divided by the peak amplitude in response to GABA EC$_{20}$ alone, multiplied by 100.

TABLE 2

Electrophysiological evaluation of the exemplary compounds at GABA$_A$-R.

| Name | GABA ($\alpha1\beta2\gamma2$) Qpatch in Ltk, % efficacy at 10 µM |
|---|---|
| 1 | C |
| 8 | B |

For Table 2. GABAA receptors $\alpha1\beta2\gamma2$ and $\alpha4\beta3\delta$ % efficacy: "A" 10-100, "B">100-500, "C">500; D indicates the data is not available or has not been determined.

What is claimed is:

1. A compound of the Formula (II):

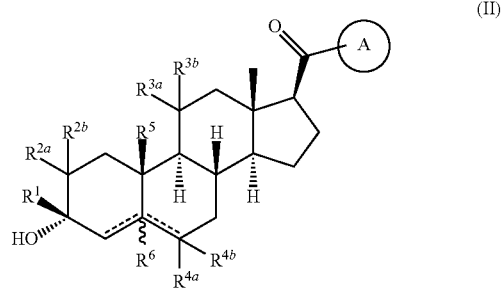

or a pharmaceutically acceptable salt thereof;
wherein:
Ring A is substituted or unsubstituted aryl or heteroaryl, wherein A is linked through a carbon atom;
$R^1$ is hydrogen, or substituted or unsubstituted $C_{1-6}$ alkyl, substituted or unsubstituted $C_{2-6}$ alkenyl, substituted or unsubstituted $C_{2-6}$ alkynyl, or substituted or unsubstituted $C_{3-6}$ carbocyclyl;
each of $R^{2a}$ and $R^{2b}$ is independently selected from hydrogen, halogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{3-6}$ carbocyclyl, substituted or unsubstituted aryl, substituted or unsubstituted heteroaryl, —N($R^A$)($R^B$), or —OR$^{A2}$, wherein each of $R^A$ and $R^B$ is independently hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{3-6}$ carbocyclyl, substituted or unsubstituted heterocyclyl, substituted or unsubstituted aryl, or substituted or unsubstituted heteroaryl, or $R^A$ and $R^B$, together with the nitrogen atom to which they are attached form a ring or $R^{2a}$ and $R^{2b}$, together with the carbon atom to which they are attached form a ring;
$R^{A2}$ is hydrogen or substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{3-6}$ carbocyclyl, substituted or unsubstituted aryl, or substituted or unsubstituted heteroaryl;

$R^{3a}$ is hydrogen, —N($R^A$)($R^B$), or —$OR^{A3}$, wherein $R^{A3}$ is hydrogen, substituted or unsubstituted $C_{1-6}$ alkyl, substituted or unsubstituted $C_{2-6}$ alkenyl, substituted or unsubstituted $C_{2-6}$ alkynyl, or substituted or unsubstituted $C_{3-6}$ carbocyclyl, substituted or unsubstituted aryl, substituted or unsubstituted heteroaryl, and $R^{3b}$ is hydrogen or —N($R^A$)C(O)$R^{A3}$; or $R^{3a}$ and $R^{3b}$ are joined to form an oxo (=O) group;

each of $R^{4a}$ and $R^{4b}$ is independently selected from hydrogen or halogen;

$R^5$ is hydrogen, unsubstituted $C_{1-6}$ alkyl, or —$CH_2OR^{A5}$, wherein $R^{A5}$ is hydrogen, substituted or unsubstituted $C_{1-6}$ alkyl, substituted or unsubstituted $C_{2-6}$ alkenyl, substituted or unsubstituted $C_{2-6}$ alkynyl, or substituted or unsubstituted $C_{3-6}$ carbocyclyl, substituted or unsubstituted aryl, substituted or unsubstituted heteroaryl;

$R^6$ is absent or hydrogen; and

===== represents a single or double bond, wherein when one of ===== is a double bond, the other ===== is a single bond; and when one of the ===== is a double bond, $R^6$ is absent.

2. A compound of the Formula (I):

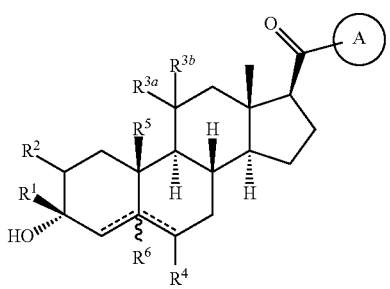

(I)

or a pharmaceutically acceptable salt thereof;
wherein:
Ring A is substituted or unsubstituted aryl or heteroaryl, wherein A is linked through a carbon atom;

$R^1$ is hydrogen, substituted or unsubstituted $C_{1-6}$ alkyl, substituted or unsubstituted $C_{2-6}$ alkenyl, or substituted or unsubstituted $C_{3-6}$ carbocyclyl;

$R^2$ is hydrogen, halogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{3-6}$ carbocyclyl, —N($R^A$)($R^B$), or —$OR^{A2}$, wherein each of $R^A$ and $R^B$ is independently hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{3-6}$ carbocyclyl, or substituted or unsubstituted heterocyclyl, or $R^A$ and $R^B$, together with the nitrogen atom to which they are attached form a ring; $R^{A2}$ is hydrogen or substituted or unsubstituted $C_{1-6}$ alkyl, substituted or unsubstituted $C_{2-6}$ alkenyl, substituted or unsubstituted $C_{2-6}$ alkynyl, or substituted or unsubstituted $C_{3-6}$ carbocyclyl;

$R^{3a}$ is hydrogen, —N($R^A$)($R^B$), or —$OR^{A3}$, wherein $R^{A3}$ is hydrogen, substituted or unsubstituted $C_{1-6}$ alkyl, substituted or unsubstituted $C_{2-6}$ alkenyl, substituted or unsubstituted $C_{2-6}$ alkynyl, or substituted or unsubstituted $C_{3-6}$ carbocyclyl, and $R^{3b}$ is hydrogen or —N($R^A$)C(O)$R^{A3}$; or $R^{3a}$ and $R^{3b}$ are joined to form an oxo (=O) group;

$R^4$ is hydrogen or halogen;

$R^5$ is hydrogen, unsubstituted $C_{1-6}$ alkyl, or —$CH_2OR^{A5}$, wherein $R^{A5}$ is hydrogen, substituted or unsubstituted $C_{1-6}$ alkyl, substituted or unsubstituted $C_{2-6}$ alkenyl, substituted or unsubstituted $C_{2-6}$ alkynyl, or substituted or unsubstituted $C_{3-6}$ carbocyclyl;

$R^6$ is absent or hydrogen; and

===== represents a single or double bond, wherein
when one of ===== is a double bond, the other ===== is a single bond; and
when one of the ===== is a double bond, $R^6$ is absent.

3. The compound of claim 2, wherein the compound of Formula (I) is a compound of Formula (I-a):

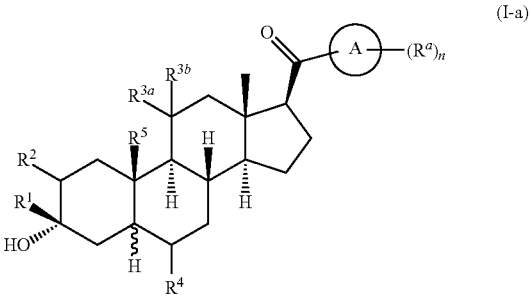

(I-a)

wherein:

n is 0, 1, 2, 3, 4, 5, or 6; and each $R^a$ is independently halogen, cyano, $C_{1-6}$ alkyl, —N($R^A$)($R^B$), —N($R^A$)C(O)$R^{A4}$, —N($R^A$)C(O)O$R^{A4}$, —$SR^{A4}$ or —$OR^{A4}$, wherein $R^{A4}$ is hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{3-6}$ carbocyclyl, substituted or unsubstituted aryl, or substituted or unsubstituted heteroaryl; or two $R^a$ groups, together with the atoms with which they are attached form a ring.

4. The compound of claim 3, wherein the compound of Formula (I) is a compound of Formula (I) is a compound of Formula (I-b):

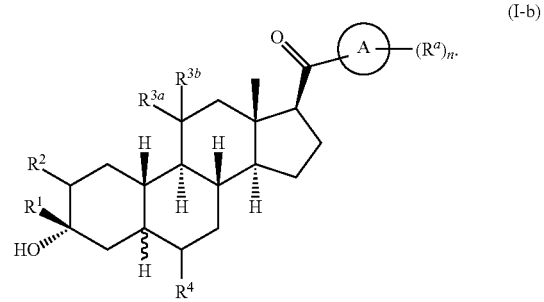

(I-b)

5. The compound of claim 3, wherein the compound of Formula (I) is a compound of Formula (I-b-i) or (I-b-ii):

(I-b-i)

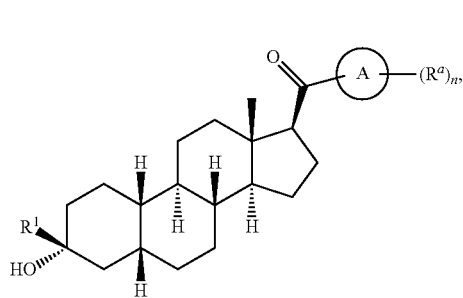

(I-b-ii)

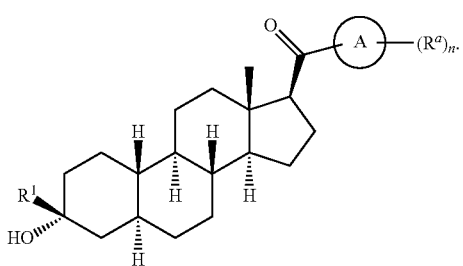

6. The compound of claim 3, wherein the compound of Formula (I) is a compound of Formula (I) is a compound of Formula (I-c):

(I-c)

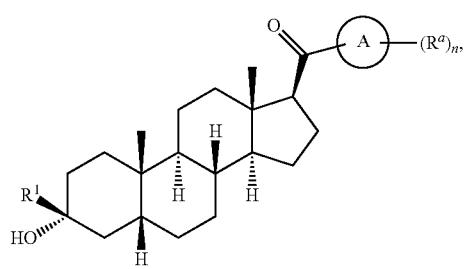

7. The compound of claim 3, wherein the compound of Formula (I) is a compound of Formula (I) is a compound of Formula (I-c-i) or (I-c-ii):

(I-c-i)

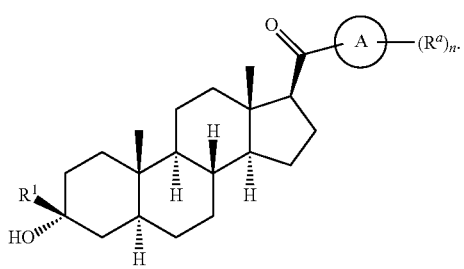

-continued (I-c-ii)

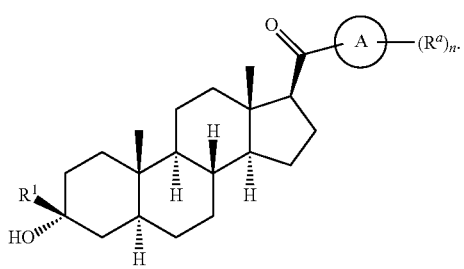

8. The compound of claim 3, wherein the compound of Formula (I) is a compound of Formula (I) is a compound of Formula (I-f):

(I-d)

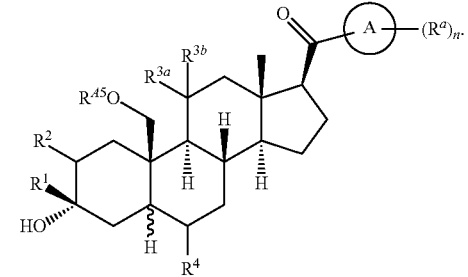

9. The compound of claim 3, wherein the compound of Formula (I) is a compound of Formula (I) is a compound of Formula (I-d-i) or (I-d-ii):

(I-d-i)

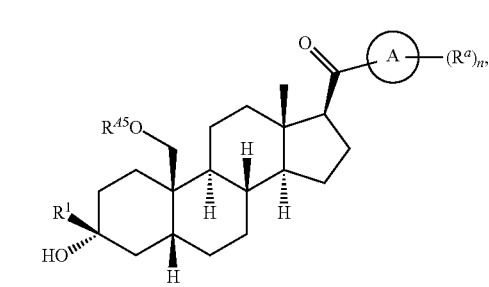

(I-d-ii)

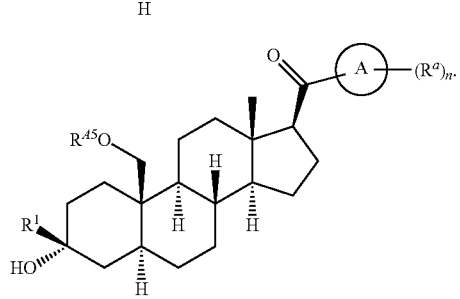

10. The compound of claim 2, wherein A is a 5-10-membered ring.

11. The compound of claim 10, wherein A is phenyl, naphthyl, furan, thiophene, thiazole, pyrrole, imidazole, pyrazole, or triazole.

12. The compound of claim 2, wherein $R^1$ is unsubstituted $C_{1-6}$ alkyl.

13. The compound of claim 12, wherein $R^1$ is —$CH_3$.

14. The compound of claim 1, wherein the compound is:
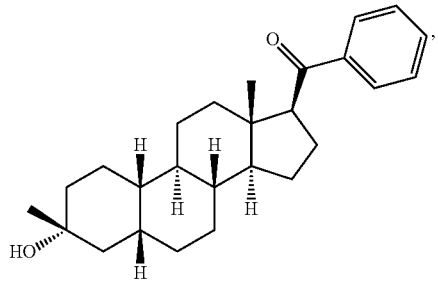,
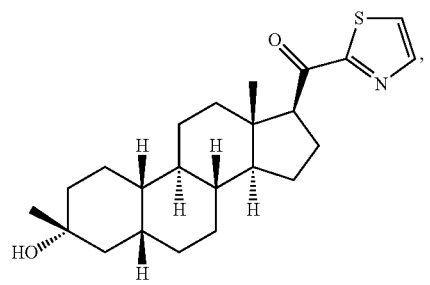,
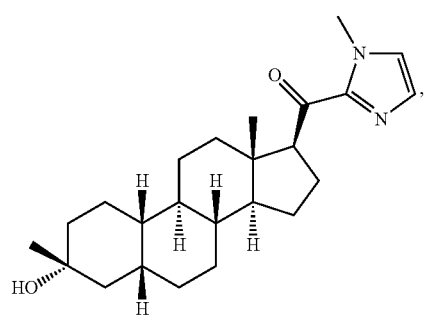,
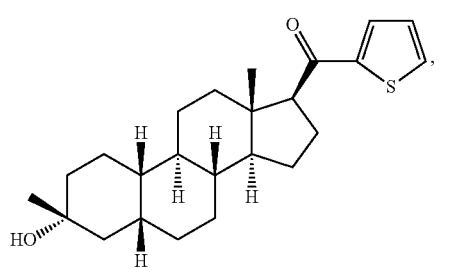,
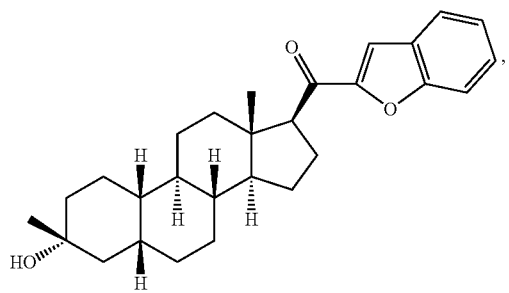,
-continued
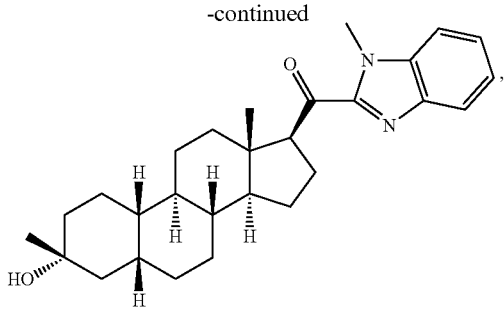,
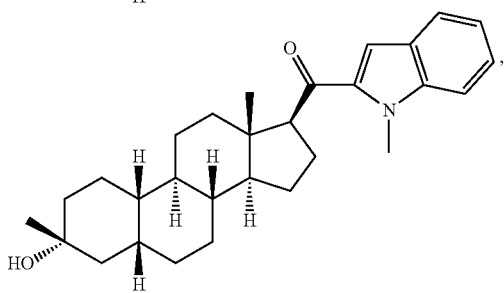,
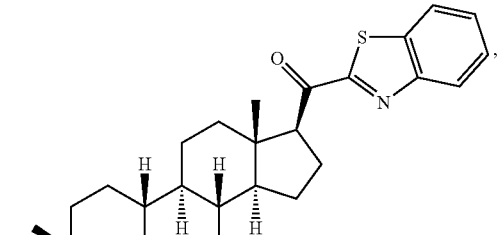,
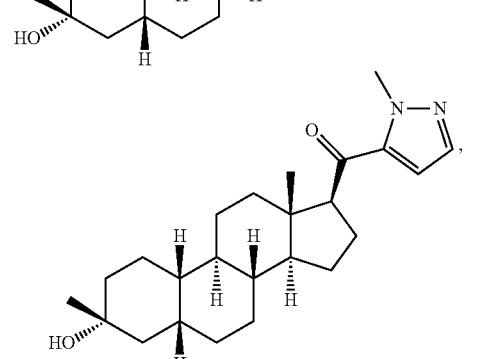,
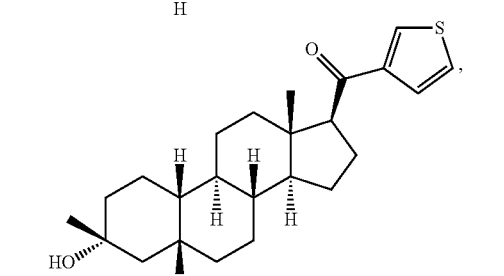,
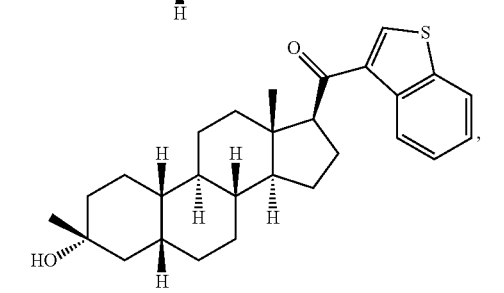,

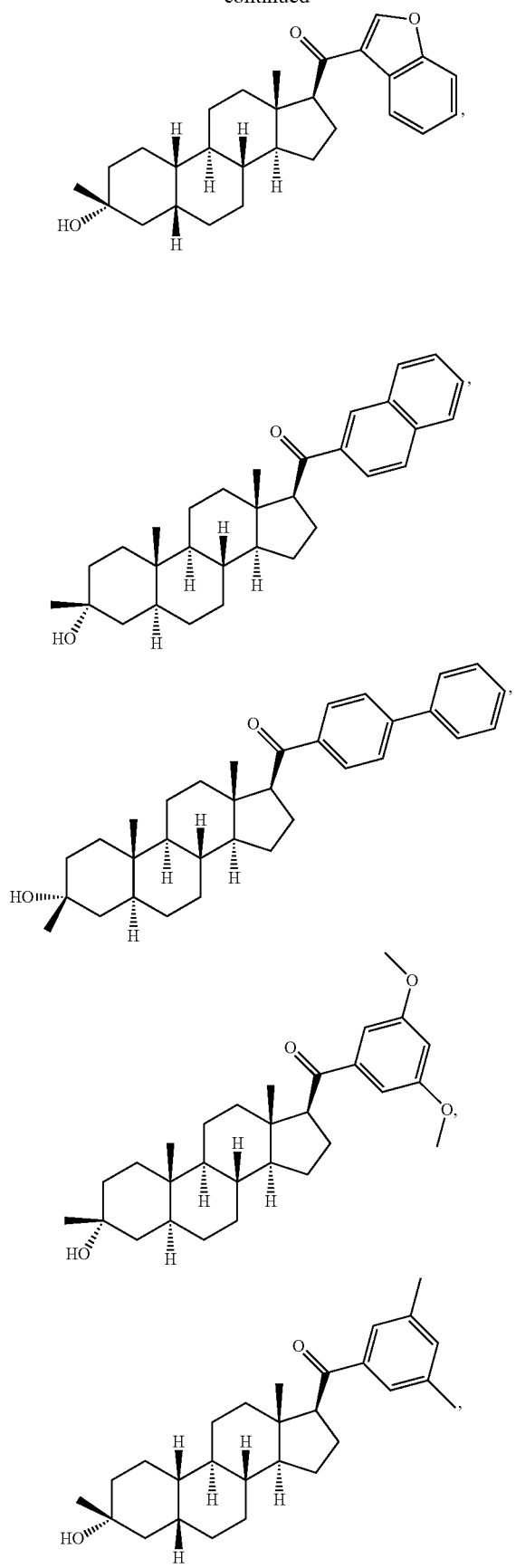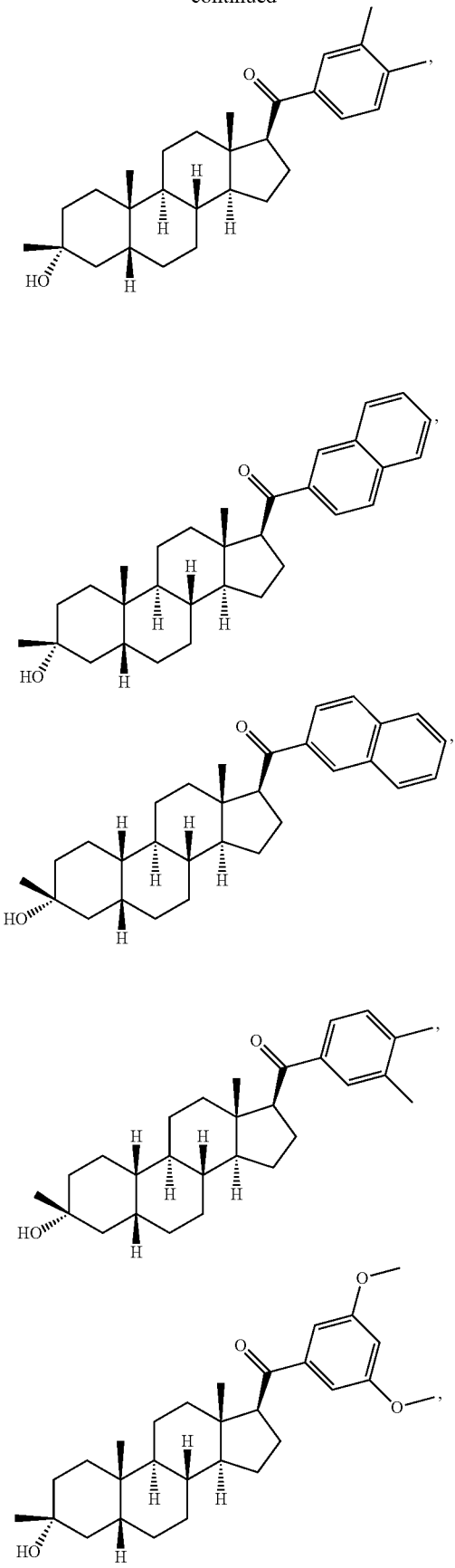

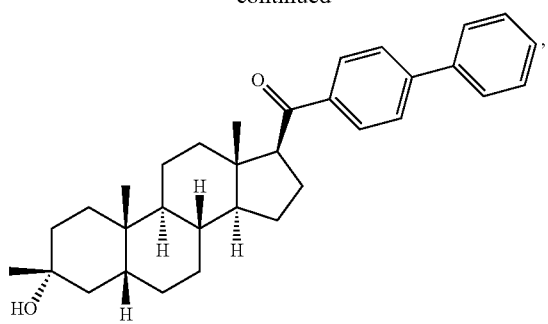
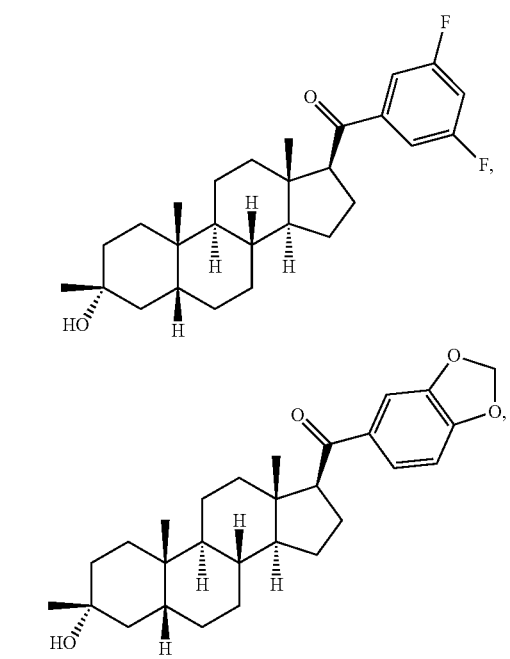
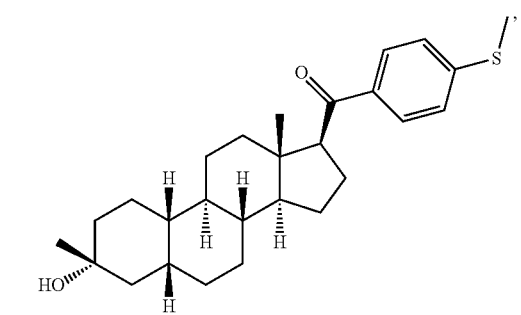
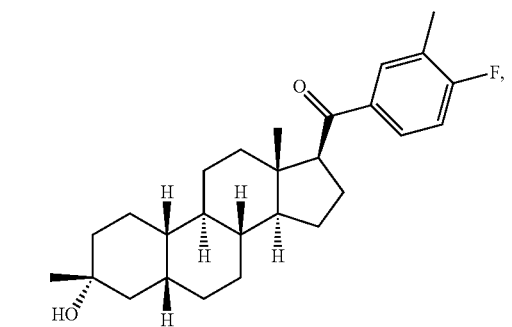
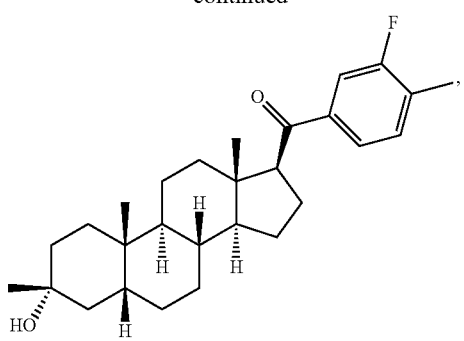
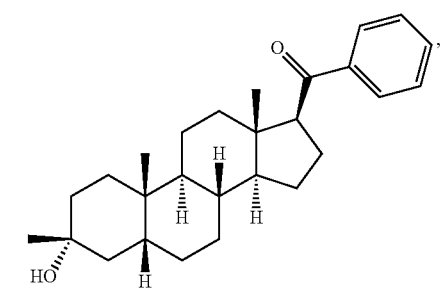
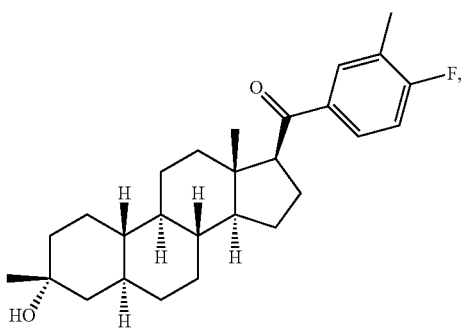
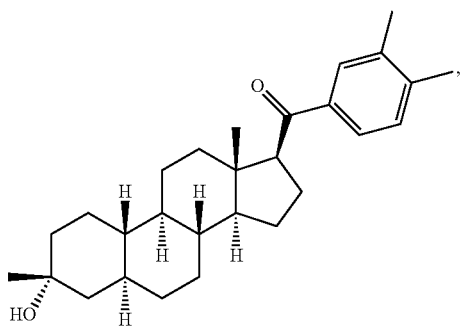
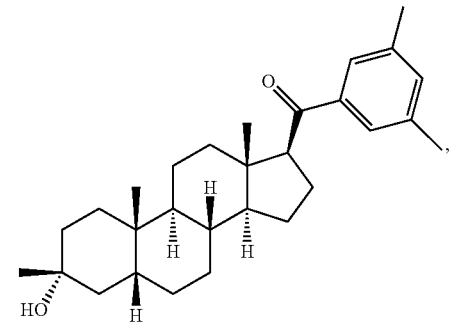

211
-continued
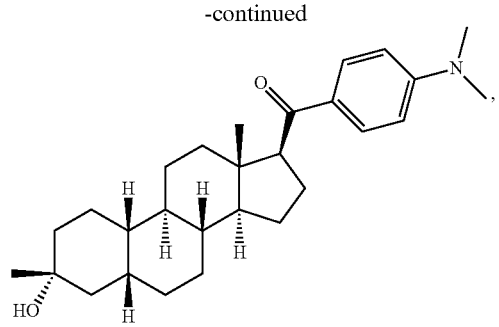
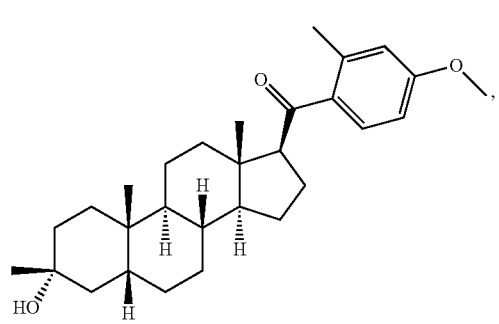
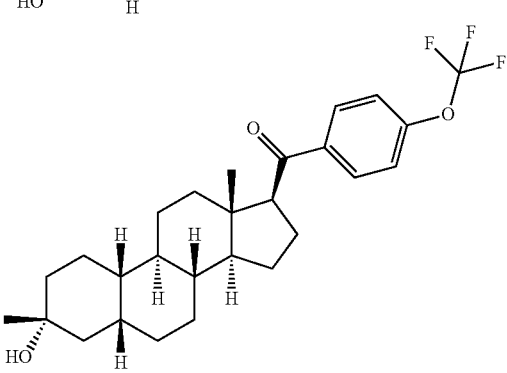
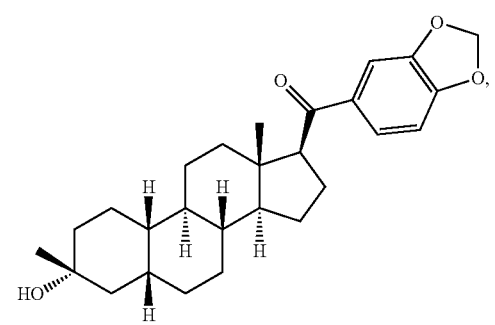
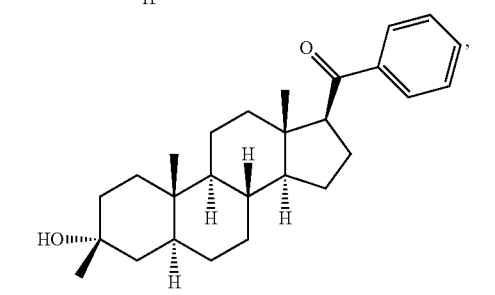
212
-continued
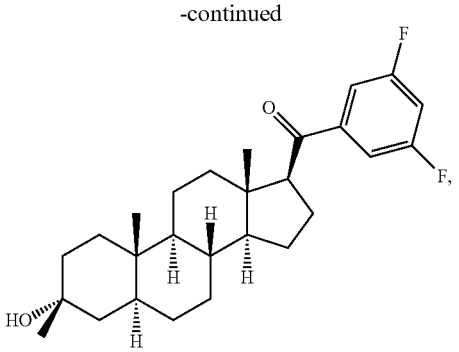
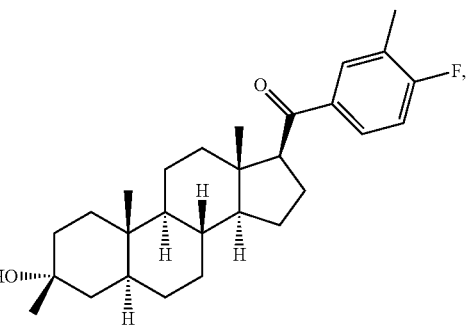
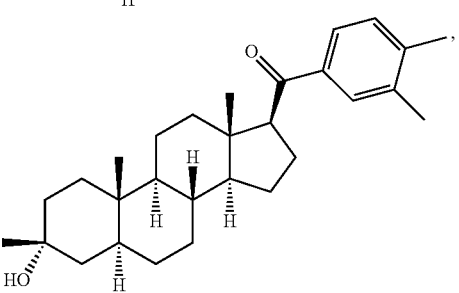
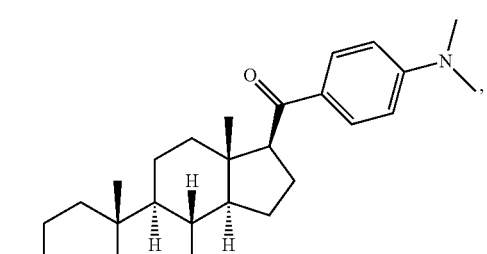
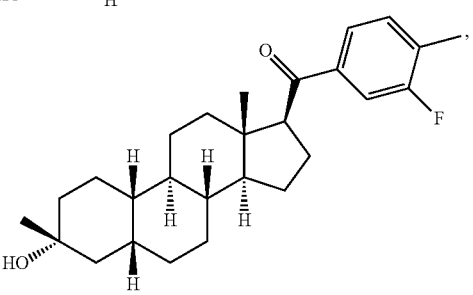

213
-continued
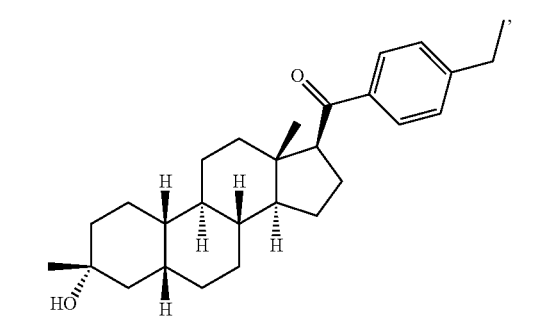
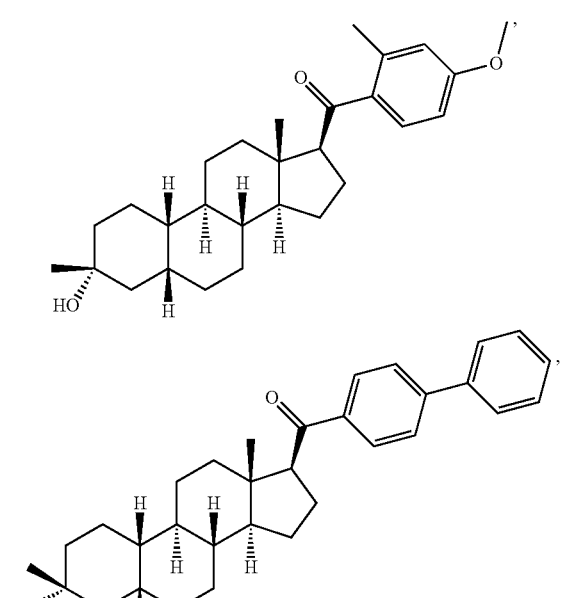
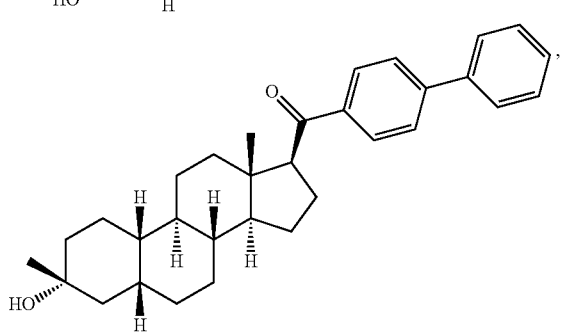
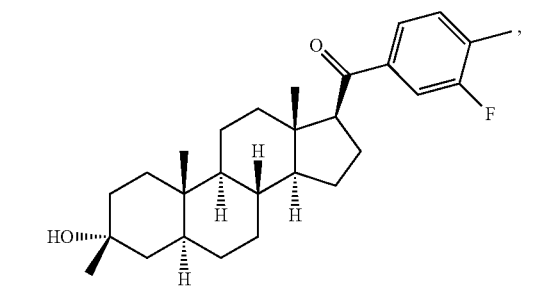
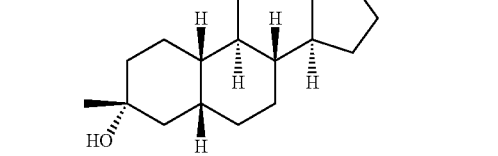
214
-continued
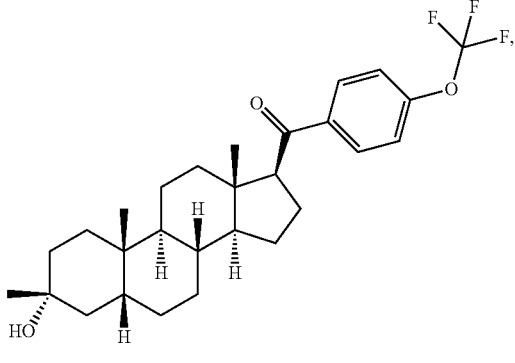
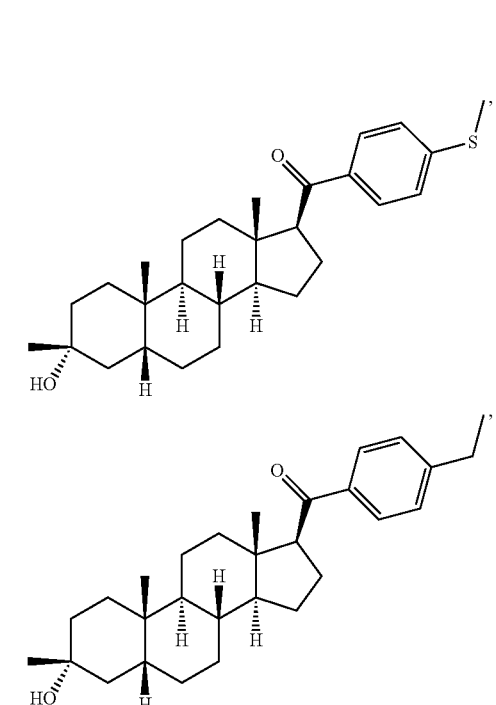
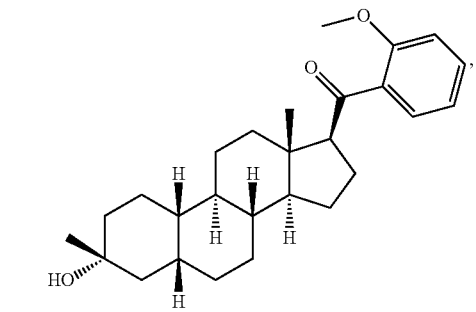
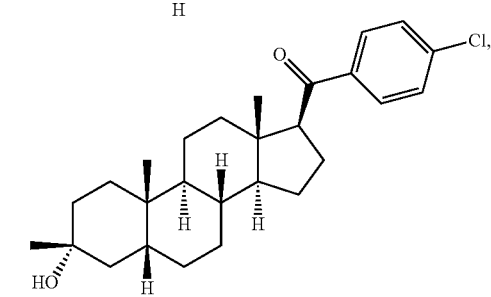

-continued
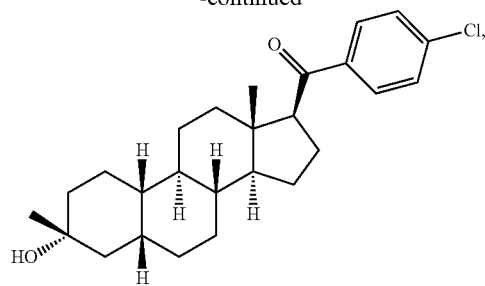
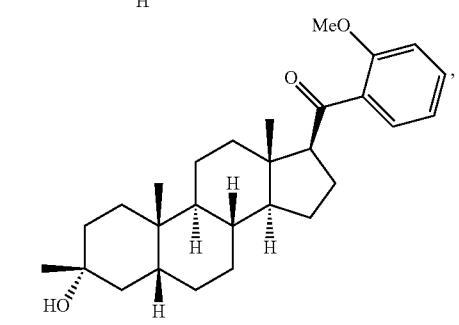
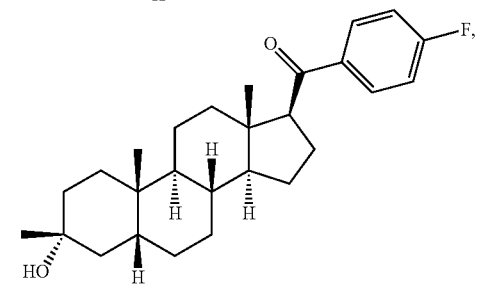
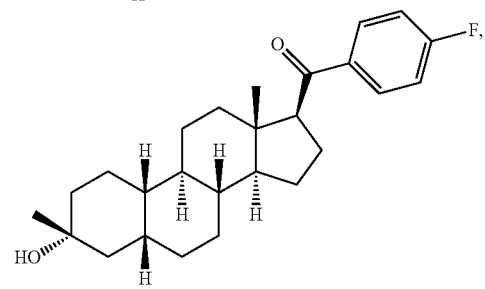
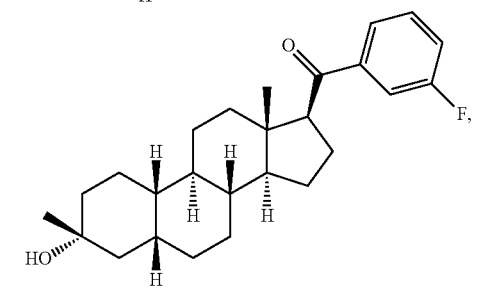
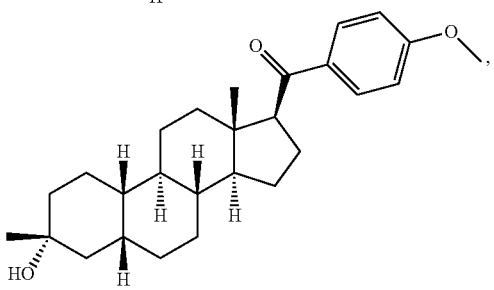
-continued
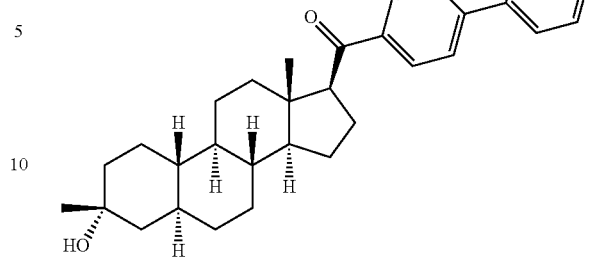
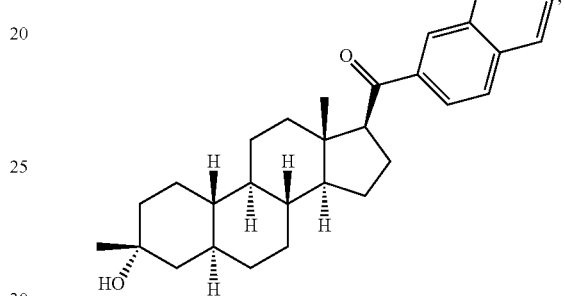
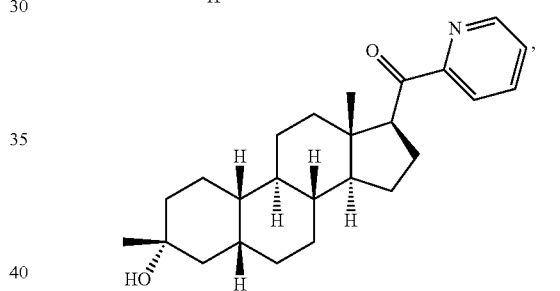
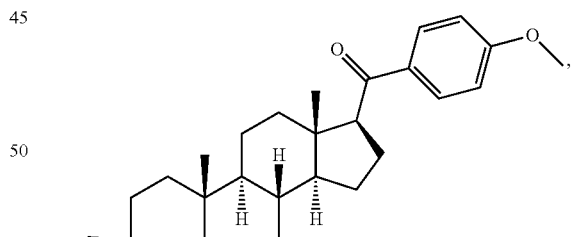
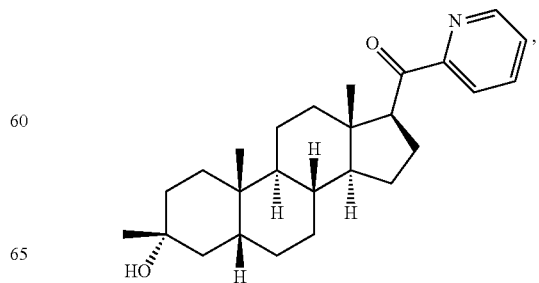

217
-continued
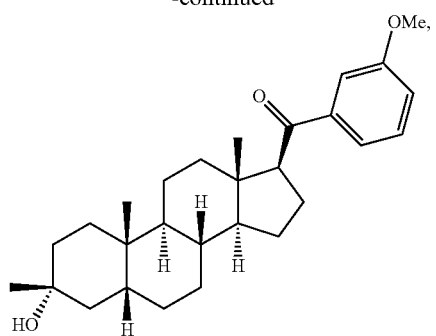
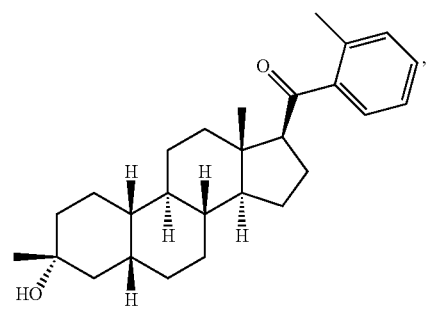
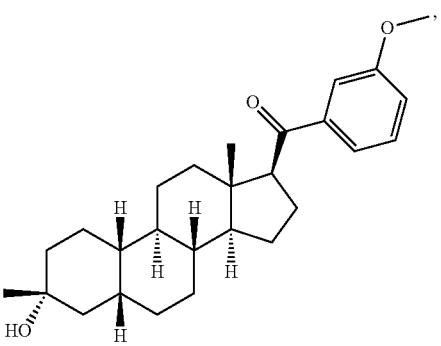
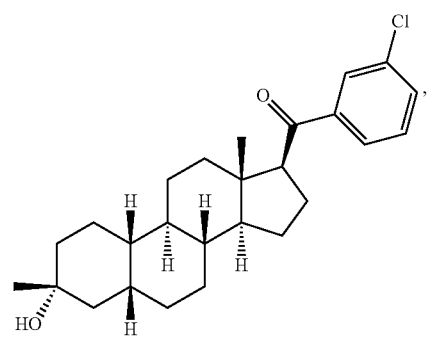
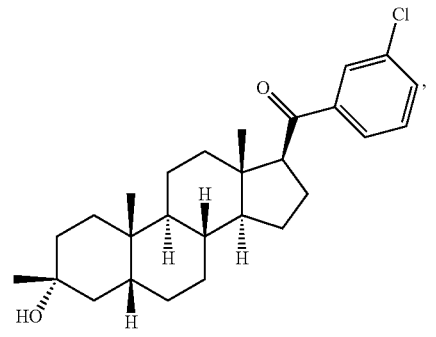
218
-continued
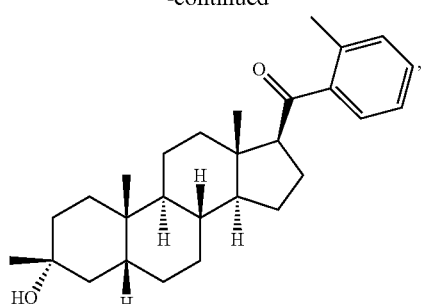
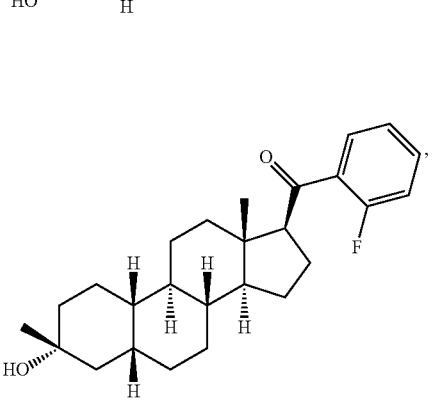
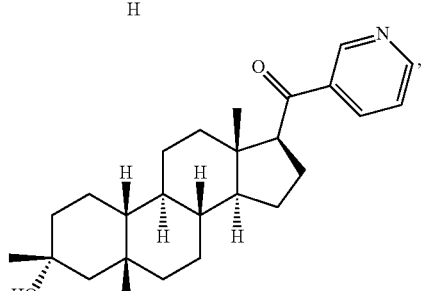
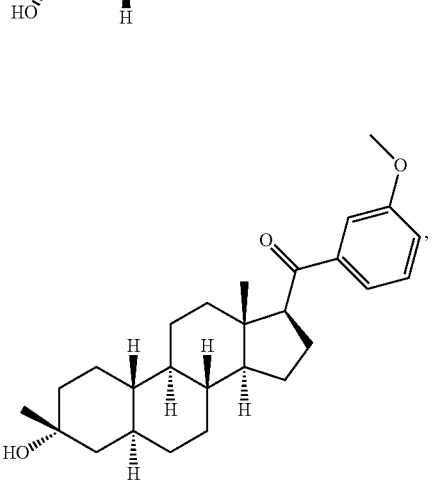
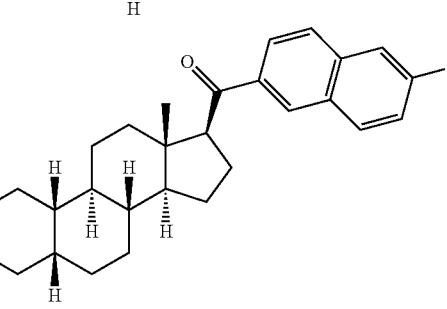

219
-continued
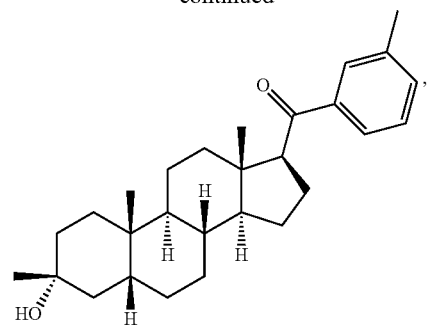
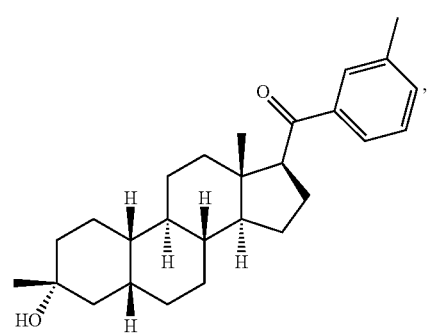
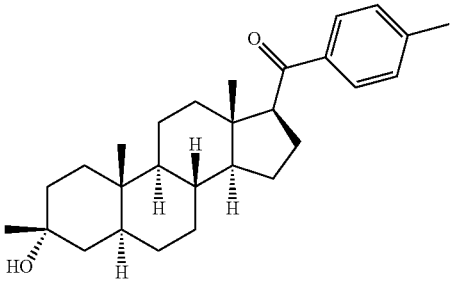
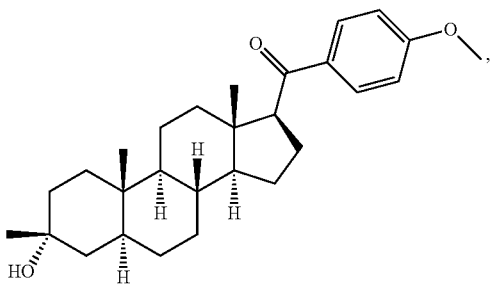
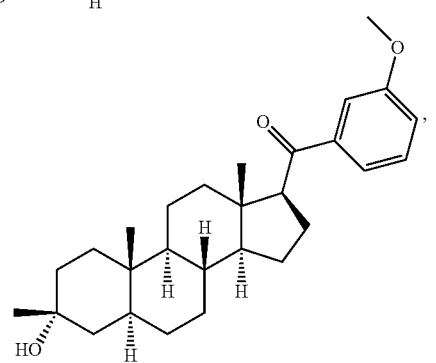
220
-continued
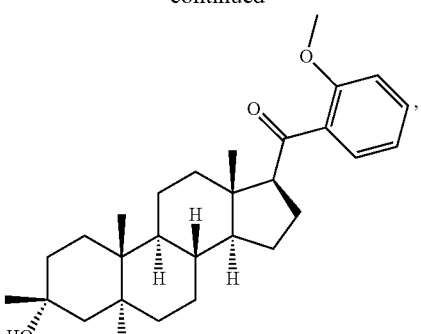
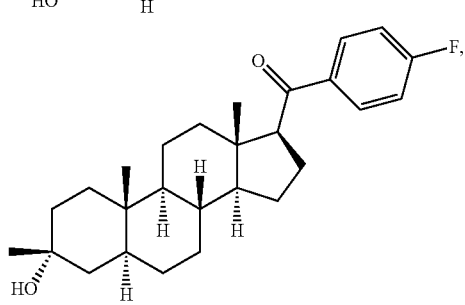
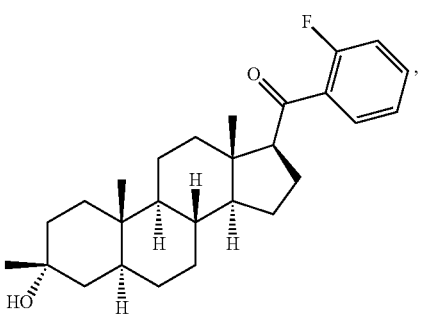
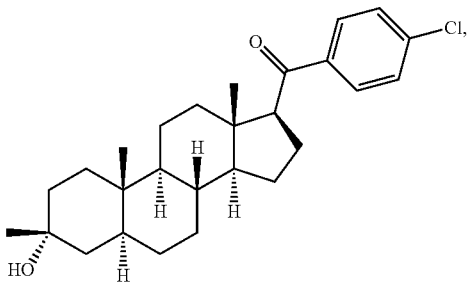
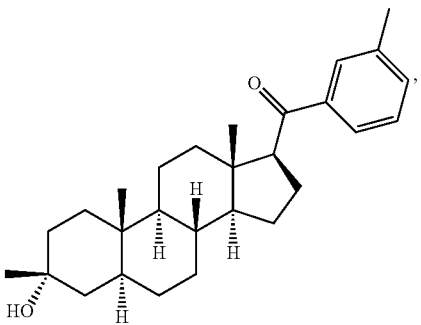

221
-continued
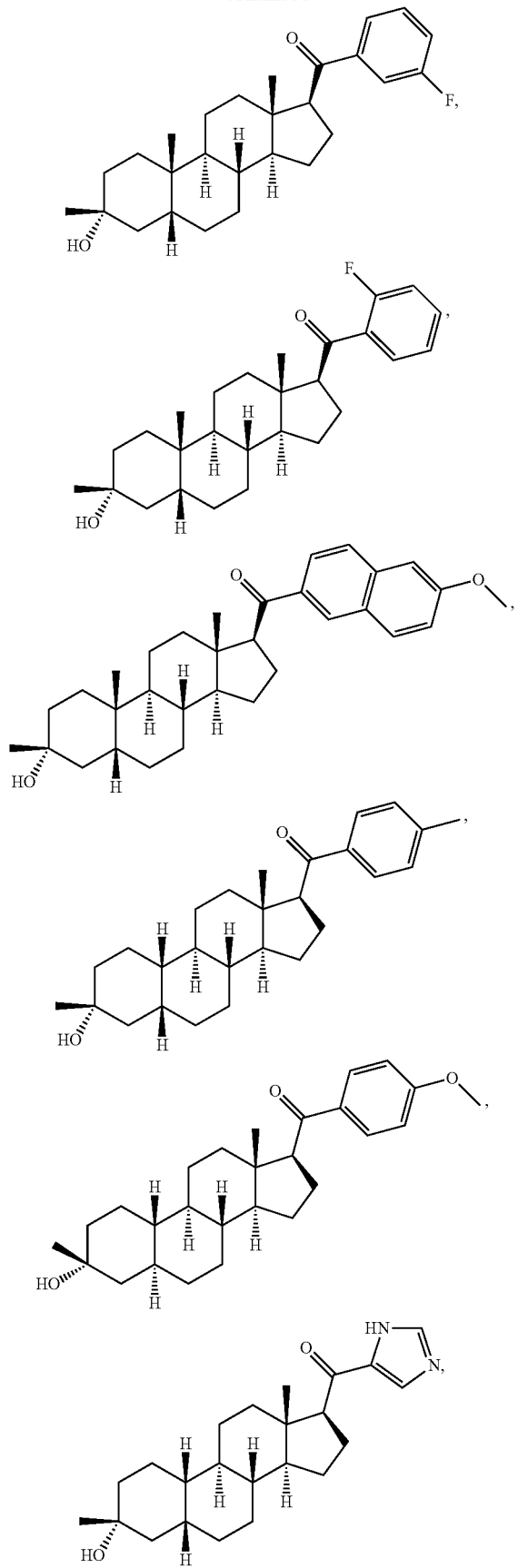
222
-continued
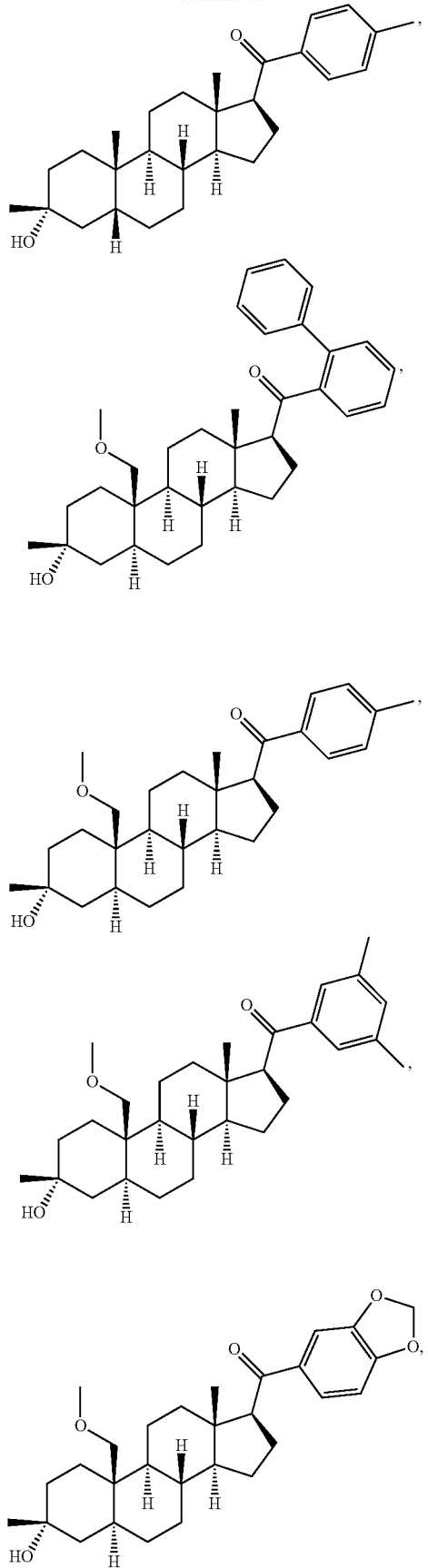

223
-continued
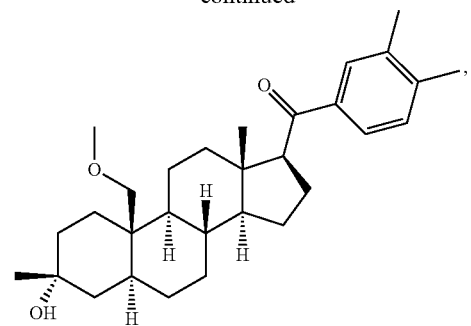
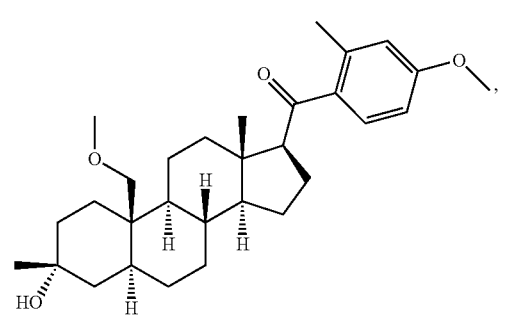
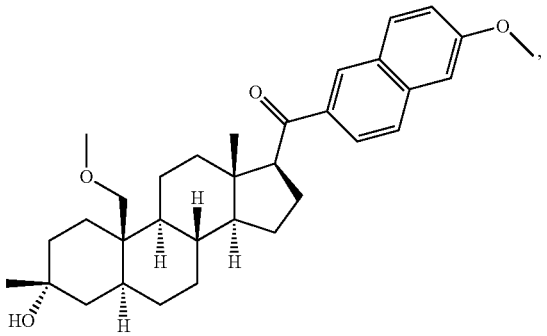
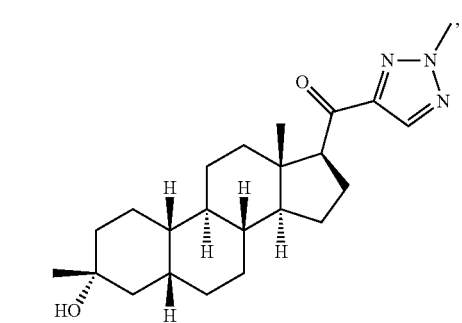
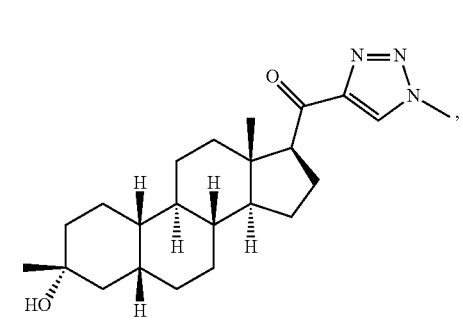
224
-continued
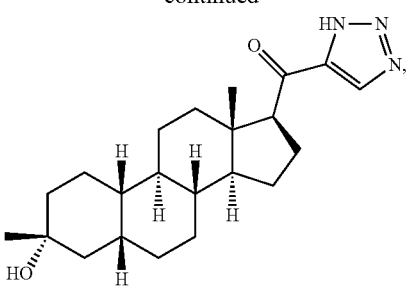
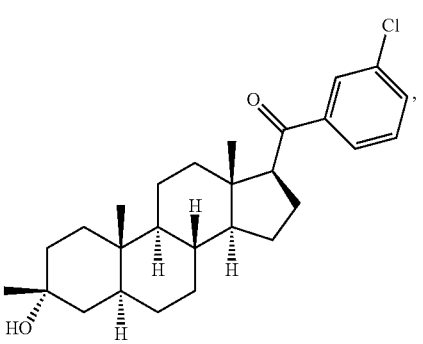
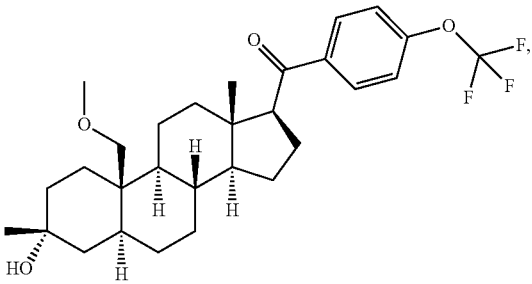
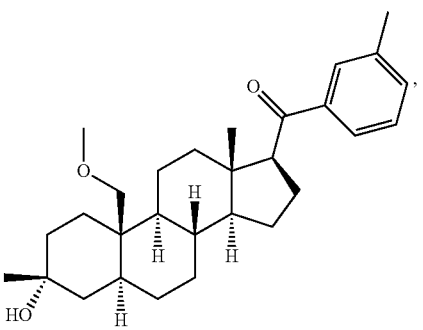
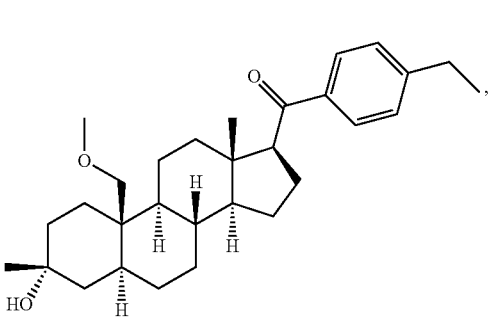

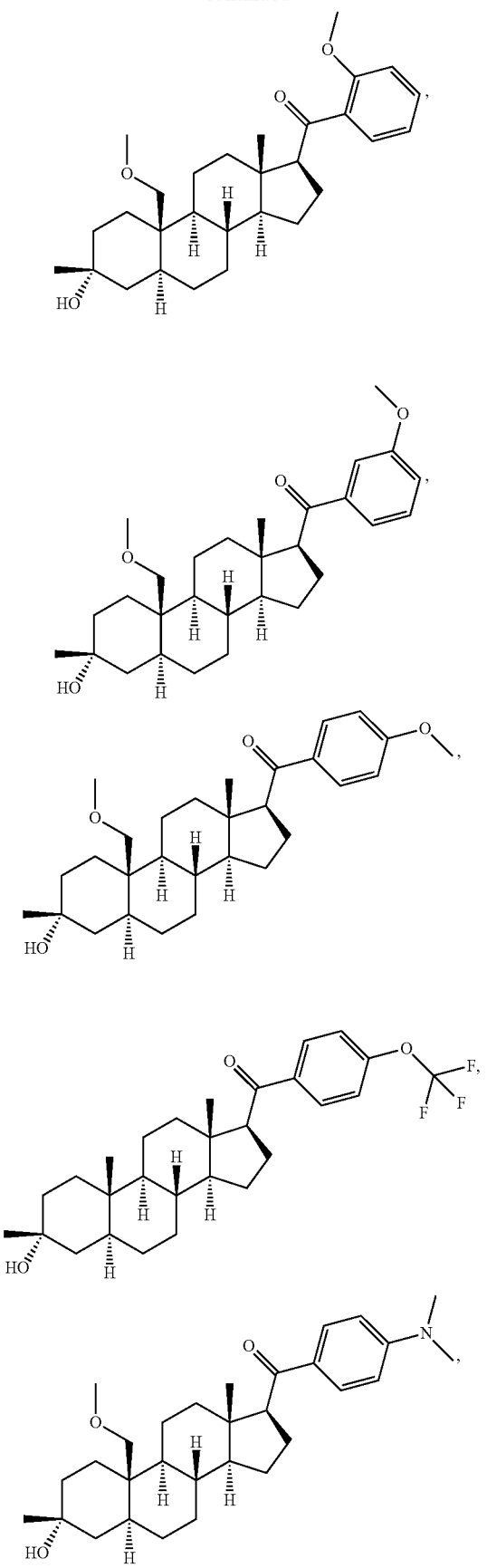
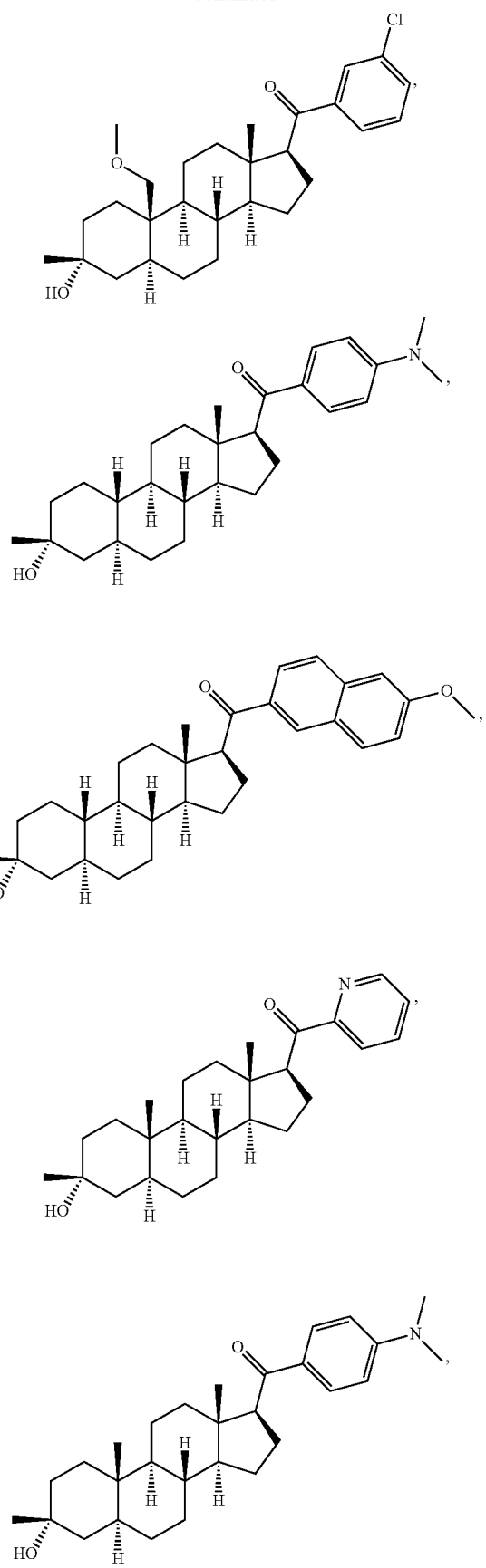

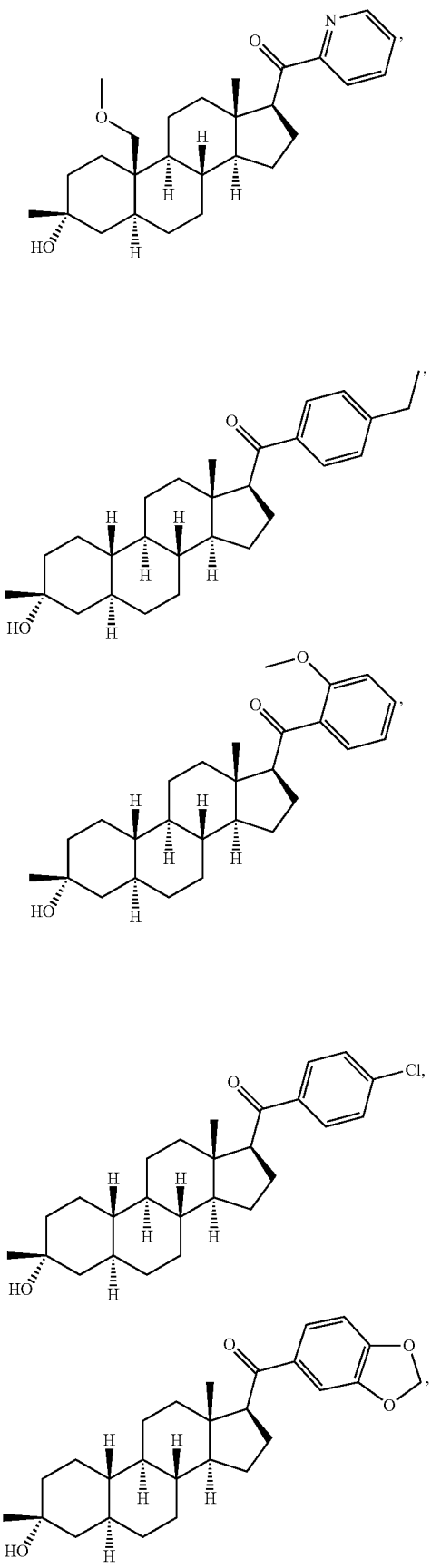
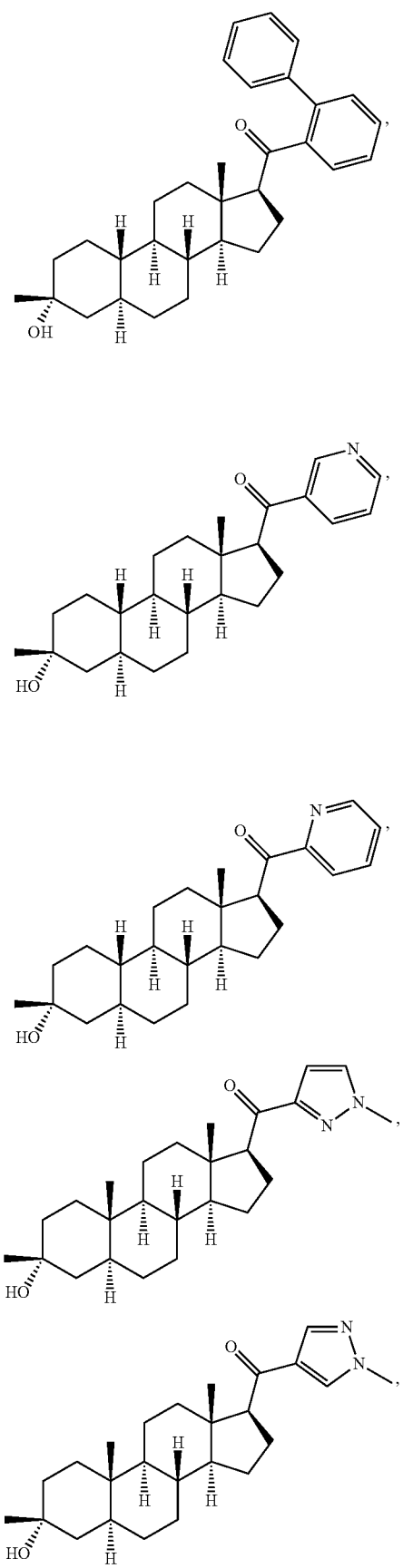

229
-continued
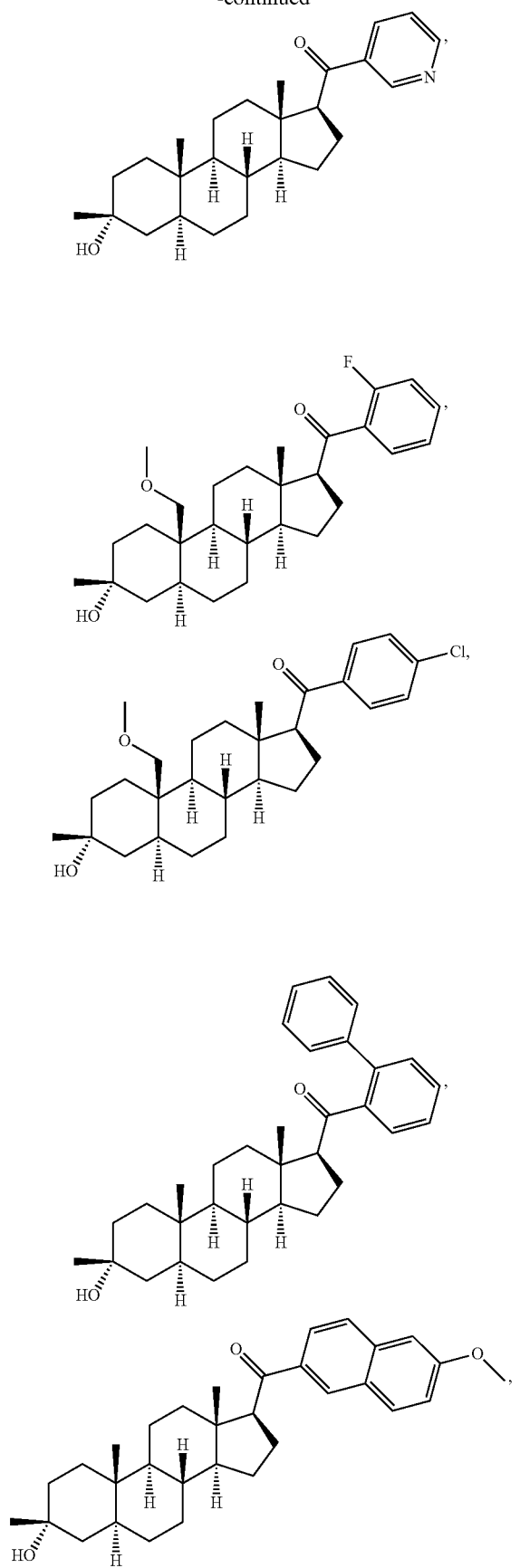
230
-continued
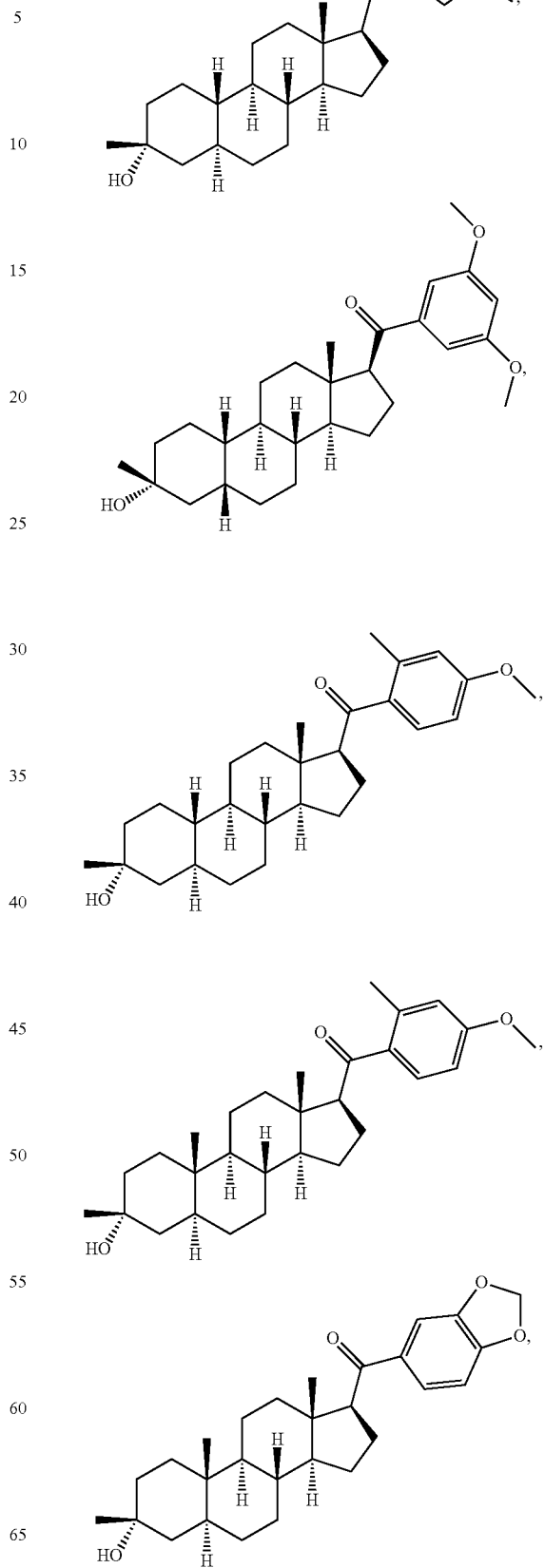

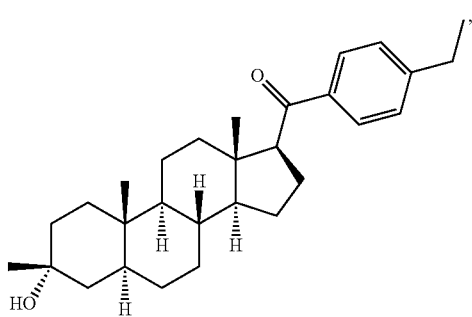

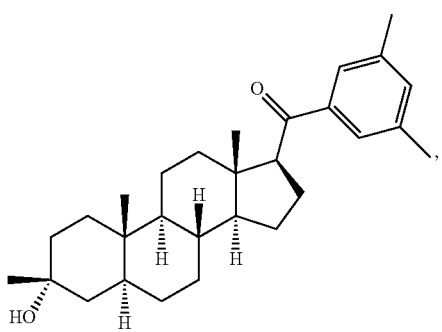

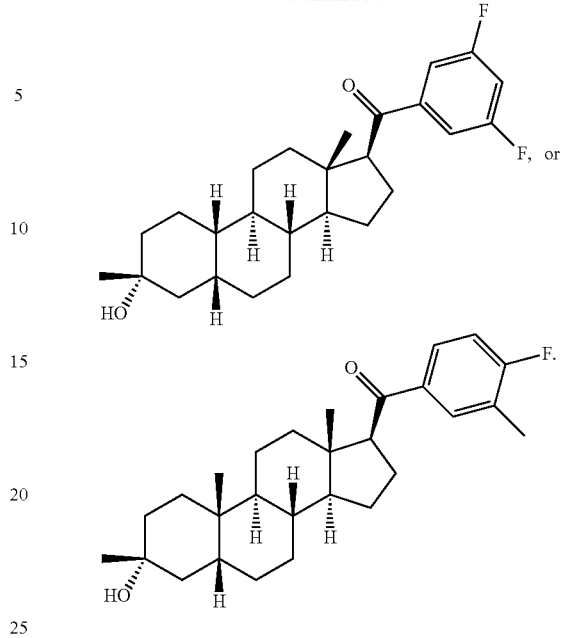

15. A pharmaceutical composition comprising a compound of claim 1 and a pharmaceutically acceptable excipient.

16. A method of treating an anxiety disorder or depression in a human subject in need thereof, comprising administering to the human subject a therapeutically effective amount of a compound of claim 1 or a pharmaceutically acceptable salt thereof.

17. The method of claim 16, wherein the anxiety disorder is a generalized anxiety disorder (GAD).

18. The method of claim 16, wherein, wherein the method is a method of treating depression.

* * * * *

UNITED STATES PATENT AND TRADEMARK OFFICE
CERTIFICATE OF CORRECTION

| | | |
|---|---|---|
| PATENT NO. | : 10,774,108 B2 | Page 1 of 1 |
| APPLICATION NO. | : 15/531313 | |
| DATED | : September 15, 2020 | |
| INVENTOR(S) | : Martinez Botella et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 132 days.

Signed and Sealed this
Thirty-first Day of January, 2023

*Katherine Kelly Vidal*

Katherine Kelly Vidal
*Director of the United States Patent and Trademark Office*